United States Patent
Winslow et al.

(10) Patent No.: US 8,002,803 B2
(45) Date of Patent: Aug. 23, 2011

(54) DEFLECTION ROD SYSTEM FOR A SPINE IMPLANT INCLUDING AN INNER ROD AND AN OUTER SHELL AND METHOD

(75) Inventors: Charles J. Winslow, Walnut Creek, CA (US); John J. Flynn, Walnut Creek, CA (US); James F. Zucherman, San Francisco, CA (US); Ken Y. Hsu, San Francisco, CA (US); Donald L. Cain, Oakland, CA (US); Henry A. Klyce, Piedmont, CA (US); H. Adam R. Klyce, Berkeley, CA (US)

(73) Assignee: Spartek Medical, Inc., Alameda, CA (US)

( * ) Notice: Subject to any disclaimer, the term of this patent is extended or adjusted under 35 U.S.C. 154(b) by 613 days.

(21) Appl. No.: 12/130,335

(22) Filed: May 30, 2008

(65) Prior Publication Data

US 2008/0306544 A1    Dec. 11, 2008

Related U.S. Application Data

(60) Provisional application No. 61/028,792, filed on Feb. 14, 2008, provisional application No. 60/942,162, filed on Jun. 5, 2007, provisional application No. 61/031,598, filed on Feb. 26, 2008, provisional application No. 61/057,340, filed on May 30, 2008.

(51) Int. Cl.
    *A61B 17/70* (2006.01)
(52) U.S. Cl. .................. 606/257; 606/246; 606/264

(58) Field of Classification Search .................. 606/257, 606/254, 255, 256, 258, 259, 246, 247, 248, 606/249, 250, 264
See application file for complete search history.

(56) References Cited

U.S. PATENT DOCUMENTS

| | | | |
|---|---|---|---|
| 4,041,939 A | 8/1977 | Hall | 128/69 |
| 4,065,817 A | 1/1978 | Branemark et al. | 3/1.91 |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |

(Continued)

FOREIGN PATENT DOCUMENTS

DE    2649042 B1    10/1976

(Continued)

OTHER PUBLICATIONS

"Flexible rods and the case for dynamic stabilization," Jason M. Highsmith, M.D., et al., *Neurosurg. Focus*, vol. 22, Jan. 2007, pp. 1-5.

(Continued)

*Primary Examiner* — Pedro Philogene
(74) *Attorney, Agent, or Firm* — Fliesler Meyer LLP

(57) ABSTRACT

A dynamic stabilization, motion preservation spinal implant system includes an anchor system, a horizontal rod system and a vertical rod system. The systems are modular so that various constructs and configurations can be created and customized to a patient.

27 Claims, 73 Drawing Sheets

U.S. PATENT DOCUMENTS

| | | | | |
|---|---|---|---|---|
| 4,604,995 A | 8/1986 | Stephens et al. | ................ | 128/69 |
| 4,611,580 A | 9/1986 | Wu | ................... | 128/69 |
| 4,611,581 A | 9/1986 | Steffee | ............................ | 128/69 |
| 4,611,582 A | 9/1986 | Duff | ................... | 128/69 |
| 4,641,636 A | 2/1987 | Cotrel | ............................ | 128/69 |
| 4,648,388 A | 3/1987 | Steffee | ............................ | 128/69 |
| 4,653,481 A | 3/1987 | Howland et al. | ................ | 128/69 |
| 4,653,489 A | 3/1987 | Tronzo | ............................ | 128/92 |
| 4,655,199 A | 4/1987 | Steffee | ............................ | 128/69 |
| 4,658,809 A | 4/1987 | Ulrich et al. | .................. | 128/92 |
| 4,696,290 A | 9/1987 | Steffee | ............................ | 128/69 |
| 4,719,905 A | 1/1988 | Steffee | ............................ | 128/69 |
| 4,763,644 A | 8/1988 | Webb | ............................ | 128/69 |
| 4,773,402 A | 9/1988 | Asher et al. | ..................... | 128/69 |
| 4,805,602 A | 2/1989 | Puno et al. | ...................... | 128/69 |
| 4,815,453 A | 3/1989 | Cotrel | ............................ | 128/69 |
| 4,887,595 A | 12/1989 | Heinig et al. | .................. | 606/61 |
| 4,913,134 A | 4/1990 | Luque | ............................ | 128/69 |
| 4,946,458 A | 8/1990 | Harms et al. | .................... | 606/61 |
| 4,950,269 A | 8/1990 | Gaines, Jr. | ....................... | 606/61 |
| 4,955,885 A | 9/1990 | Meyers | ............................ | 606/53 |
| 4,987,892 A | 1/1991 | Krag et al. | ...................... | 606/61 |
| 5,005,562 A | 4/1991 | Cotrel | ............................ | 128/69 |
| 5,024,213 A | 6/1991 | Asher et al. | ..................... | 128/69 |
| 5,030,220 A | 7/1991 | Howland | ........................ | 606/61 |
| 5,042,982 A | 8/1991 | Harms et al. | .................... | 606/61 |
| 5,047,029 A | 9/1991 | Aebi et al. | ........................ | 606/61 |
| 5,067,955 A | 11/1991 | Cotrel | ............................ | 606/61 |
| 5,074,864 A | 12/1991 | Cozad et al. | .................... | 606/54 |
| 5,084,049 A | 1/1992 | Asher et al. | ..................... | 606/61 |
| 5,092,866 A | 3/1992 | Breard et al. | .................... | 606/61 |
| 5,102,412 A | 4/1992 | Rogozinski | ..................... | 606/61 |
| 5,112,332 A | 5/1992 | Cozad et al. | .................... | 606/61 |
| 5,113,685 A | 5/1992 | Asher et al. | ..................... | 72/458 |
| 5,127,912 A | 7/1992 | Ray et al. | ........................ | 606/61 |
| 5,129,388 A | 7/1992 | Vignaud et al. | ................ | 606/61 |
| 5,129,900 A | 7/1992 | Asher et al. | ..................... | 606/61 |
| 5,147,359 A | 9/1992 | Cozad et al. | .................... | 606/61 |
| 5,154,718 A | 10/1992 | Cozad et al. | .................... | 606/61 |
| 5,176,680 A | 1/1993 | Vignaud et al. | ................ | 606/61 |
| 5,180,393 A | 1/1993 | Commarmond | ............... | 623/13 |
| 5,190,543 A | 3/1993 | Schläpfer | ........................ | 606/61 |
| 5,201,734 A | 4/1993 | Cozad et al. | .................... | 606/62 |
| 5,207,678 A | 5/1993 | Harms et al. | .................... | 606/61 |
| 5,261,911 A | 11/1993 | Carl | ................................ | 606/61 |
| 5,261,912 A | 11/1993 | Frigg | ............................... | 606/61 |
| 5,261,913 A | 11/1993 | Marnay | ............................ | 606/61 |
| 5,281,222 A | 1/1994 | Allard et al. | .................... | 606/54 |
| 5,282,801 A | 2/1994 | Sherman | ........................ | 606/61 |
| 5,282,863 A | 2/1994 | Burton | ............................ | 623/17 |
| 5,290,289 A | 3/1994 | Sanders et al. | ................. | 606/61 |
| 5,312,402 A | 5/1994 | Schläpfer et al. | ............... | 606/53 |
| 5,312,404 A | 5/1994 | Asher et al. | ..................... | 606/61 |
| 5,344,422 A | 9/1994 | Frigg | ............................... | 606/61 |
| 5,346,493 A | 9/1994 | Stahurski et al. | ............... | 606/61 |
| 5,360,429 A | 11/1994 | Jeanson et al. | ................. | 606/61 |
| 5,360,431 A | 11/1994 | Puno et al. | ...................... | 606/72 |
| 5,380,325 A | 1/1995 | Lahille et al. | .................... | 606/61 |
| 5,380,326 A | 1/1995 | Lin | ................................ | 606/61 |
| 5,382,248 A | 1/1995 | Jacobson et al. | ............... | 606/60 |
| 5,385,583 A | 1/1995 | Cotrel | ............................ | 623/17 |
| 5,387,213 A | 2/1995 | Breard et al. | .................... | 606/61 |
| 5,415,661 A | 5/1995 | Holmes | ............................ | 606/69 |
| 5,429,639 A | 7/1995 | Judet | ............................... | 606/61 |
| 5,437,672 A | 8/1995 | Alleyne | | |
| 5,443,467 A | 8/1995 | Biedermann et al. | ........... | 606/65 |
| 5,466,237 A | 11/1995 | Byrd, III et al. | ................ | 606/61 |
| 5,474,555 A | 12/1995 | Puno et al. | ...................... | 606/73 |
| 5,487,742 A | 1/1996 | Cotrel | ............................ | 606/61 |
| 5,496,321 A | 3/1996 | Puno et al. | ...................... | 606/61 |
| 5,498,264 A | 3/1996 | Schlapfer et al. | ............... | 606/72 |
| 5,520,689 A | 5/1996 | Schläpfer et al. | ............... | 606/61 |
| 5,534,001 A | 7/1996 | Schlapfer et al. | ............... | 606/61 |
| 5,536,268 A | 7/1996 | Griss | ............................... | 606/61 |
| 5,540,688 A | 7/1996 | Navas | ............................. | 606/61 |
| 5,545,167 A | 8/1996 | Lin | ................................ | 606/61 |
| 5,549,607 A | 8/1996 | Olson et al. | ..................... | 606/61 |
| 5,562,737 A | 10/1996 | Graf | ................................ | 623/17 |
| 5,569,248 A | 10/1996 | Mathews | ........................ | 606/61 |
| 5,609,592 A | 3/1997 | Brumfield et al. | ............... | 606/61 |
| 5,609,593 A | 3/1997 | Errico et al. | ..................... | 606/61 |
| 5,611,800 A | 3/1997 | Davis et al. | ..................... | 606/61 |
| 5,624,441 A | 4/1997 | Sherman et al. | ................ | 606/61 |
| 5,628,740 A | 5/1997 | Mullane | ........................ | 606/61 |
| 5,630,816 A | 5/1997 | Kambin | ......................... | 606/61 |
| 5,643,260 A | 7/1997 | Doherty | ........................ | 606/61 |
| 5,645,599 A | 7/1997 | Samani | ............................ | 623/17 |
| 5,651,789 A | 7/1997 | Cotrel | ............................ | 606/61 |
| 5,653,708 A | 8/1997 | Howland | ........................ | 606/61 |
| 5,658,284 A | 8/1997 | Sebastian et al. | ............... | 606/61 |
| 5,667,506 A | 9/1997 | Sutterlin | ......................... | 606/61 |
| 5,667,507 A | 9/1997 | Corin et al. | ..................... | 606/61 |
| 5,669,910 A | 9/1997 | Korhonen et al. | .............. | 606/61 |
| 5,672,175 A | 9/1997 | Martin | ............................. | 606/61 |
| 5,672,176 A | 9/1997 | Biedermann et al. | ........... | 606/61 |
| 5,676,665 A | 10/1997 | Bryan | ............................. | 606/61 |
| 5,676,703 A | 10/1997 | Gelbard | ......................... | 623/17 |
| 5,681,311 A | 10/1997 | Foley et al. | ..................... | 606/61 |
| 5,681,319 A | 10/1997 | Biedermann et al. | ......... | 606/104 |
| 5,683,391 A | 11/1997 | Boyd | ............................... | 606/61 |
| 5,683,392 A | 11/1997 | Richelsoph et al. | ............ | 606/61 |
| 5,683,393 A | 11/1997 | Ralph | ............................. | 606/61 |
| 5,688,272 A | 11/1997 | Montague et al. | ............... | 606/61 |
| 5,688,273 A | 11/1997 | Errico et al. | ..................... | 606/61 |
| 5,690,629 A | 11/1997 | Asher et al. | ..................... | 606/61 |
| 5,690,632 A | 11/1997 | Schwartz et al. | ............... | 606/73 |
| 5,690,633 A | 11/1997 | Taylor et al. | .................... | 606/73 |
| 5,693,053 A | 12/1997 | Estes | ............................... | 606/61 |
| 5,697,929 A | 12/1997 | Mellinger | ....................... | 606/61 |
| 5,700,292 A | 12/1997 | Margulies | ....................... | 623/17 |
| 5,702,392 A | 12/1997 | Wu et al. | ......................... | 606/61 |
| 5,702,394 A | 12/1997 | Henry et al. | ..................... | 606/61 |
| 5,702,395 A | 12/1997 | Hopf | ................................ | 606/61 |
| 5,702,396 A | 12/1997 | Hoenig et al. | .................... | 606/69 |
| 5,702,399 A | 12/1997 | Kilpela et al. | .................... | 606/72 |
| 5,702,452 A | 12/1997 | Argenson et al. | ............... | 623/17 |
| 5,713,900 A | 2/1998 | Benzel et al. | .................... | 606/61 |
| 5,713,904 A | 2/1998 | Errico et al. | ..................... | 606/73 |
| 5,716,355 A | 2/1998 | Jackson et al. | ................. | 606/61 |
| 5,716,356 A | 2/1998 | Biedermann et al. | ........... | 606/61 |
| 5,716,357 A | 2/1998 | Rogozinski | ..................... | 606/61 |
| 5,716,358 A | 2/1998 | Ochoa et al. | ..................... | 606/62 |
| 5,716,359 A | 2/1998 | Ojima et al. | ..................... | 606/76 |
| 5,720,751 A | 2/1998 | Jackson | .......................... | 606/86 |
| 5,725,528 A | 3/1998 | Errico et al. | ..................... | 606/61 |
| 5,725,582 A | 3/1998 | Bevan et al. | ..................... | 623/17 |
| 5,728,098 A | 3/1998 | Sherman et al. | ................ | 606/61 |
| 5,733,286 A | 3/1998 | Errico et al. | ..................... | 606/61 |
| 5,735,851 A | 4/1998 | Errico et al. | ..................... | 606/61 |
| 5,741,254 A | 4/1998 | Henry et al. | ..................... | 606/61 |
| 5,743,907 A | 4/1998 | Asher et al. | ..................... | 606/61 |
| 5,743,911 A | 4/1998 | Cotrel | ............................ | 606/61 |
| 5,752,957 A | 5/1998 | Ralph et al. | ..................... | 606/61 |
| 5,766,254 A | 6/1998 | Gelbard | ......................... | 623/17 |
| 5,776,135 A | 7/1998 | Errico et al. | ..................... | 606/61 |
| 5,782,833 A | 7/1998 | Haider | ............................ | 606/61 |
| 5,785,711 A | 7/1998 | Errico et al. | ..................... | 606/61 |
| 5,797,911 A | 8/1998 | Sherman et al. | ................ | 606/61 |
| 5,800,435 A | 9/1998 | Errico et al. | ..................... | 606/61 |
| 5,810,819 A | 9/1998 | Errico et al. | ..................... | 606/61 |
| 5,863,293 A | 1/1999 | Richelsoph | ..................... | 606/61 |
| 5,879,350 A | 3/1999 | Sherman et al. | ................ | 606/61 |
| 5,885,286 A | 3/1999 | Sherman et al. | ................ | 606/61 |
| 5,891,145 A | 4/1999 | Morrison et al. | ............... | 606/61 |
| 5,899,904 A | 5/1999 | Errico et al. | ..................... | 606/61 |
| RE36,221 E | 6/1999 | Breard et al. | .................... | 606/61 |
| 5,910,142 A | 6/1999 | Tatar | ............................... | 606/61 |
| 5,925,047 A | 7/1999 | Errico et al. | ..................... | 606/65 |
| 5,928,231 A | 7/1999 | Klein et al. | ...................... | 606/60 |
| 5,928,232 A | 7/1999 | Howland et al. | ............... | 606/61 |
| 5,928,233 A | 7/1999 | Apfelbaum et al. | ............. | 606/61 |
| 5,947,965 A | 9/1999 | Bryan | ............................. | 606/61 |
| 5,947,969 A | 9/1999 | Errico et al. | ..................... | 606/61 |
| 5,954,725 A | 9/1999 | Sherman et al. | ................ | 606/78 |
| 5,961,517 A | 10/1999 | Biedermann et al. | ........... | 606/61 |
| 5,964,760 A | 10/1999 | Richelsoph | ..................... | 606/61 |
| 5,980,521 A | 11/1999 | Montague et al. | ............... | 606/61 |

| | | | |
|---|---|---|---|
| 5,980,523 A | 11/1999 | Jackson | 606/61 |
| 5,984,922 A | 11/1999 | McKay | 606/61 |
| 5,989,251 A | 11/1999 | Nichols | 606/61 |
| 5,989,254 A | 11/1999 | Katz | 606/73 |
| 6,001,098 A | 12/1999 | Metz-Stavenhagen et al. | 606/61 |
| 6,004,322 A | 12/1999 | Bernstein | 606/61 |
| 6,010,503 A | 1/2000 | Richelsoph et al. | 606/61 |
| 6,015,409 A | 1/2000 | Jackson | 606/61 |
| 6,036,693 A | 3/2000 | Yuan et al. | 606/61 |
| 6,050,997 A | 4/2000 | Mullane | 606/61 |
| 6,053,917 A | 4/2000 | Sherman et al. | 606/61 |
| 6,063,089 A | 5/2000 | Errico et al. | 606/61 |
| 6,077,262 A | 6/2000 | Schläpfer et al. | 606/61 |
| 6,086,588 A | 7/2000 | Ameil et al. | 606/61 |
| 6,090,111 A | 7/2000 | Nichols | 606/61 |
| 6,096,039 A | 8/2000 | Stoltenberg et al. | 606/61 |
| 6,113,600 A | 9/2000 | Drummond et al. | 606/61 |
| 6,113,601 A | 9/2000 | Tatar | 606/61 |
| 6,127,597 A | 10/2000 | Beyar et al. | 623/16 |
| 6,132,430 A | 10/2000 | Wagner | 606/61 |
| 6,132,434 A | 10/2000 | Sherman et al. | 606/78 |
| 6,136,000 A | 10/2000 | Louis et al. | 606/61 |
| 6,146,383 A | 11/2000 | Studer et al. | 606/61 |
| 6,171,311 B1 | 1/2001 | Richelsoph | 606/61 |
| 6,193,720 B1 | 2/2001 | Yuan et al. | 606/61 |
| 6,197,028 B1 | 3/2001 | Ray et al. | 606/61 |
| 6,210,413 B1 | 4/2001 | Justis et al. | 606/61 |
| 6,217,578 B1 | 4/2001 | Crozet et al. | 606/61 |
| 6,248,106 B1 | 6/2001 | Ferree | 606/61 |
| 6,254,602 B1 | 7/2001 | Justis | 606/61 |
| 6,261,287 B1 | 7/2001 | Metz-Stavenhagen | 606/61 |
| 6,273,888 B1 | 8/2001 | Justis | 606/61 |
| 6,273,914 B1 | 8/2001 | Papas | 623/17.11 |
| 6,280,443 B1 | 8/2001 | Gu et al. | 606/61 |
| 6,287,311 B1 | 9/2001 | Sherman et al. | 606/78 |
| 6,293,949 B1 | 9/2001 | Justis et al. | 606/61 |
| 6,302,882 B1 | 10/2001 | Lin et al. | |
| 6,302,888 B1 | 10/2001 | Mellinger et al. | 606/73 |
| 6,309,391 B1 | 10/2001 | Crandall et al. | 606/61 |
| 6,325,802 B1 | 12/2001 | Frigg | 606/61 |
| 6,328,740 B1 | 12/2001 | Richelsoph | 606/61 |
| 6,344,057 B1 | 2/2002 | Rabbe et al. | 623/17 |
| 6,355,040 B1 | 3/2002 | Richelsoph et al. | 606/61 |
| 6,379,354 B1 | 4/2002 | Rogozinski | 606/61 |
| 6,402,749 B1 | 6/2002 | Ashman | 606/61 |
| 6,402,751 B1 | 6/2002 | Hoeck et al. | 606/61 |
| 6,402,752 B2 | 6/2002 | Schaffler-Wachter et al. | 606/61 |
| 6,413,257 B1 | 7/2002 | Lin et al. | 606/61 |
| 6,416,515 B1 | 7/2002 | Wagner | 606/61 |
| 6,423,064 B1 | 7/2002 | Kluger | 606/61 |
| 6,440,169 B1 | 8/2002 | Elberg et al. | 623/17.16 |
| 6,451,021 B1 | 9/2002 | Ralph et al. | 606/61 |
| 6,454,773 B1 | 9/2002 | Sherman et al. | 606/78 |
| 6,458,131 B1 | 10/2002 | Ray | 606/61 |
| 6,458,132 B2 | 10/2002 | Choi | 606/61 |
| 6,468,276 B1 | 10/2002 | McKay | 606/61 |
| 6,471,705 B1 | 10/2002 | Biedermann et al. | 606/61 |
| 6,478,797 B1 | 11/2002 | Paul | 606/61 |
| 6,482,207 B1 | 11/2002 | Errico | 606/61 |
| 6,485,491 B1 | 11/2002 | Farris et al. | 606/61 |
| 6,488,681 B2 | 12/2002 | Martin et al. | 606/61 |
| 6,520,962 B1 | 2/2003 | Taylor et al. | 606/61 |
| 6,520,990 B1 | 2/2003 | Ray | 623/17.11 |
| 6,537,276 B2 | 3/2003 | Metz-Stavenhagen | 606/61 |
| 6,540,748 B2 | 4/2003 | Lombardo | 606/61 |
| 6,540,749 B2 | 4/2003 | Schäfer et al. | 606/61 |
| 6,547,789 B1 | 4/2003 | Ventre et al. | 606/61 |
| 6,554,832 B2 | 4/2003 | Shluzas | 606/61 |
| 6,554,834 B1 | 4/2003 | Crozet et al. | 606/65 |
| 6,565,565 B1 | 5/2003 | Yuan et al. | 606/61 |
| 6,565,566 B1 | 5/2003 | Wagner et al. | 606/61 |
| 6,565,567 B1 | 5/2003 | Haider | 606/61 |
| 6,565,605 B2 | 5/2003 | Goble et al. | 623/17.11 |
| 6,572,617 B1 | 6/2003 | Senegas | 606/61 |
| 6,572,653 B1 | 6/2003 | Simonson | 623/17.13 |
| 6,579,290 B1 | 6/2003 | Hardcastle et al. | 606/61 |
| 6,585,737 B1 | 7/2003 | Baccelli et al. | 606/61 |
| 6,616,669 B2 | 9/2003 | Ogilvie et al. | 606/61 |
| 6,623,485 B2 | 9/2003 | Doubler et al. | 606/61 |
| 6,626,905 B1 | 9/2003 | Schmiel et al. | 606/61 |
| 6,626,908 B2 | 9/2003 | Cooper et al. | 606/61 |
| 6,645,207 B2 | 11/2003 | Dixon et al. | 606/61 |
| 6,652,526 B1 | 11/2003 | Arafiles | 606/61 |
| 6,656,181 B2 | 12/2003 | Dixon et al. | 606/69 |
| 6,660,004 B2 | 12/2003 | Barker et al. | 606/61 |
| 6,660,005 B2 | 12/2003 | Toyama et al. | 606/61 |
| 6,695,845 B2 | 2/2004 | Dixon et al. | 606/70 |
| 6,706,045 B2 | 3/2004 | Lin et al. | 606/61 |
| 6,709,434 B1 | 3/2004 | Gournay et al. | 606/61 |
| 6,716,213 B2 | 4/2004 | Shitoto | 606/61 |
| 6,716,214 B1 | 4/2004 | Jackson | 606/61 |
| 6,726,689 B2 | 4/2004 | Jackson | 606/73 |
| 6,736,820 B2 | 5/2004 | Biedermann et al. | 606/73 |
| 6,740,086 B2 | 5/2004 | Richelsoph | |
| 6,749,614 B2 | 6/2004 | Teitelbaum et al. | 606/61 |
| 6,752,807 B2 | 6/2004 | Lin et al. | 606/61 |
| 6,755,829 B1 | 6/2004 | Bono et al. | 606/61 |
| 6,755,835 B2 | 6/2004 | Schultheiss et al. | 606/73 |
| 6,761,719 B2 | 7/2004 | Justis et al. | 606/61 |
| 6,783,526 B1 | 8/2004 | Lin et al. | 606/61 |
| 6,783,527 B2 | 8/2004 | Drewry et al. | 606/61 |
| 6,786,907 B2 | 9/2004 | Lange | 606/61 |
| 6,793,656 B1 | 9/2004 | Mathews | 606/61 |
| 6,805,695 B2 | 10/2004 | Keith et al. | 606/61 |
| 6,805,714 B2 | 10/2004 | Sutcliffe | 623/17.11 |
| 6,811,567 B2 | 11/2004 | Reiley | 623/17.11 |
| 6,832,999 B2 | 12/2004 | Ueyama et al. | 606/61 |
| 6,840,940 B2 | 1/2005 | Ralph et al. | 606/61 |
| 6,843,791 B2 | 1/2005 | Serhan | 606/61 |
| 6,852,128 B2 | 2/2005 | Lange | 623/17.11 |
| 6,858,030 B2 | 2/2005 | Martin et al. | 606/61 |
| 6,869,433 B2 | 3/2005 | Glascott | 606/73 |
| 6,875,211 B2 | 4/2005 | Nichols et al. | 606/61 |
| 6,881,215 B2 | 4/2005 | Assaker et al. | 606/61 |
| 6,883,520 B2 | 4/2005 | Lambrecht et al. | 128/898 |
| 6,887,242 B2 | 5/2005 | Doubler et al. | 606/61 |
| 6,899,714 B2 | 5/2005 | Vaughan | 606/61 |
| 6,918,911 B2 | 7/2005 | Biedermann et al. | 606/61 |
| 6,932,817 B2 | 8/2005 | Baynham et al. | 606/61 |
| 6,945,974 B2 | 9/2005 | Dalton | 606/70 |
| 6,951,561 B2 | 10/2005 | Warren et al. | 606/73 |
| 6,964,666 B2 | 11/2005 | Jackson | 606/61 |
| 6,966,910 B2 | 11/2005 | Ritland | 606/61 |
| 6,986,771 B2 | 1/2006 | Paul et al. | 606/61 |
| 6,991,632 B2 | 1/2006 | Ritland | 606/61 |
| 7,008,423 B2 | 3/2006 | Assaker et al. | 606/61 |
| 7,011,685 B2 | 3/2006 | Arnin et al. | 623/17.16 |
| 7,018,378 B2 | 3/2006 | Biedermann et al. | 606/61 |
| 7,018,379 B2 | 3/2006 | Drewry et al. | 606/61 |
| 7,022,122 B2 | 4/2006 | Amrein et al. | 606/61 |
| 7,029,475 B2 | 4/2006 | Panjabi | 606/61 |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,214,227 B2 | 5/2007 | Colleran et al. | 606/61 |
| 7,250,052 B2 | 7/2007 | Landry et al. | 606/61 |
| 7,282,064 B2 | 10/2007 | Chin | 623/17.15 |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,326,210 B2 | 2/2008 | Jahng et al. | 606/61 |
| 7,335,201 B2 | 2/2008 | Doubler et al. | 606/61 |
| 7,776,071 B2 * | 8/2010 | Fortin et al. | 606/257 |
| 7,811,309 B2 * | 10/2010 | Timm et al. | 606/257 |
| 7,875,059 B2 * | 1/2011 | Patterson et al. | 606/261 |

| Publication No. | Date | Inventor(s) |
|---|---|---|
| 2002/0013586 A1 | 1/2002 | Justis et al. |
| 2002/0026192 A1 | 2/2002 | Schmiel et al. |
| 2002/0068975 A1 | 6/2002 | Teitelbaum et al. |
| 2002/0082603 A1 | 6/2002 | Dixon et al. |
| 2002/0120271 A1 | 8/2002 | Dixon et al. |
| 2002/0143329 A1 | 10/2002 | Serhan et al. |
| 2002/0169450 A1 | 11/2002 | Lange |
| 2003/0004511 A1 | 1/2003 | Ferree |
| 2003/0073996 A1 | 4/2003 | Doubler et al. |
| 2003/0073997 A1 | 4/2003 | Doubler et al. |
| 2003/0083657 A1 | 5/2003 | Drewry et al. |
| 2003/0125742 A1 | 7/2003 | Yuan et al. |
| 2003/0171749 A1 | 9/2003 | Le Couedic et al. |
| 2004/0015166 A1 | 1/2004 | Gorek |
| 2004/0030337 A1 | 2/2004 | Alleyne et al. |
| 2004/0039384 A1 | 2/2004 | Boehm, Jr. et al. |
| 2004/0097925 A1 | 5/2004 | Boehm, Jr. et al. |
| 2004/0097933 A1 | 5/2004 | Lourdel et al. |
| 2004/0111088 A1 | 6/2004 | Picetti et al. |
| 2004/0116929 A1 | 6/2004 | Barker et al. |
| 2004/0122425 A1 | 6/2004 | Suzuki et al. |
| 2004/0138662 A1 | 7/2004 | Landry et al. |
| 2004/0143264 A1 | 7/2004 | McAfee |
| 2004/0143265 A1 | 7/2004 | Landry et al. |
| 2004/0147928 A1 | 7/2004 | Landry et al. |
| 2004/0153077 A1 | 8/2004 | Biedermann et al. |
| 2004/0158245 A1 | 8/2004 | Chin |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172024 A1 | 9/2004 | Gorek |
| 2004/0215192 A1 | 10/2004 | Justis et al. |
| 2004/0225289 A1 | 11/2004 | Biedermann et al. |
| 2004/0230192 A1 | 11/2004 | Graf |
| 2004/0236327 A1 | 11/2004 | Paul et al. |
| 2004/0236330 A1 | 11/2004 | Purcell et al. |
| 2005/0033441 A1 | 2/2005 | Lambrecht et al. |
| 2005/0049589 A1 | 3/2005 | Jackson |
| 2005/0065515 A1 | 3/2005 | Jahng |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085813 A1 | 4/2005 | Spitler et al. |
| 2005/0090822 A1 | 4/2005 | DiPoto |
| 2005/0096652 A1 | 5/2005 | Burton |
| 2005/0096659 A1 | 5/2005 | Freudiger |
| 2005/0107788 A1 | 5/2005 | Beaurain et al. |
| 2005/0113927 A1 | 5/2005 | Malek |
| 2005/0113929 A1 | 5/2005 | Cragg et al. |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz, IV et al. |
| 2005/0131406 A1 | 6/2005 | Reiley et al. |
| 2005/0143737 A1 | 6/2005 | Pafford et al. |
| 2005/0143823 A1 | 6/2005 | Boyd et al. |
| 2005/0171537 A1 | 8/2005 | Mazel et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler et al. |
| 2005/0192569 A1 | 9/2005 | Nichols et al. |
| 2005/0192571 A1 | 9/2005 | Abdelgany |
| 2005/0192572 A1 | 9/2005 | Abdelgany et al. |
| 2005/0203514 A1 | 9/2005 | Jahng et al. |
| 2005/0203517 A1 | 9/2005 | Jahng et al. |
| 2005/0203518 A1 | 9/2005 | Biedermann et al. |
| 2005/0222570 A1 | 10/2005 | Jackson |
| 2005/0228375 A1 | 10/2005 | Mazda et al. |
| 2005/0228382 A1 | 10/2005 | Richelsoph et al. |
| 2005/0228385 A1 | 10/2005 | Iott et al. |
| 2005/0234451 A1 | 10/2005 | Markworth |
| 2005/0234454 A1 | 10/2005 | Chin |
| 2005/0234557 A1 | 10/2005 | Lambrecht et al. |
| 2005/0240180 A1 | 10/2005 | Vienney et al. |
| 2005/0240265 A1 | 10/2005 | Kuiper et al. |
| 2005/0240266 A1 | 10/2005 | Kuiper et al. |
| 2005/0261770 A1 | 11/2005 | Kuiper et al. |
| 2005/0267470 A1 | 12/2005 | McBride |
| 2005/0267472 A1 | 12/2005 | Biedermann et al. |
| 2005/0277922 A1 | 12/2005 | Trieu et al. |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0288670 A1 | 12/2005 | Panjabi et al. |
| 2005/0288671 A1 | 12/2005 | Yuan et al. |
| 2006/0004357 A1 | 1/2006 | Lee et al. |
| 2006/0025771 A1 | 2/2006 | Jackson |
| 2006/0030839 A1 | 2/2006 | Park et al. |
| 2006/0036242 A1 | 2/2006 | Nilsson et al. |
| 2006/0036324 A1 | 2/2006 | Sachs et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058787 A1 | 3/2006 | David |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0069391 A1 | 3/2006 | Jackson |
| 2006/0074419 A1 | 4/2006 | Taylor et al. |
| 2006/0079894 A1 | 4/2006 | Colleran et al. |
| 2006/0079896 A1 | 4/2006 | Kwak et al. |
| 2006/0084978 A1 | 4/2006 | Mokhtar |
| 2006/0084980 A1 | 4/2006 | Melkent et al. |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084990 A1 | 4/2006 | Gournay et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0095035 A1 | 5/2006 | Jones et al. |
| 2006/0095038 A1 | 5/2006 | Jackson |
| 2006/0100621 A1 | 5/2006 | Jackson |
| 2006/0100622 A1 | 5/2006 | Jackson |
| 2006/0106380 A1 | 5/2006 | Colleran et al. |
| 2006/0106383 A1 | 5/2006 | Biedermann et al. |
| 2006/0111712 A1 | 5/2006 | Jackson |
| 2006/0111715 A1 | 5/2006 | Jackson |
| 2006/0116676 A1 | 6/2006 | Gradel et al. |
| 2006/0122597 A1 | 6/2006 | Jones et al. |
| 2006/0122599 A1 | 6/2006 | Drewry et al. |
| 2006/0122620 A1 | 6/2006 | Kim |
| 2006/0129147 A1 | 6/2006 | Biedermann et al. |
| 2006/0129148 A1 | 6/2006 | Simmons et al. |
| 2006/0129149 A1 | 6/2006 | Iott et al. |
| 2006/0142761 A1 | 6/2006 | Landry et al. |
| 2006/0149231 A1 | 7/2006 | Bray |
| 2006/0149232 A1 | 7/2006 | Sasing |
| 2006/0149234 A1 | 7/2006 | de Coninck |
| 2006/0149237 A1 | 7/2006 | Markworth et al. |
| 2006/0149238 A1 | 7/2006 | Sherman et al. |
| 2006/0149240 A1 | 7/2006 | Jackson |
| 2006/0149242 A1 | 7/2006 | Kraus et al. |
| 2006/0149244 A1 | 7/2006 | Amrein et al. |
| 2006/0149380 A1 | 7/2006 | Lotz et al. |
| 2006/0155277 A1 | 7/2006 | Metz-Stavenhagen |
| 2006/0155278 A1 | 7/2006 | Warnick |
| 2006/0161153 A1 | 7/2006 | Hawkes et al. |
| 2006/0173456 A1 | 8/2006 | Hawkes et al. |
| 2006/0189983 A1 | 8/2006 | Fallin et al. |
| 2006/0195093 A1 | 8/2006 | Jahng |
| 2006/0200128 A1 | 9/2006 | Mueller |
| 2006/0200130 A1 | 9/2006 | Hawkins et al. |
| 2006/0200131 A1 | 9/2006 | Chao et al. |

| | | |
|---|---|---|
| 2006/0200133 A1 | 9/2006 | Jackson |
| 2006/0217716 A1 | 9/2006 | Baker et al. |
| 2006/0229606 A1 | 10/2006 | Clement et al. |
| 2006/0229607 A1 | 10/2006 | Brumfield |
| 2006/0229613 A1 | 10/2006 | Timm et al. |
| 2006/0229615 A1 | 10/2006 | Abdou |
| 2006/0229616 A1 | 10/2006 | Albert et al. |
| 2006/0235385 A1 | 10/2006 | Whipple |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241594 A1 | 10/2006 | McCarthy et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241603 A1 | 10/2006 | Jackson |
| 2006/0241757 A1 | 10/2006 | Anderson |
| 2006/0247623 A1 | 11/2006 | Anderson et al. |
| 2006/0247624 A1 | 11/2006 | Banouskou et al. |
| 2006/0247628 A1 | 11/2006 | Rawlins et al. |
| 2006/0247631 A1 | 11/2006 | Ahn et al. |
| 2006/0247636 A1 | 11/2006 | Yuan et al. |
| 2006/0247637 A1 | 11/2006 | Colleran et al. |
| 2006/0253118 A1 | 11/2006 | Bailey |
| 2006/0264935 A1 | 11/2006 | White |
| 2006/0264937 A1 | 11/2006 | White |
| 2006/0276897 A1 | 12/2006 | Winslow et al. |
| 2006/0282073 A1 | 12/2006 | Simanovsky |
| 2006/0282078 A1 | 12/2006 | Labrom et al. |
| 2007/0005062 A1 | 1/2007 | Lange et al. |
| 2007/0005063 A1 | 1/2007 | Bruneau et al. |
| 2007/0016190 A1 | 1/2007 | Martinez et al. |
| 2007/0016194 A1 | 1/2007 | Shaolian et al. |
| 2007/0016201 A1 | 1/2007 | Freudiger |
| 2007/0032123 A1 | 2/2007 | Timm et al. |
| 2007/0043356 A1 | 2/2007 | Timm et al. |
| 2007/0043358 A1 | 2/2007 | Molz, IV et al. |
| 2007/0049936 A1 | 3/2007 | Colleran et al. |
| 2007/0073289 A1 | 3/2007 | Kwak et al. |
| 2007/0083200 A1 | 4/2007 | Gittings et al. |
| 2007/0088359 A1 | 4/2007 | Woods et al. |
| 2007/0093814 A1 | 4/2007 | Callahan, II et al. |
| 2007/0093820 A1 | 4/2007 | Freudiger |
| 2007/0093821 A1 | 4/2007 | Freudiger |
| 2007/0093829 A1 | 4/2007 | Abdou |
| 2007/0118122 A1* | 5/2007 | Butler et al. .................. 606/61 |
| 2007/0123861 A1 | 5/2007 | Dewey et al. |
| 2007/0123871 A1 | 5/2007 | Jahng |
| 2007/0156143 A1 | 7/2007 | Lancial |
| 2007/0161994 A1 | 7/2007 | Lowery et al. |
| 2007/0161997 A1 | 7/2007 | Thramann et al. |
| 2007/0162007 A1 | 7/2007 | Shoham |
| 2007/0167947 A1 | 7/2007 | Gittings |
| 2007/0168035 A1 | 7/2007 | Koske |
| 2007/0198014 A1 | 8/2007 | Graf et al. |
| 2007/0213714 A1 | 9/2007 | Justis |
| 2007/0213719 A1 | 9/2007 | Hudgins et al. |
| 2007/0233068 A1 | 10/2007 | Bruneau et al. |
| 2007/0233072 A1 | 10/2007 | Dickinson et al. |
| 2007/0233075 A1 | 10/2007 | Dawson |
| 2007/0233090 A1 | 10/2007 | Naifeh et al. |
| 2007/0233091 A1 | 10/2007 | Naifeh et al. |
| 2007/0233092 A1 | 10/2007 | Falahee |
| 2007/0233093 A1 | 10/2007 | Falahee |
| 2007/0233094 A1 | 10/2007 | Colleran et al. |
| 2007/0244481 A1 | 10/2007 | Timm |
| 2007/0250061 A1 | 10/2007 | Chin et al. |
| 2007/0270819 A1 | 11/2007 | Justis et al. |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0276380 A1 | 11/2007 | Jahng et al. |
| 2007/0288009 A1 | 12/2007 | Brown et al. |
| 2007/0288012 A1 | 12/2007 | Colleran et al. |
| 2008/0009864 A1 | 1/2008 | Forton et al. |
| 2008/0021285 A1 | 1/2008 | Drzyzga et al. |
| 2008/0021459 A1 | 1/2008 | Lim |
| 2008/0021461 A1 | 1/2008 | Barker et al. |
| 2008/0033433 A1 | 2/2008 | Implicito |
| 2008/0039838 A1 | 2/2008 | Landry et al. |
| 2008/0045951 A1 | 2/2008 | Fanger et al. |
| 2008/0045957 A1 | 2/2008 | Landry et al. |
| 2008/0051787 A1 | 2/2008 | Remington et al. |
| 2008/0065073 A1 | 3/2008 | Perriello et al. |
| 2008/0065075 A1 | 3/2008 | Dant et al. |
| 2008/0065079 A1 | 3/2008 | Bruneau et al. |
| 2008/0071273 A1 | 3/2008 | Hawkes et al. |
| 2008/0077139 A1 | 3/2008 | Landry et al. |

FOREIGN PATENT DOCUMENTS

| | | |
|---|---|---|
| DE | 3639810 A1 | 5/1988 |
| EP | 0128058 A1 | 12/1984 |
| EP | 0669109 B1 | 8/1995 |
| EP | 1281362 A2 | 2/2003 |
| EP | 1330987 A1 | 7/2003 |
| FR | 2612070 A1 | 9/1988 |
| FR | 2615095 A1 | 11/1988 |
| FR | 2880256 B1 | 7/2006 |
| GB | 780652 | 8/1957 |
| GB | 2173104 | 10/1986 |
| GB | 2382304 | 5/2003 |
| WO | WO 87/07134 | 12/1987 |
| WO | WO 94/21185 | 9/1994 |
| WO | WO 98/27884 | 7/1998 |
| WO | WO 01/45576 | 6/2001 |
| WO | WO 01/91656 | 12/2001 |
| WO | WO 02/07621 | 1/2002 |
| WO | WO 02/07622 | 1/2002 |
| WO | WO 02/17803 | 3/2002 |
| WO | WO 02/39921 | 5/2002 |
| WO | WO 02/43603 | 6/2002 |
| WO | WO 02/102259 | 12/2002 |
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO 2004/024011 | 3/2004 |
| WO | WO 2004/034916 | 4/2004 |
| WO | WO 2006/033503 | 3/2006 |
| WO | WO 2006/066685 | 6/2006 |
| WO | WO 2006/105935 | 10/2006 |
| WO | WO 2007/080317 | 7/2007 |
| WO | WO 2008/034130 | 3/2008 |

OTHER PUBLICATIONS

"The Spinous Process: The Forgotten Appendage," Kenneth R. Kattan, M. D. eta l., *Skeletal Radiology*, vol. 6, 1981, pp. 199-204.

"Morphological and functional changes of the lumbar spinous processes in the elderly," R. Scapinelli, *Surgical Radiologic Anatomy*, vol. 11, 1989, pp. 129-133.

"The Paraspinal Sacrospinalis-Splitting Approach to the Lumbar Spine," Leon L. Wiltse et al., *The Journal of Bone & Joint Surgery*, vol. 50-A, No. 5, Jul. 1968 pp. 919-926.

*Dynamic Reconstruction of the Spine*, D.H. Kim et al., 2006, cover through p. xix.

"Historical Review of Spinal Arthroplasty and Dynamic Stabilizations," K M. Shibata et al., *Dynamic Reconstruction of the Spine*, Section I, Motion Preservation of the Spine, Chapter 1, 2006, pp. 3-15.

"Current Concepts in Spinal Fusion versus Nonfusion," D.H. Walker et al., *Dynamic Reconstruction of the Spine*, Section I, Motion Preservation of the Spine, Chapter 2, 2006, pp. 16-23.

"Biomechanical Aspects Associated with Cervical Disk Arthroplasty," D.J. DiAngelo et al., *Dynamic Reconstruction of the Spine*, Section II, Restoration of Cervical Motion Segment, Chapter 3, 2006, pp. 27-32.

"Biomechanical Testing Protocol for Evaluating Cervical Disk Arthroplasty," D.J. DiAngelo et al., *Dynamic Reconstruction of the Spine*, Section II, Restoration of Cervical Motion Segment, Chapter 4, 2006, pp. 33-41.

"Cervical Disk Arthroplasty: Rationale, Indications, and Clinical Experience," M.R. Lim et al., *Dynamic Reconstruction of the Spine*, Section II, Restoration of Cervical Motion Segment, Chapter 5, 2006, pp. 42-51.

"Spinal Kinetics Cervical Disc," D.H. Kim et al., *Dynamic Reconstruction of the Spine*, Section II, Restoration of Cervical Motion Segment, Chapter 6, 2006, pp. 52-58.

"Bryan Cervical Disc Device," R. Hacker, *Dynamic Reconstruction of the Spine*, Section II, Restoration of Cervical Motion Segment, Chapter 7, 2006, pp. 59-66.

"Prestige Cervical Artificial Disk," J.T. Robertson, *Dynamic Reconstruction of the Spine*, Section II, Restoration of Cervical Motion Segment, Chapter 8, 2006, pp. 67-71.

"ProDisc-C Cervical Artificial Disk" G.K. Jeong et al., *Dynamic Reconstruction of the Spine*, Section II, Restoration of Cervical Motion Segment, Chapter 9, 2006, pp. 72-77.

"PCM (Porous Coated Motion) Artificial Cervical Disc," L Pimenta et al., *Dynamic Reconstruction of the Spine*, Section II, Restoration of Cervical Motion Segment, Chapter 10, 2006, pp. 78-85.

"Cervidisc Concept: Six-Year Follow-Up and Introducing Cervidisc II: DISCOCERV," A.S. Ramadan et al., *Dynamic Reconstruction of the Spine*, Section II, Restoration of Cervical Motion Segment, Chapter 11, 2006, pp. 86-91.

"CerviCore Cervical Intervertebral Disk Replacement," S.S. Lee et al., *Dynamic Reconstruction of the Spine*, Section II, Restoration of Cervical Motion Segment, Chapter 12, 2006, pp. 92-95.

"Prosthetic Disk Nucleus Partial Disk Replacement: Pathobiological and Biomechanical Rationale for Design and Function," C.D. Ray et al., *Dynamic Reconstruction of the Spine*, Section III, Restoration of Lumbar Motion Segment, A. Lumbar Nucleus Replacement, Chapter 13, 2006, pp. 99-104.

"The Raymedica Prosthetic Disk Nucleus (PDN): Stabilizing the Degenerated Lumbar Vertebral Segment without Fusion or Total Disk Replacement," C.D. Ray, *Dynamic Reconstruction of the Spine*, Section III, Restoration of Lumbar Motion Segment, A. Lumbar Nucleus Replacement, Chapter 14, pp. 105-113.

"Functional Lumbar Artificial Nucleus Replacement: The DASCOR System," J.E. Sherman et al., *Dynamic Reconstruction of the Spine*, Section III, Restoration of Lumbar Motion Segment, A. Lumbar Nucleus Replacement, Chapter 15, 2006, pp. 114-121.

"NeuDisc," R. Bertagnoli et al., *Dynamic Reconstruction of the Spine*, Section III, Restoration of Lumbar Motion Segment, A. Lumbar Nucleus Replacement, Chapter 16, 2006, pp. 122-126.

"Pioneer Surgical Technology NUBAC Artificial Nucleus," Q. Bao et al., *Dynamic Reconstruction of the Spine*, Section III, Restoration of Lumbar Motion Segment, A. Lumbar Nucleus Replacement, Chapter 17, 2006, pp. 128-136.

"SINUX (Sinitec)," J. Zoeliner, *Dynamic Reconstruction of the Spine*, Section III, Restoration of Lumbar Motion Segment, A. Lumbar Nucleus Replacement, Chapter 18, 2006, pp. 137-141.

"Nucore Injectable Disk Nucleus," S.H. Kitchel et al., *Dynamic Reconstruction of the Spine*, Section III, Restoration of Lumbar Motion Segment, A. Lumbar Nucleus Replacement, Chapter 19, 2006, pp. 142-146.

"Biomechanical Considerations for Total Lumbar Disk Replacement," J. LeHuec et al., *Dynamic Reconstruction of the Spine*, Section III, Restoration of Lumbar Motion Segment, B. Lumbar Total Disk Replacement, Chapter 20, 2006, pp. 149-153.

"Indications for Total Lumbar Disk Replacement," R. Bertagnoli, *Dynamic Reconstruction of the Spine*, Section III, Restoration of Lumbar Motion Segment, B. Lumbar Total Disk Replacement, Chapter 21, 2006, pp. 154-159.

"Charté Artificial Disc," F.H. Geisler, *Dynamic Reconstruction of the Spine*, Section III, Restoration of Lumbar Motion Segment, B. Lumbar Total Disk Replacement, Chapter 22, 2006, pp. 160-178.

"ProDisc Lumbar Artificial Disk," J.E.Zigler et al., *Dynamic Reconstruction of the Spine*, Section III, Restoration of Lumbar Motion Segment, B. Lumbar Total Disk Replacement, Chapter 23, 2006, pp. 179-185.

"Maverick Total Disc Replacement," M.F.Gornet, *Dynamic Reconstruction of the Spine*, Section III, Restoration of Lumbar Motion Segment, B. Lumbar Total Disk Replacement, Chapter 24, 2006, pp. 186-195.

"The Mobidisc Prosthesis," J.P. Steib et al., *Dynamic Reconstruction of the Spine*, Section III, Restoration of Lumbar Motion Segment, B. Lumbar Total Disk Replacement, Chapter 25, 2006, pp. 196-203.

"Activ-L Lumbar (Aesculap) Total Disk Arthroplasty," J.J.Yue et al., *Dynamic Reconstruction of the Spine*, Section III, Restoration of Lumbar Motion Segment, B. Lumbar Total Disk Replacement, Chapter 26, 2006, pp. 204-211.

"The FlexiCore Disk," A.D. Sharan et al., *Dynamic Reconstruction of the Spine*, Section III, Restoration of Lumbar Motion Segment, B. Lumbar Total Disk Replacement, Chapter 27, 2006, pp. 212-220.

"Management of Vascular and Surgical Approach—Related Complications for Lumbar Total Disk Replacement," S.H. Lee et al., *Dynamic Reconstruction of the Spine*, Section III, Restoration of Lumbar Motion Segment, B. Lumbar Total Disk Replacement, Chapter 28, 2006, pp. 221-226.

"Complications of Lumbar Disk Arthroplasty," SH Lee et al., *Dynamic Reconstruction of the Spine*, Section III, Restoration of Lumbar Motion Segment, B. Lumbar Total Disk Replacement, Chapter 29, 2006, pp. 227-233.

"Rationale for Dynamic Stabilization," D.S. McNally, *Dynamic Reconstruction of the Spine*, Section III, Restoration of Lumbar Motion Segment, C. Dynamic Posterior Stabilization, Chapter 30, 2006, pp. 237-243.

"Rationale for Dynamic Stabilization II—SoftFlex System," D.K. Sengupta, *Dynamic Reconstruction of the Spine*, Section III, Restoration of Lumbar Motion Segment, C. Dynamic Posterior Stabilization, Chapter 31, 2006, pp. 244-250.

"The X Stop Interspinous Process Decompression System for the Treatment of Lumbar Neurogenic Claudication," R.M. Thunder et al., *Dynamic Reconstruction of the Spine*, Section III, Restoration of Lumbar Motion Segment, C. Dynamic Posterior Stabilization, Chapter 32, 2006, pp. 251-257.

"Dynamic Lumbar Stabilization with the Wallis Interspinous Implant," J. Sénégas, *Dynamic Reconstruction of the Spine*, Section III, Restoration of Lumbar Motion Segment, C. Dynamic Posterior Stabilization, Chapter 33, 2006, pp. 258-267.

"Coflex," ES Kim et al., *Dynamic Reconstruction of the Spine*, Section III, Restoration of Lumbar Motion Segment, C. Dynamic Posterior Stabilization, Chapter 34, 2006, pp. 268-273.

DIAM (Device for Intervertebral Assisted Motion) Spinal Stabilization System, K. Singh et al., *Dynamic Reconstruction of the Spine*, Section III, Restoration of Lumbar Motion Segment, C. Dynamic Posterior Stabilization, Chapter 35, 2006, pp. 274-283.

"Tension Band System," SH Lee et al., *Dynamic Reconstruction of the Spine*, Section III, Restoration of Lumbar Motion Segment, C. Dynamic Posterior Stabilization, Chapter 36, 2006, pp. 284-291.

"Shape Memory Implant (KIMPF-DI Fixing) System,"YS Kim et al., *Dynamic Reconstruction of the Spine*, Section III, Restoration of Lumbar Motion Segment, C. Dynamic Posterior Stabilization, Chapter 37, 2006, pp. 292-298.

"Treatment of Mobile Vertebral Instability with Dynesys," G. Dubois et al., *Dynamic Reconstruction of the Spine*, Section III, Restoration of Lumbar Motion Segment, C. Dynamic Posterior Stabilization, Chapter 38, 2006, pp. 299-304.

"Graf Soft Stabilization: Graf Ligamentoplasty," YS Kim et al., *Dynamic Reconstruction of the Spine*, Section III, Restoration of Lumbar Motion Segment, C. Dynamic Posterior Stabilization, Chapter 39, 2006, pp. 305-311.

"Isobar TTL Dynamic Instrumentation," A.E. Castellvi et al., *Dynamic Reconstruction of the Spine*, Section III, Restoration of Lumbar Motion Segment, C. Dynamic Posterior Stabilization, Chapter 40, 2006, pp. 312-322.

"Minimally Invasive Posterior Dynamic Stabilization System," L. Pimenta et al., *Dynamic Reconstruction of the Spine*, Section III, Restoration of Lumbar Motion Segment, C. Dynamic Posterior Stabilization, Chapter 41, 2006, pp. 323-329.

"Nonfusion Stabilization of the Degenerated Lumbar Spine with Cosmic," A. von Strempel, *Dynamic Reconstruction of the Spine*, Section III, Restoration of Lumbar Motion Segment, C. Dynamic Posterior Stabilization, Chapter 42, 2006, pp. 330-339.

"BioFlex Spring Rod Pedicle Screw System," YS Kim et al., *Dynamic Reconstruction of the Spine*, Section III, Restoration of Lumbar Motion Segment, C. Dynamic Posterior Stabilization, Chapter 43, 2006, pp. 340-344.

"Facet Replacement Technologies," M.R. Lim et al., *Dynamic Reconstruction of the Spine*, Section III, Restoration of Lumbar Motion Segment, D. Facet Replacement, Chapter 44, 2006, pp. 347-353.

"TOPS—Total Posterior Facet Replacement and Dynamic Motion Segment Stabilization System," L.T. Khoo et al., *Dynamic Reconstruction of the Spine*, Section III, Restoration of Lumbar Motion Segment, D. Facet Replacement, Chapter 45, 2006, pp. 354-363.

"Total Facet Arthroplasty System (TFAS)," S. Webb, *Dynamic Reconstruction of the Spine*, Section III, Restoration of Lumbar Motion Segment, D. Facet Replacement, Chapter 46, 2006, pp. 364-371.

"Indications and Techniques in Annuloplasty," M.Y. Wang, *Dynamic Reconstruction of the Spine*, Section III, Restoration of Lumbar Motion Segment, E. Annular Repair, Chapter 47, 2006, pp. 375-379.

"Molecular Therapy of the Intervertebral Disk," S.T. Yoon, *Dynamic Reconstruction of the Spine*, Section IV, Future Biological Approaches to Disk Repair, Chapter 48, 2006, pp. 383-388.

*Dynamic Reconstruction of the Spine*, D.H. Kim et al., 2006, Index, pp. 389-402.

International Search Report for PCT/US07/70981 dated 23 Apr. 2008, 7 pages.

International Search Report for PCT/US/08/65435 dated Sep. 2, 2008, 4 pages.

International Search Report for PCT/US/08/65443 dated Sep. 16, 2008, 4 pages.

International Search Report for PCT/US/08/65444 dated Sep. 16, 2008, 4 pages.

International Search Report for PCT/US/08/65434 dated Oct. 9, 2008, 4 pages.

\* cited by examiner

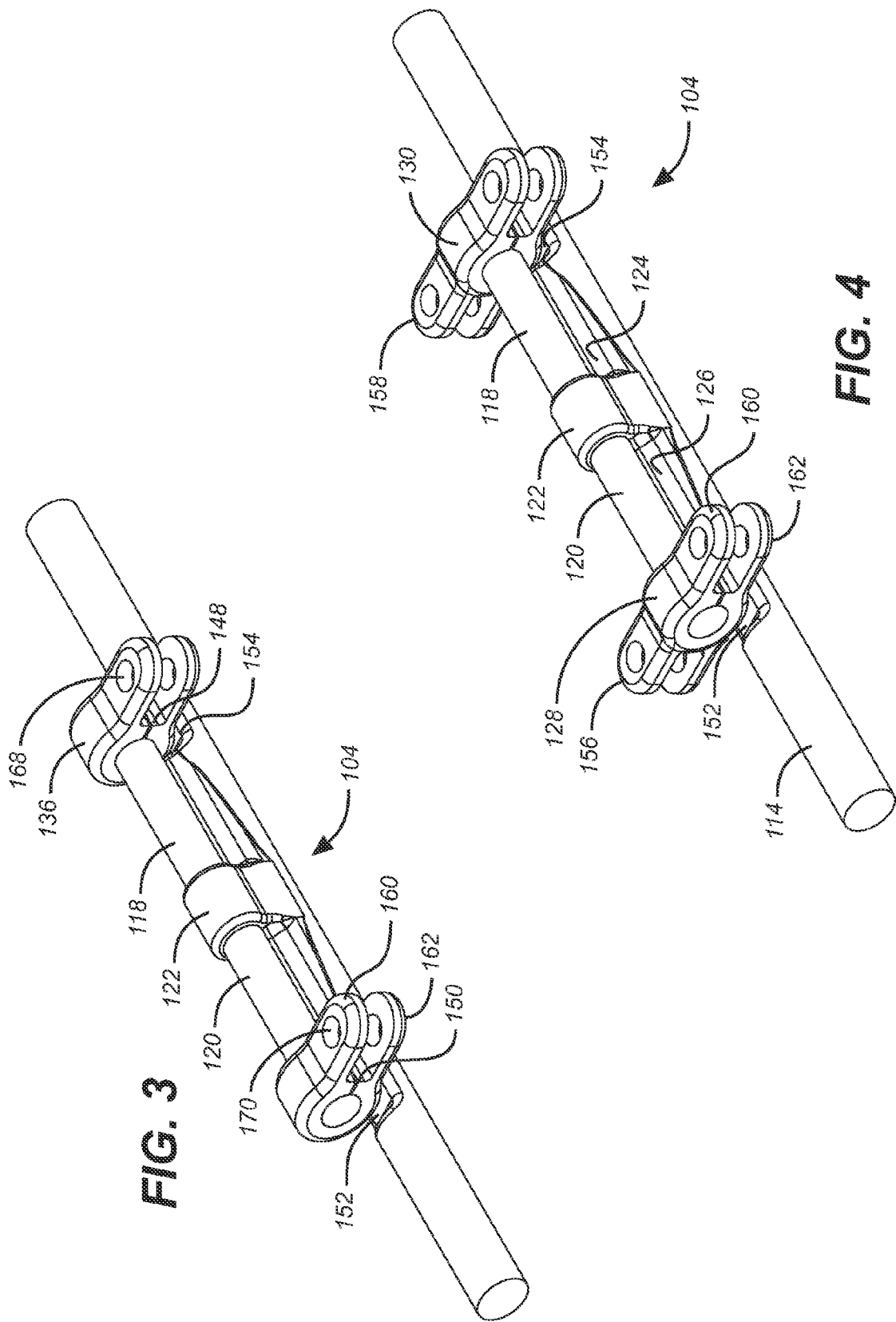

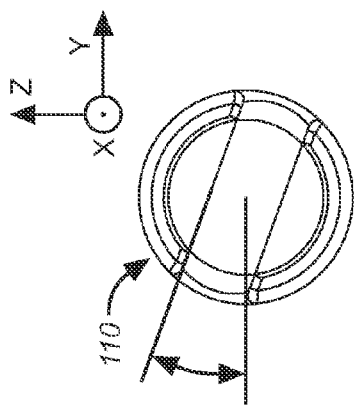
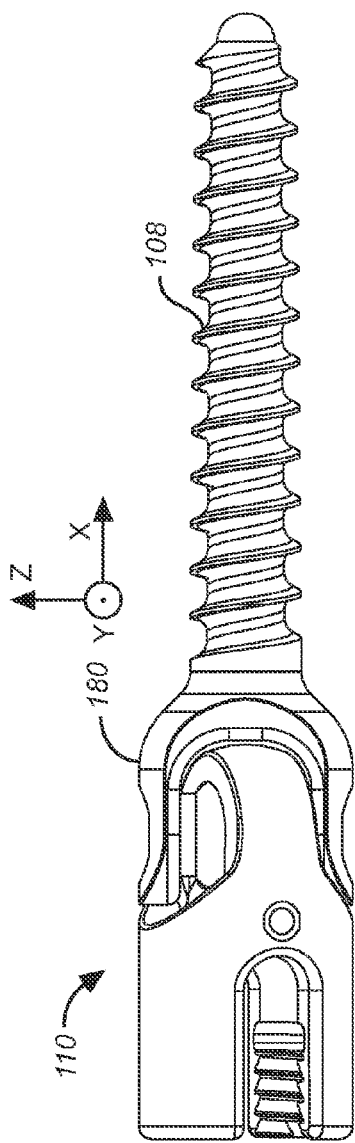
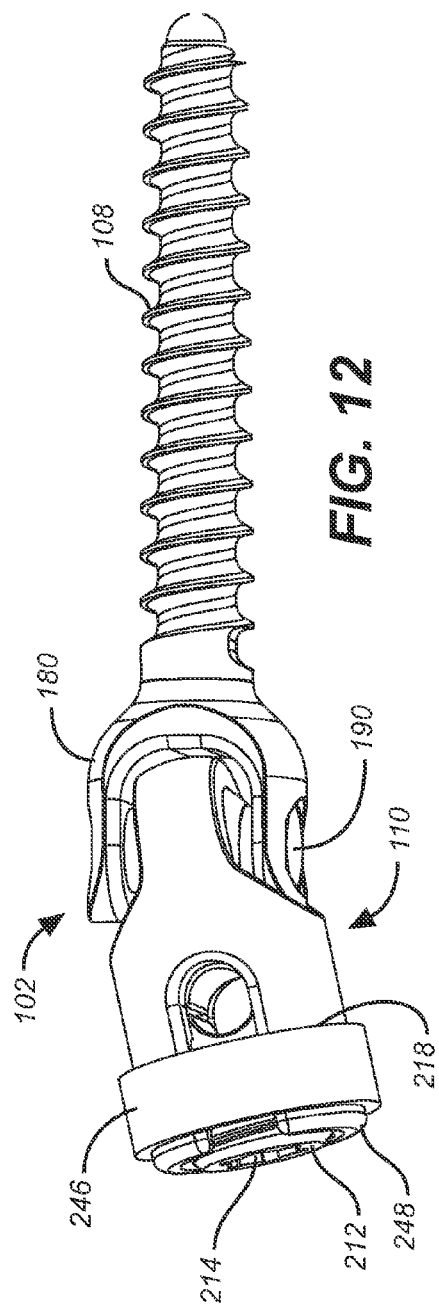

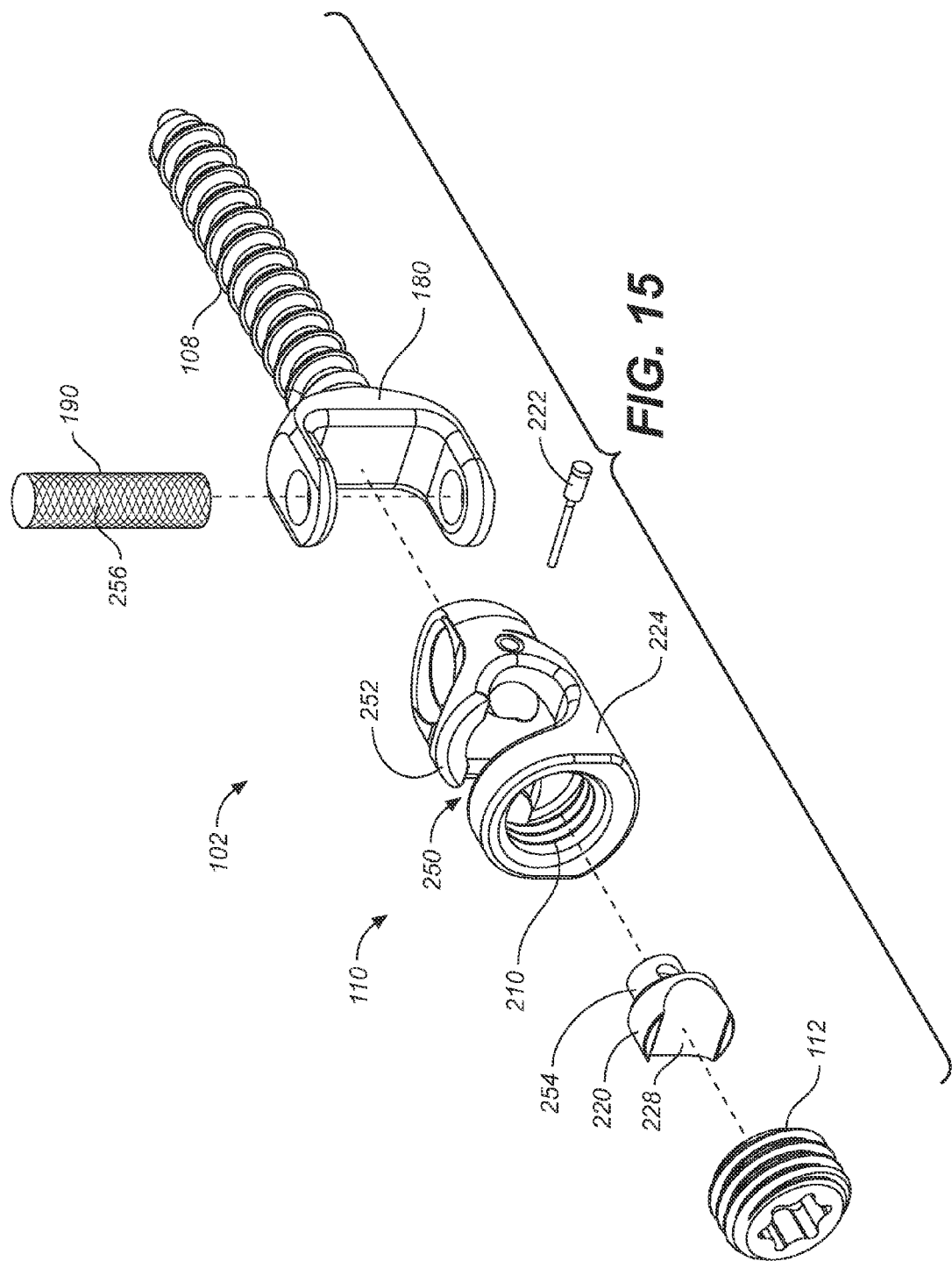

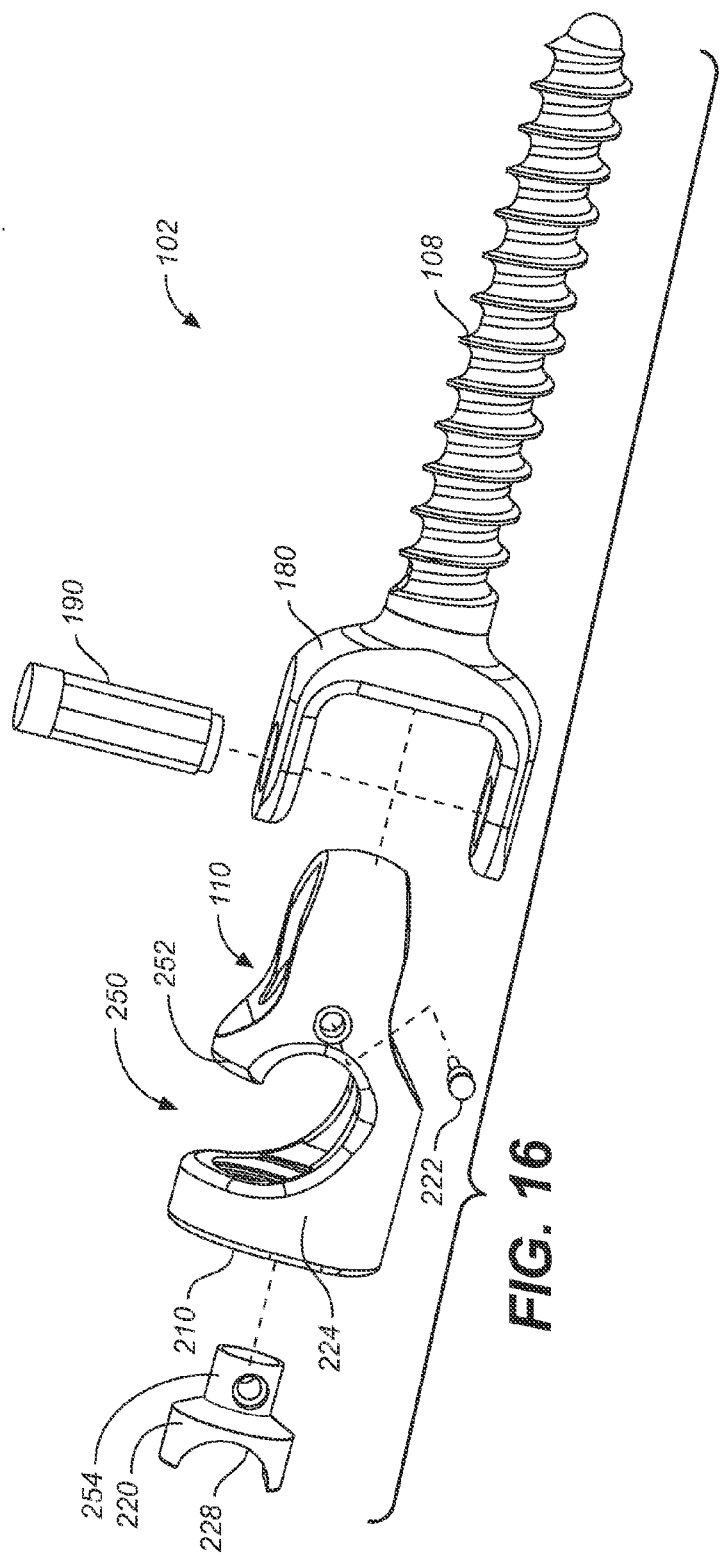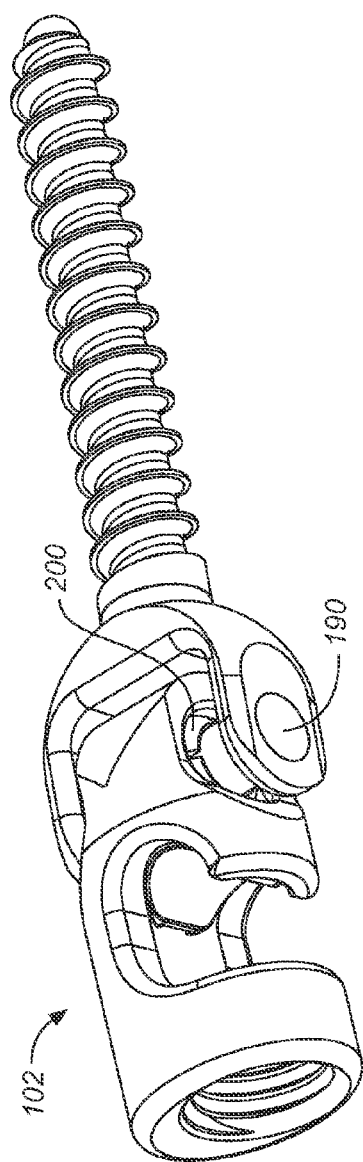

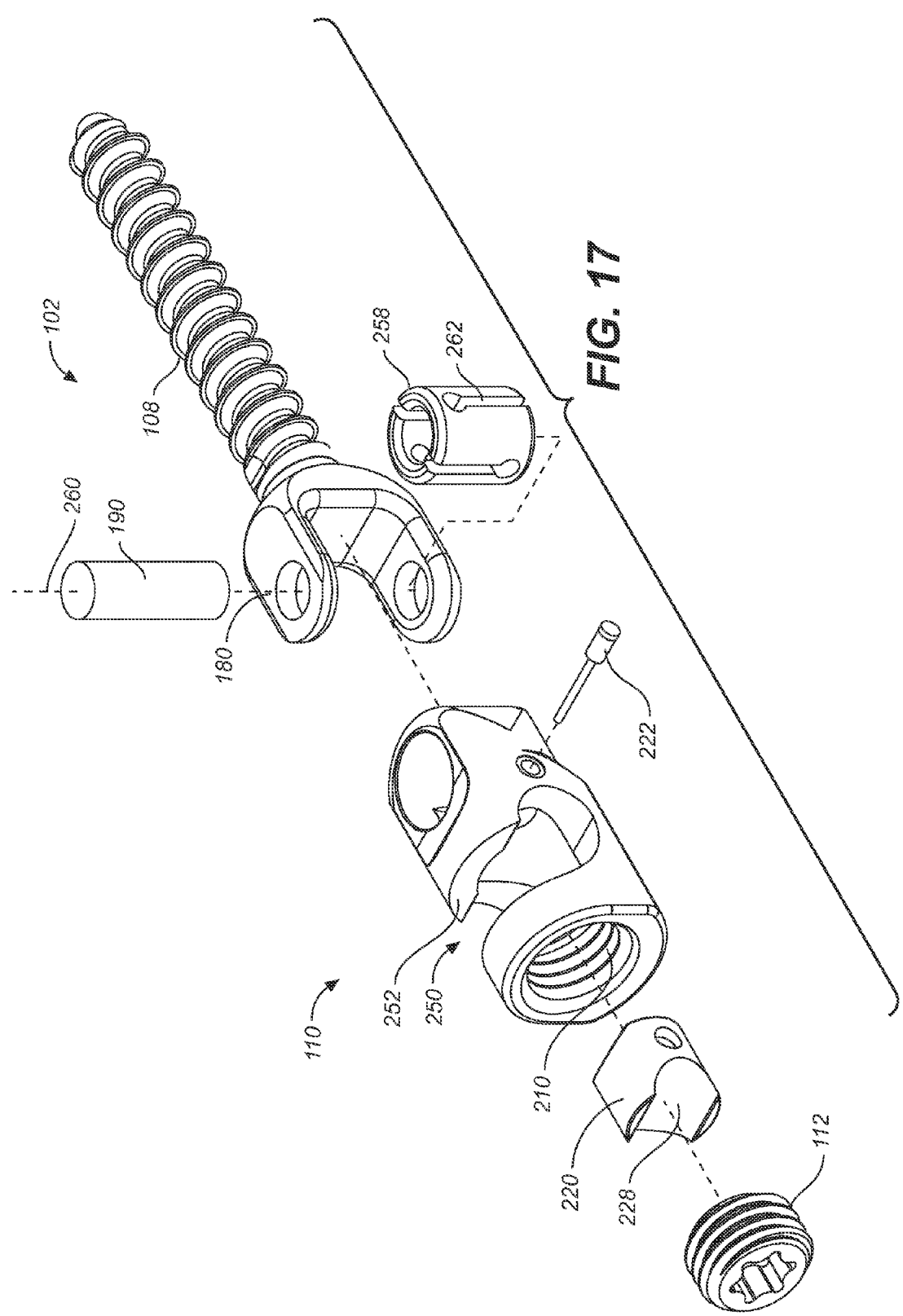

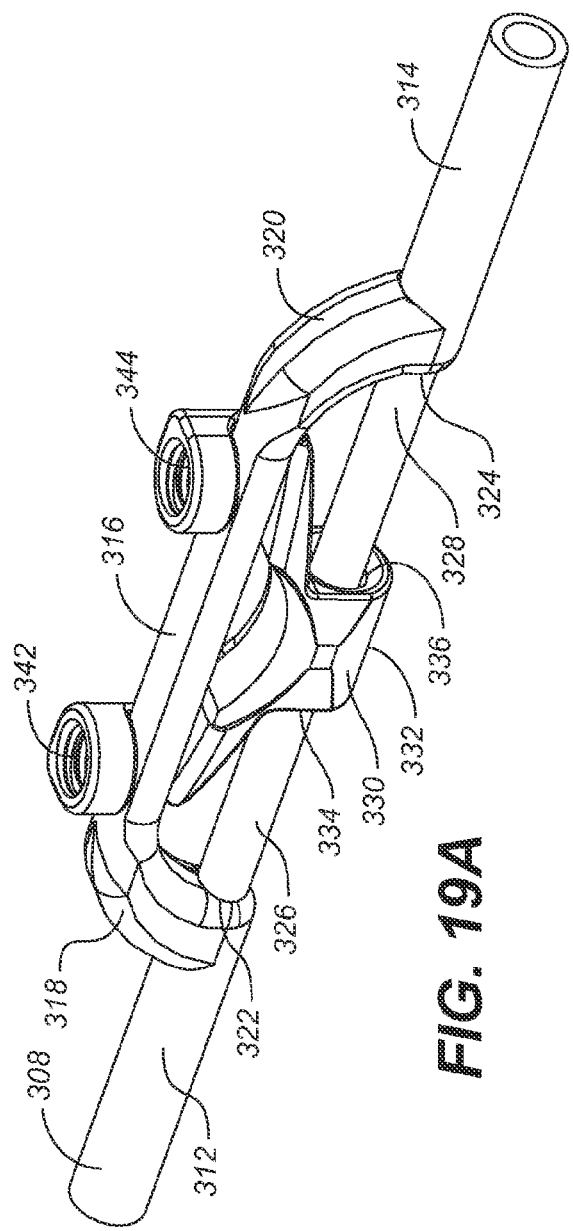
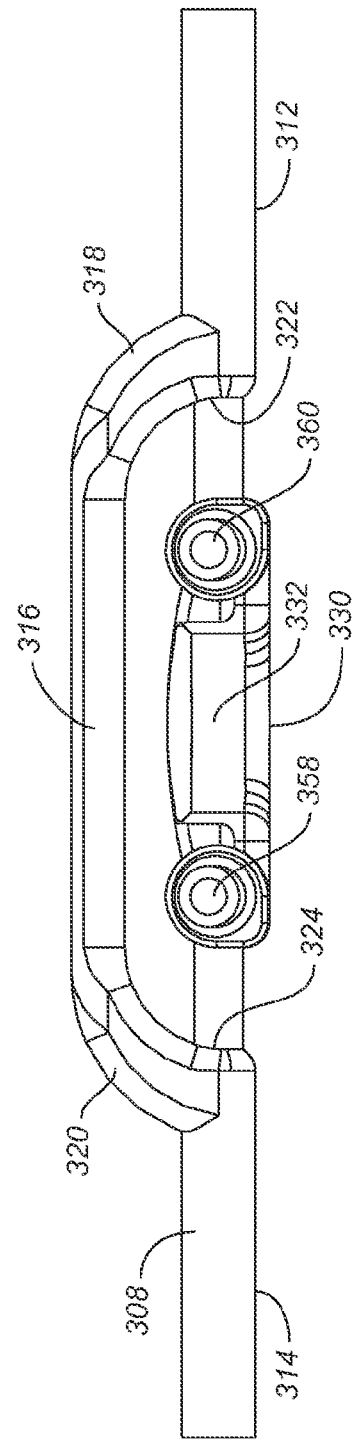
FIG. 19A
FIG. 19C

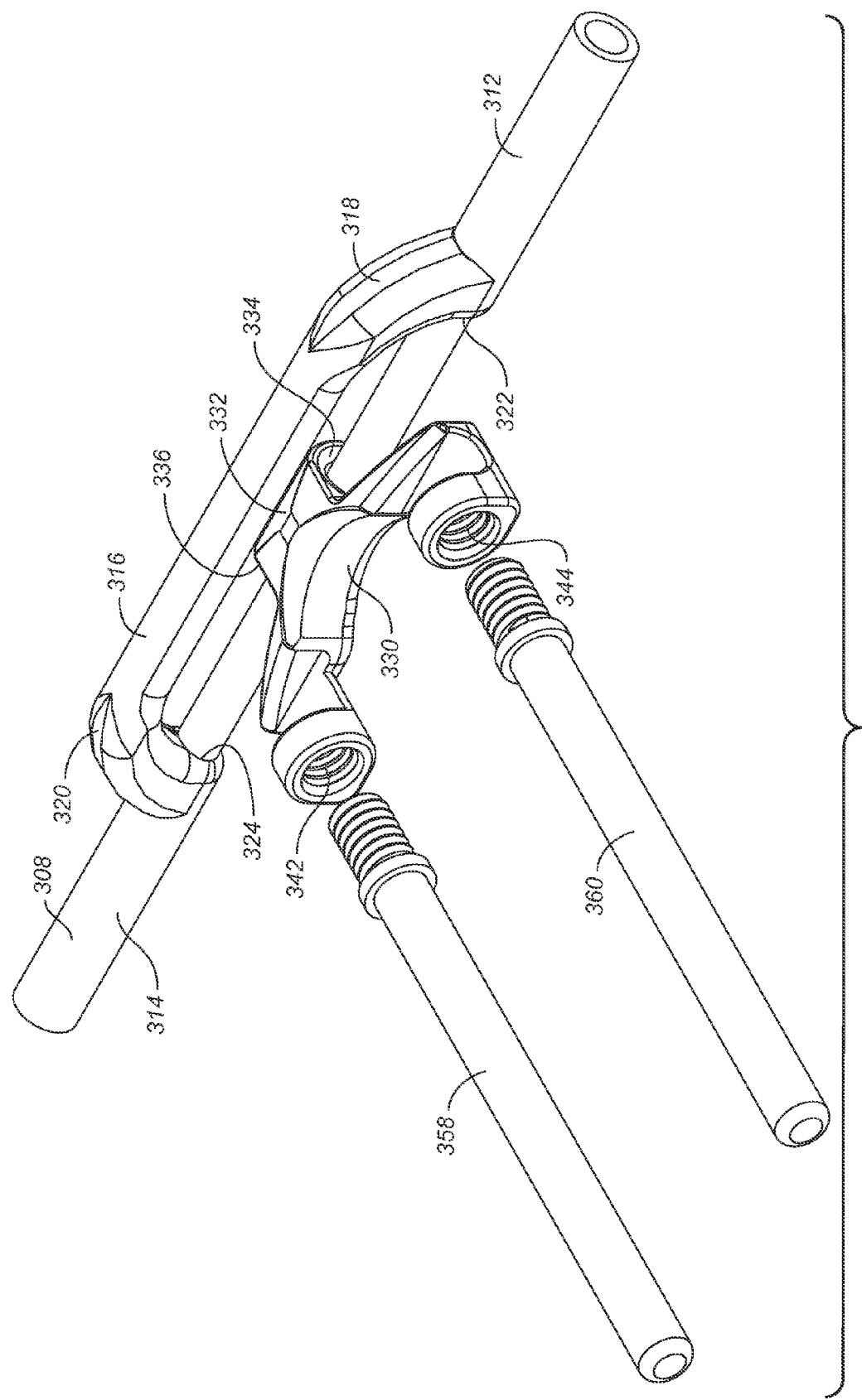

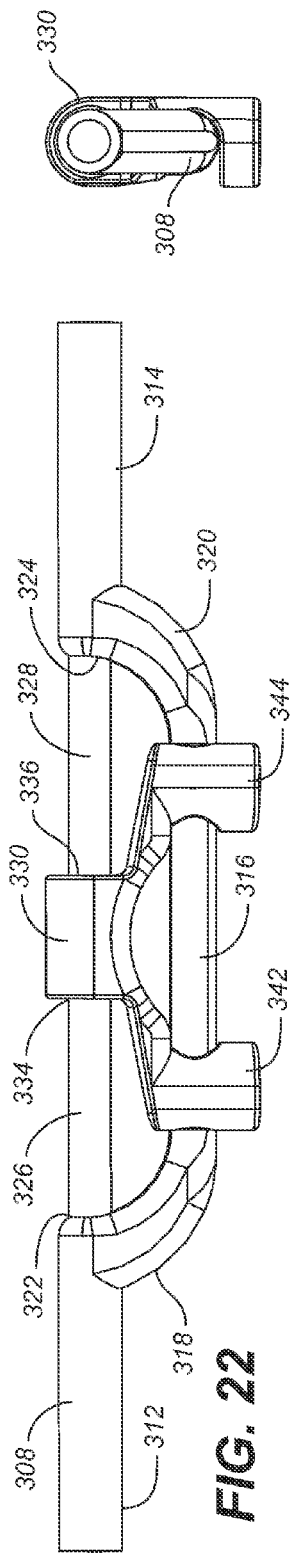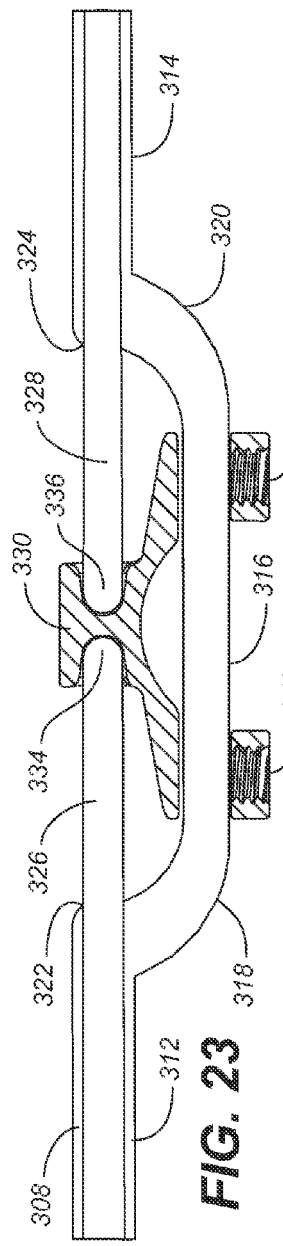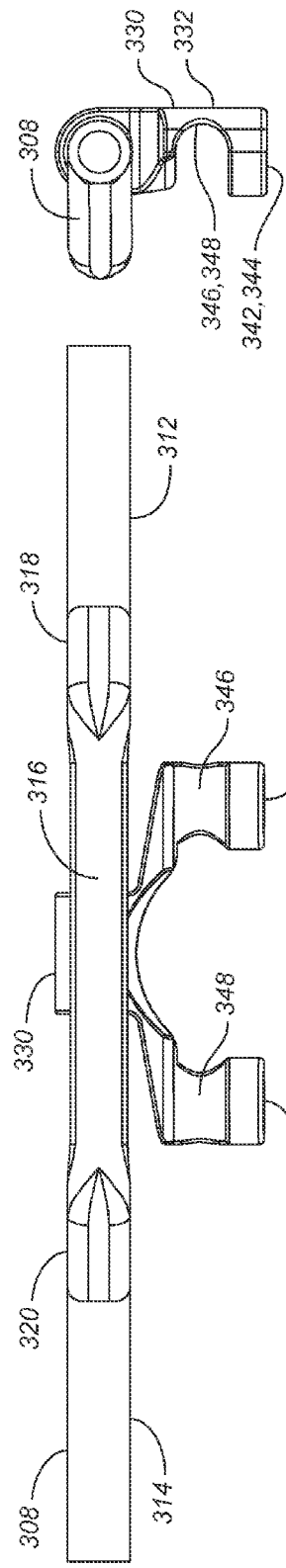

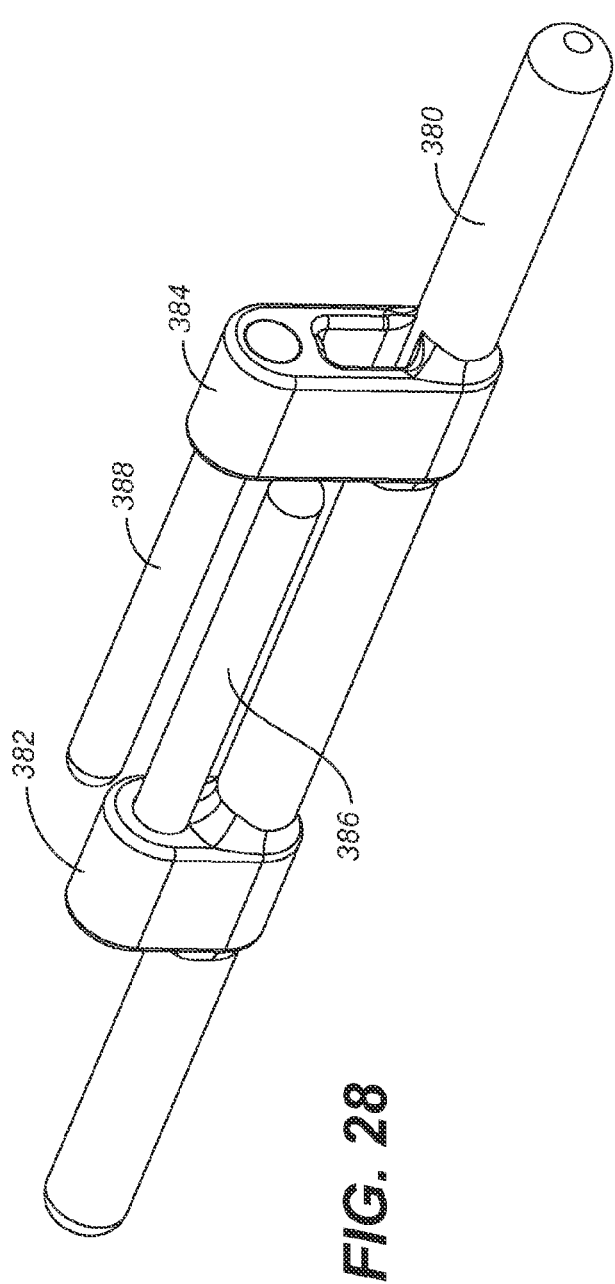
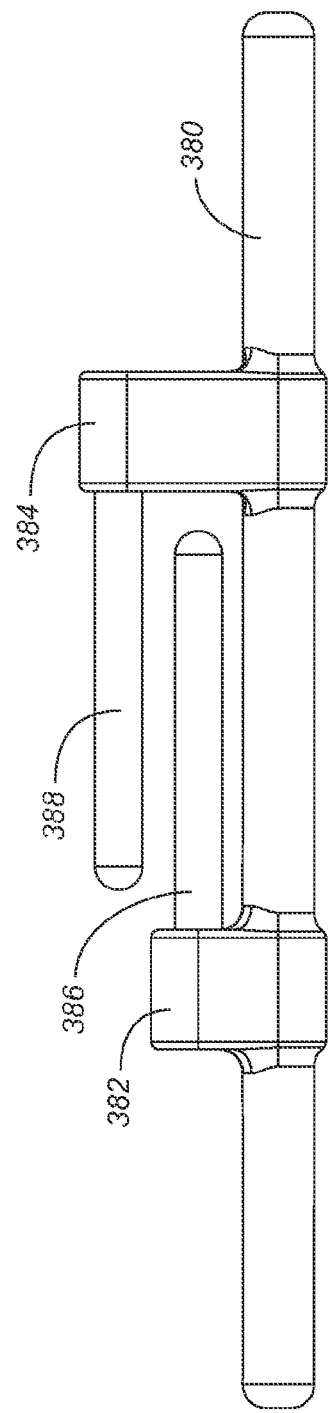
FIG. 28
FIG. 29

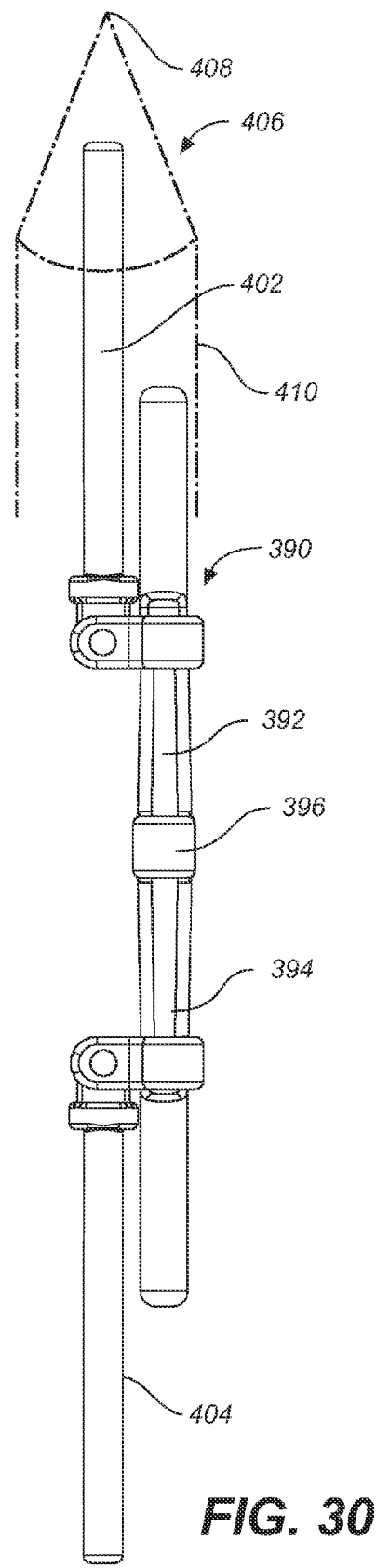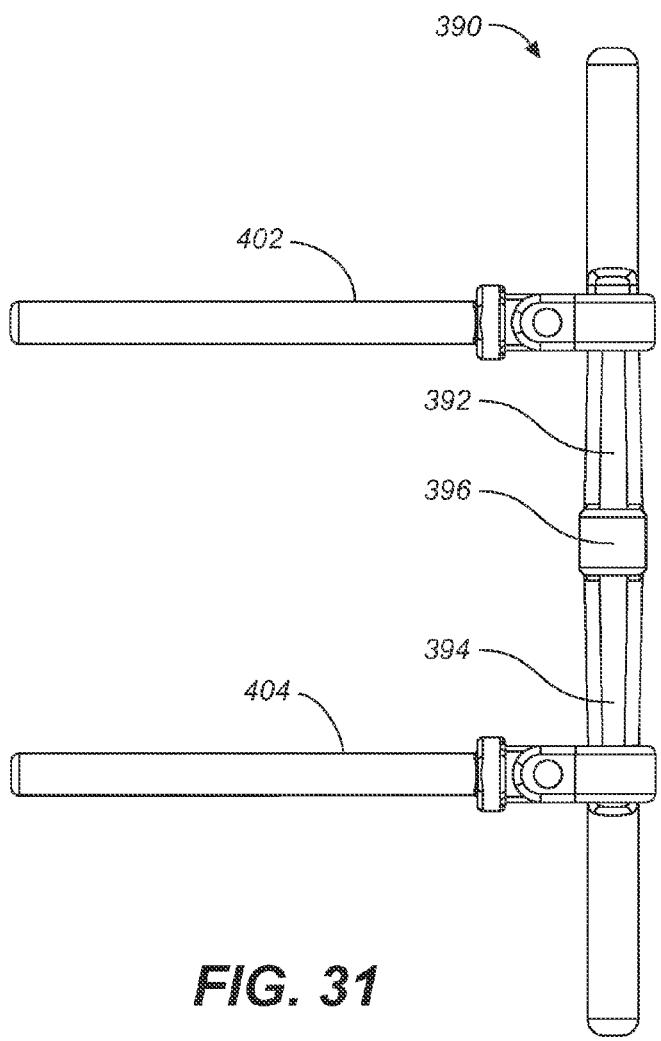
FIG. 30
FIG. 31

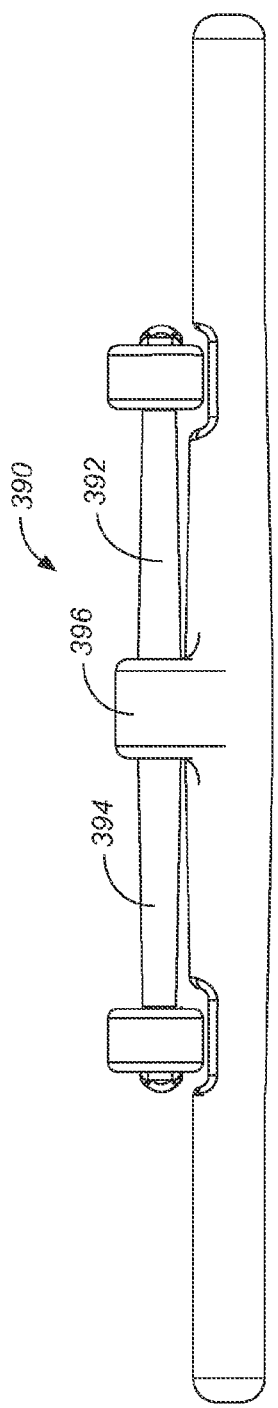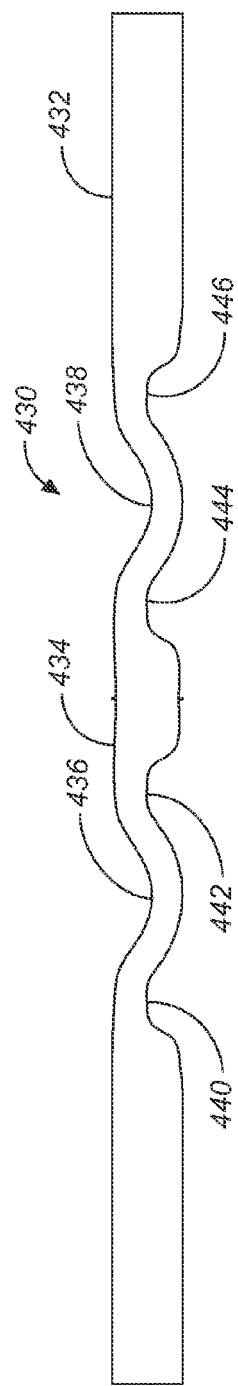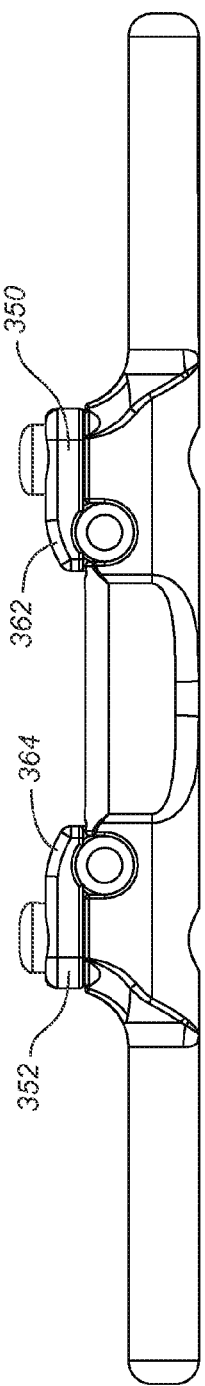

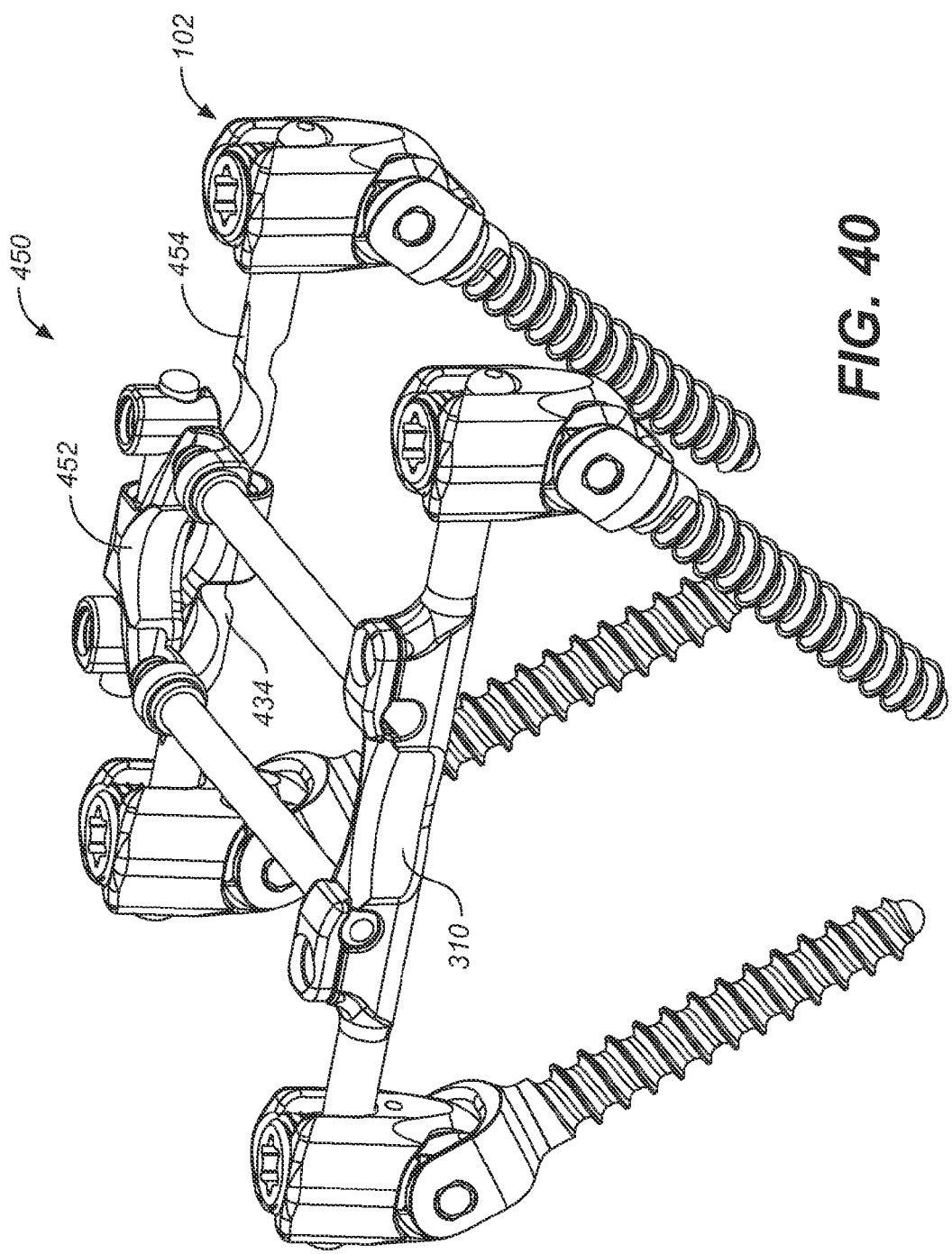

DEFLECTION ROD SYSTEM FOR A SPINE IMPLANT INCLUDING AN INNER ROD AND AN OUTER SHELL AND METHOD

CLAIM TO PRIORITY

This application claims priority to all of the following applications including U.S. Provisional Application No. 60/942,162, filed Jun. 5, 2007, entitled "Dynamic Stabilization and Motion Preservation Spinal Implantation System and Method", U.S. patent application Ser. No. 11/832,260, filed Aug. 1, 2007, entitled "Shaped Horizontal Rod for Dynamic Stabilization and Motion Preservation Spinal Implantation System and Method", U.S. patent application Ser. No. 11/832,273, filed Aug. 1, 2007, entitled "Multi-directional Deflection Profile for a Dynamic Stabilization and Motion Preservation Spinal Implantation System and Method", U.S. patent application Ser. No. 11/832,305, filed Aug. 1, 2007, entitled "A Horizontal Rod with a Mounting Platform for a Dynamic Stabilization and Motion Preservation Spinal Implant System and Method", U.S. patent application Ser. No. 11/832,330, filed Aug. 1, 2007, entitled "Multi-dimensional Horizontal Rod for a Dynamic Stabilization and Motion Preservation Spinal Implantation System and Method", U.S. patent application Ser. No. 11/832,338, filed Aug. 1, 2007, entitled "A Bone Anchor With a Yoke-Shaped anchor head for a Dynamic Stabilization and Motion Preservation Spinal Implantation System and Method", U.S. patent application Ser. No. 11/832,358, filed Aug. 1, 2007, entitled "A Bone Anchor With a Curved Mounting Element for a Dynamic Stabilization and Motion Preservation Spinal Implantation System and Method", U.S. patent application Ser. No. 11/832,377, filed Aug. 1, 2007, entitled "Reinforced Bone Anchor for a Dynamic Stabilization and Motion Preservation Spinal Implantation System and Method", U.S. patent application Ser. No. 11/832,400, filed Aug. 1, 2007, entitled "A Bone Anchor With a Compressor Element for Receiving a Rod for a Dynamic Stabilization and Motion Preservation Spinal Implantation System and Method", U.S. patent application Ser. No. 11/832,413, filed Aug. 1, 2007, entitled "Dynamic Stabilization and Motion Preservation Spinal Implantation System and Method with a Deflection Rod", U.S. patent application Ser. No. 11/832,426, filed Aug. 1, 2007, entitled "Dynamic Stabilization and Motion Preservation Spinal Implantation System and Method with a Deflection Rod Mounted in Close Proximity to a Mounting Rod", U.S. patent application Ser. No. 11/832,436, filed Aug. 1, 2007, entitled "Dynamic Stabilization and Motion Preservation Spinal Implantation System and Method", U.S. patent application Ser. No. 11/832,446, filed Aug. 1, 2007, entitled "Super-Elastic Deflection Rod for a Dynamic Stabilization and Motion Preservation Spinal Implantation System and Method", U.S. patent application Ser. No. 11/832,470, filed Aug. 1, 2007, entitled "Revision System and Method for a Dynamic Stabilization and Motion Preservation Spinal Implantation System and Method", U.S. patent application Ser. No. 11/832,485, filed Aug. 1, 2007, entitled "Revision System for a Dynamic Stabilization and Motion Preservation Spinal Implantation System and Method", U.S. patent application Ser. No. 11/832,494, filed Aug. 1, 2007, entitled "Dynamic Stabilization and Motion Preservation Spinal Implantation System and Method", U.S. patent application Ser. No. 11/832,517, filed Aug. 1, 2007, entitled "Implantation Method for Dynamic Stabilization and Motion Preservation Spinal Implantation System and Method", U.S. patent application Ser. No. 11/832,527, filed Aug. 1, 2007, entitled "Modular Spine Treatment Kit for Dynamic Stabilization and Motion Preservation of the Spine", U.S. patent application Ser. No. 11/832,534, filed Aug. 1, 2007, entitled "Horizontally Loaded Dynamic Stabilization and Motion Preservation Spinal Implantation System and Method", U.S. patent application Ser. No. 11/832,548, filed Aug. 1, 2007, entitled "Dynamic Stabilization and Motion Preservation Spinal Implantation System with Horizontal Deflection Rod and Articulating Vertical Rods", U.S. patent application Ser. No. 11/832,557, filed Aug. 1, 2007, entitled "An Anchor System for a Spine Implantation System That Can Move About three Axes", U.S. patent application Ser. No. 11/832,562, filed Aug. 1, 2007, entitled "Rod Capture Mechanism for Dynamic Stabilization and Motion Preservation Spinal Implantation System and Method", U.S. Provisional Application No. 61/028,792, filed Feb. 14, 2008, entitled "A Deflection Rod System for a Dynamic Stabilization and Motion Preservation Spinal Implantation System and Method", U.S. Provisional Application 61/031,598, filed Feb. 26, 2008, entitled "A Deflection Rod System for a Dynamic Stabilization and Motion Preservation Spinal Implantation System and Method", and U.S. Provisional Application No. 61/057,340, filed May 30, 2008, entitled "A Spine Implant With A Deflection Rod System Aligned With A Bone Anchor And Method".

All of the afore-mentioned applications are incorporated herein by reference in their entireties.

CROSS-REFERENCE TO RELATED APPLICATIONS

This application is related to all of the following applications including U.S. patent application Ser. No. 12/130,335, filed May 30, 2008, entitled "A Deflection Rod System For A Spine Implant Including An Inner Rod And An Outer Shell And Method";

U.S. patent application Ser. No. 12/130,359, filed May 30, 2008, entitled "A Deflection Rod System With A Deflection Contouring Shield For A Spine Implant And Method";

U.S. patent application Ser. No. 12/130,367, filed May 30, 2008, entitled "Dynamic Stabilization And Motion Preservation Spinal Implantation System With A Shielded Deflection Rod System And Method";

U.S. patent application Ser. No. 12/130,377, filed May 30, 2008, entitled "A Deflection Rod System For Spine Implant With End Connectors And Method";

U.S. patent application Ser. No. 12/130,383, filed May 30, 2008, entitled "A Deflection Rod System For A Dynamic Stabilization And Motion Preservation Spinal Implantation System And Method";

U.S. patent application Ser. No. 12/130,395, filed May 30, 2008, entitled "A Deflection Rod System With Mount For Dynamic Stabilization And Motion Preservation Spinal Implantation System And Method";

U.S. patent application Ser. No. 12/130,411, May 30, 2008, entitled "A Deflection Rod System With Mount For Dynamic Stabilization And Motion Preservation Spinal Implantation System And Method";

U.S. patent application Ser. No. 12/130,423, filed May 30, 2008, entitled "A Deflection Rod System With A Non-Linear Deflection To Load Characteristic For Dynamic Stabilization And Motion Preservation Spinal Implantation System And Method";

U.S. patent application Ser. No. 12/130,454, filed May 30, 2008, entitled "A Deflection Rod System Dimensioned For Deflection To A Load Characteristic For Dynamic Stabilization And Motion Preservation Spinal Implantation System And Method";

U.S. patent application Ser. No. 12/130,457, filed May 30, 2008, entitled "A Deflection Rod System For Use With A Vertebral Fusion Implant For Dynamic Stabilization And Motion Preservation Spinal Implantation System And Method";

U.S. patent application Ser. No. 12/130,467, filed May 30, 2008, entitled "A Dual Deflection Rod System For Dynamic Stabilization And Motion Preservation Spinal Implantation System And Method";

U.S. patent application Ser. No. 12/130,475, filed May 30, 2008, entitled "Method For Implanting A Deflection Rod System And Customizing The Deflection Rod System For A Particular Patient Need For Dynamic Stabilization And Motion Preservation Spinal Implantation System";

U.S. patent application Ser. No. 12/130,032, filed May 30, 2008 entitled "A Spine Implant With A Deflection Rod System Anchored To A Bone Anchor And Method";

U.S. patent application Ser. No. 12/130,095, filed May 30, 2008, entitled "A Spine Implant With A Deflection Rod System Including A Deflection Limiting Shield Associated With A Bone Screw And Method";

U.S. patent application Ser. No. 12/130,127, filed May 30, 2008, entitled "A Spine Implant With A Dual Deflection Rod System Including A Deflection Limiting Shield Associated With A Bone Screw And Method"; and U.S. patent application Ser. No. 12/130,152, filed May 30, 2008, entitled "A Spine Implant With A Deflection Rod System And Connecting Linkages And Method".

All of the afore-mentioned applications are incorporated herein by reference in their entireties.

BACKGROUND OF INVENTION

The most dynamic segment of orthopedic and neurosurgical medical practice over the past decade has been spinal devices designed to fuse the spine to treat a broad range of degenerative spinal disorders. Back pain is a significant clinical problem and the annual costs to treat it, both surgical and medical, is estimated to be over $2 billion. Motion preserving devices to treat back and extremity pain has, however, created a treatment alternative to or in combination with fusion for degenerative disc disease. These devices offer the possibility of eliminating the long term clinical consequences of fusing the spine that is associated with accelerated degenerative changes at adjacent disc levels.

BRIEF DESCRIPTION OF THE DRAWINGS

FIG. 3 is a perspective view of an embodiment of a horizontal rod system of the invention for use with a dynamic spine stabilization system such as depicted in FIG. 1.

FIG. 4 is a perspective view of an alternative embodiment of a horizontal rod system of the invention for use with a dynamic spine stabilization system such as depicted in FIG. 1.

FIG. 11 is a side view of the anchor system of FIG. 7 depicting yet another degree of freedom of movement of the anchor system of FIG. 7.

FIG. 11A is an end view of the anchor system of FIG. 11.

FIG. 12 is a perspective view of yet another embodiment of the anchor system of the invention.

FIG. 15 is an exploded perspective view of the embodiment of the anchor system of the invention of FIG. 14.

FIG. 16 is another exploded perspective view of the embodiment of the anchor system of the invention of FIG. 14.

FIG. 17 is an exploded perspective view of another embodiment of the anchor system of the invention.

FIG. 18 is a perspective view of yet another embodiment of the anchor system of the invention.

FIG. 19A is a perspective view of another horizontal rod system of the invention as depicted in FIG. 19 and partially shown in phantom form.

FIG. 19B is an exploded perspective view of the embodiment of FIG. 19.

FIG. 19C is a side view of the embodiment of FIG. 19.

FIG. 22 is a side view the embodiment of the horizontal rod system of the invention as depicted in FIG. 19 configured in a closed position for implantation.

FIG. 22A is an end view of the embodiment depicted in FIG. 22.

FIG. 23 is a side view partially in phantom form of the horizontal rod system of FIG. 22.

FIG. 24 is a side view of the embodiment of FIG. 22 in an open position as used when the embodiment is deployed in a spine.

FIG. 25 is an end view of the embodiment depicted in FIG. 24.

FIG. 28 is a perspective view of still another embodiment of the horizontal rod system of the invention.

FIG. 29 is a side view of the embodiment of the horizontal rod system of the invention of FIG. 28.

FIG. 30 is a top view of another embodiment of the horizontal rod system of the invention as depicted in FIG. 1 with the horizontal rod system in an undeployed position ready for implantation.

FIG. 31 is a top view of the embodiment of the horizontal rod system of FIG. 30 in a deployed position after implantation.

FIG. 32 is a side view, partially in phantom of the embodiment depicted in FIG. 30.

FIG. 33 is a side view of an alternative embodiment of the horizontal rod system of the invention.

FIG. 33A is a side view of yet another embodiment of the horizontal rod system of the invention.

FIG. 34 is a side view of another alternative embodiment of the horizontal rod system of the invention.

FIG. 40 is a perspective view of another embodiment of a dynamic spine stabilization system of the invention.

DETAILED DESCRIPTION OF THE PREFERRED EMBODIMENTS

Figure 1:
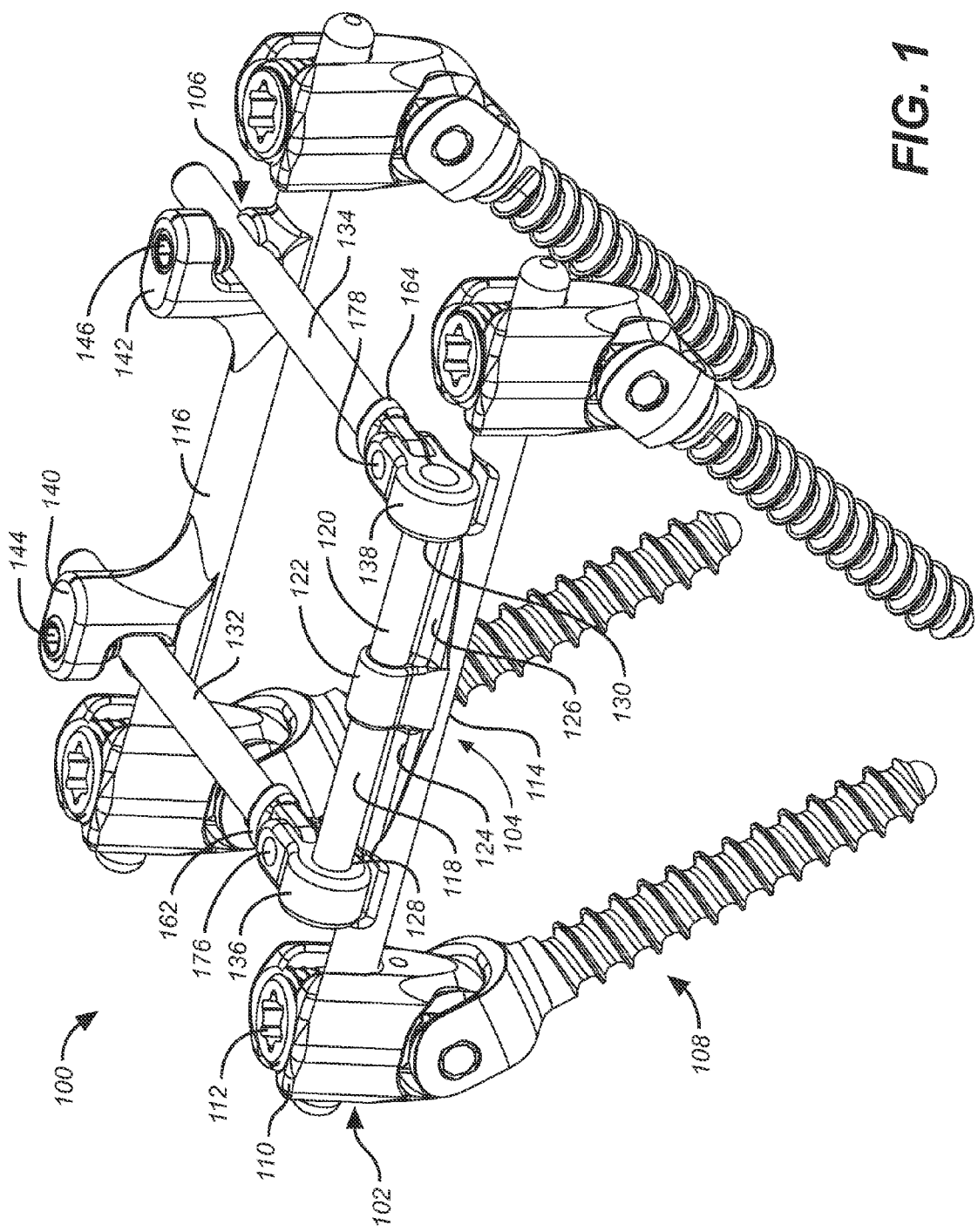
FIG. 1 is a perspective view of an embodiment of a dynamic spine stabilization system of the invention.

Embodiments of the present invention include a system or implant and method that can dynamically stabilize the spine while providing for preservation of spinal motion. Alternative embodiments can be used for spine fusion.

Embodiments of the invention include a construct with an anchoring system, a horizontal rod system that is associated with the anchoring system and a vertical rod system that is associated with the anchoring system and the horizontal rod system.

An advantage and aspect of the system is that the anchoring system includes a head or saddle that allows for appropriate, efficient and convenient placement of the anchoring system relative to the spine in order to reduce the force that is placed on the anchoring system. The anchor system has enhanced degrees of freedom which contribute to the ease of implantation of the anchor system. Accordingly, the anchor system is designed to isolate the head and the screw from the rest of the dynamic stabilization system and the forces that the rest of the dynamic stabilization system can place on the anchor system and the anchor system/bone interface. Thus, the anchor system can provide a secure purchase in the spine.

Another advantage and aspect of the system is that the horizontal rod system is in part comprised of a super elastic material that allows for convenient positioning of the horizontal rod system relative to the anchor system and allows for isolation of the horizontal rod system from the anchor system so that less force is placed on the anchor system from the horizontal rod system and on the anchor system/bone interface. Accordingly, unlike prior devices the anchor system stays secure in the bone of the spine.

An aspect and advantage of the invention is the ability to maximize the range of motion of the spine after embodiments of the dynamic stabilization, motion preservation implant of the invention are implanted in a patient. While traditional solutions to back pain include fusion, discectomy, and artificial implants that replace spine structure, embodiments of the present invention preserve the bone and ligament structure of the spine and preserve a wide range of motion of the spine, while stabilizing spines that were heretofore unstable due to degenerative and other spinal diseases.

Still another aspect of the invention is the preservation of the natural motion of the spine and the maintenance of the quality of motion as well as the wide range of motion so that the spine motion is as close to that of the natural spine as possible. The present embodiments of the invention allow for the selection of a less stiff, yet dynamically stable implant for use in a non-fusion situation. A less stiff, yet dynamically stable implant relates directly to a positive patient outcome, including patient comfort and the quality of motion of the spine.

In another aspect of the invention, load sharing is provided by the embodiment, and, in particular, the deflection rod or loading rod of the embodiment. For embodiments of this invention, the terms "deflection rod" and "loading rod" can be used interchangeably. Accordingly this aspect of the invention is directed to restoring the normal motion of the spine. The embodiment provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod or loading rod in order to match the load sharing desired. By selecting the appropriate stiffness of the deflection rod or loading rod to match the physiology of the patient and the loads that the patient places on the spine, a better outcome is realized for the patient. Prior to implantation of the embodiment, the stiffness of the implant of the system can be selected among a number of loading rods. In other words, the stiffness is variable depending on the deflection rod or loading rod selected. In another aspect, the load sharing is between the spine and the embodiment of the invention.

In another aspect of the invention, the deflection rod or loading rod is cantilevered. In another aspect the deflection rod or loading rod is cantilevered from a horizontal rod. In yet another aspect the deflection rod or loading rod is cantilevered from a horizontal rod that is connected between two anchors that are affixed to the same vertebra. In yet another aspect the deflection rod or loading rod is about parallel to the horizontal rod in a resting position. In still a further, aspect the deflection rod or loading rod is cantilevered from a mount on the horizontal rod and said deflection rod or loading rod is about parallel to the horizontal rod in a resting position.

In another aspect of the invention the horizontal rod attached directly to opposite anchors is stiff and rigid, and the cantilevered deflection rod or cantilevered loading rod shares the load with the spine resulting from the motions of the body of the patient.

In another aspect of embodiments of the invention, the load being absorbed or carried by the embodiment is being distributed along at least part of the length of the deflection rod or loading rod. In another aspect of the invention, the load being absorbed or carried by the embodiment is distributed along at least part of the length of the horizontal cantilevered deflection rod or horizontal cantilevered loading rod.

As the load is carried horizontally along the deflection rod or loading rod, rather than vertically, the embodiments of the invention can be made smaller in order to fit in more spaces relative to the spine. Advantageously, the embodiments can fit in the L5-S1 space of the spine.

An aspect of the invention is to preserve and not restrict motion between the pedicles of the spine through the use of appropriately selected horizontal and vertical rods of embodiments of the invention.

An aspect of the invention is to provide for load bearing on horizontal elements such as horizontal rods instead of vertical elements or rods, and, in particular, vertical elements that are connected between bone anchoring systems.

An aspect of the invention is the use of horizontal rods in the embodiments of the invention in order to isolate each level of the implantation system from the other so as not to put undue force and/or torque on anchoring systems of embodiment of the invention and associated bone, and so as to allow customization of the implantation system to the need of the patient. Accordingly, an aspect of the invention is to provide for minimized loading on the bone/implantation system interface. Customization, in preferred embodiments, can be achieved by the selection of the horizontal rod with the desired stiffness and stiffness characteristics. Different materials and different implant configurations enable the selection of various stiffness characteristics.

Another aspect of the invention is the ability to control stiffness for extension, flexion, lateral bending and axial rotation, and to control stiffness for each of these motions independently of the other motions.

An aspect of the invention is to use the stiffness and load bearing characteristics of super elastic materials.

Another aspect of the invention is to use super elastic materials to customize the implant to the motion preservation and the dynamic stabilization needs of a patient. An aspect of such embodiments of the invention is to provide for a force plateau where motion of the implantation system continues without placement of additional force of the bone anchor system, or, in other words, the bone/implantation system interface.

Thus, an aspect of the invention is to use the horizontal bar to offset loading on the anchor system and on the implantation system in general.

Accordingly, an aspect of the invention is to be able to selectively vary the stiffness and selectively vary the orientation and direction that the stiffness is felt by varying the structure of the implantation system of the invention, and, in particular, to vary the stiffness of the horizontal rod system of the invention.

Another aspect of embodiments of the invention is to prevent any off-axis implantation by allowing the implantation system to have enhanced degrees of freedom of placement of the implant. Embodiments of the invention provide for off-axis placement of bone anchor or pedicle screw systems.

A further aspect of embodiments of the invention is to control stabilized motion from micro-motion to broad extension, flexion, axial rotation, and lateral bending motions of the spine.

Yet another aspect of the embodiments of the invention is to be able to revise a dynamic stabilization implant should a fusion implant be indicated. This procedure can be accomplished by, for example, the removal of the horizontal rods of the implantation system and replacement of such rods with stiffer rods. Accordingly, an aspect of the invention is to provide for a convenient path for a revision of the original implantation system, if needed.

A further aspect of the invention, due to the ease of implanting the anchoring system and the ease of affixing vertical rods to the horizontal rods of the invention, is the ability to accommodate the bone structure of the spine, even if adjacent vertebra are misaligned with respect to each other.

A further aspect of the invention is that the implant is constructed around features of the spine such as the spinous processes and, thus, such features do not need to be removed and the implant does not get in the way of the normal motion of the spine features and the spine features do not get in the way of the operation of the implant.

Another aspect of embodiments of the invention is the ability to stabilize two, three and/or more levels of the spine by the selection of appropriate embodiments and components of embodiments of the invention for implantation in a patient. Further embodiments of the invention allow for fused levels (in conjunction with, if desired, bone graphs) to be placed next to dynamically stabilized levels with the same implantation system. Such embodiments of the invention enable vertebral levels adjacent to fusion levels to be shielded by avoiding an abrupt change from a rigid fusion level to a dynamically stable, motion preserved, and more mobile level.

Accordingly, another aspect of the embodiments of the invention is to provide a modular system that can be customized to the needs of the patient. Horizontal rods can be selectively chosen for the particular patient as well the particular levels of the vertebrae of the spine that are treated. Further, the positioning of the various selected horizontal rods can be selected to control stiffness and stability.

Another aspect of embodiments of the invention is that embodiments can be constructed to provide for higher stiffness and fusion at one level while allowing for lower stiffness and dynamic stabilization at another adjacent level.

Yet a further aspect of the invention is to provide for dynamic stabilization and motion preservation while preserving the bone and tissues of the spine in order to lessen trauma to the patient and to use the existing functional bone and tissue of the patient as optimally as possible in cooperation with embodiments of the invention.

Another object of the invention is to implant the embodiments of the invention in order to unload force from the spinal facets and other posterior spinal structures and also the intervertebral disk.

A further aspect of the invention is to implant the embodiment of the invention with a procedure that does not remove or alter bone or tear or sever tissue. In an aspect of the invention the muscle and other tissue can be urged out of the way during the inventive implantation procedure.

Accordingly, an aspect of the invention is to provide for a novel implantation procedure that is minimally invasive.

Figure 1A:
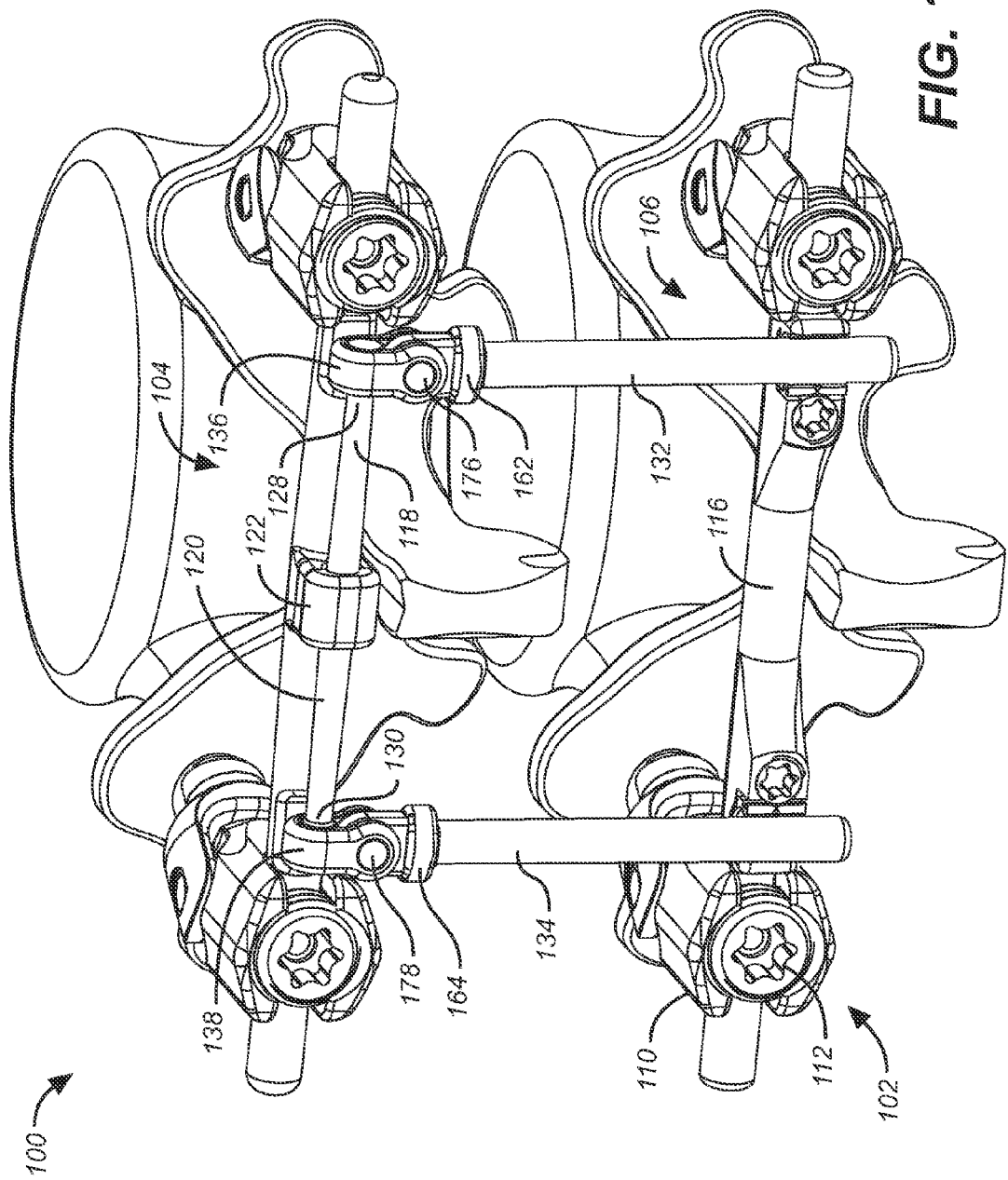
FIG. 1A is a posterior view of the embodiment of FIG. 1 implanted in a spine.

Dynamic Stabilization, Motion Preservation System for the Spine:

A dynamic stabilization, motion preservation system 100 embodiment of the invention is depicted in FIG. 1 and includes an anchor system 102, a horizontal rod system 104, and a vertical rod system 106. For these embodiments horizontal refers to a horizontal orientation with respect to a human patient that is standing and vertical refers to a vertical orientation with respect to a patient that is standing (FIG. 1A). As will be more fully disclosed herein below, one embodiment for the anchor system 102 includes a bone screw 108 which is mounted to a head or saddle 110. Alternatively, the bone screw 108 can be replaced by a bone hook as more fully described in U.S. Provisional Patent Application No. 60/801, 871, entitled "An Implant Position Between the Lamina to Treat Degenerative Disorders of the Spine," which was filed on Jun. 14, 2006, and is incorporated herein by reference and in its entirety. The mounting of the head or saddle 110 to the bone screw 108 allows for multiple degrees of freedom in order that the bone screw 108 may be appropriately, conveniently, and easily placed in the bone of the spine and in order to assist in isolating the bone screw 108 from the remainder of the system 100 so that less force is placed on the anchor system 102 and on the bone screw/bone interface. Some prior art devices, which use such bone screws, have, on occasion, had the bone screws loosen from the spine, and the present embodiment is designed to reduce the force on the bone screw and on the bone screw/bone interface. Preferably, the anchor system 102 is comprised of titanium. However, other biocompatible materials such as stainless steal and/or PEEK can be used.

In the embodiment of FIG. 1, the horizontal bar system 104 is preferably secured through the head 110 of the anchor system 102 with a locking set screw 112. This embodiment includes a first horizontal rod 114 and a second horizontal rod 116. The first horizontal rod 114 has first and second deflection rods or loading rods 118 and 120 secured thereto. In a preferred embodiment, the first horizontal rod can be comprised of titanium, stainless steel or PEEK or another biocompatible material, and the first and second deflection rods or loading rods can be comprised of a super elastic material. Preferably, the super elastic material is comprised on Nitinol (NiTi). In addition to Nitinol or nickel-titanium (NiTi), other super elastic materials include copper-zinc-aluminum and copper-aluminum-nickel. However, for biocompatibility, the nickel-titanium is the preferred material.

Such an arrangement allows for the horizontal rod system 104 to isolate forces placed thereon from the anchor system 102 and, thus, isolate forces that could be placed on the bone screw 108 and the bone screw/bone interface of the spine, and, thus, prevent the loosening of the bone screw 108 in the spine. As shown in FIG. 1 the deflection rods or loading rods 118 and 120, in this preferred embodiment, are mounted in the center of the first horizontal rod 114 to a mount 122. Preferably, the deflection rods or loading rods 118 and 120 are force fit into the mount 122. Alternatively, the deflection rods or loading rods may be screwed, glued, or laser welded to the mount 122 and to bores placed in the mount 122. Other fastening techniques are within the scope and spirit of the invention. As can be seen in FIGS. 1, 3, and 4, the first horizontal rod 114 includes first and second ridges 124, 126 located on either side of the mount 122 and extend at least partially along the length of the first horizontal rod 114 toward the respective ends of the horizontal rod 114. These ridges 124, 126 add rigidity to the mount 122 relative to the rest of the horizontal rod system 104.

As seen in FIG. 1, the deflection rods or loading rods 118, 120 have a constant diameter extending outwardly toward the respective ends 128, 130 of the deflection rods or loading rods 118, 120. Alternatively, the deflection rods or loading rods 118, 120 can have a varying diameter as the rods 118, 120 approach their respective ends 128, 130. Preferably, as depicted and discussed below, the rods 118 and 120 can have a decreasing diameter as the rods approach the respective ends 128, 130. The decreasing diameter allows the super elastic rods 118, 120 to be more flexible and bendable along the length of the rods as the rods approach the ends 128, 130 and to more evenly distribute the load placed on the system 100 by the spine. Preferably, the diameter of the deflection rods or loading rods continuously decreases in diameter. However, it can be understood that the diameter can decrease in discrete steps along the length, with the diameter of one step not being continuous with the diameter of the next adjacent step. Alternatively, for different force and load carrying criteria the diameters of the deflection rods or loading rods can continuously increase in diameter or can have discreet step increases in diameter along the length of the deflection rods or loading rods as the rods extent toward the respective ends 128, 130. Still further, the rods can have at least one step of decreasing diameter and at least one step of increasing diameter in any order along the length of the deflection rods or loading rods as the rods approach the respective ends 128, 130, as desired for the force and load carrying characteristics of the deflection rods or loading rods 118, 120.

With respect to FIG. 3, for example, the horizontal rod system 104, and, in particular, the deflection rods 118, 120, share the load carried by the spine. This load sharing is directed to restoring the normal motion of the spine. This embodiment, and, in particular, the deflection rods or loading rods 118, 120, provide stiffness and support where needed to support the loads exerted on the spine during spine motion, which loads, the soft tissues of the spine are no longer able to accommodate since these spine tissues are either degenerated or damaged. Such load sharing is enhanced by the ability to select the appropriate stiffness of the deflection rods or loading rods 118, 120 in order to match the load sharing desired. By selecting the appropriate stiffness of the deflection or loading rods, to match the physiology of the patient, and the loads that the patient places on the spine, a better outcome is realized by the patient. Prior to implantation, the stiffness of the deflection or loading rods can be selected from a number of deflection or loading rods. The stiffness is variable depending on the deflection or load rod selected. As indicated herein, the stiffness of the deflection or loading rod can be varied by the shape of the rod and the selection of the material. Shape variations can include diameter, taper, direction of taper, stepped tapering, and material variation can include composition of material, just to name a few variations.

It is to be understood that the load carried by the deflection or loading rods is distributed along at least part of the length of the deflection or loading rods. Preferably, the load is distributed along the entire length of the deflection or loading rods. Further, as the load is carried horizontally and the stiffness can be varied along a horizontal member, rather than vertically, the embodiments of the invention can be made smaller in order to fit in more spaces relative to the spine. Advantageously, embodiments can fit, for example, in the L5-S1 space of the spine in addition to generally less constrained spaces such as the L4-L5 space of the spine.

With respect to the embodiment of the horizontal rod system of the invention as depicted for example in FIG. 3, the deflection rods or loading rods 118, 120 are cantilevered from mount 122. Thus, these deflection rods 118, 120 have a free end and an end fixed by the mount 112, which mount is located on the horizontal rod 114. As is evident in FIG. 3, the cantilevered deflection rods 118, 120 are about parallel in a rested position to the horizontal rod 114, and, in this embodiment, the horizontal rod is directly connected to the anchor systems and, in particular, to the heads or saddles of the anchor system. Preferably, the horizontal rod 114 is stiff and rigid and, particularly, in comparison to the deflection rods. In this arrangement, the horizontal rod system and, in particular, the deflection rods 118, 120 share the load resulting from the motions of the body of the patient.

Figure 43:
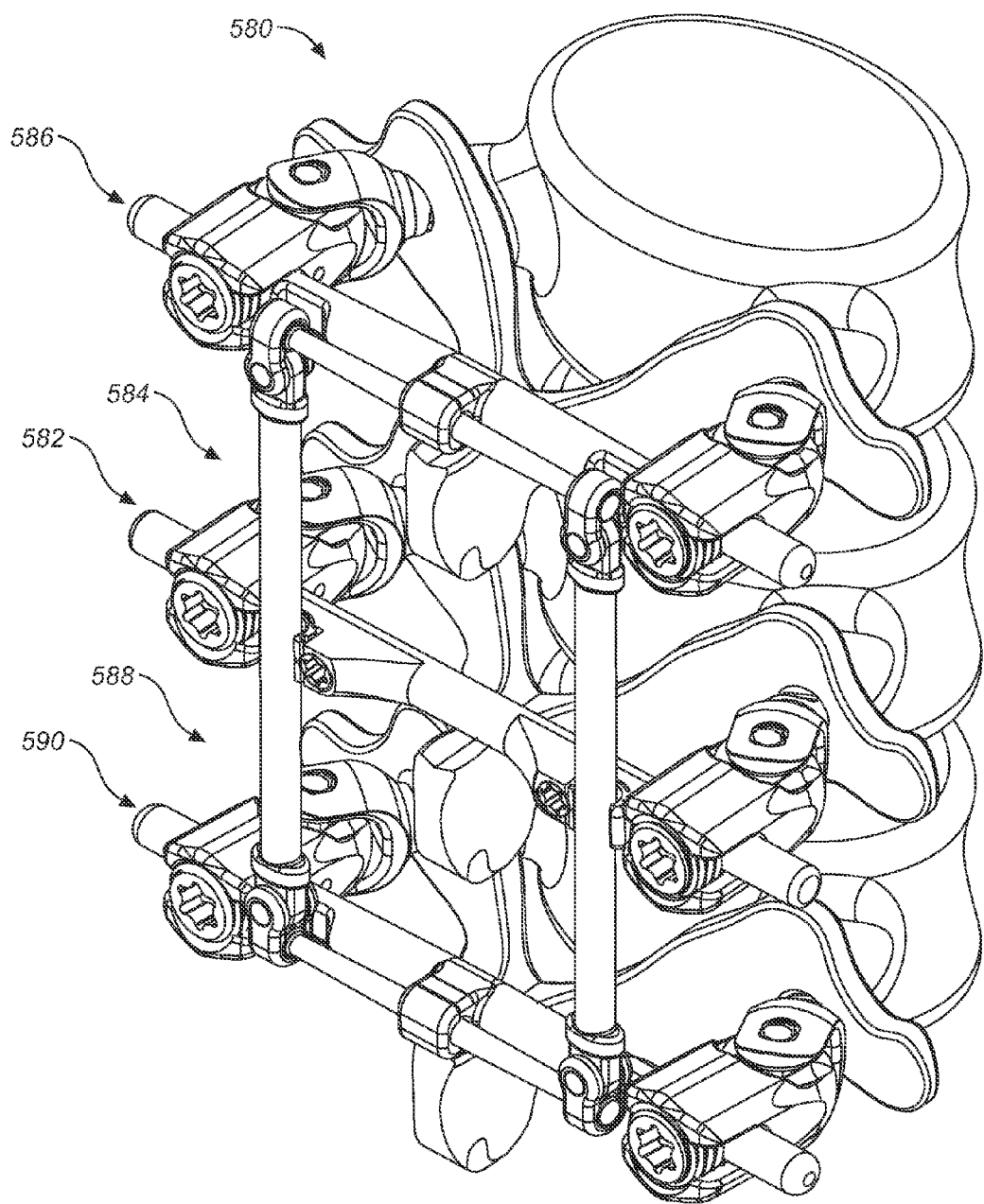
FIG. 43 is a side view of yet another embodiment of a two level dynamic spine stabilization system of the invention.
Figure 43A:
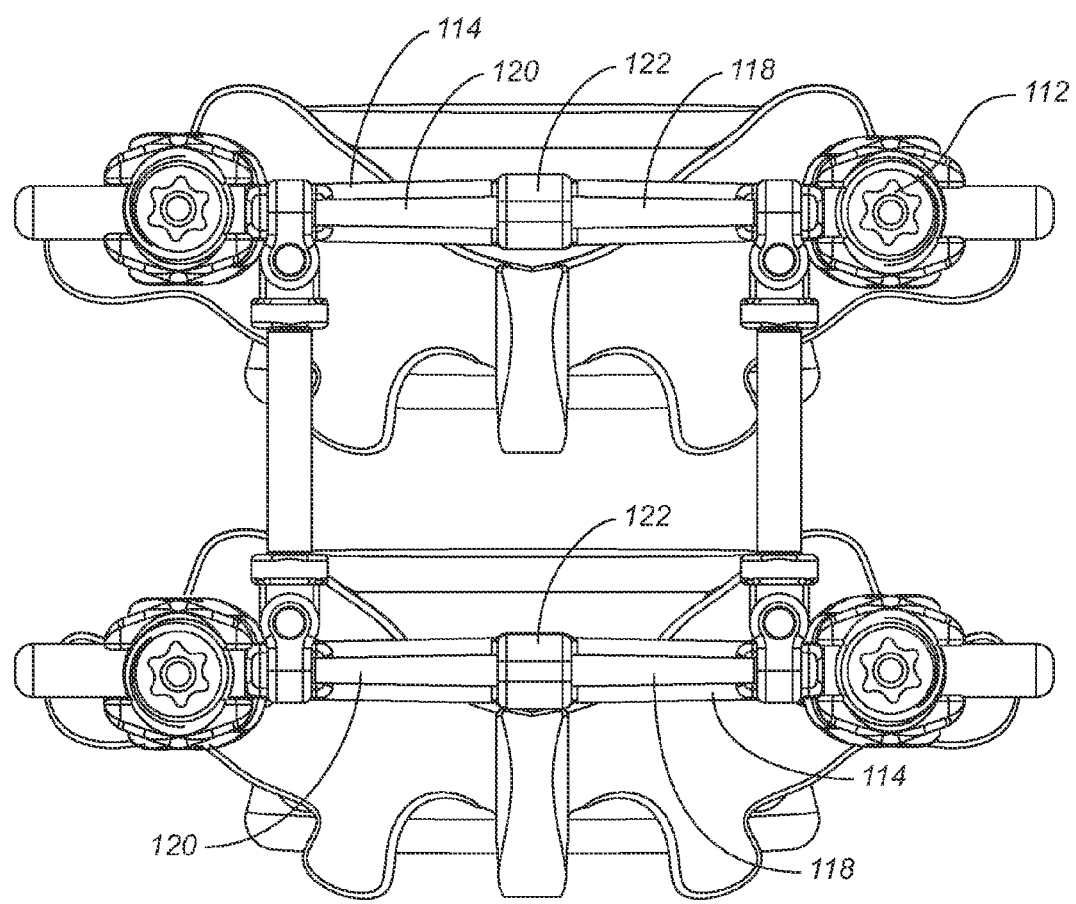
FIG. 43A is a side view of an alternative embodiment of a dynamic spine stabilization system of the invention.

As an alternate embodiment, the second horizontal rod 116 could be replaced with a horizontal rod 114 which has deflection rods or loading rods (FIG. 43A). Thus, both horizontal rods would have deflection rods or loading rods. The deflection rods or loading rods mounted on one horizontal rod would be connected to vertical rods and the vertical rods would be connected to deflection rods or loading rods mounted on the other horizontal rod. Such an embodiment provides for more flexibility. Further, the deflection rods or loading rods 118, 120 can have other configurations and be within the spirit and scope of the invention.

Further, as can be seen in FIG. 1, the vertical rod system is comprised of, in this embodiment, first and second vertical rods 132, 134 which are secured to first and second connectors 136, 138 located at the ends 128, 130 of the first and second deflection rods or loading rods 118, 120. As will be described below, the vertical rods 132, 134 are preferably connected in such a way as to be pivotal for purposes of implantation in a patient and for purposes of adding flexibility and dynamic stability to the system as a whole. These vertical rods 132, 134 are preferably made of titanium. However, other bio-compatible materials can be used. The vertical rods 132, 134 are also connected to the second horizontal rod 116 by being received in C-shaped mounts 140, 142 located on the second horizontal rods and in this embodiment, held in place by set screws 144, 146. It is to be understood by one of ordinary skill in the art that other structures can be used to connect the vertical rods to the horizontal rods.

Preferably, the vertical rods are only connected to the horizontal rods and not to the anchoring system 102 in order to isolate the anchor system 102 and, in particular, the heads 110 from stress and forces that could be placed on the heads, and from forces transferred to the heads where the vertical rods connect to the heads. Thus, the system 100 through the vertical and horizontal rods allow for dynamic stability, and a wide range of motion without causing undue force to be placed on the heads of the anchor systems. These embodiments also allow for each level of the spine to move as freely as possible without being unduly restrictively tied to another level.

More lateral placement of the vertical rods toward the heads of the anchor system provides for more stiffness in lateral bending and an easier implant approach by, for example, a Wiltse approach as described in "The Paraspinal Sacraspinalis-Splitting Approach to the Lumber Spine," by Leon L. Wiltse et al., *The Journal of Bone & Joint Surgery*, Vol. 50-A, No. 5, July 1968, which is incorporated herein by reference.

The stiffness of the system 100 can preferably be adjusted by the selection of the materials and placement and diameters of the horizontal and vertical rods and also the deflection rods or loading rods. Larger diameter rods would increase the resistance of the system 100 to flexion, extension rotation, and bending of the spine, while smaller diameter rods would decrease the resistance of the system 100 to flexion, extension, rotation and bending of the spine. Further, continually or discretely changing the diameter of the rods such as the deflection rods or loading rods along the length of the rods changes the stiffness characteristics. Thus, with the deflection rods or loading rods 118, 120 tapered from the mount 122 toward the ends 128, 130, the system can have more flexibility in flexion and extension of the spine. Further, using a super elastic material for the horizontal rods and the vertical rods in addition to the horizontal deflection rods or loading rods adds to the flexibility of the system 100. Further, all of the horizontal and vertical rods, in addition to the deflection rods or loading rods, can be made of titanium or stainless steel or PEEK should a stiffer system 100 be required. Thus, it can be appreciated that the system 100 can easily accommodate the desired stiffness for the patient depending on the materials uses, and the diameter of the materials, and the placement of the elements of the system 100.

Should an implanted system 100 need to be revised, that can be accomplished by removing and replacing the horizontal and/or vertical rods to obtain the desired stiffness. By way of example only, should a stiffer revised system be desired, more akin to a fusion, or, in fact, a fusion, then the horizontal rods having the deflection rods or loading rods can be removed and replaced by horizontal rods having deflection rods or loading rods made of titanium, or stainless steel, or non-super elastic rods to increase the stiffness of the system. This can be accomplished by leaving the anchor system 102 in place and removing the existing horizontal rods from the heads 110 and replacing the horizontal rods with stiffer horizontal rods and associated vertical rods.

FIG. 3 depicts a view of the horizontal rod 104 as previously described. In this embodiment the connectors 136, 138 are shown on the ends of the deflection rods or loading rods 118, 120. The connectors can be forced-fitted to the deflection rods or fastened in other methods known in the art for this material and as further disclosed below. The connectors 136, 138 have slits 148, 150 to aid in placing the connectors onto the ends of the deflection rods. As is evident from FIG. 3, the connectors 136, 138 each include upper and lower arms 160, 162 which can capture there between the vertical rods 132, 134. The arms each include an aperture 168, 170 that can accept a pin or screw 176, 178 (FIG. 1) for either fixedly or pivotally securing the vertical rods 132, 134. In this embodiment the vertical rods include a head 162, 164 that can be force fit or screwed onto the rest of the vertical rods. The heads include apertures 172, 174 for accepting the pins or screws 176, 178.

In order that the system 100 has as low a profile as possible and extends from the spine as little as possible, it is advantageous to place the deflection rods or loading rods 118, 120 as close to the first horizontal rod 114 as possible. In order to accomplish this low profile, preferably notches 152, 154 are placed in horizontal rod 114 to accommodate the connectors 136, 138.

Accordingly, the purpose for the notches is to provide for a horizontal rod with a low profile when implanted relative to the bones and tissues of the spine so that there is, for example, clearance for implant and the motion of the implant, and to keep the deflection rods or loading rods as close as possible to the horizontal rods in order to reduce any potential moment arm relative to the mounts on the horizontal rod.

Figure 46:
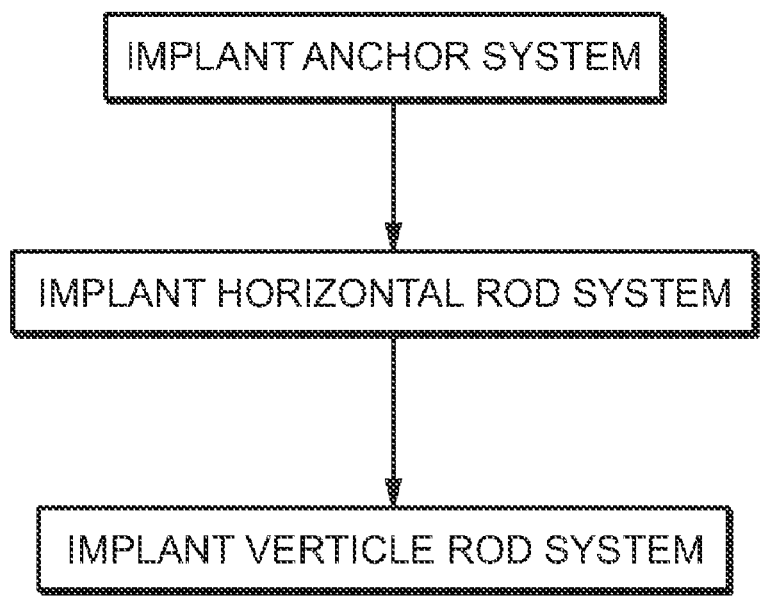
FIG. 46 is a flow chart of an embodiment of the method of the invention.

FIG. 4 depicts another embodiment of the horizontal rod 114 with deflection rods or loading rods 118, 120 and with different connectors 156, 158. Connectors 156, 158 each include two pairs of upper and lower arms 160, 162 extending in opposite directions in order for each connector 156, 158 to mount an upper and a lower vertical rod as presented with respect to FIG. 46. This configuration allows for a three level system as will be described below.

Figure 5:
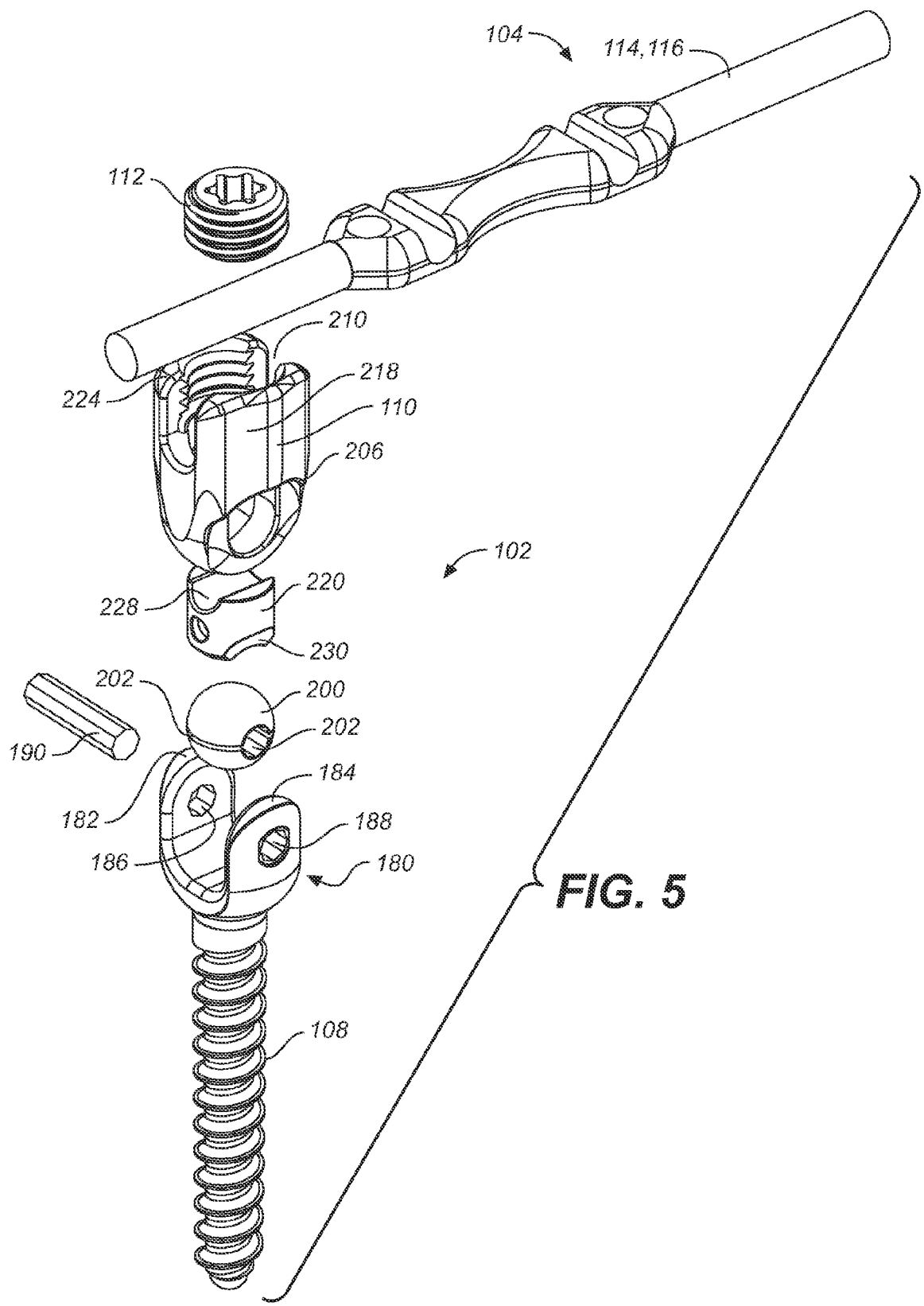
FIG. 5 is a perspective view of an embodiment of an anchor system of the invention for use with a dynamic spine stabilization system such as depicted in FIG. 1.
Figure 7:
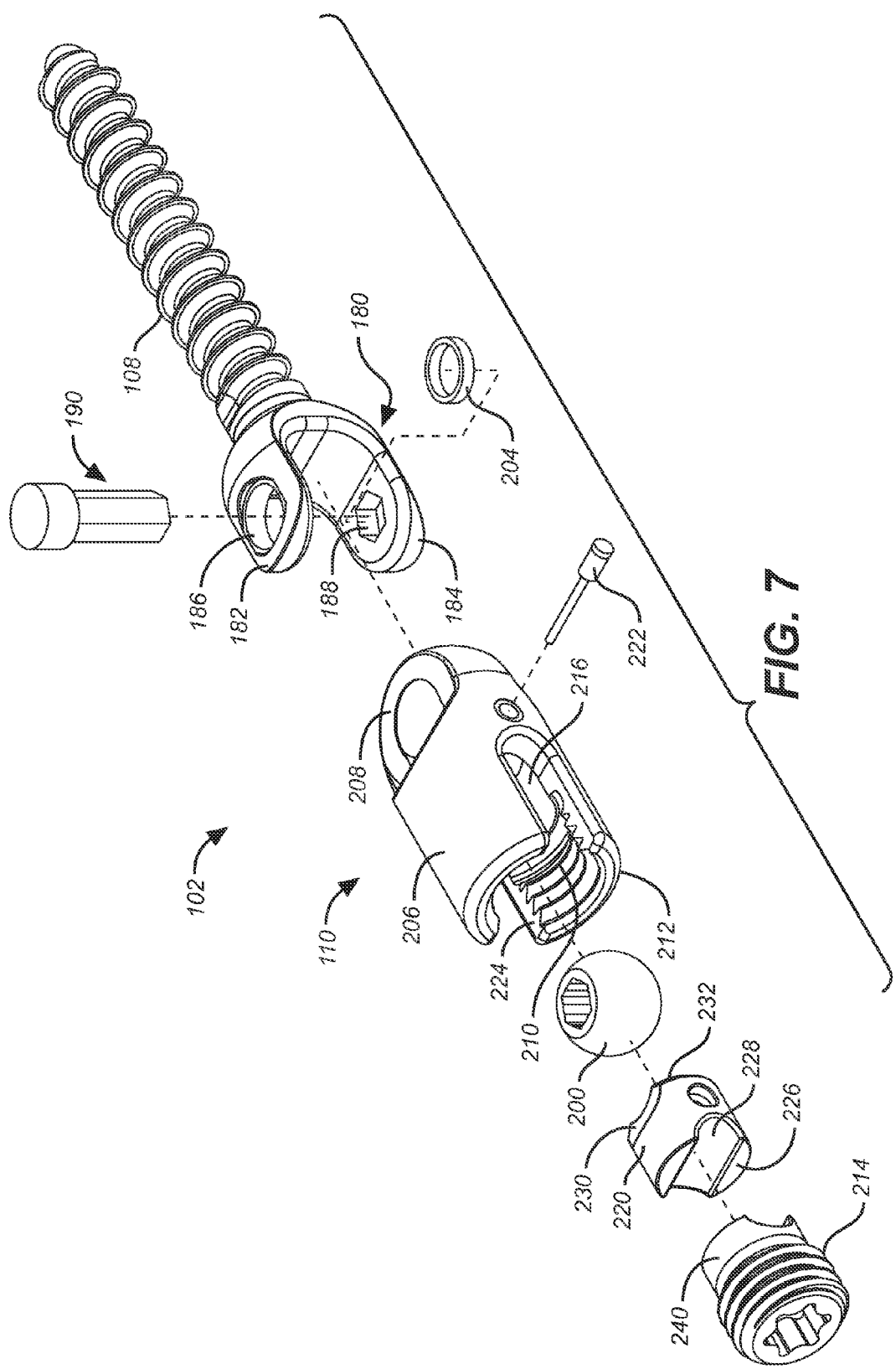
FIG. 7 is an exploded perspective view of an alternative embodiment of the anchor system of the invention for use with a dynamic spine stabilization system such as depicted in FIG. 1.
Figure 8:
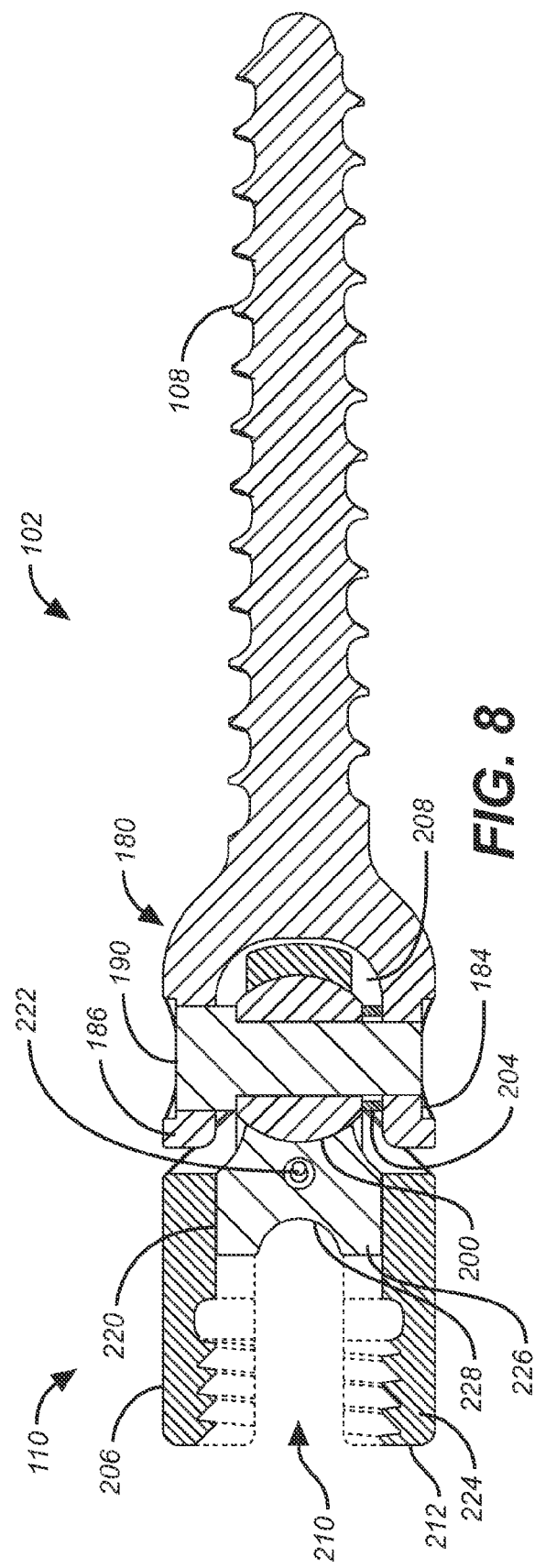
FIG. 8 is a sectioned view of a portion of embodiment of the alternative anchor system of FIG. 7 of the invention.

Embodiments of the Anchor System of the Invention:

A preferred embodiment of the anchor system 102 invention can be seen in FIG. 5. This is similar to the anchor system 102 depicted in FIG. 1. In particular, this anchor system 102 includes a bone screw 108 with a head 110 in the form of a U-shaped yoke 180 with arms 182, 184. As will be discussed further, a hook, preferably with bone engaging barbs or projections, can be substituted for the bone screw 108. The hook embodiment is further described in the above referenced and incorporated provisional application. The hooks are used to hook to the bone, such as the vertebra instead of having screws anchored into the bone. Each of the arms 182, 814 of yoke 180 includes an aperture 186, 188 through which a pin 190 can be placed. The pin 190 can be laser welded or force fit or glued into the yoke 180, as desired. The pin 190 can be smooth or roughened as discussed below. Further, the pin 190 can be cylindrical or be comprised of a multiple sides as shown in FIG. 7. In FIG. 7, pin 190 has six sides and one or more of the accommodating apertures 186, 188 can also include mating sides in order to fix the position of the pin 190 in the yoke 180. A compression sphere 200 is placed over the pin 190. The compression sphere 200 can have a roughened surface if desired to assist in locking the sphere in place as described below. The compression sphere 200 can include one or more slits 202 to assist in compressing the sphere 200 about the pin 190. The compression sphere 200 can have an inner bore that is cylindrical or with multiple sides in order conform to and be received over the pin 190. As can be seen in FIG. 8, one or more spacer rings 204 can be used to space the compression ring from the yoke 180 in order to assist in providing the range of motion and degrees of freedom that are advantageous to the embodiments of the invention.

Mounted about the compression sphere 200 is the head or saddle 110. Head 110 in FIGS. 7, 8 is somewhat different from head 110 in FIG. 1 as will be described below. Head 110 in FIGS. 7, 8 includes a cylindrical body 206 with a lower end having an aperture 208 that can receive the compression sphere 200. The aperture 208 can have a concave surface as depicted in FIGS. 7, 8. Accordingly, the compression sphere 200 fits inside of the concave surface of aperture 208 and is free to move therein until restrained as described below. As is evident from the figures, the lower end of the cylindrical body 206 about the aperture 208 has some of the material that comprised wall 224 removed in order to accommodate the motion of the yoke 180 of the bone screw 108. Essentially, the portion of the wall 224 adjacent to the arms 182, 184 of the yoke 180 has been removed to accommodate the yoke 180 and the range of motion of the yoke.

The head 110 of the anchor system 102 includes an internal cylindrical bore 210 which is preferably substantially parallel to a longitudinal axis of the head 110. This bore 210 is open to the aperture 208 and is open and preferably substantially perpendicular to the distal end 212 of the head 110. At the distal end 212 of the head 110, the bore 210 is threaded and can accept the set screw 112. Along the side of the head 110 are defined aligned U-shaped slots that extend through the head 110 from the outer surface to the bore 210. These U-shaped slots are also open to the distal end 212 of the head 110 in order to have the set screw 112 accepted by the threads of the bore 210. Located in the bore 210 between the set screw 112 and the compression sphere 200 is a compressor element or cradle 220. The compressor element or cradle 220 can slide somewhat in the bore 210, but the compressor element or cradle 220 is restrained by a pin 222 (FIG. 7) received through the wall 224 of the head 110 and into the compressor element or cradle 220. Thus, the compressor element or cradle 220, until locked into position, can move somewhat in the bore 210.

The compressor element or cradle 220 has a generally cylindrical body so that the compressor element 220 can fit into bore 210. An upper end 226 of the compressor element 220 includes a concave surface 228. This surface 228 is shaped to fit the horizontal rod system 104 and, in particular, a horizontal rod 114, 116. The lower end of the compressor element 220 includes a concave surface 230 which can accommodate the compression sphere 200. The lower end of the compressor element 220 adjacent to the concave surface 230 has an additional concave surface 232 (FIG. 8) which is used to accommodate the motion of the upper end of the yoke 180 as the head 110 is moved relative to the bone screw 108. The concave surfaces 228 and 230 can be roughened, if desired, to assist in locking the head 110 relative to the bone screw 108. In this embodiment (FIGS. 5, 6) there is no top compression element or cradle (see, for example, FIGS. 7, 13) in order to reduce the profile of the head of the anchor system.

As is evident from the figures, with the anchor system 102 assembled and with a horizontal rod 114, 116 received in the U-shaped slot 216, the set screw can press against the horizontal rod 114, 116, which horizontal rod 114, 116, can press against the compressor element or cradle 220, which compressor element or cradle 220 can press against the compression sphere 220, which compression sphere can press against the pin 190 in order to lock the horizontal rod 114, 116 relative to the head 110 and to lock the head 110 relative to the bone screw 108. It is to be understood that all of the surfaces that are in contact, can be roughened to enable this locking, if desired. Alternatively, the surfaces may be smooth with the force of the set screw 112 urging of the elements together and the resultant locking.

Figure 6:
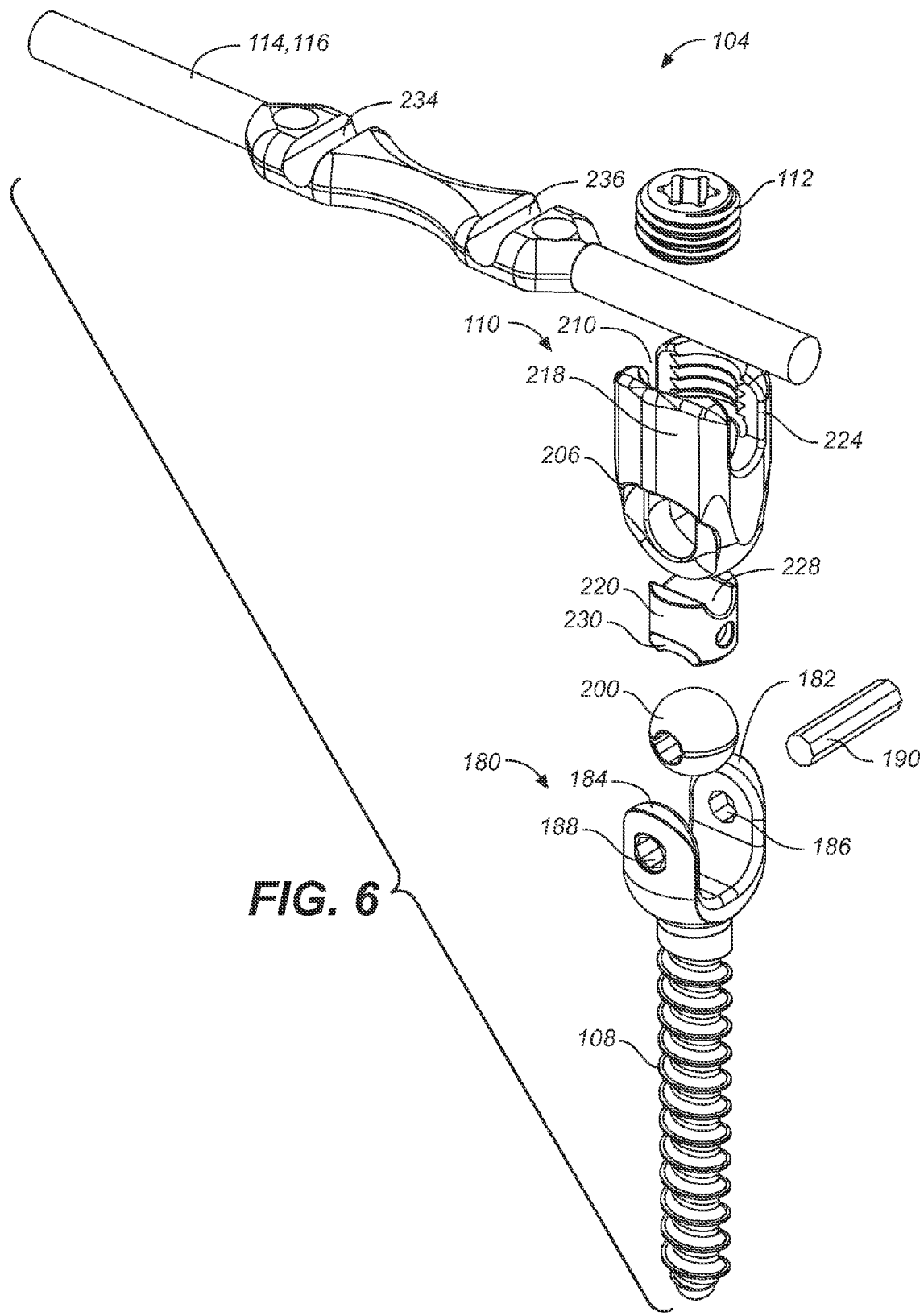
FIG. 6 is another perspective view of the embodiment of the anchor system of FIG. 5.

As can be seen in FIGS. 5, 6 an alternative horizontal rod 114, 116 is depicted. This alternative horizontal rod 114, 116 includes first and second concave openings 234, 236 which can receive vertical rods such as vertical rods 132, 134 (FIG. 1). The horizontal rod 114, 116 is substantially cylindrical with the areas around the concave openings 234, 236 bulked up or reinforced as desired to support the forces. Additionally, threaded bores are provided adjacent to the concave openings 234, 236 and these bores can receive screws that have heads that can be used to lock vertical rods in place. Alternatively, the screws can retain short bars that project over the concave openings 234, 236 in order to hold the vertical rods in place (FIG. 34). If desired, the short retaining bars can also have concave openings that conform to the shape of, and receive at least part of, the vertical rods in order to retain the vertical rods in place with the system 100 implanted in a patient.

Figure 2:
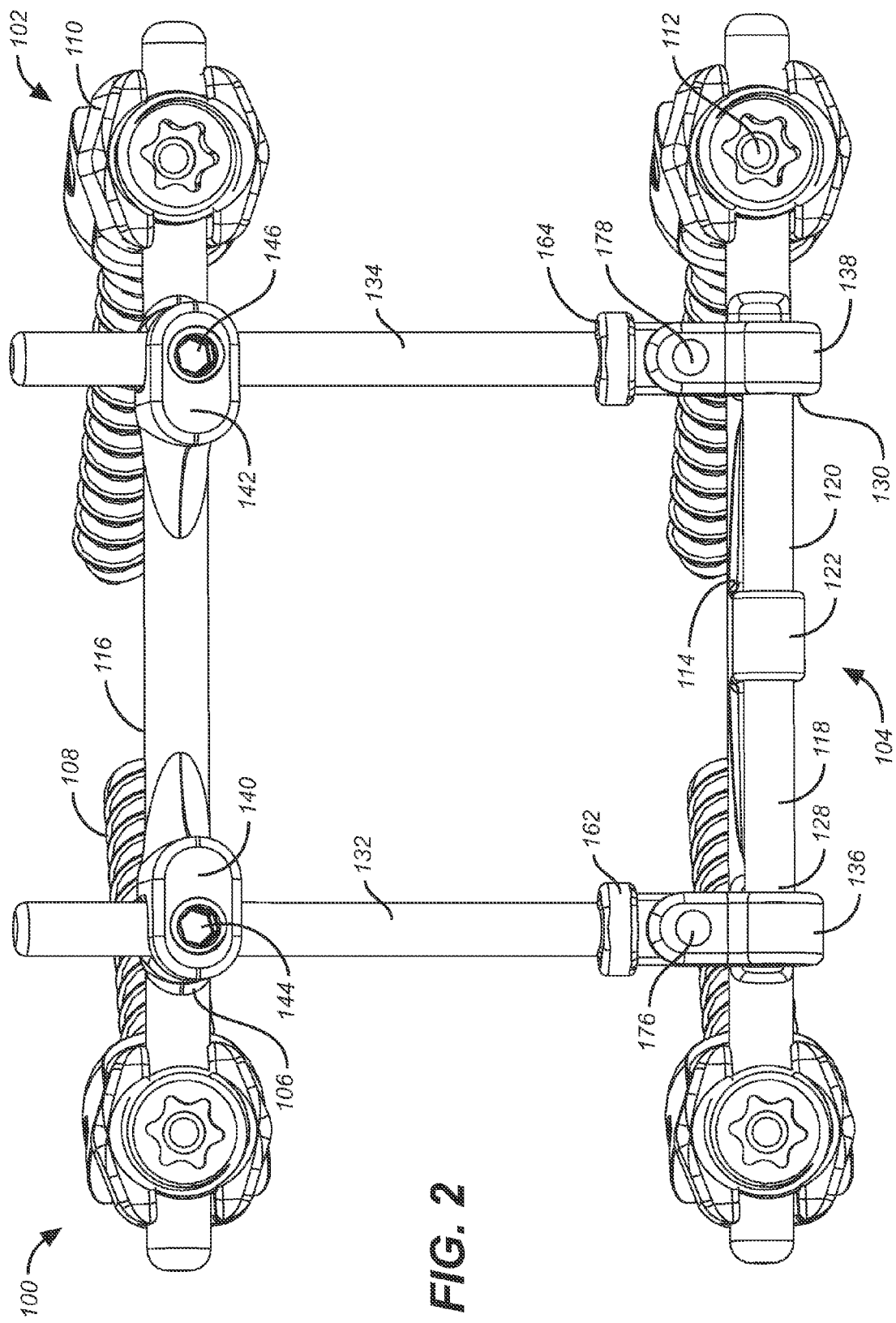
FIG. 2 is a top view of the embodiment of FIG. 1.

Turning again to FIGS. 1, 2, 5, 6, the head 110 depicted is a preferred embodiment and is somewhat different from the head 110 as seen in FIG. 8. In particular the head body 206, the outer surface 218 of the head and the head wall 224, have been configured in order to prevent splaying of the head 110 when the set screw 112 locks the anchor system 102 as explained above. As seen in FIGS. 1, 2, the head 110 and, in particular, the wall 224 is reinforced about the U-shaped slot 216 that received the horizontal bar system 104. By reinforcing or bulking up the area of the wall about the U-shaped slot 216, splaying of the head 110 when force is applied to the set screw 214, in order to lock the anchor system 102, is avoided. The head 110 can use a number of shapes to be reinforced in order to prevent splaying. The exemplary embodiment of FIGS. 1, 2, includes a pitched roof shape as seen in the top view looking down on distal end 212 of the head 110. In particular, the wall about the U-shaped slot 216 is thickened, while the portion of the head distal from the U-shaped slot can be less thick if desired in order to reduce the bulk and size of the head 110 and, thus, give the head 110 a smaller profile relative to the bone and tissue structures when implanted in a patient. Further, the small profile allows greater freedom of motion of the system 100 as described below. Also, it is to be understood that due to the design of the anchor system 102, as described above, the head 110 can be shorter and, thus, stand less prominently out of the bone when the bone screw 108 in implanted in a spine of a patient for example.

Freedom of Motion of the Embodiments of the Anchor System of the Invention:

In order to accommodate embodiments of the horizontal rod systems 104 of the invention, to allow greater freedom in placing the horizontal rod systems and the anchor systems 102 relative to, for example, the spine of a patient, and to provide for a smaller implanted profile in a patient, the anchor system 102 includes a number of degrees of freedom of motion. These degrees of freedom of motion are depicted in FIGS. 9, 9A, 10, 10A, and 11, 11A.

Figure 9A:
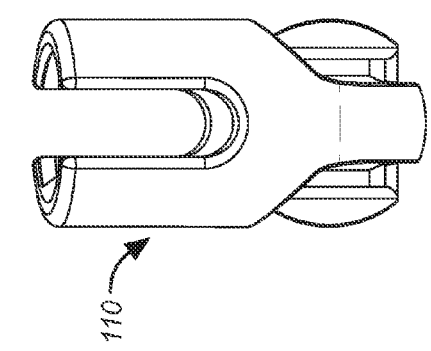
FIG. 9A is an end view of the anchor system of FIG. 9.
Figure 10A:
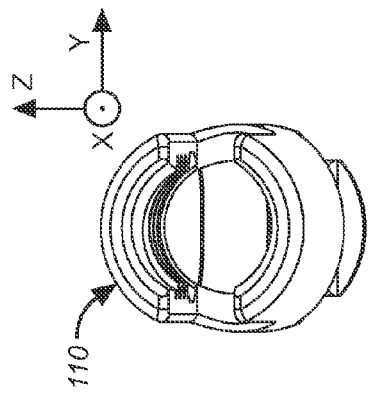
FIG. 10A is an end view of the anchor system of FIG. 10.
Figure 9:
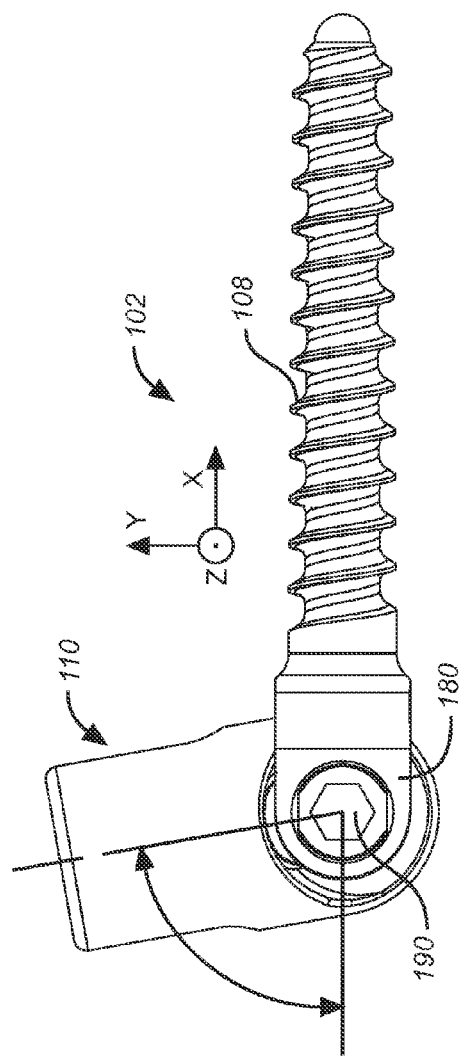
FIG. 9 is a side view of the anchor system of FIG. 7 depicting a degree of freedom of movement of the anchor system of FIG. 7.
Figure 10:
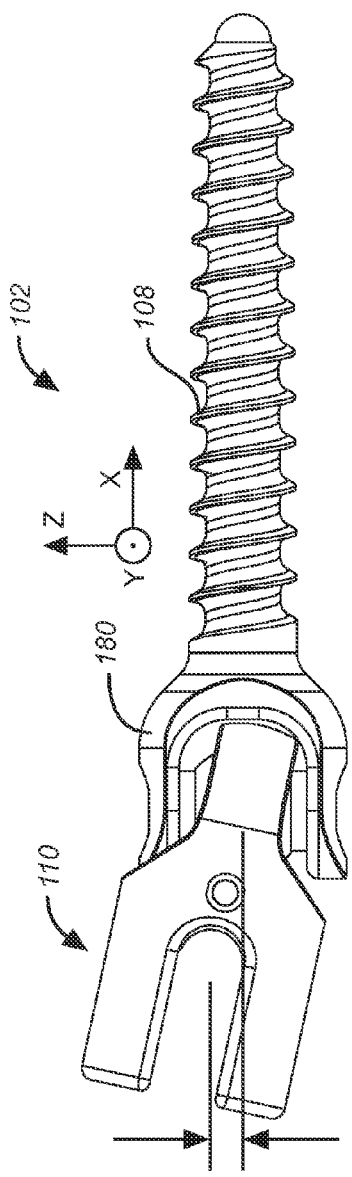
FIG. 10 is a side view of the anchor system of FIG. 7 depicting another degree of freedom of movement of the anchor system of FIG. 7.

FIG. 9 establishes a frame of reference including a longitudinal axis x which is along the longitudinal length of the bone screw 108, a y axis that extends perpendicular to the x axis, and a lateral axis z which is perpendicular to both the x axis and the y axis and extends outwardly from and parallel to the pin 190 of the yoke 180 of the anchor system 102. As depicted in the figures and, in particular, FIGS. 9, 9A, the system 100 due to the embodiments as disclosed herein is able to have the head 110 rotate about the z axis from about 80 degrees to about zero degrees and, thus, in line with the x axis and from the zero degree position to about 80 degrees on the other side of the x axis. Accordingly, the head is able to rotate about 160 degrees about the z axis relative to the bone screw 108. As seen in FIGS. 10, 10A the head 110 is able to tilt about 0.08 inches (2 mm) relative to and on both sides of the x axis. Accordingly, the head 110 can tilt from about 12 degrees to zero degrees where the head 110 is about parallel to the x axis and from zero degrees to 12 degrees about the y axis and on the other side of the x axis. Thus, the head can tilt through about 24 degrees about the y axis. As can be seen in FIGS. 11, 11A, the head 110 can swivel for a total of about 40 degrees about the x axis. With respect FIG. 11A, the head 110 can swivel about the x axis from about 20 degrees to one side of the z axis to zero degrees and from zero degrees to about 20 degrees on the other side of the z axis. The head is able to substantially exercise all of these degrees of freedom at once and, thus, can have a compound position relative to the bone screw by simultaneously moving the head within the ranges of about 160 degrees about the z axis (FIG. 9), about 24 degrees from the y axis (FIG. 10) and about 40 degrees about the x axis (FIG. 11A).

Thus, with respect to FIGS. 9, 9A the range of motion in the axial plane is about 180 degrees or about 90 degrees on each side of the centerline. In FIGS. 10, 10A the range of motion in the Caudal/Cephalad orientation is about 4 mm or about 2 mm on each side of the centerline or about 24 degrees or about 12 degrees on each side of the centerline. In FIGS. 11, 11A the range of motion in the coronal plane is about 40 degrees or about 20 degrees on each side of the centerline.

Figure 13:
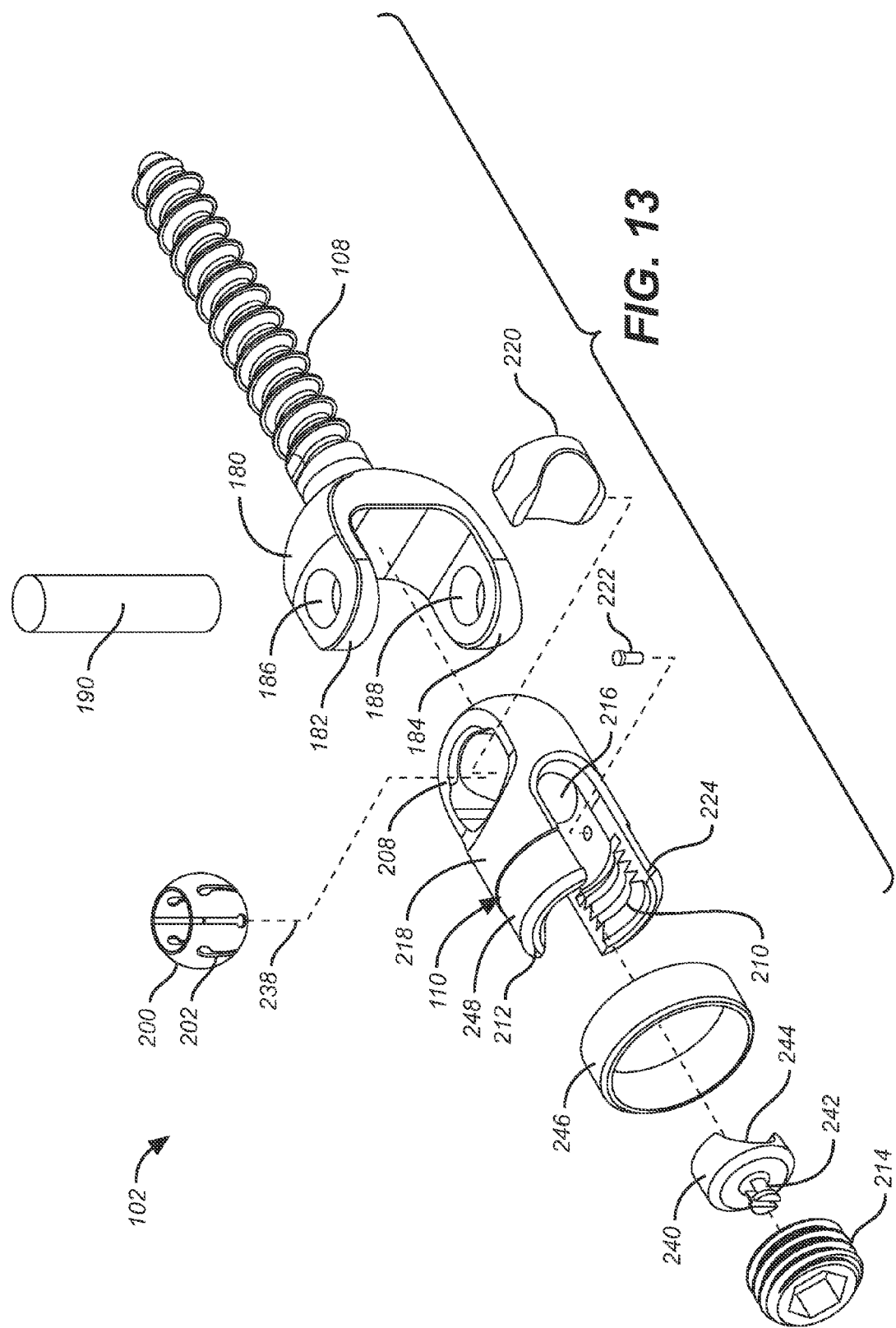
FIG. 13 is an exploded perspective view of the embodiment of the anchor system of the invention of FIG. 12.

FIGS. 12, 13 depict yet another embodiment of the anchor system 102 of the invention where elements that are similar to elements of other embodiments and have similar reference numbers.

As can be seen in FIG. 13, this embodiment includes a lower cradle or compressor element 220 that is similar to the cradle or compressor element 220 of the embodiment of FIG. 7 with the head 110 similar to the head 110 as seen in FIG. 7. The compression sphere 200 is similar to the compression sphere 200 in FIG. 7 with the compression sphere including a plurality of slits provided about the axis of rotation 238 of the sphere 200. In this embodiment, the slits 202 have openings that alternate between facing the north pole of the axis of rotation of the sphere 200 and facing the south pole of the axis of rotation of the sphere 200. Alternatively, the slits can be provided in the sphere and have no opening relative to the north or south pole of the axis of rotation of the sphere 200. Still further, the slits can open relative to only one of the north or south poles.

In the embodiment of FIGS. 12, 13, there is also an upper cradle or compressor element 240 which is positioned adjacent to the set screw 214 (see also FIG. 7). The upper cradle or compressor element 240 has a generally cylindrical body which can slide in the cylindrical bore of the head 110 with an upper end having fingers 242 extending therefrom. The fingers 242 can spring over a bore formed in the lower surface of the set screw 214 in order to retain the cradle 240 relative to the set screw 214 and to allow the cradle 240 to rotate relative to the set screw 214. The lower surface of the cradle 240 includes a concave surface 244 which can mate with a horizontal rod 114, 116 in order to lock the rod relative the head 110 and the head 110 relative to the bone screw 108. If desired, the concave surface 244 can be roughened to assist in locking the system 100.

Further, in FIGS. 12, 13, a retaining ring 246 is depicted. The retaining ring can be force fit over the outer surface 218 of the head 110, or pop over and snap under a ridge 248 at the distal end 212 of the head 110, or can have internal threads that mate with external threads located on the outer surface of the 218 of the head 110. With the anchor system 102 in place in a patient and with the horizontal rod 114, 116 received in the anchor system, before the set screw 214 is tightened in order to lock the horizontal rod and the anchor system, the retaining ring 246 can be attached to the head 110 in order to prevent splaying of the head 110 as the set screw 214 locks the system 110.

Figure 14:
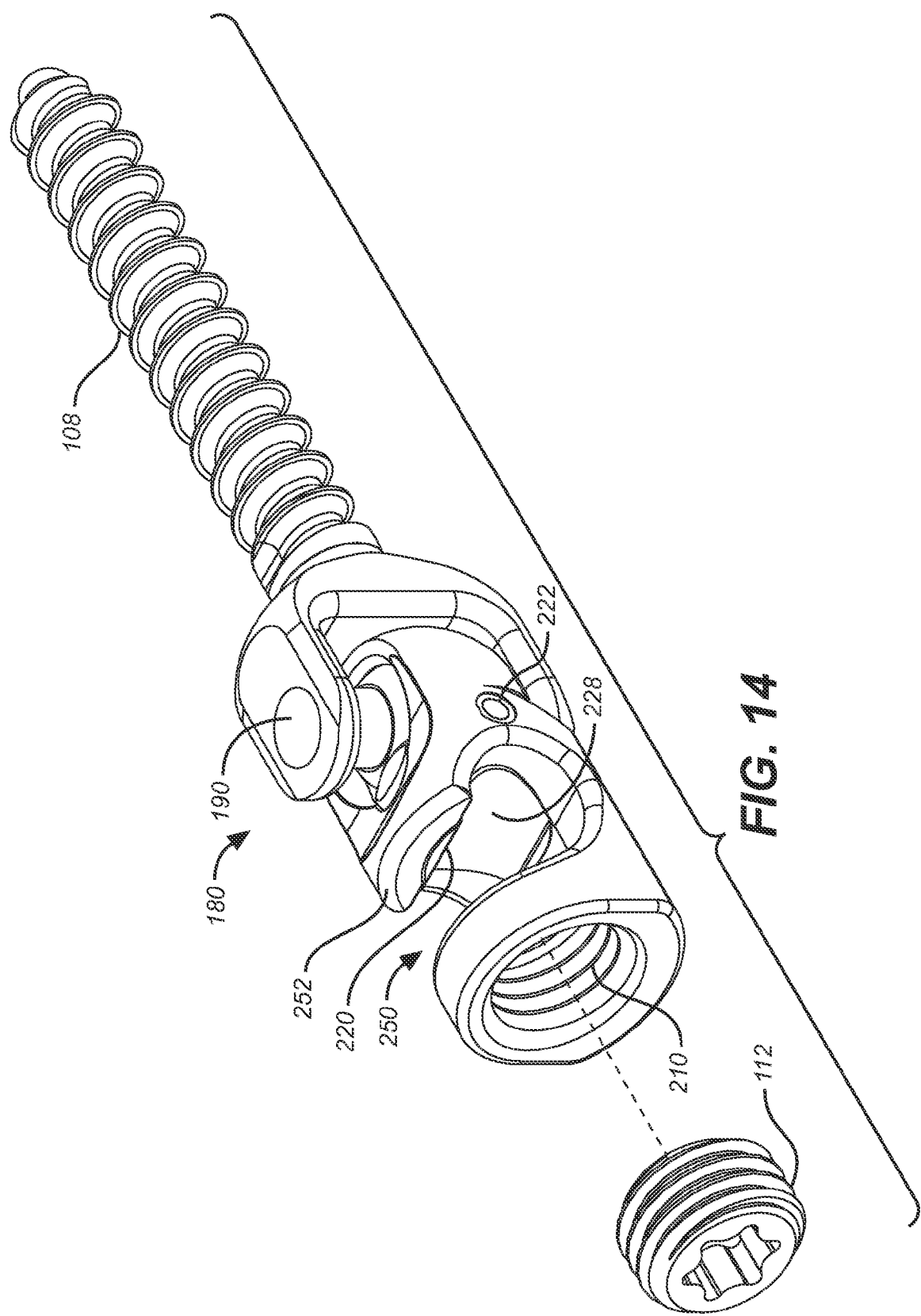
FIG. 14 is a perspective view of yet another embodiment of the anchor system of the invention.

Further embodiments of the anchor system 102 which can side load the horizontal rods 114, 116 are seen in FIGS. 14, 15, and 16, where similar elements from other embodiments of the anchor system are given similar numeral references. With respect to the embodiment in FIG. 15, the head side wall 224 includes a lateral or side opening 250 which communicates with the cylindrical bore 210 which is located in head 110. The lateral or side opening preferably extends more than 180 degrees about the outer surface of the head. The side opening 250 includes a lip 252 and the side opening extends down below the lip into communication with the cylindrical bore 210 and follows the outline of the concave surface 228 of the cradle 220. Accordingly, a horizontal rod 114, 116, can be positioned through the side opening 250 and urged downwardly into contact with the concave surface 228 of the cradle 220. In this embodiment the cradle 220 includes a downward projecting post 254. Also, this embodiment does not include a compression sphere, and instead the pin 190, which can have a larger diameter than a pin 190 in other embodiments, comes in direct contact with the post 254 when the set screw 112 locks the anchor system 100. If desired the pin 190 can have a roughened surface 256 to assist in the locking of the anchor system 100. As is evident from FIGS. 14, 15, 16, as this embodiment has a side loading head 110, the distal end of the head is a fully cylindrical without communicating with any lateral U-shaped slots of the other embodiments. Accordingly, this embodiment does not include any retaining ring or reinforced areas that can be used to prevent splaying.

FIG. 17 depicts yet another embodiment of the anchor system 102 that has a lateral or side loading head 110. In this embodiment, a compression cylinder 258 is placed over the pin 190. Such a compression cylinder 258 may offer less freedom of motion of the anchor system 100 with added stability. The compression cylinder 258 can slide along the longitudinal axis 260 of the pin 190, if desired. The head 110 can rotate about the pin 190 and the compression cylinder 258. The head 110 can also slide or translate along the longitudinal axis 260 of the pin as well as the longitudinal axis of the compression cylinder 258. Compression cylinder 258 has slits 262 that can be configured similarly as the slits 202 of the other embodiments of the anchor system 100 described and depicted herein.

FIG. 18 depicts still another embodiment of the anchor system 100 that has a lateral or side loading head 110. This embodiment includes a compression sphere 200 provided over a pin 190 which is similar to the other compression spheres 200 depicted and described herein. Accordingly, this embodiment has the freedom of motion described with respect to the other embodiments which use a compression sphere.

It is to be understood that although each embodiment of the anchor system does not necessarily depict all the elements of another embodiment of the anchor system, that one of ordinary skill in the art would be able to use elements of one embodiment of the anchor system in another embodiment of the anchor system.

Embodiments of the Horizontal Rod System of the Invention:

Embodiments of the horizontal rod system 104 of the invention include the embodiments describes above, in addition to the embodiments that follow. An aspect of the horizontal rod system 104 is to isolate the anchor system 102 and reduce the stress and forces on the anchor system. This aspect is accomplished by not transmitting such stresses and forces placed on the horizontal rod system by, for example, flexion, extension, rotation or bending of the spine to the anchor system. This aspect thus maintains the integrity of the placement of the anchor system in, for example, the spine and prevents loosening of the bone screw or bone hook of the anchor system. In addition, various horizontal rod systems can be used to control the rigidity, stiffness and/or springiness of the dynamic stabilization system 100 by the various elements that comprise the horizontal rod system. Further the horizontal rod system can be used to have one level of rigidity, stiffness and/or springiness in one direction and another level in a different direction. For example, the horizontal rod system can offer one level of stiffness in flexion of the spine and a different level of stiffness in extension of the spine. Additionally, the resistance to lateral bending can be controlled by the horizontal rod system. Select horizontal rod systems allow for more resistance to lateral bending with other select horizontal rod systems allow for less lateral bending. As discussed below, placement of the vertical rods also effects lateral bending. The more laterally the vertical rods are placed, the more stiff the embodiment is to lateral bending.

As is evident from the figures, the horizontal rod system connects to the heads of the anchor system without the vertical rod system connecting to the heads. Generally, two anchor systems are secured to each vertebral level with a horizontal rod system connected between the two anchor systems. This further ensures that less stress and force is placed on the anchor systems secured to each level and also enables dynamic stability of the vertebra of the spine. Accordingly, movement of the vertebra relative to each other vertebra, as the spine extends, flexes, rotates and bends, is stabilized by the horizontal rods and the entire system 100 without placing excessive force or stress on the anchor system as there are no vertical rods that connect the anchor systems of one vertebra level with the anchor system of another vertebra.

Figure 19:
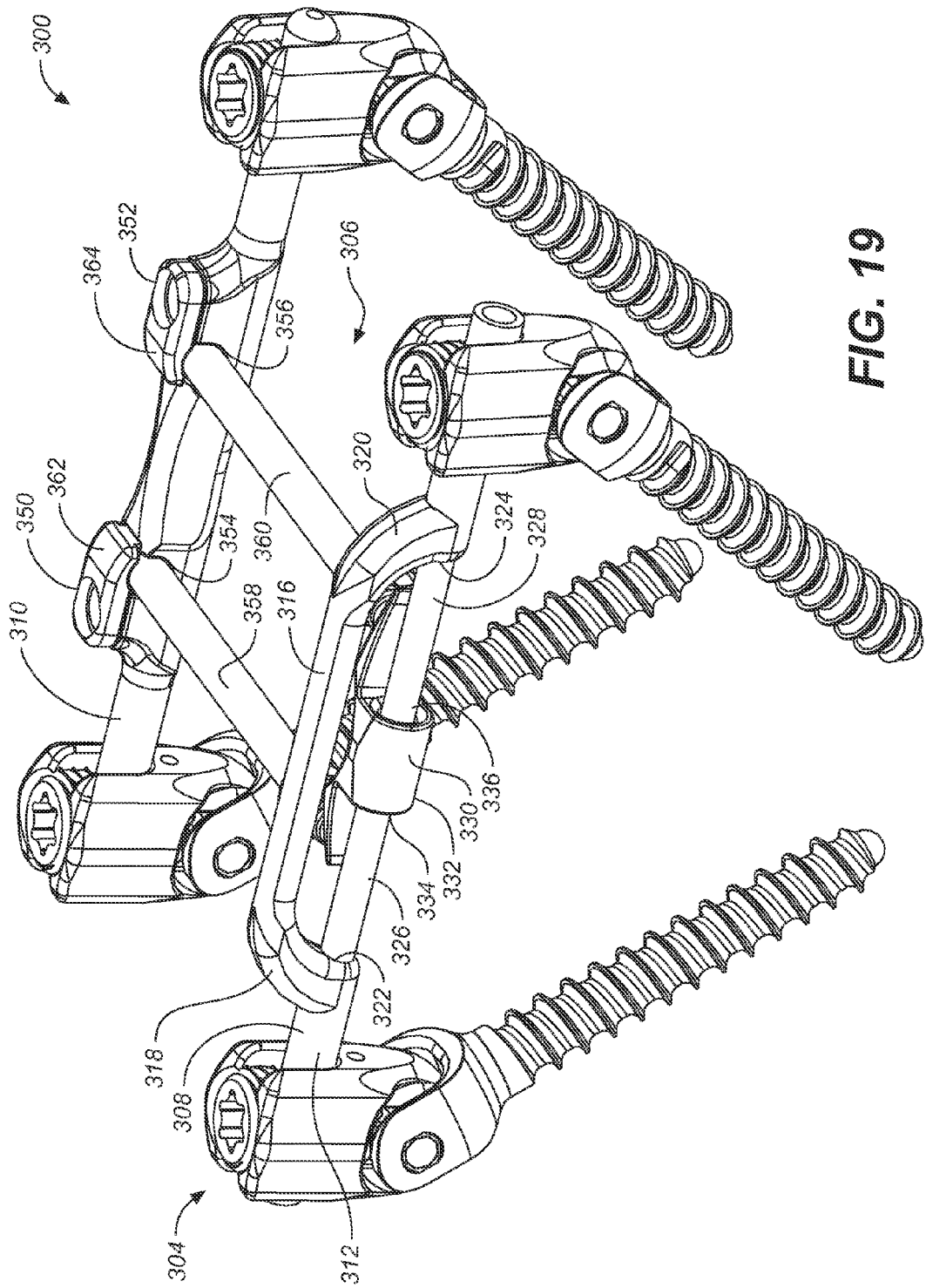
FIG. 19 is a perspective view of another embodiment of a dynamic spine stabilization system of the invention with another horizontal rod system.
Figure 20:
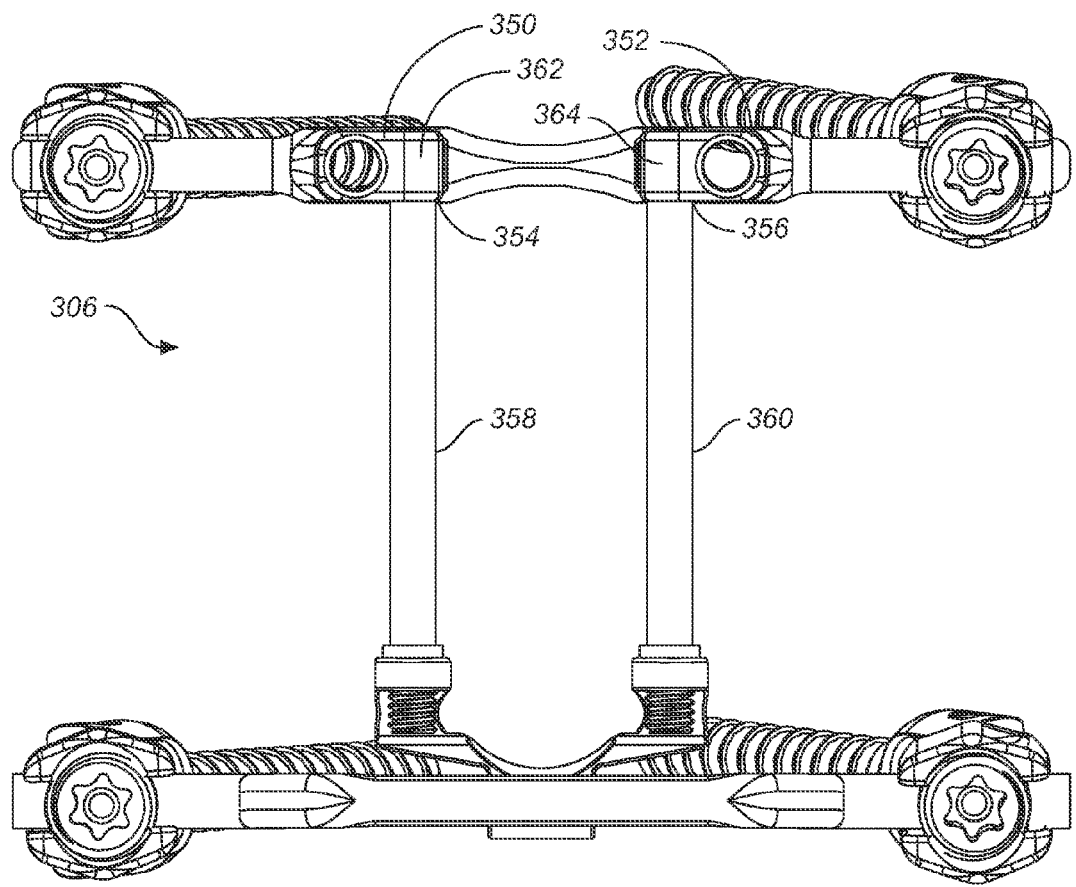
FIG. 20 is a top view of another embodiment of the dynamic spine stabilization of the system of the invention of FIG. 19.
Figure 20A:
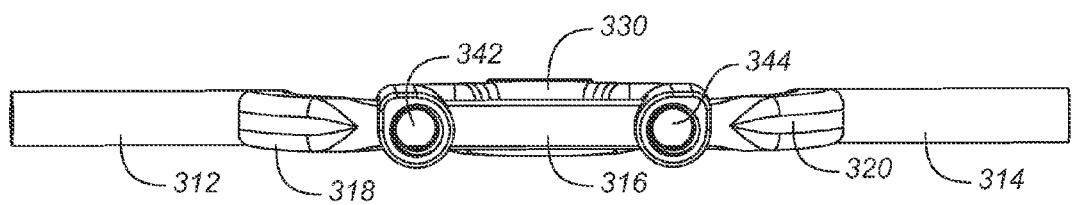
FIG. 20A is a top side of the embodiment depicted in FIG. 19A.
Figure 21:
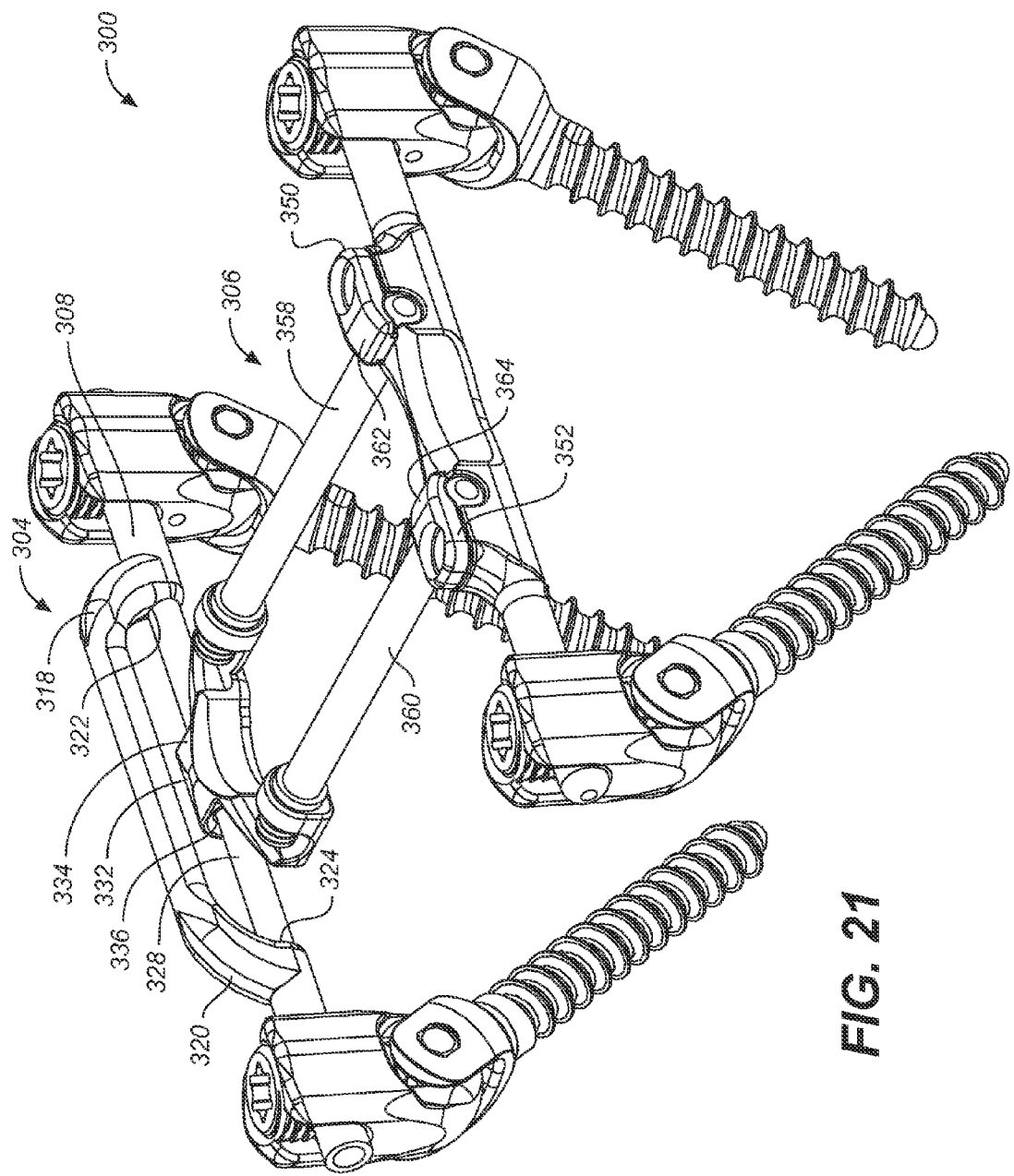
FIG. 21 is another perspective view of the embodiment of the dynamic spine stabilization of the invention of FIG. 19.

With respect to FIG. 19 through FIG. 25 another embodiment of the horizontal rod system 304 of the dynamic stabilization system 300 is depicted as used with an anchor system 102 of the embodiment depicted in FIG. 1. Also shown in FIGS. 19, 19A, is the vertical rod system 306. The horizontal rod system 304 includes first and second horizontal rods 308, 310. It is to be understood that FIG. 19A shows a second image of only the horizontal rod 308 in a first undeployed position and that FIG. 19 shows a deployed position with the horizontal rod 308 connected with vertical rods 306 and, thus, the entire system 300.

The horizontal rod 308 includes first and second aligned end rods 312, 314 which are connected together with an offset rod 316 located between the first and second end rods 312, 314. In this embodiment, the horizontal rod 308 looks much like a yoke with the offset rod joining each of the end rods 312, 314 with a curved section 318, 320. At the junction of the first end rod 312 and the offset rod 316 is a first bore 322 which is aligned with the first end rod 312, and at the junction of the second end rod 314 and the offset rod 316 is a second bore 324 which is aligned with the second end rod 314 and, thus, aligned with the first end rod 312. Positioned in and extending from the first bore 322 is a first deflection rod or loading rod 326 and positioned in and extending from the second bore 324 is a second deflection rod or loading rod 328. As with the other deflection rods or loading rods, preferably deflection rods or loading rods 324, 328 are made of a super elastic material such as, for example, Nitinol (NiTi) and the rest of system 300 is comprised of titanium, stainless steel, a biocompatible polymer such as PEEK or other biocompatible material. In addition to Nitinol or nickel-titanium (NiTi), other super elastic materials include copper-zinc-aluminum and copper-aluminum-nickel. However, for biocompatibility the nickel-titanium is the desired material. The super elastic material has been selected for the deflection rods as the stress or force/deflection chart for a super elastic material has a plateau where the force is relatively constant as the deflection increases. Stated differently, a super elastic rod has a load (y) axis/deflection (x) axis curve which has a plateau at a certain level where the load plateaus or flattens out with increased deflection. In other words, the rod continues to deflect with the load staying constant at the plateau. In one embodiment, the load plateau is about 250 Newtons to about 300 Newtons. It is to be understood that the plateau can be customized to the needs of the patient by the selection of the type and composition of the super elastic material. For some patients, the plateau should be lower, and, for others, the plateau should be higher. Accordingly, and, for example, at the plateau, additional force is not put on the anchor system 102 and, thus, additional force is not put on the area of implantation of the bone screw 108 and the surrounding bone of the spine where the bone screw 108 is implanted. The deflection rods or loading rods 326, 328 are force fit, screwed, welded, or glued into the bores 322, 324 as desired.

The first and second deflection rods or loading rods 326, 328 extend from the respective bores 322, 324 toward each other and are joined by a Y-shaped connector 330. The Y-shaped connector 330 includes a base 332 which has opposed and aligned bores 334, 336 that can receive the deflection rods or loading rods 326, 328 in a manner that preferably allows the Y-shaped connector to pivot about the longitudinal axis defined by the aligned first and second deflection rods or loading rods 326, 328. The Y-shaped connector 330 includes first and second arms that preferably end in threaded bores 342, 344 that can receive the threaded ends of the vertical bar system 306 as described below. Just behind the threaded bores 342, 344 are recesses 346, 348 (FIG. 24) which are shaped to accept the offset rod 316 with the horizontal rod 308 in the undeployed configuration depicted in FIG. 19A. In the undeployed configuration, the horizontal rod 308 can be more easily implanted between the tissues and bones of the spine and, in particular, guided between the spinous processes. Once the first horizontal rod 308 is implanted, the Y-shaped connector 330 can be deployed by rotating it about 90 degrees or as required by the anatomy of the spine of the patient and connected with the vertical rod system 306.

The second horizontal rod 310 is similar to the second horizontal rod 116 of the embodiment of FIG. 1. This second horizontal rod 310 is preferably comprised of titanium or other biocompatible material and includes first and second mounts 350, 352 which can receive the ends of the vertical rod system 306. The mounts 350, 352 include respective recesses 354, 356 which can receive the vertical rods 358, 360 of the vertical rod system 306. The mounts 350, 352 also include tabs 362, 364 which can capture the vertical rods 358, 360 in the respective recesses 354, 356. The tabs 362, 364 can be secured to the mounts 350, 352 with screws or other appropriate fastening devices.

The first and second vertical rods 358, 360 are preferably comprised of titanium or other biocompatible material and include a threaded end and a non-threaded end. The threaded end can be formed on the end of the rod or threaded elements can be force fit or glued to the end of the vertical rods 358, 360. Once the first and second horizontal rods are deployed in the patient, the first and second vertical rods can be screwed into or otherwise captured by the Y-shaped connector 330 of the first horizontal bar 308 and the first and second vertical rods can be captured or otherwise secured to the second horizontal bar 310.

Figure 26:
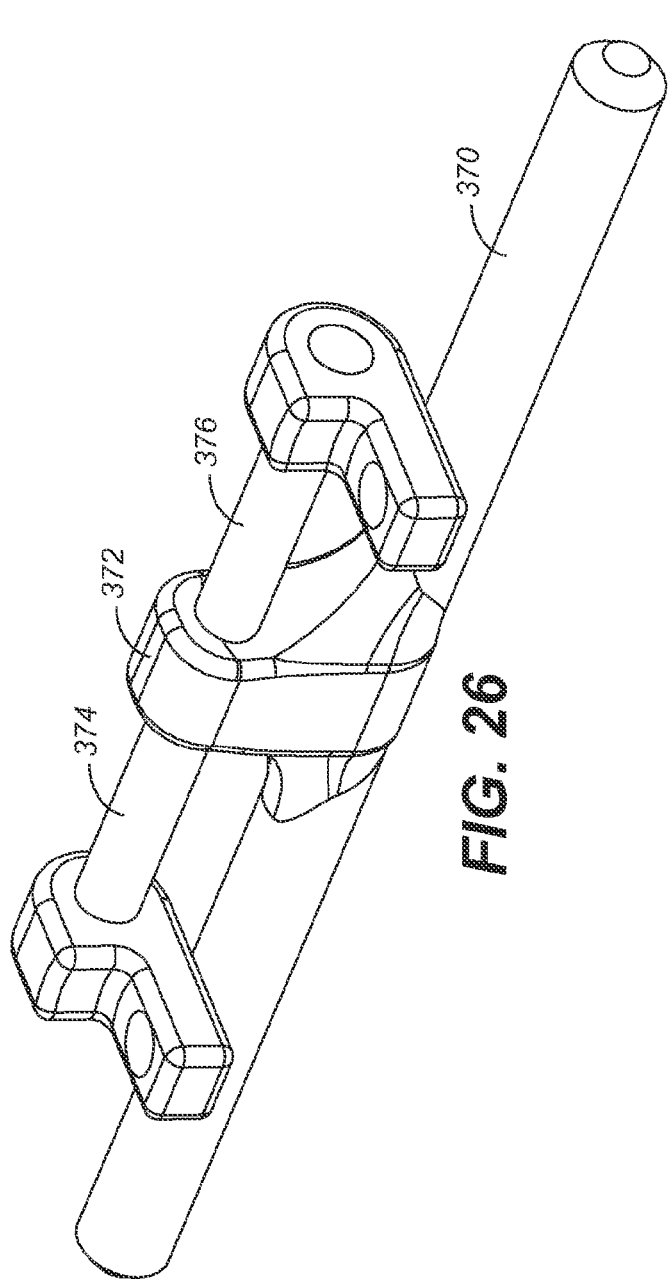
FIG. 26 is a perspective view of yet another embodiment of the horizontal rod system of the invention.
Figure 27:
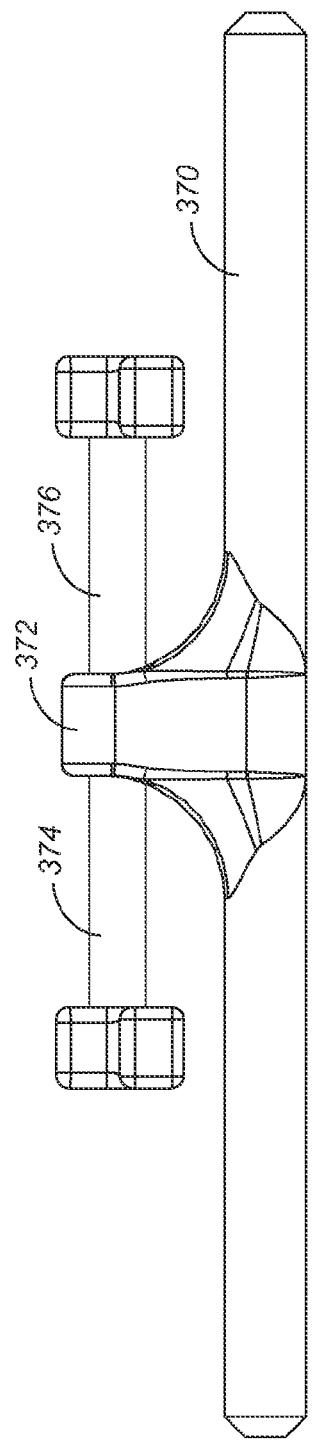
FIG. 27 is a side view of the embodiment of the horizontal rod system of the invention of FIG. 26.

FIGS. 26, 27, and FIGS. 28, 29 depict yet more alternative embodiments of the horizontal rod systems of the invention. The horizontal rod 370 in FIG. 26, 27 is similar to the horizontal rod 118 in FIG. 1. Horizontal rod 370 includes a mount 372 which has bores that can receive first and second deflection rods or loading rods 374, 376 which are preferably made of a super elastic material. At the ends of the first and second deflection rods or loading rods 374, 376 are connectors which include a tab having a threaded bore therethrough. The connectors can be used to connect vertical rods to the deflection rods or loading rods.

FIGS. 28, 29 depict a horizontal rod 380 with first mount 382 and second mount 384. Each of the mounts 382, 884, includes a bore that is substantially parallel to the horizontal rod 380. First and second deflection rods or loading rods 386, 388 extend respectively from the bores of the first and second mounts 382, 382. In the embodiment depicted the deflection rods or loading rods 386, 388 are parallel to the horizontal rod 380 and are directed toward each other. Alternatively, the deflection rods or loading rods 386, 388 can be directed away from each other. In that configuration, the mounts 382, 384 would be spaced apart and the deflection rods or loading rods would be shorter as the deflection rods or loading rods extended parallel to and toward the ends of the horizontal rod 380.

FIGS. 30, 31, 32 depict yet another embodiment of the horizontal rod system 390 of the invention which is similar to the horizontal bar system 104 as depicted in FIG. 1. Horizontal bar system 390 includes tapered deflection rods or loading rods 392, 394. The deflection rods or loading rods are tapered and reduce in diameter from the mount 396 toward the ends of the horizontal rod 390. As previously discussed the deflection rods or loading rods can taper continuously or in discrete steps and can also have an decreasing diameter from the ends of the deflection rods or loading rods towards the mount 396. In other words, a reverse taper than what is depicted in FIG. 30. Connected to the deflection rod or loading rods 392, 394 are the vertical rods 402, 404. The vertical rods 402, 404 are connected to the deflection rods or loading rods 392, 394 as explained above.

The conically shaped or tapered deflection rods or loading rods can be formed by drawing or grinding the material which is preferably a super elastic material. The tapered shape of the deflection rods or loading rods distributes the load or forces placed by the spine on the system evenly over the relatively short length of the deflection rods or loading rods as the rods extend from the central mount outwardly toward the ends of the horizontal rod. In this embodiment, in order to be operatively positioned relative to the spine and between the anchor systems, the deflection rods or loading rods are less than half the length of the horizontal rods.

FIG. 30 depicts the vertical rods 402, 404 in undeployed positions that are about parallel to the horizontal rod 390 and with the vertical rods 402, 404 directed away from each other and toward the respective ends of the horizontal rod 390. In this position the horizontal rod 390 can be more conveniently directed through the bone and tissue of the spine and, for example, directed between the spinous processes to the implant position. Once in position, the vertical rods 402, 404 can be deployed so that the vertical rods are parallel to each other and about parallel to the horizontal rod 390 as depicted in FIG. 31. Accordingly, this embodiment can be inserted from the side of the spine in the undeployed configuration depicted in FIG. 30 and then the vertical rods can be rotated or deployed by about 90 degrees (from FIG. 30 to FIG. 31) each into the coronal plane of the patient. The vertical rods are also free to rotate about 180 degrees about the deflection rods and in the sagittal plane of patient. This allows this embodiment to conform to the different sagittal contours that may be encountered relative to the spine of a patient. The deflection rods or loading rods are rigidly connected to the horizontal rod allowing for an easier surgical technique as sections of the spine and, in particular, the spinous processes and associated ligaments and tissues do not have to be removed in order to accommodate the implantation system 100. The moving action of the system, and, in particular, the flexing of the deflection rods and the motion of the vertical rods connected to the deflection rods or loading rods, takes place about the spinous processes and associated tissues and ligaments, and, thus, the spinous processes do not interfere with this motion. Further, having the horizontal rods more lateral than central also allows for a more simple surgical technique through, for example, a Wiltse approach.

To assist in implantation, a cone 406 can be slipped over the end of the horizontal rod 390 and the vertical rod 402 to assist in urging the tissues and bone associated with the spine out of the way. Once the horizontal rod is implanted the cone 406 can be removed. The cone 406 includes an end 408 which can be pointed or bulbous and the cone 406 has an increasing diameter in the direction to the sleeve 410 portion of the cone 406. The sleeve can be cylindrical and receive the end of the horizontal rod and the end of the deflection rod or loading rod 402.

FIG. 32 depicts how the connectors 412, 414 are secured to the respective deflection rods 392, 394. The deflection rods have flanges, such as spaced apart flange 416, 418 on the deflection rod 392. The connectors 412, 414 can snap over and be retained between respective pairs of flanges.

FIG. 33 depicts yet another embodiment of the horizontal rod system 430 of the invention. The horizontal rod system 430 includes horizontal rod 432 which is preferably comprised of a super elastic material such as Nitinol. The horizontal rod 432 includes a generally central platform 434, and on each side of the central platform 434 are first and second upwardly facing scallops or recesses 436, 438. On each side of the upwardly facing scallop or recess 436 are downwardly facing scallops or recesses 440, 442. On each side of the upwardly facing scallop or recess 438 are downwardly facing scallops or recesses 444, 446. The platform 434 accepts a connector for connecting the horizontal rod to vertical rods (FIG. 40) as will be explained below, and the scallops 436, 440, 442 on one side of the platform 434 act as a spring and the scallop 438, 444, 446 on the other side of the platform 434 acts as a spring. These springs assist the platform in carrying the load that the spine can place on the horizontal rod and isolate the anchor systems 102 from that load. That isolation has the advantage of preventing loosening of the anchor system as implanted in the patient. It is to be understood that by varying the pattern of the scallops, that the stiffness or rigidity of the horizontal bar can be varied and customized for each patient. Fewer scallops will generally result in a more stiff horizontal bar and more scallops will generally result in a less rigid horizontal bar. Additionally, the stiffness can be different depending on the direction of the force that is placed on the horizontal bar depending on the orientation and location of the scallops. For the embodiment depicted in FIG. 33, with the scallops 436, 438 pointed upward to the head of a patient and the scallops 440, 442, 444, 446 pointed downward toward the feet of a patient, the horizontal bar is stiffer in extension and less stiff in flexion. It is noted that in this embodiment the rod is of a uniform diameter, although the diameter can be non-uniform as, for example, being larger where the platform 434 is and tapering to the ends of the horizontal rod 432, or having a large diameter at the ends of the horizontal rod 432, tapering to a smaller diameter at the platform 434. In this embodiment with a substantially uniform diameter, the scallops are formed within the uniform diameter. In other forms, the scallops are molded into the horizontal rod or machined out of the preformed horizontal rod. With this configuration, the horizontal rod is more easily inserted into the spine and between bones and tissues of the spine. Further, this horizontal rod can be more easily delivered to the spine through a cannula due to the substantially uniform diameter. For purposes of forming the scallops a machining technique known as wire electric discharge machining or wire EDM can be used. Thus, an approach for shaping the super elastic material is through wire EDM followed by electro-polishing. Additionally, the super elastic material in this and the other embodiments can be cold rolled, drawn or worked in order to increase the super elastic property of the material.

In this embodiment, the deflection takes place almost exclusively in the middle portion of the horizontal rod and principally at the platform and spring thus relieving the load or force on the ends of the horizontal rod and on the anchor system/bone interface.

Accordingly, in this preferred embodiment, there are two superior scallops pointing upwardly having a relatively gentler radius compared to the tighter radii of the inferior scallops pointing downwardly. It is to be understood that in this preferred embodiment, the inferior scallops are not symmetrical the way the superior scallops are. The lateral most cuts in both of the most lateral inferior scallops are steep and not radiused. These cuts allow the rod to bend at these points enhancing the spring effect. The ratio of the radii of the superior scallop to the inferior scallop in this preferred embodiment is two to one. The result is to create two curved and flat (in cross-section) sections, one on each side of the platform and these two flat sections in this preferred embodiment have about the same uniform thickness. Again, in this embodiment, the scallops and the platform is formed into an otherwise uniformly diametered cylindrical rod. Accordingly, none of these formed elements in this preferred embodiment extend beyond the diameter of the rod. In this preferred embodiment, the diameter of the horizontal rod is about 4 mm.

If desired, the rod could be bent in such a way that the platform and/or the scallops extend outside of the diameter of the cylindrical rod. However that configuration would not be as suitable for implantation through a cannula or percutaneously as would the horizontal rod as shown in FIG. 33 and described above.

Figure 47:
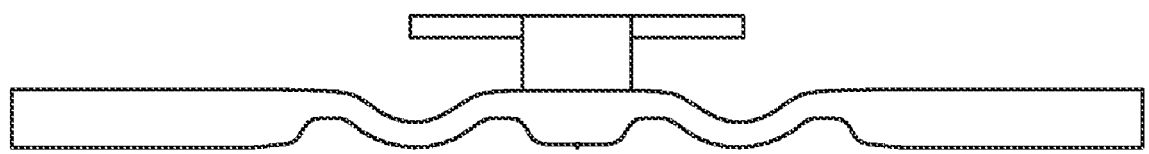
FIG. 47 is yet another embodiment of the horizontal rod system of the invention.

It is to be understood that to have enhanced flexibility, that the torsion rod and connector elements used in the horizontal rod embodiment of FIG. 1 can be used with the horizontal rod of FIG. 33. In this embodiment (FIG. 47), the connector is secured to the platform of the horizontal rod of FIG. 33 with the two deflection rods or loading rods extending toward the ends of the horizontal rod of FIG. 33 and about parallel to that horizontal rod.

Another embodiment of the horizontal rod 433 is depicted in FIG. 33A. In this embodiment the horizontal rod 433 is similar to the horizontal rod in FIG. 33 with the exception that the platform and scallops are replaced with a reduced diameter central portion 448. Each end of the central portion 448 gradually increases in diameter until the diameter is the full diameter of the ends of the horizontal rod 433. This embodiment can be formed of a super elastic material and ground to the reduced diameter shape from a rod stock of the super elastic material. The rod stock could also be drawn to this shape. Generally after such operations the horizontal rod would be electro polished. In this embodiment, a connector such as the connector shown in FIG. 40 could be used to connect vertical rods to preferably the middle of the central portion 448.

Figures 34A, 34B:
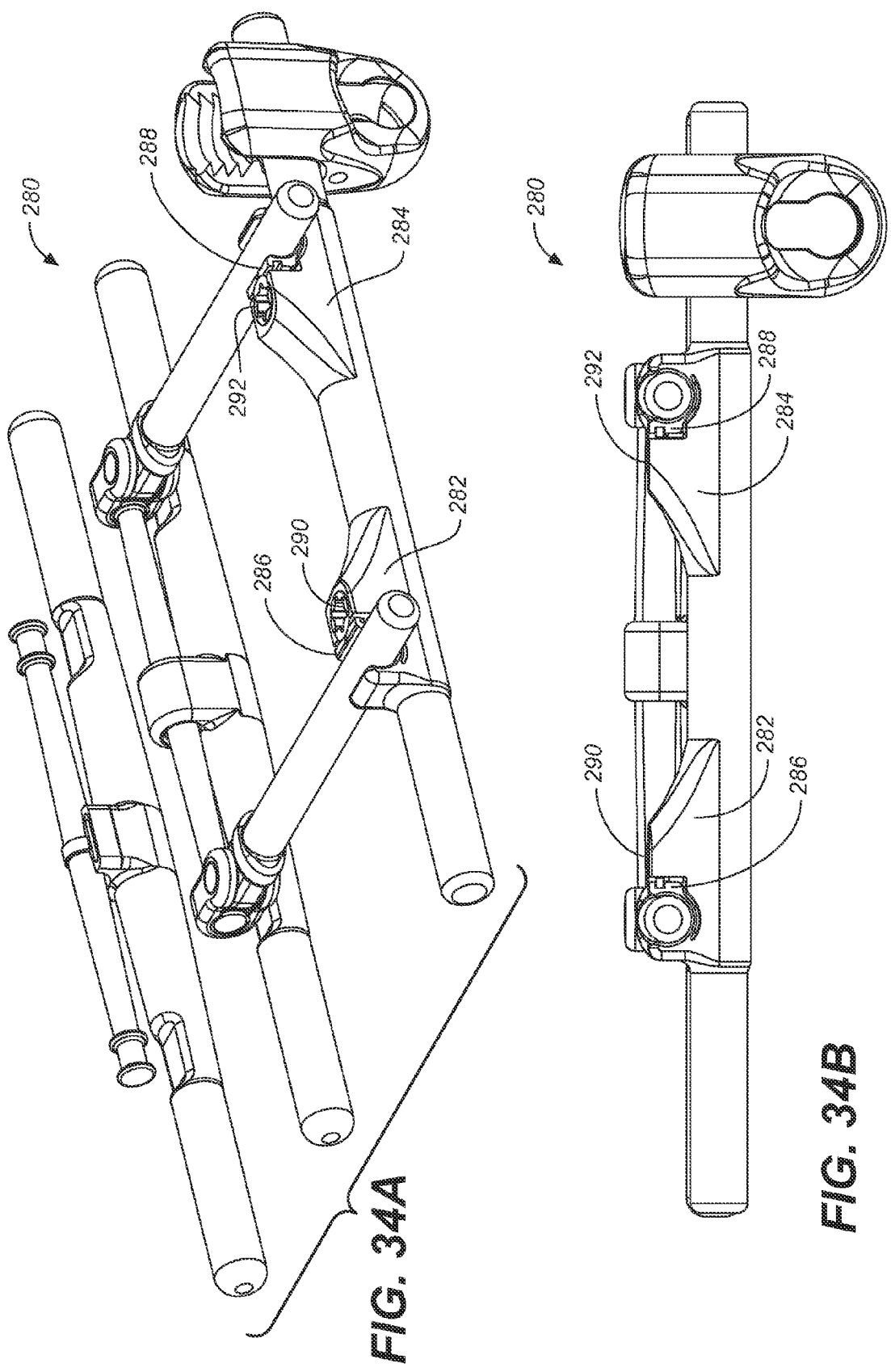
FIG. 34A is a perspective view of yet another embodiment of the horizontal rod system of the invention.
FIG. 34B is a side view of the embodiment of FIG. 34A.
Figure 34C:
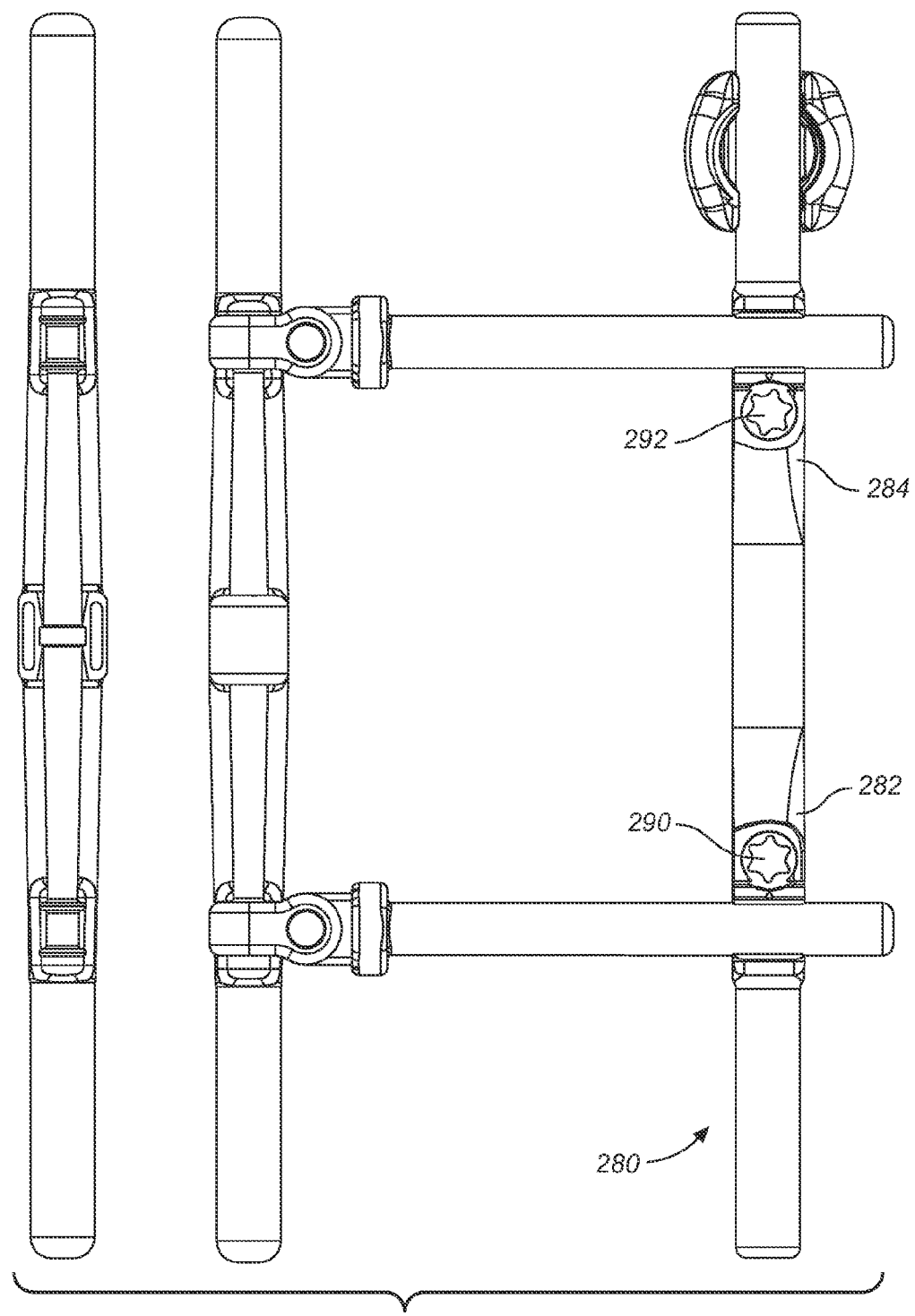
FIG. 34C is a top view of the embodiment of FIG. 34A.

FIGS. 34A, 34B, 34C depict yet an alternative embodiment of a horizontal rod 280 such as horizontal rod 116 as shown in FIG. 1 that is meant to rigidly hold the vertical rods secured thereto. The mounts 282, 284 formed in this horizontal rod 280 include a body that can be formed with the rod 280. The mounts are then provided with a movable capture arm 286, 288 that have recesses, which capture arms are formed out of the mount preferably using a wire EDM process that leaves the capture arm still connected to the horizontal rod with a living hinge. Eccentric headed set screws 290, 292 are mounted on the horizontal bar. With vertical rods captured in the recesses of the capture arms, the eccentric set screws can be turned to urge the capture arms against the living hinge, and thereby capturing the vertical rods in the recesses of the capture arms.

FIG. 40 depicts a dynamic stabilization system 450 that uses the horizontal rod system 454 of the invention. The system 450 additionally uses the anchor system 102 as depicted in FIG. 1 and the other horizontal rod 310 as depicted in FIGS. 19, 34. A connector 452 is secured to the platform 434 of the horizontal rod 454 and vertical rods are connected to the connector and to the other horizontal rod 310. In FIG. 40 for the horizontal rod 454, the scallops are formed by bending a bar and not by forming the scallops in a straight horizontal bar as depicted in the horizontal bar 432 of FIG. 33. The horizontal rod 430 of FIG. 33 could also be used in the embodiment of FIG. 40.

Figure 35:
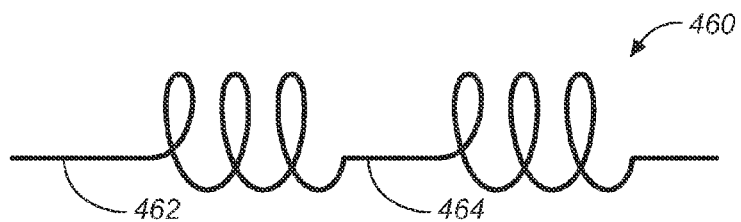
FIG. 35 is a side view of still another alternative embodiment of the horizontal rod system of the invention.

FIG. 35 depicts an alternative embodiment of a horizontal rod system 460 of the invention. Horizontal rod system 460 includes a horizontal rod 462 with a central platform 464 and first and second spring regions 466, 468 located on either side of the platform 464. Extending outwardly from each spring region are respective ends of the horizontal rod 462. The spring regions include coils that are wound about the longitudinal axis of the horizontal rod 462. If desired, the entire horizontal rod 462 can be comprised of a rod wound around a longitudinal axis with the platform 464 and the ends of the horizontal rod being more tightly wound and/or with a smaller diameter and the spring regions 466, 468 more loosely wound and/or with a larger diameter. Such a horizontal rod 462 can preferably be comprised of super elastic material such as Nitinol or alternatively titanium or other biocompatible material which demonstrates the ability to flex repeatedly.

Figure 36:
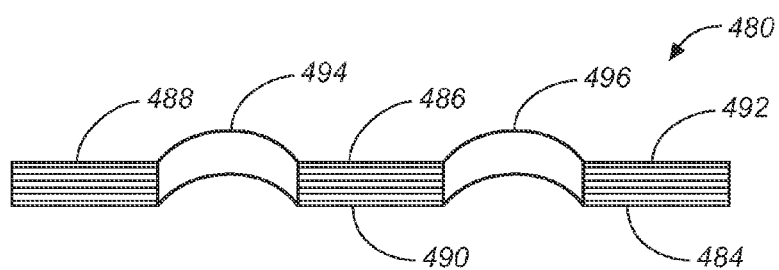
FIG. 36 is a side view of yet another alternative embodiment of the horizontal rod system of the invention.

FIG. 36 depicts yet another alternative embodiment of a horizontal rod system 480 which includes first and second horizontal rods 482, 484 which can be flat rods if desired. The horizontal rods 482, 484, include spring region 494, 496. In the spring region the horizontal rod is formed into an arc, much like a leaf spring. Located at the ends and at the central platform 486 and between the horizontal rods 482, 484 are spacers 488, 490, 492. The spacers are glued, bonded, welded or otherwise secured between the first and second horizontal rods 482, 484 in order to form the horizontal rod system 480. This system 480 can be comprised of super elastic materials or other materials that are biocompatible with the patient.

Figure 37:
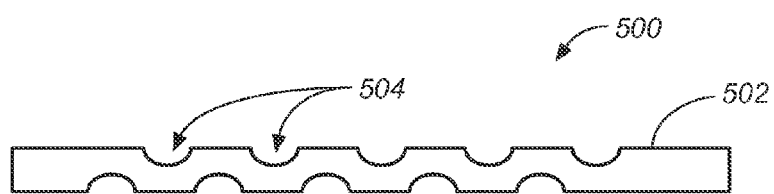
FIG. 37 is a side view of another alternative embodiment of the horizontal rod system of the invention.

FIG. 37 depicts another embodiment of the horizontal rod system 500 including a horizontal rod 502. In this embodiment, recesses 504 are formed in the horizontal rod in order to define the stiffness of the horizontal rod 502. This system can be formed of a super elastic material or other biocompatible material.

Figure 38:
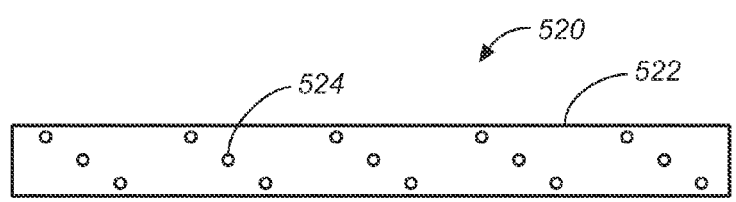
FIG. 38 is a side view of another alternative embodiment of the horizontal rod system of the invention.

FIG. 38 depicts still another embodiment of the horizontal rod system 520 of the invention with a horizontal rod 522. The horizontal rod 522 includes dimples 524 distributed around and along the horizontal rod 522. As this other embodiment, depending on the distribution of the dimples, the stiffness of the horizontal rod 522 can be determined. Further is more dimples are placed on the lower surface than on the upper surface, when placed in a patient, the horizontal rod 522 would tend to be stiffer in extension and less stiff in flexion. This horizontal rod 522 can also be made of a super elastic material or other biocompatible material.

Figure 39:
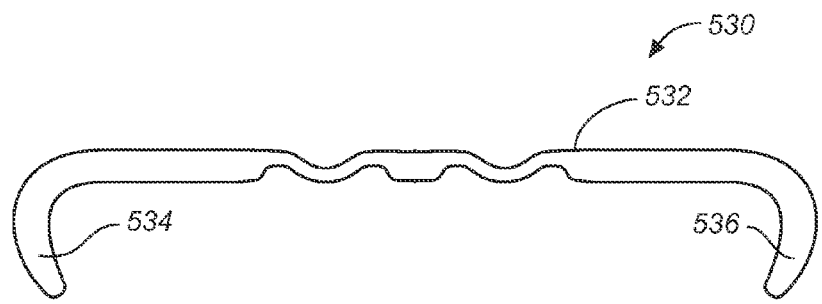
FIG. 39 is a side view of yet another alternative embodiment of the horizontal rod system of the invention.

FIG. 39 depicts another embodiment of the horizontal rod system 530 of the invention which has a horizontal rod 532 which is similar to the horizontal rod 432 of FIG. 33 and, thus, similar elements will number with similar numbers. In addition, the ends 534, 536 of the horizontal rod 532 are curved so as to create hooks that can fit around portions of the vertebra so as to secure the horizontal rod 532 to the vertebra. In this embodiment, preferably the rod is comprised of super elastic material or other biocompatible material. In order to implant the rod, the hooks at ends 534, 536 are sprung open and allowed to spring closed around the vertebra. An anchor system which includes a hook (as discussed above) could be used with this system.

Figure 39A:
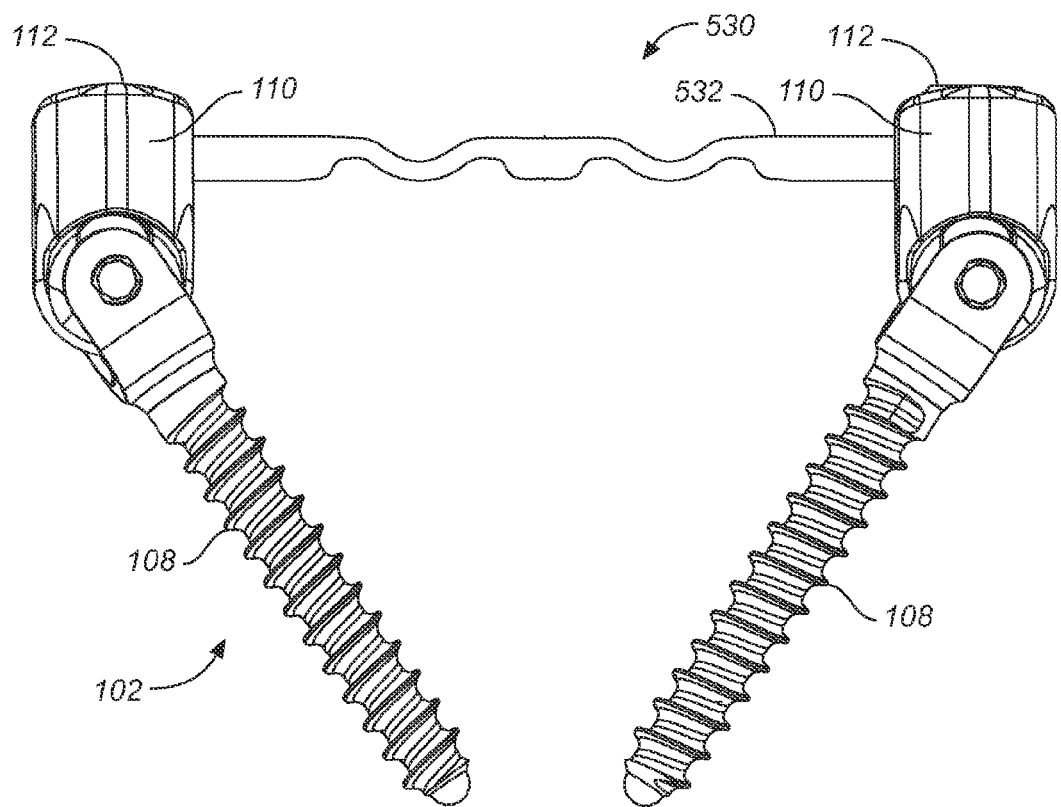
FIG. 39A is still another embodiment of the horizontal rod system and the anchor system of the invention.
Figure 39B:
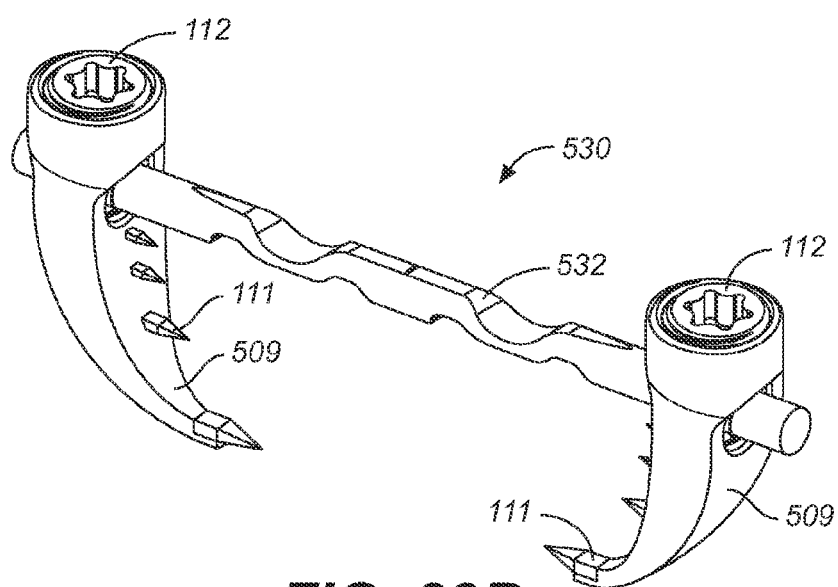
FIG. 39B is yet another embodiment of the horizontal rod system and the anchor system of the invention.

FIGS. 39A, 39B are similar to FIG. 39. In FIGS. 39A, 39B, a horizontal rod 532 is held in place relative to the spine by two anchor systems 102. The anchor systems are similar to the anchor systems depicted in FIG. 1. The anchor systems 102 include an anchor or bone screw 108 or bone hook 109 with spikes 111 (FIG. 39B), as well as the head 110 into which the horizontal rod is received. A set screw 112 secures the horizontal rod relative to the anchor systems.

Figure 41:
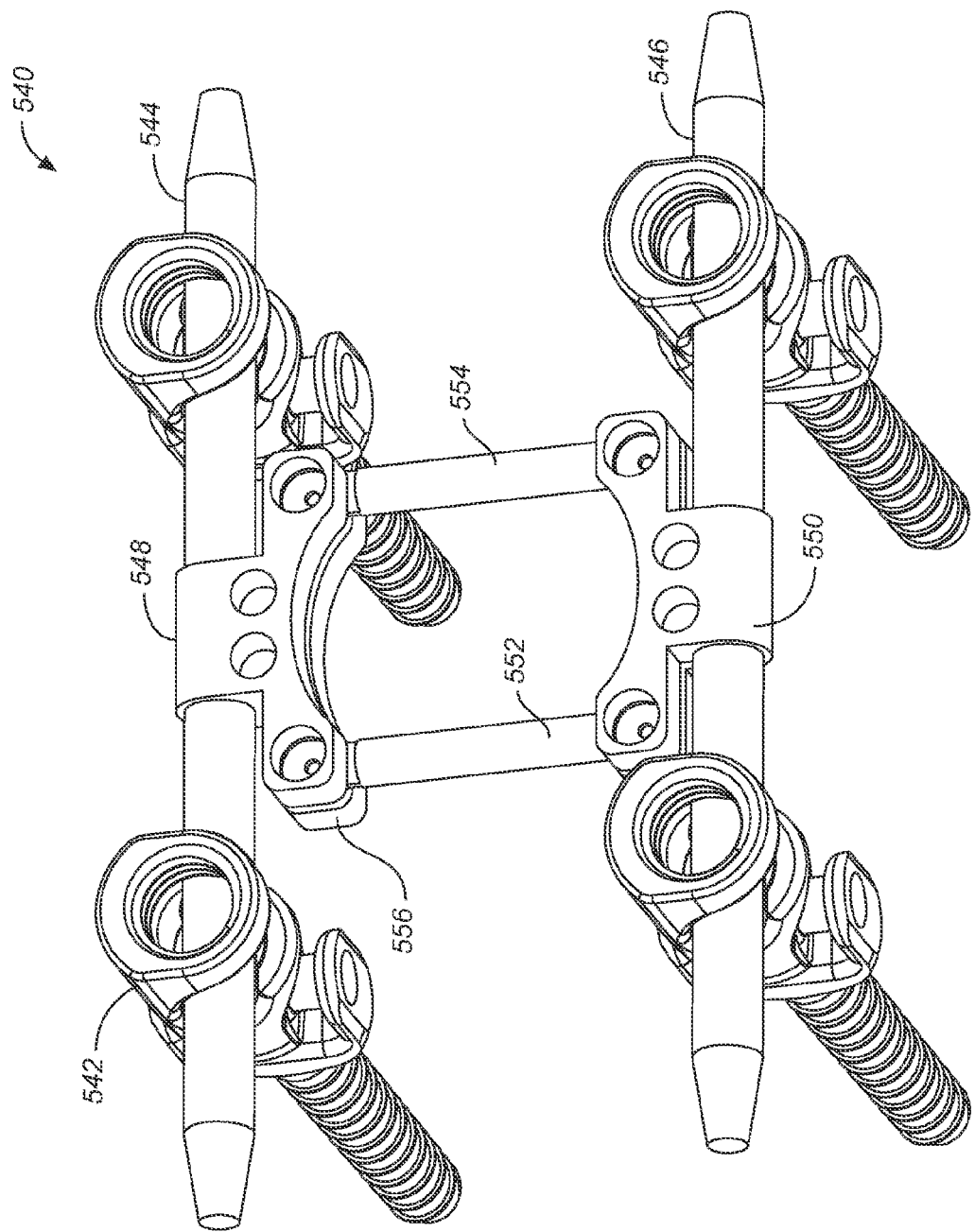
FIG. 41 is a perspective view of still another embodiment of a dynamic spine stabilization system of the invention.

FIG. 41 depicts another embodiment of the dynamic stabilization system 540 of the invention. This embodiment includes side loading anchor systems 542 as described above, although top loading anchor systems would also be appropriate for this embodiment. In this embodiment the horizontal rods 544, 546 are preferably comprised of a polymer such as PEEK and mounted on the horizontal rods 544, 546 are first and second connectors 548, 550. Vertical rods 552 and 554 are connected to the first and second connectors 548, 550 at points 556 with screws, rivets or other devices so that the connection is rigid or, alternatively, so that the vertical rods 552, 554 can pivot or rotate about the points. As the horizontal rods are comprised of PEEK, the system tends to be more rigid than if the rods were comprised of a super elastic material. Rigidity also depends on the diameter of the rod.

Embodiments of the Vertical Rod System of the Invention:

Embodiments of vertical rod systems of the invention such as vertical rod system 106 are presented throughout this description of the invention. Generally, the vertical rod systems are comprised of vertical rods that can be pivoted or inserted into position after the horizontal rods are deployed in the patient. The vertical rods are preferably connected to the horizontal rods and not to the anchor systems in order to reduce the forces and stress on the anchor systems. The vertical rods are connected to the horizontal rod systems, which horizontal rod systems include mechanisms as described herein that reduce the forces and stresses on the anchor systems. The vertical rods can generally be comprised of titanium, stainless steel, PEEK or other biocompatible material. Should more flexibility be desired, the vertical rods can be comprised of a super elastic material.

Figure 42:
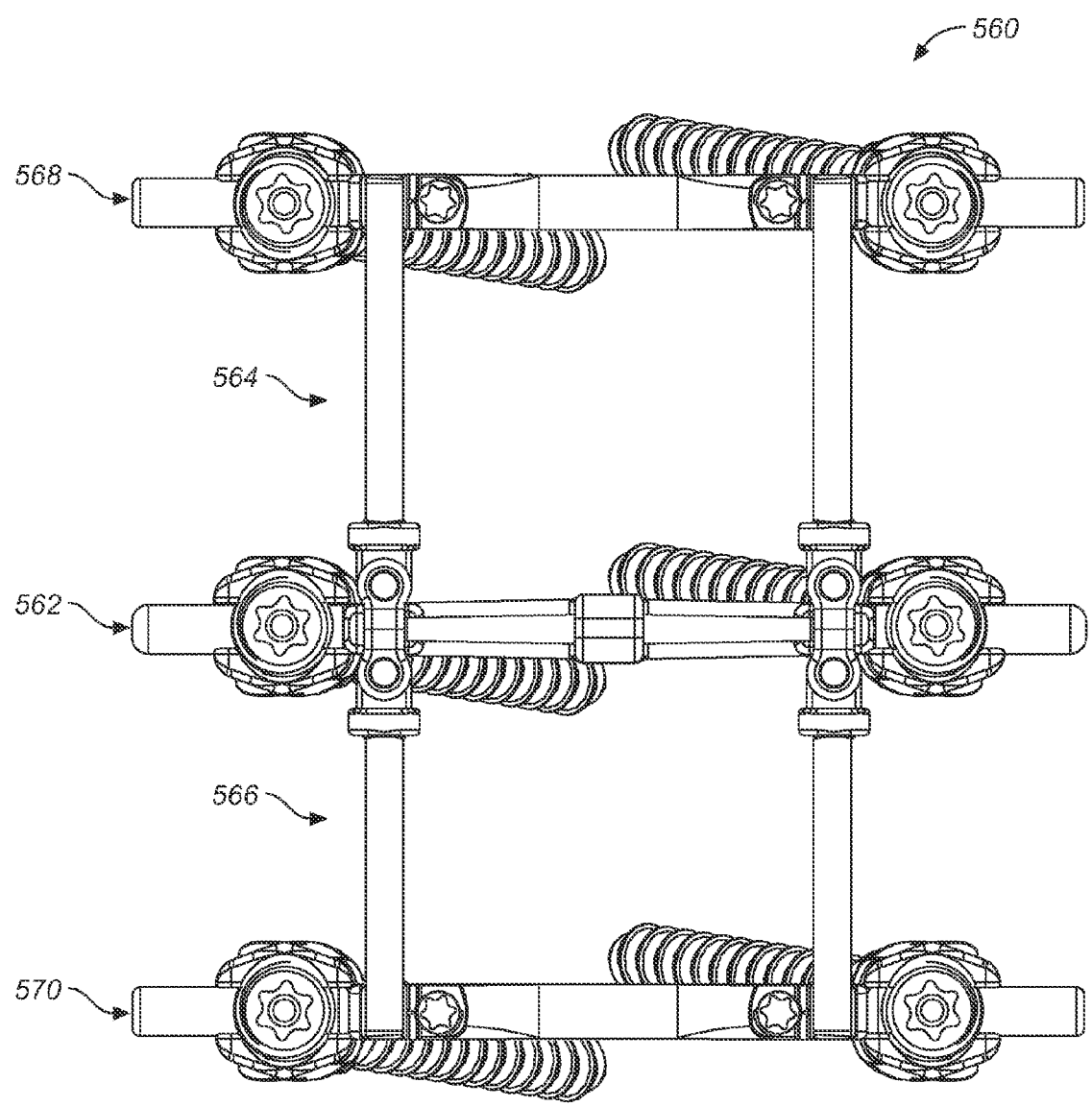
FIG. 42 is a side view of an embodiment of a two level dynamic spine stabilization system of the invention.

Embodiments of Alternative Multi-Level Dynamic Stabilization Systems for the Spine:

FIGS. 42 and 43 depict multi-level dynamic stabilization systems 560, 580. Each of these systems 560, 580 are two level systems. All of these systems use anchor systems as described herein. In system 560 of FIG. 42 the middle level horizontal rod 562 is secured to a vertebra and includes a horizontal rod system 104 having first and second deflection rods or loading rods such as that depicted in FIG. 4, whereby a first pair of vertical rods 564 can extend upwardly from horizontal rod system and a second pair of vertical rods 566 can extend downwardly from the horizontal rod system. The vertical rods that extend upwardly are connected to an upper horizontal rod 568 such as depicted in FIG. 34 and the vertical rods that extend downward are connected to a lower horizontal rod 568 such as depicted in FIG. 34. The upper horizontal rod 568 is secured with anchor systems to a vertebra located above the vertebra to which the middle level horizontal rod 562 is secured. The lower horizontal rod 570 is secured with anchor systems to a vertebra located below the vertebra to which the middle level horizontal rod 562 is secured. This embodiment offers more stability for the middle level vertebra relative to the upper and lower vertebra while allowing for extension, flexion, rotation and bending relative to the middle level vertebra.

FIG. 43 depicts another multi-level dynamic stabilization system 580. All of these systems use anchor systems as described herein. In system 580 of FIG. 43, the middle level horizontal rod 582 is secured to a vertebra and includes a horizontal rod such as that depicted in FIG. 34. The upper and lower horizontal rods 586, 590 can be similar to the horizontal rod 114 including the deflection rods or loading rods and deflection rod or loading rod mount depicted in FIG. 3. Vertical rods are pivotally and rotationally mounted to the upper and lower horizontal rods 586, 590 and, respectively, to the deflection or loading rods thereof and are also rigidly mounted to the middle level horizontal rod 582. The upper horizontal rod 586 is secured with anchor systems to a vertebra located above the vertebra to which the middle level horizontal rod 582 is secured. The lower horizontal rod 590 is secured with anchor systems to a vertebra located below the vertebra to which the middle level horizontal rod 582 is secured. This embodiment offers more dynamic stability for the upper and lower vertebra relative to the middle level vertebra while allowing for extension, flexion, rotation and bending relative to the middle level vertebra. Alternatively, the middle level horizontal rod 582 has four mounts instead of the two mounts depicted in FIG. 34 or FIG. 34A so that a first pair of vertical rods 588 can extend upwardly from a lower horizontal rod 590 and a second pair of vertical rods 566 extending downwardly from the upper horizontal rod 586, can be secured to the middle level horizontal rod 582.

Figure 44:
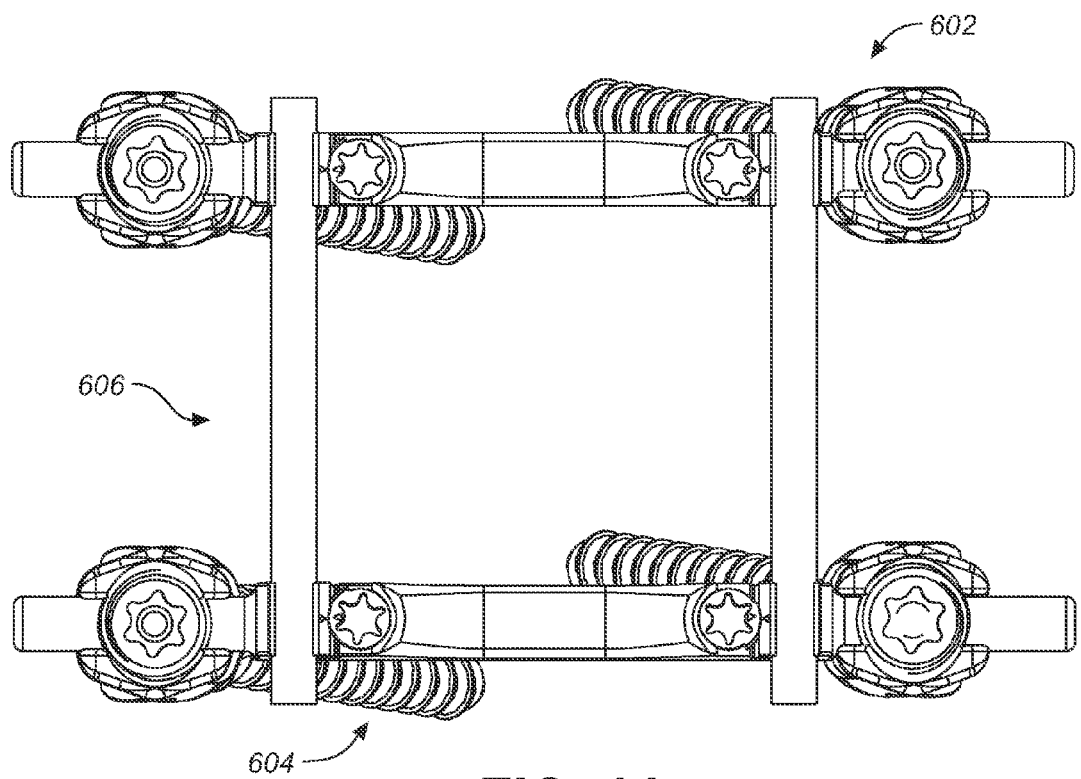
FIG. 44 is a side view of an embodiment of a fusion system of the invention.
Figure 45:
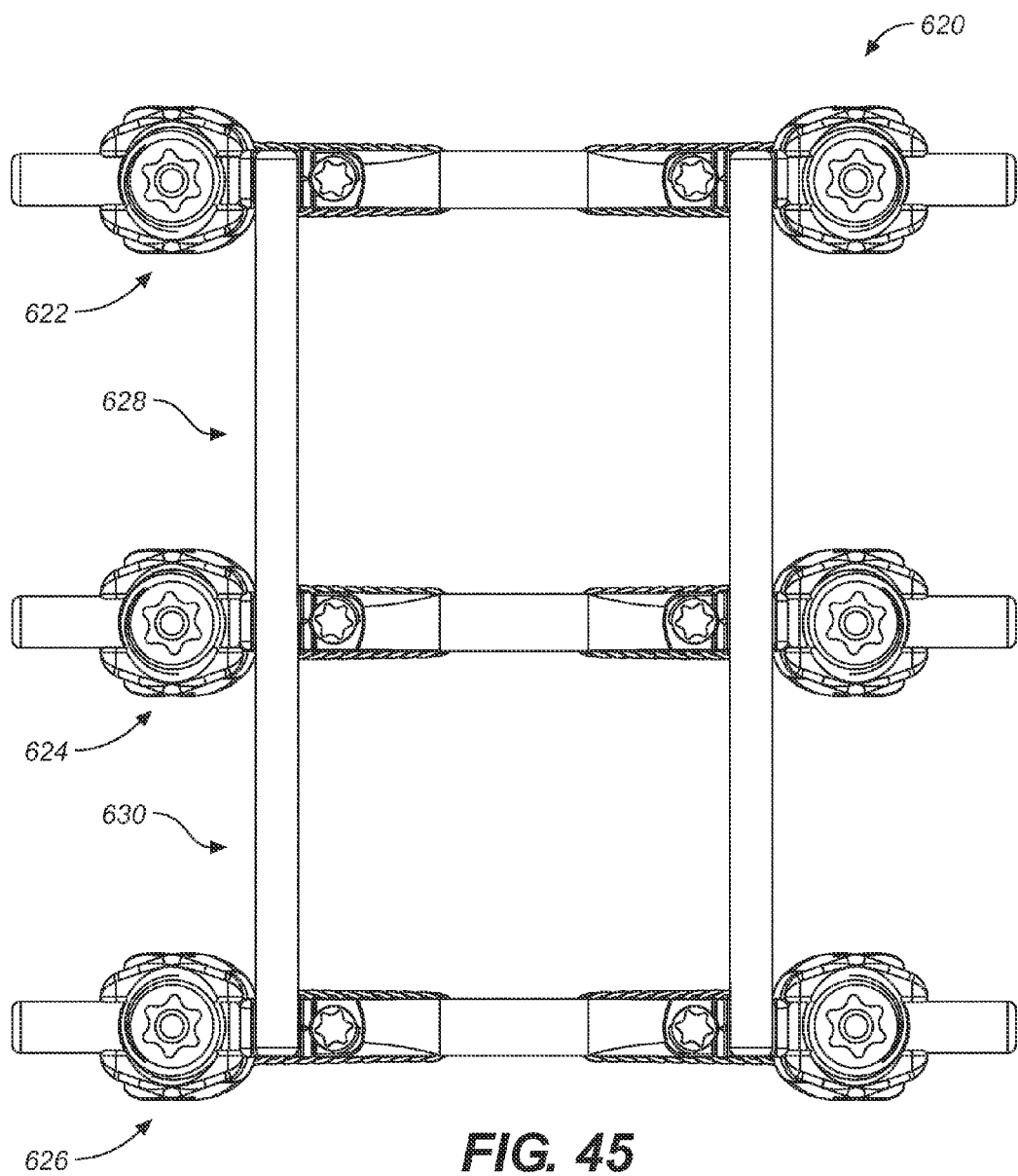
FIG. 45 is a side view of an embodiment of a two level fusion system of the invention.

Embodiments of Spine Fusion Systems of the Invention:

FIGS. 44, 45 depict one and two level systems that are more preferably used for fusion. The system 600 depicted in FIG. 44 resembles the system depicted in FIG. 41. When PEEK is used for the horizontal rods 602, 604, the system is substantially rigid and can be used in conjunction with spine fusion. For example, this system can be used with the placement of bone or a fusion cage between vertebra to which this system is attached. In fusion, bone can be placed between the vertebral bodies or, alternatively, fusion can be accomplished by placing bone in the valleys on each side of the spinous processes. The horizontal rods 602, 604 an also be comprised of titanium, or other biocompatible material and be used for spine fusion. For this embodiment, the vertical rods 606 can be rigidly attached to the horizontal rods through the use of a horizontal rod with mounts, as depicted in FIG. 34, so that the vertical rods 606 do not move or pivot with respect to the horizontal rods.

FIG. 45 depicts a two level system 620 that is more preferably used for a two level fusion. Each level can use an anchor system for example described with respect to anchor system 102 of FIG. 1. The horizontal rods 622, 624, 626 are can be similar to the horizontal rod in FIG. 34 with either two vertical rod mounts for the upper and lower horizontal rods 622, 626 or four vertical rod mounts for the middle level horizontal rod 624. For this embodiment, the vertical rods 628, 630 can be rigidly attached to the horizontal rods through the use of a horizontal rod with mounts as depicted in FIG. 34 so that the vertical rods 628, 630 do not move or pivot with respect to the horizontal rods. Vertical rods 628 extend between the upper and middle horizontal rods 622, 624, and vertical rods 630 extend between the middle and lower horizontal rods 624, 626. The system 620 depicted in FIG. 44 resembles the system depicted in FIG. 41, but with respect to three levels. When PEEK is used for the horizontal rods 622, 624, 626, the system is substantially rigid and can be used in conjunction with spine fusion. For example, this system can be used with the placement of bone or a fusion cage between vertebra to which this system is attached. Bone can also be placed along the valleys on either side of the spinous processes for this system. The horizontal rods 622, 624, 626 can also be comprised of titanium, PEEK or other biocompatible material and be used for spine fusion.

Figure 45A:
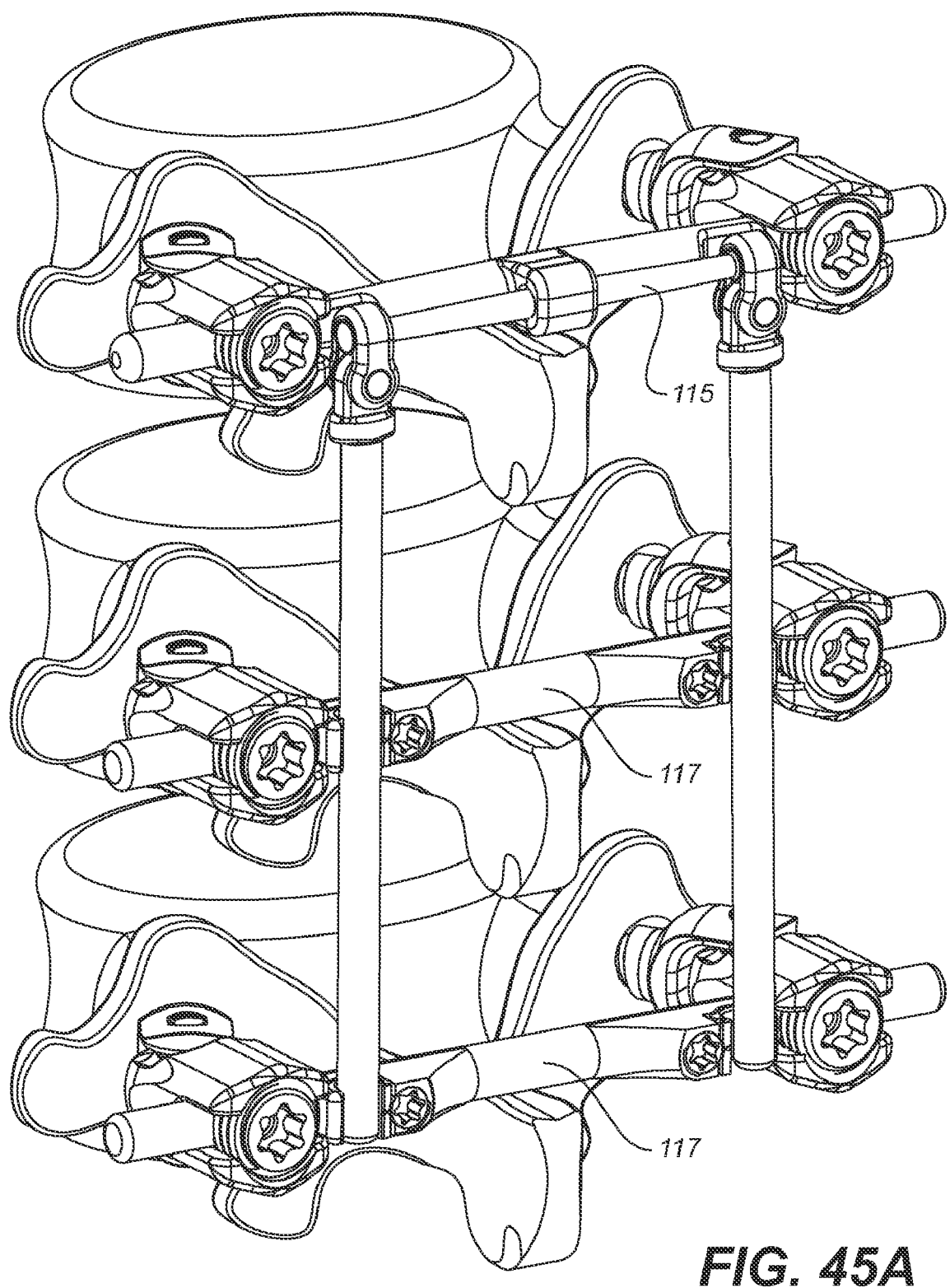
FIGS. 45A, 45B are perspective and side views of still another fusion system of an embodiment of the invention that has a transition level.
Figure 45B:
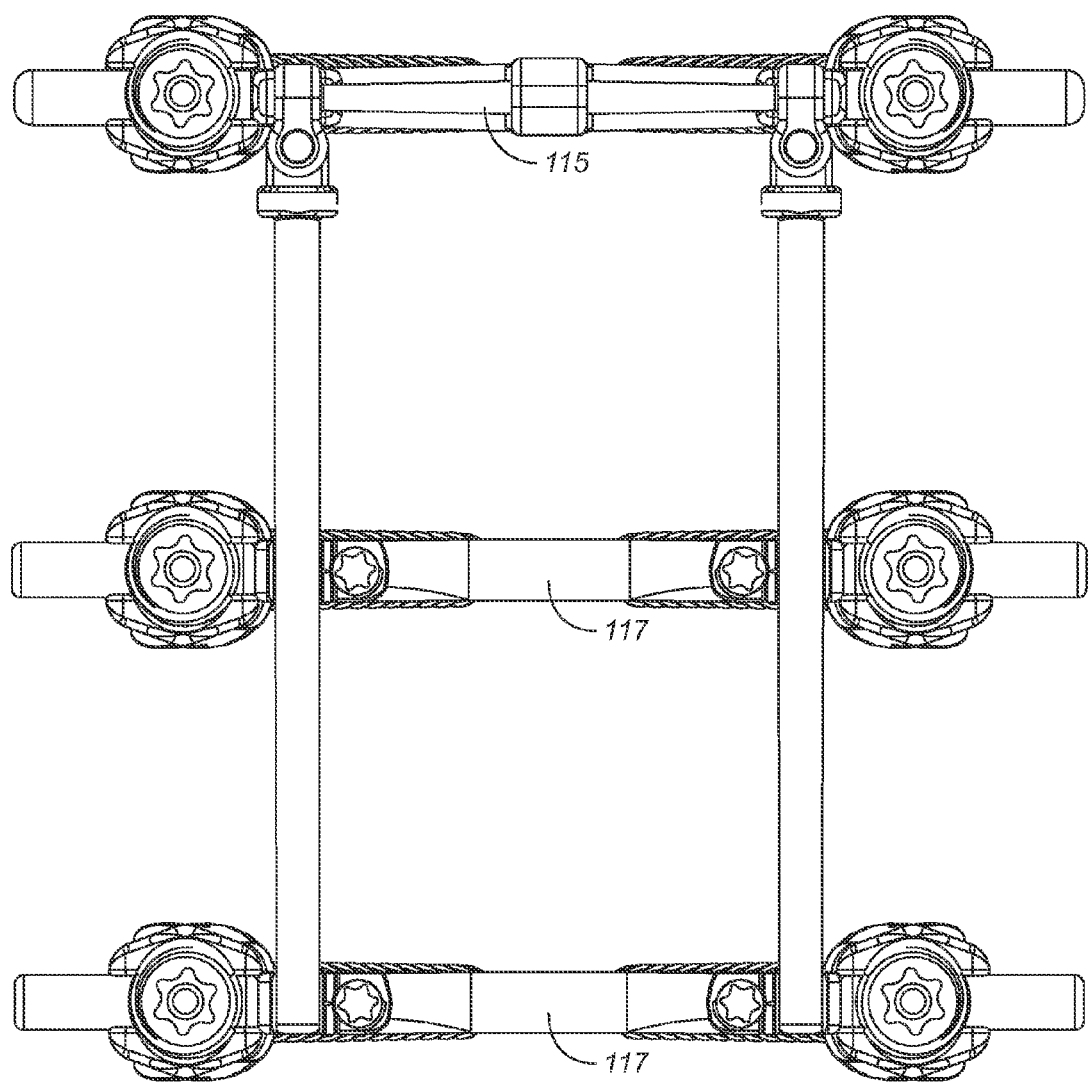

With respect to FIG. 45, to ease the transition to a one level fused area of the spine this two level system can be modified by replacing the horizontal rod 622 with a horizontal rod 115 (FIGS. 45A, 45B), which is much like horizontal rod 104 with deflection or loading rods 118, 120 of FIG. 1. This embodiment is depicted in FIG. 45A. Thus, fusion is accomplished between the two lower horizontal rods 117 which rods are like those depicted in FIG. 34, or like horizontal rods 116 in FIG. 1, and made of, preferably, titanium, and flexibility is provided by the upper horizontal rod 115 that is like horizontal rod 114 with deflection or loading rods that are shown in FIG. 1. Accordingly, there is more gradual transition from a healthier portion of the spine located above horizontal rod 115 through horizontal rod 115 to the fused part of the spine located between horizontal rod 624 and horizontal rod 606 of FIG. 45 or between the horizontal rods 117 (FIG. 45A).

Figure 48:
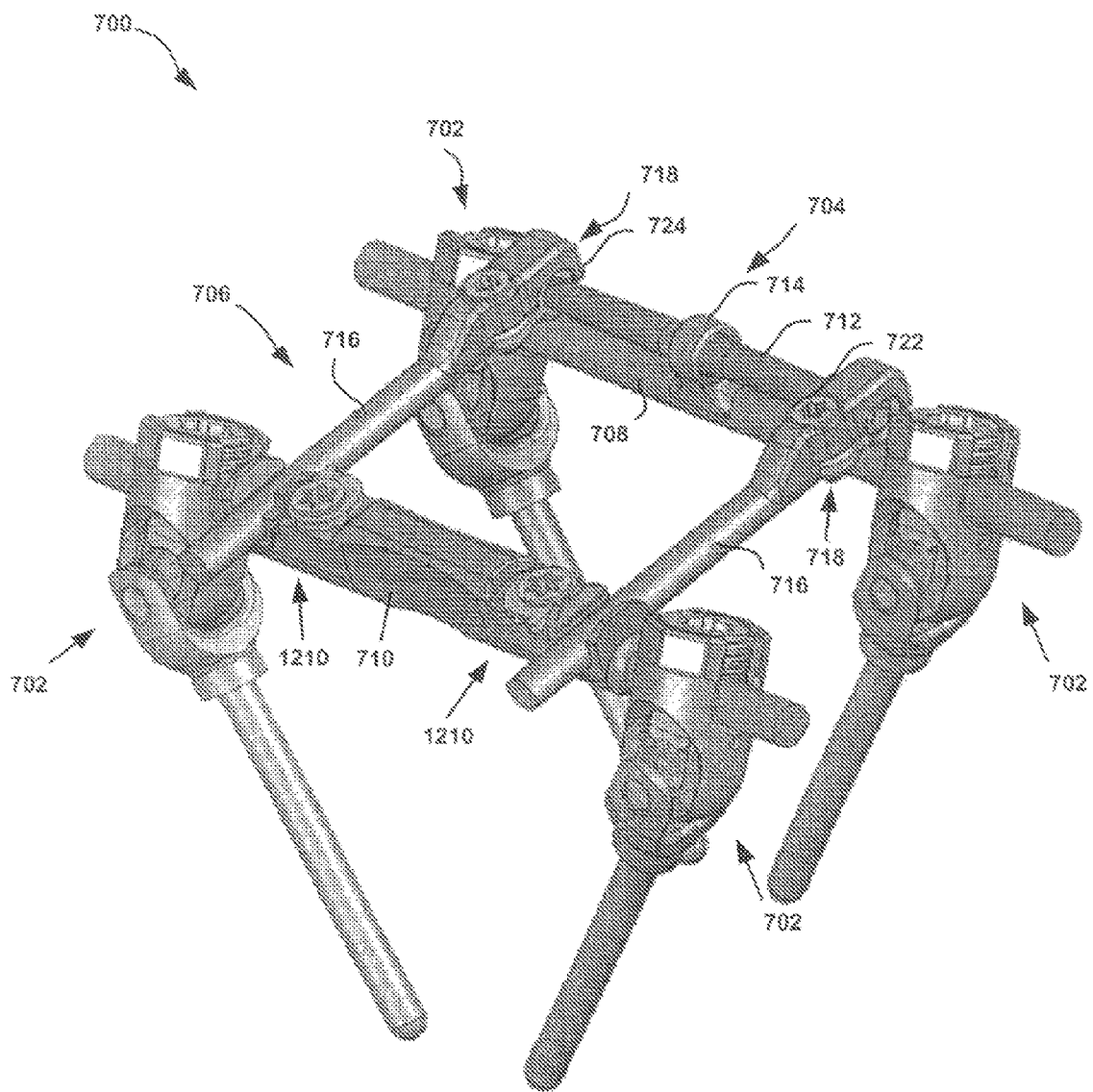
FIG. 48 is a perspective view of an embodiment of a dynamic spine stabilization system of the invention.
Figure 49:
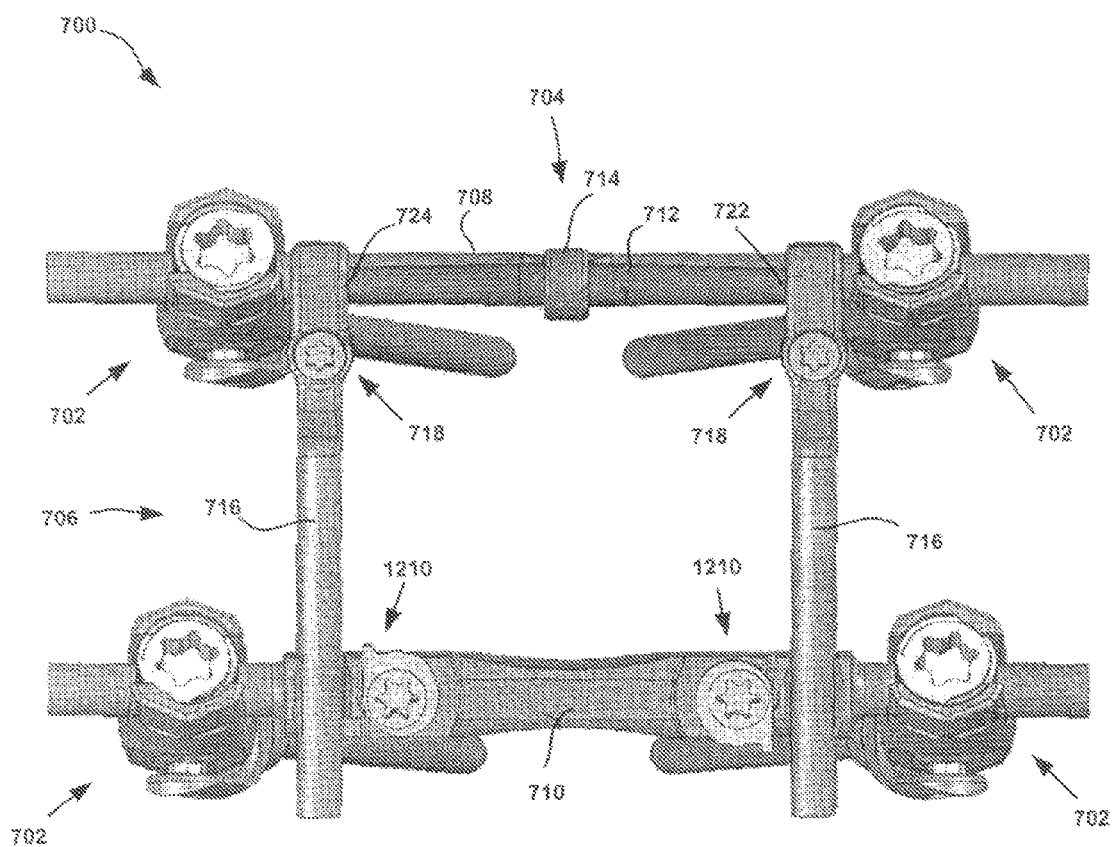
FIG. 49 is a posterior view of an embodiment of a dynamic spine stabilization system of the invention.
Figure 50A:
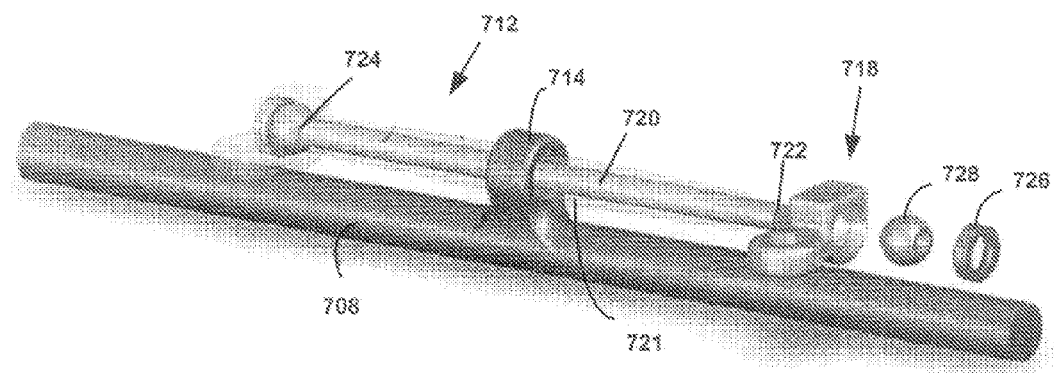
FIG. 50A is a perspective view of an embodiment of the horizontal rod system and a connector of the invention.
Figure 50B:
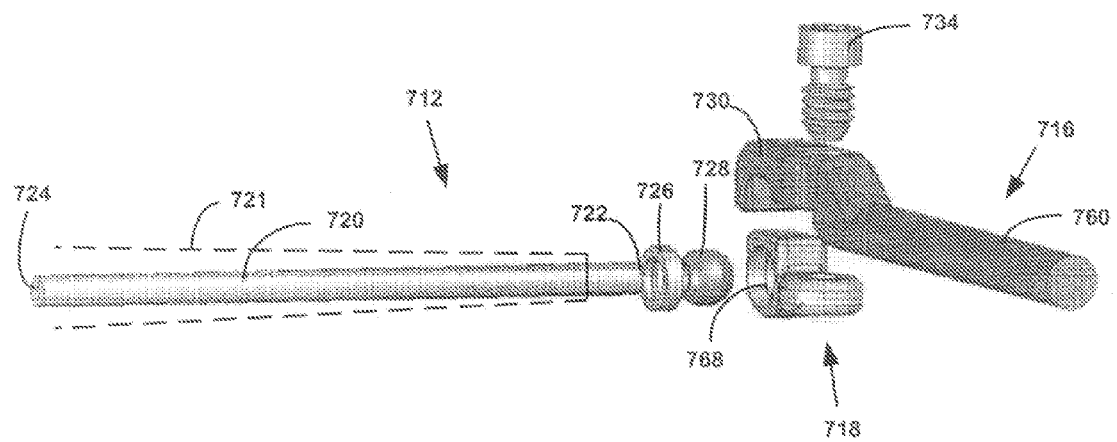
FIG. 50B is a perspective view of an embodiment of a horizontal rod system, a vertical rod system and a connector of the invention.

Further Embodiments of the Dynamic Stabilization System And Embodiments of the Connectors, the Horizontal Rod System, and the Vertical Rod System:

Various embodiments of the dynamic stabilization system have been shown and described above. FIGS. 48-85 provide further embodiments of the dynamic stabilization system. Referring now to FIGS. 48 and 49, perspective and posterior views of another embodiment of a dynamic stabilization system 700 can be seen. Generally, as with the embodiments described above, the dynamic stabilization system 700 includes an anchor system 702, a horizontal rod system 704 and a vertical rod system 706. For these embodiments horizontal refers to a horizontal orientation with respect to a human patient that is standing and vertical refers to a vertical orientation with respect to a patient that is standing. The horizontal rod system 704 can include a first horizontal rod 708, a second horizontal rod 710 and a deflection rod system 712. The vertical rod system 706 can include vertical rods 716 which are used with separate connectors 718 to attach the vertical rods 716 to the deflection rod system 712 attached to the first horizontal rod 708 and can use connector 1210 to attach vertical rods 716 to the second horizontal rod 710.

As shown in FIGS. 48-49, the deflection rod system 712 is attached, in this embodiment, to the center of the first horizontal rod 708 within a mount 714, while being connected to the vertical rods 716 at the ends 722, 724 of the deflection rod system 712. The deflection rod system 712 is positioned about parallel to the first horizontal rod 708, the first horizontal rod 708 being attached to the anchor systems 702 and, in particular, to the heads or saddles of the anchor system 702. Preferably, the horizontal rods 708, 710 are stiff and rigid (and made of titanium, for example), particularly in comparison to the deflection rod system 712 (which can be made of a super elastic material such as Nitinol (inner deflection rod 720 (FIG. 50A) and a polymer such as PEEK (outer shell 721), for example). In this configuration, the horizontal rod system 704 and, in particular, the deflection rod system 712 shares and distributes the load resulting from the motions of the body of the patient. Various embodiments of the vertical rods 716, the connectors 718, 1210, the deflection rod system 712, and the horizontal rods 708, 710 can be utilized as a part of the dynamic stabilization system 700 as will be described in greater detail below.

Figure 51:
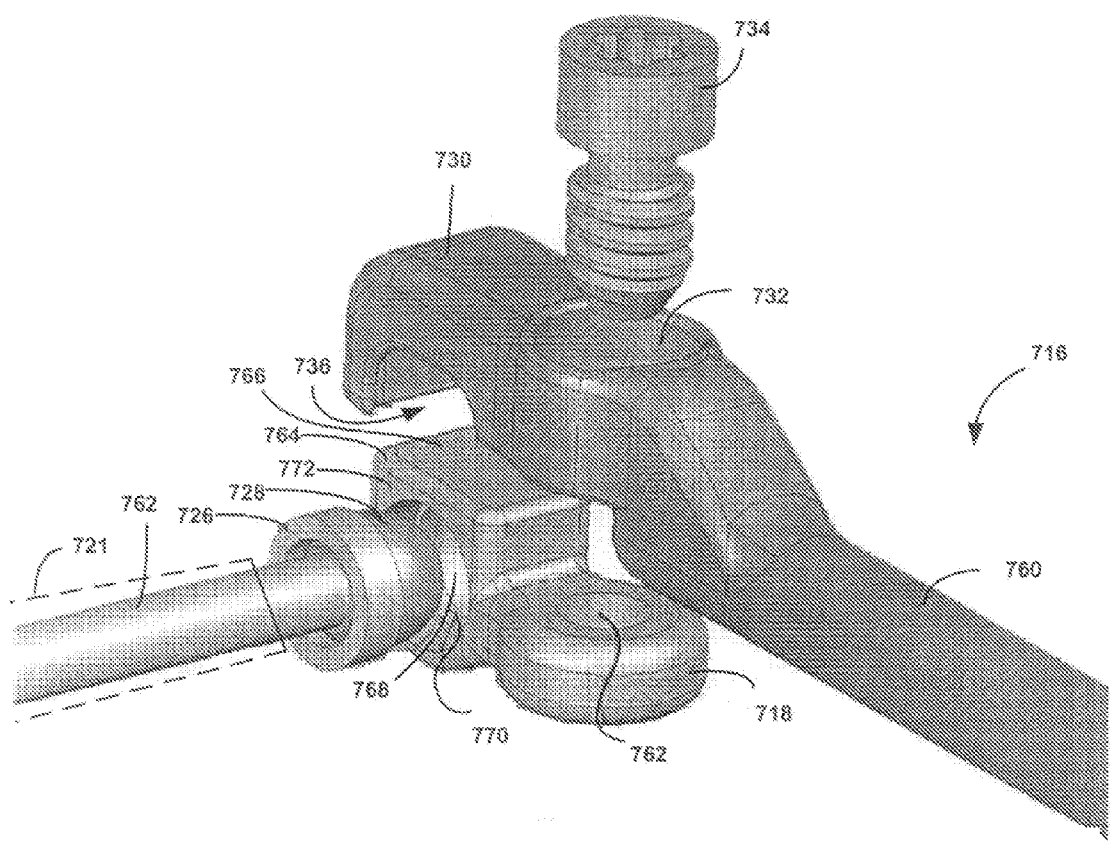
FIG. 51 is a perspective view of an embodiment of a horizontal rod system, a vertical rod system and a connector of the invention.
Figure 52:
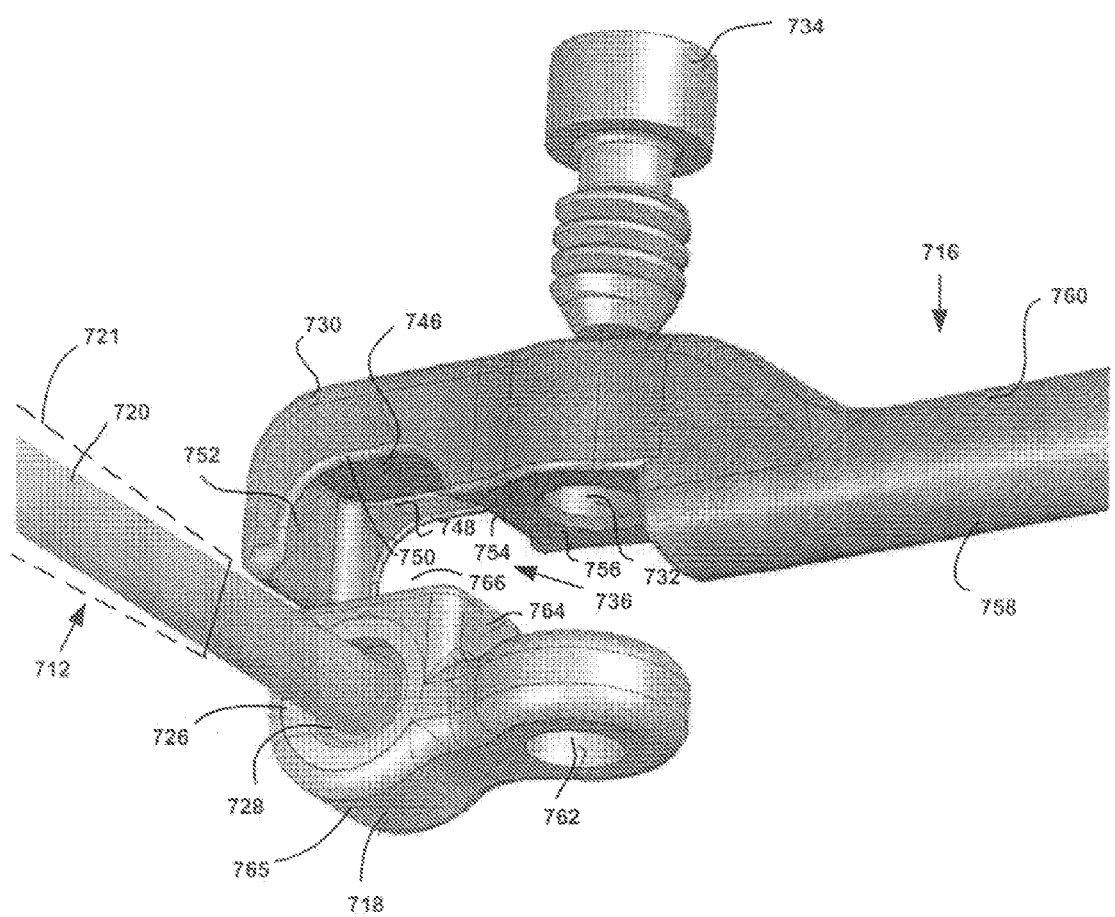
FIG. 52 is a perspective view of an embodiment of a horizontal rod system, a vertical rod system and a connector of the invention.

FIGS. 50A-55B illustrate an embodiment of a deflection rod system 712, a vertical rod 716 and a connector 718 used within the dynamic stabilization system 700. Referring now to FIGS. 50A-55B, the deflection rod system 712 includes an inner deflection rod 720 having a first end 722 and a second end 724, a retaining ring 726 and a spherical ball or joint 728. As will be further described with regard to FIGS. 68-71, the deflection rod system 712 includes an inner rod 720 preferably made of, for example, a super elastic material such as Nitinol, and an outer shell 721 made of a polymer such as PEEK. In this embodiment, the first end 722 of the inner deflection rod 720 of the deflection rod system 712 can be passed through the retaining ring 726 and attached to the spherical ball or joint 728 (as shown in FIG. 51) using threading, fusing, gluing, press fit and/or laser welding techniques, for example. In this embodiment, the spherical ball or joint 728 is only connected to the deflection rod 720 and not to the outer shell 721 of the deflection rod system 712. The spherical joint 728 can then be positioned within the socket chamber 768 of the connector 718. Once the spherical joint 728 is positioned within the connector 718, the retaining ring 726 can be threaded, fused, glued, press fit and/or laser welded, for example, to the connector 718, thereby securing the deflection rod 712 to the connector 718 (as shown in FIG. 52) in a ball joint type connection. In this configuration, the deflection rod system 712 is allowed to rotate and/or have tilting and/or swiveling movements about a center which corresponds with the center of the spherical ball or joint 728.

Figure 53:
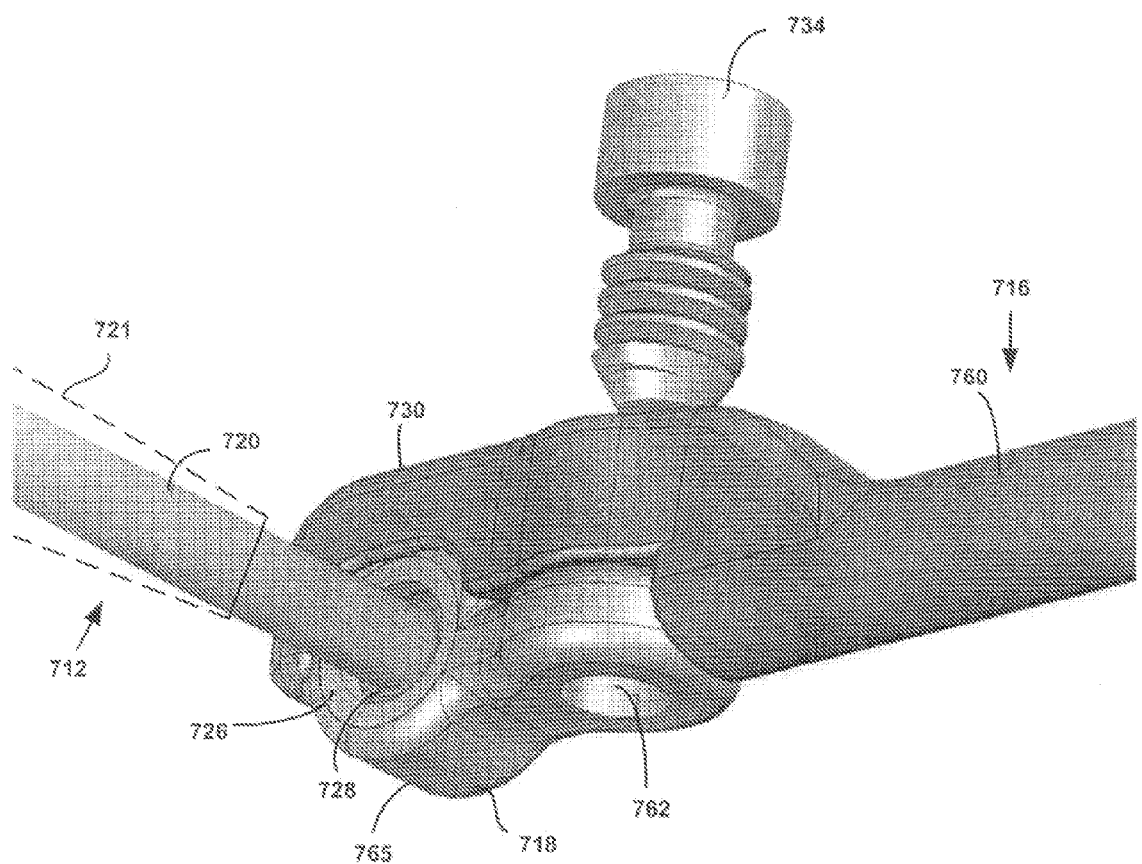
FIG. 53 is a perspective view of an embodiment of a horizontal rod system, a vertical rod system and a connector of the invention.
Figure 54:
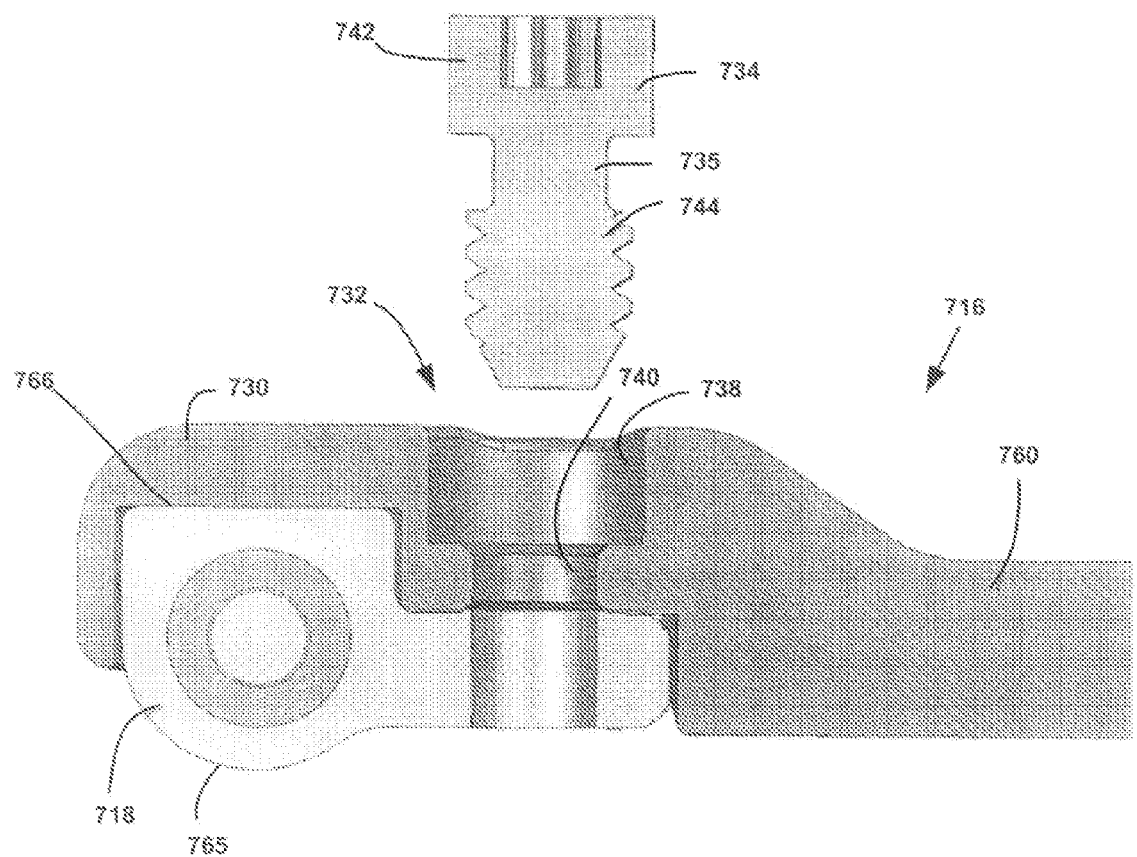
FIG. 54 is a sectional view of an embodiment of a horizontal rod system, a vertical rod system and a connector of the invention.

Referring to FIGS. 51 and 52, the vertical rod 716 used in this embodiment of the dynamic stabilization system 700 includes a head 730 having an aperture 732 that can accept a screw 734 and a rectangular shell or recess 736 for accepting the connector 718. Turning additionally to FIGS. 53 and 54, the aperture 732 of the vertical rod 716 includes a first bore 738 and a second bore 740. The first bore 738 of the aperture 732 can be configured to encase the head 742 of the connector screw 734 while the second section 740 can be configured to capture the neck 735 of the screw 734. Accordingly, the first section 738 of the aperture 732 has a larger diameter than the second bore 740 of the aperture 732, the overall shape of the aperture 732 conforming to the shape of the connector screw 734.

Referring back to FIG. 52, the rectangular shell or recess 736 of the vertical rod head 730 is configured to fixedly receive and encase the connector 718. Accordingly, the inner surface of the rectangular shell or recess 736 includes a top surface 746, inner side surfaces 748, 750, and inner front and back surfaces 752, 754. In this embodiment, the top 746, front 752 and back 754 inner surfaces are flat and rectangular in shape, while the inner sides surfaces 748, 750 are flat with a saddle-shaped cut-out which can allow for movement of the deflection rod system 712 and/or the vertical rod 716 relative to each other. Also in this embodiment, the bottom surface 756 of the head 730 is elevated from the bottom surface 758 of the vertical rod shaft 760 in order to provide a space for the connector 718 to be attached to the bottom of the head 730. The extent of elevation can vary depending on the size of the connector 718 attached thereto.

Referring back to FIG. 51, the connector 718 used in this embodiment of the dynamic stabilization system 700 includes a threaded aperture 762 for accepting the connector screw 734 and a housing 764 for accepting the deflection rod system 712. In its deployed position, the aperture 762 within the connector 718 is lined up with and placed adjacent to the aperture 732 located on the vertical rod 716, the connector screw 734 being inserted into both apertures 732, 762 to secure the connector 718 to the vertical rod 716.

FIGS. 51 and 52 further illustrates the housing 764 of the connector 718 as having a generally cylindrical exterior surface 765 with a flat top surface 766. The housing 764 also includes an opening 770 on the front face 772 of the connector 718 leading to a socket or spherical chamber 768 formed within the housing 764. The socket or spherical chamber 768 can be configured to engage the spherical ball or joint 728 of the deflection rod system 712. In this configuration, the spherical ball or joint 728 of the deflection rod system 712 is allowed to be pivotally engaged to the connector 718 within the socket or spherical chamber 768 while the deflection rod 720 is allowed to extend away from the connector 718 through the opening 770 of the front face 772 of the housing 764. The retaining ring 726 holds the ball 728 in place in the connector 718.

Referring back to FIG. 52, as the aperture 732 in the vertical rod 716 is aligned with the aperture 762 in the connector 718, the vertical rod recess or shell 736 can also be aligned with the housing 764 of the connector 718. The connector housing 764 can be inserted into the vertical rod recess or shell 736 until the connector housing 764 engages the top 750 and sides 748, 750, 752, 754 along the inner surface of the vertical rod shell 736. In this configuration, movement of the connector 718 within the head 730 of the vertical rod 716 is minimized and/or eliminated. This configuration also allows the vertical rod shell 736 to absorb any pressure resulting from movements of the deflection rod system 712 and vertical rod 716 during use, thereby limiting the pressure placed on the screw 734 during use.

Figure 55A:
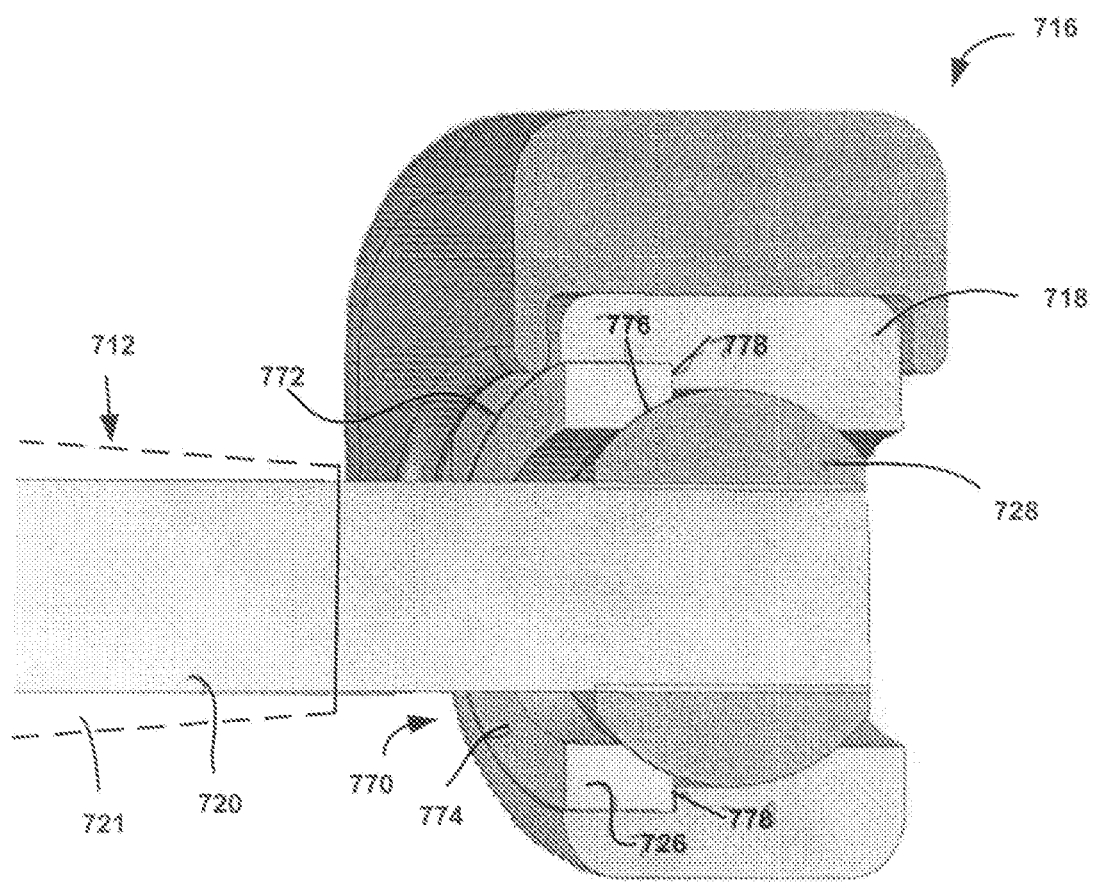
FIG. 55A is a sectional view of an embodiment of a horizontal rod system, a vertical rod system and a connector of the invention.

FIG. 55A further illustrates the connection between the deflection rod system 712, the connector 718 and the vertical rod 716 in this embodiment. As can be seen in FIG. 55A, the retainer ring 726 has an outer diameter which is slightly smaller than the diameter of the opening 770 on the front face 772 of the connector 718. The retainer ring 726 has a flat front surface 774, while the inner surface of the retaining ring 726 includes a curved section 776, the radius of curvature for the curved section 776 being the same as the radius of curvature of the spherical ball or joint 728. Accordingly, the retaining ring 726 can be inserted into the opening 770 through the front face 772 of the connector 718 until it is in sliding engagement with the spherical joint ball or 728. The connector 718 can also include a ridge 778 on its inner surface which limits the depth of insertion of the retainer ring 726 into the connector 718. The retainer ring 726 can then be screwed, fused, glued, force fit, and/or laser welded to the connector 718.

Figure 55B:
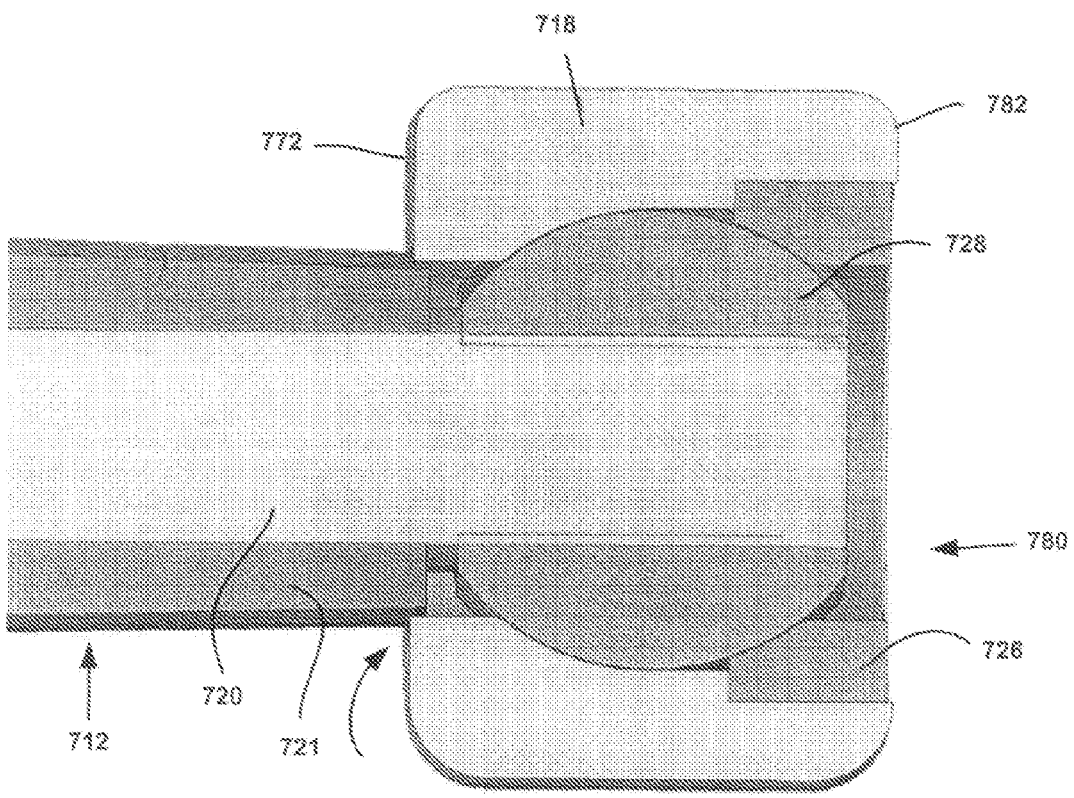
FIG. 55B is a sectional view of an embodiment of a horizontal rod system, a vertical rod system and a connector of the invention.

FIG. 55B illustrates an alternative fastening technique. In this embodiment, the spherical ball or joint 728 is inserted into the connector 718 through an opening 780 on the back face 780 of the connector 718 while the deflection rod 720 is inserted into the connector 718 through an opening 770 on the front face 772 of the connector 718. Once the parts have been inserted, the spherical joint 728 and the deflection rod 720 are connected within the connector 718. Alternatively, the spherical ball or joint 728 and the deflection rod 720 can be preassembled by, for example, screwing, gluing, force fitting and/or laser welding before the spherical joint 728 is placed in the connector 718. A retainer ring 726 can then be used to prevent the spherical joint 728 from exiting the connector 718 through the opening 780 on the back face 782 of the connector 718. The retainer ring 726 may be screwed, fused, glued, force fit and/or laser welded to the connector 718. Other fastening techniques are also within the scope and spirit of the invention.

Once the deflection rod system 712 is secured to the connector 718, the connector 718 can then be secured to the vertical rod 716 as shown in FIG. 53. In this configuration, the connector 718 is mated with the head 730 of the vertical rod 716. When mating the connector 718 to the head 730 of the vertical rod 716, the aperture 732 in the vertical rod 716 is aligned with the aperture 762 of the connector 718. The connector screw 734 then can secure the vertical rod 716 to the connector 718.

FIGS. 56A-59 illustrate another embodiment of a deflection rod system 800, a vertical rod 802 and a connector 804 that can be used within the dynamic stabilization system 700. In this embodiment, a cylindrically-shaped connector 804 including a U-shaped slot 810 is used to attach the vertical rod 802 to the deflection rod system 800 as will be described in greater detail below.

Figure 56A:
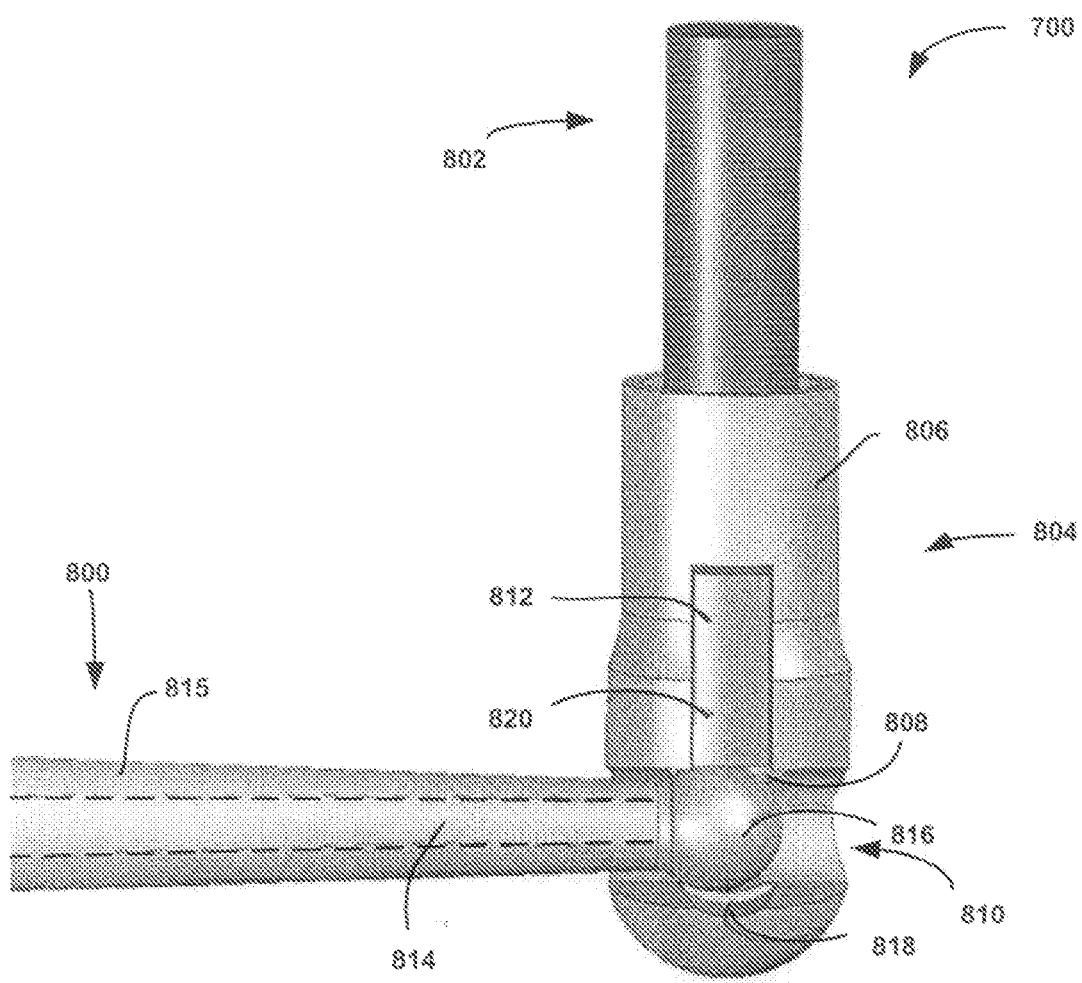
FIG. 56A is a front view of an embodiment of a horizontal rod system, a vertical rod system and a connector of the invention.
Figure 56B:
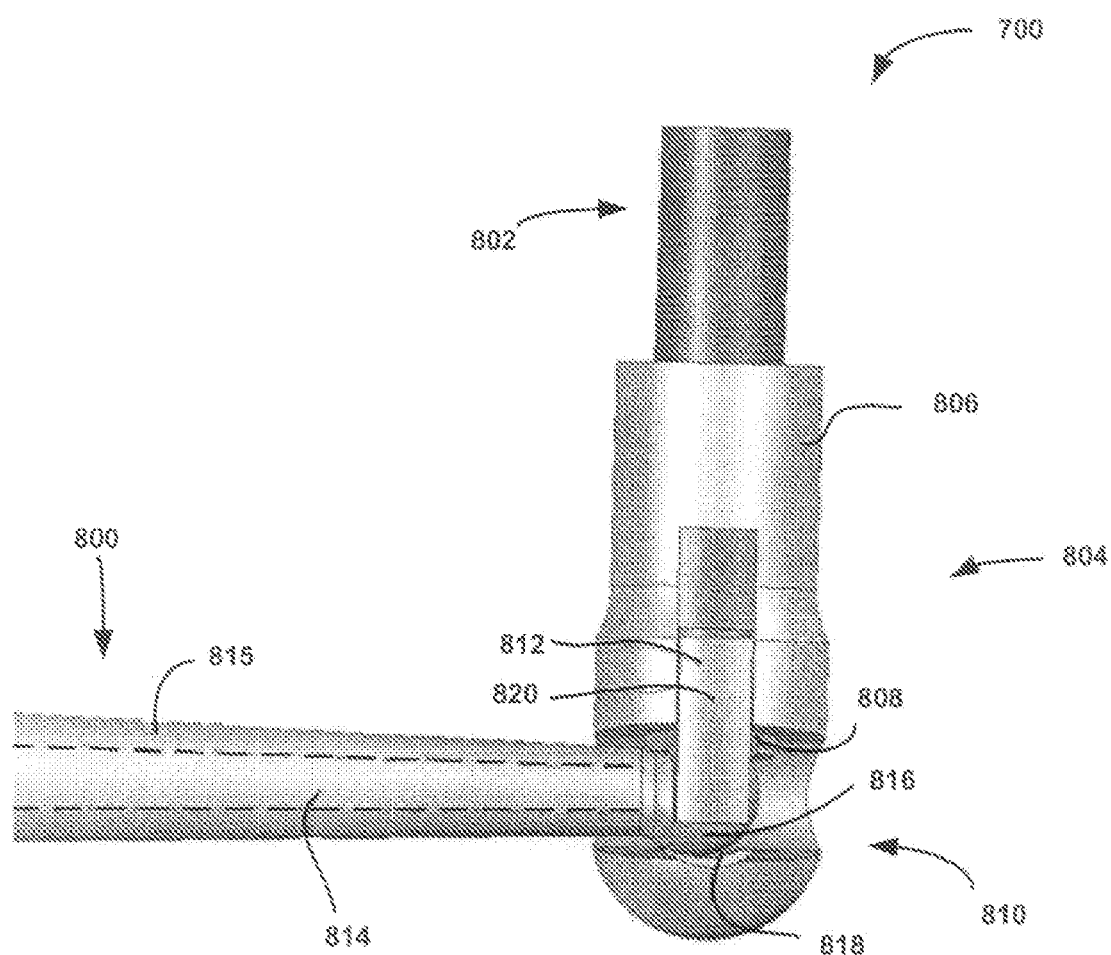
FIG. 56B is a front view of an embodiment of a horizontal rod system, a vertical rod system and a connector of the invention.
Figure 59:
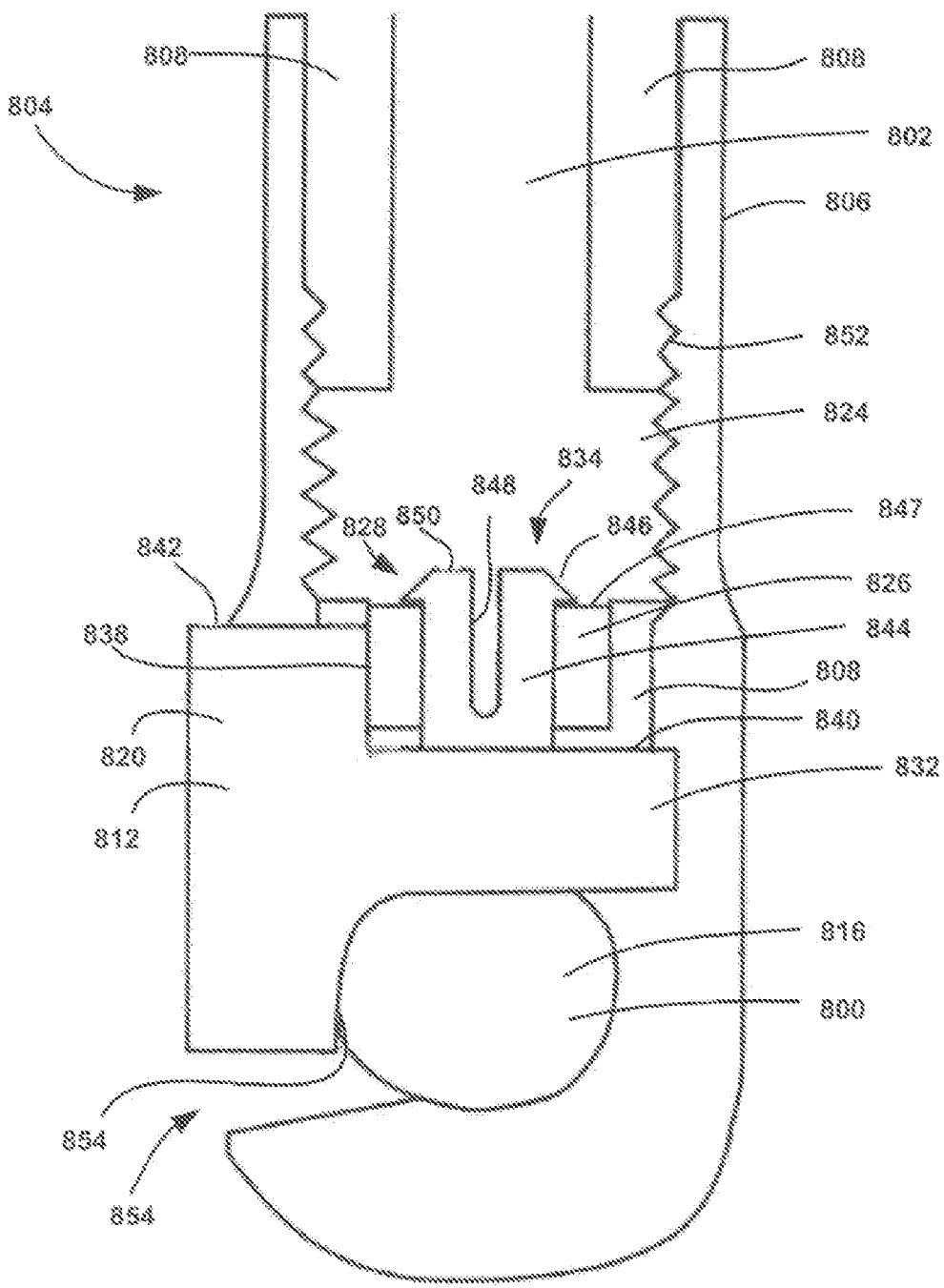
FIG. 59 is a sectional view of an embodiment of a vertical rod system and a connector of the invention.

Referring now to FIGS. 56A and 56B, the connector 804 in this embodiment is shown as including a cylindrical body 806 having an internal cylindrical bore 808, a U-shaped slot 810 and a lock tab 812. The deflection rod system 800 in this embodiment includes a deflection rod 814 (preferably made of Nitinol, Niti or other super elastic material) having an outer shell 815 (preferably made of PEEK or other comparable polymer) and a spherical ball or joint 816. The connector 804 includes a socket chamber 818 which is formed within the U-shaped slot 810 for receiving the spherical ball or joint 816 of the deflection rod system 800. Once the spherical ball or joint 816 of the deflection rod system 800 is positioned within the socket chamber 818, the exterior panel 820 of the lock tab 812 can be moved from its open, undeployed configuration (as shown in FIG. 56A) to its closed, deployed configuration (as shown in FIG. 56B), thereby closing the opening of the U-shaped slot 810 around the spherical ball or joint 816 of the deflection rod system 800 to secure the deflection rod system 800 to the connector 804. The specific mechanism employed to move the exterior panel 820 of the lock tab 812 in this embodiment of the invention is illustrated in FIG. 59, which is described in greater detail below. In the deployed configuration of the connector 804, the deflection rod system 800 is pivotally engaged to the connector 804 within the socket chamber 818 while the deflection rod shaft 814 extends away from the connector 804. Consequently, the vertical rod 802 is allowed to rotate and/or have tilting and/or swiveling movements about a center that corresponds with the center of the spherical joint 816.

Figure 57:
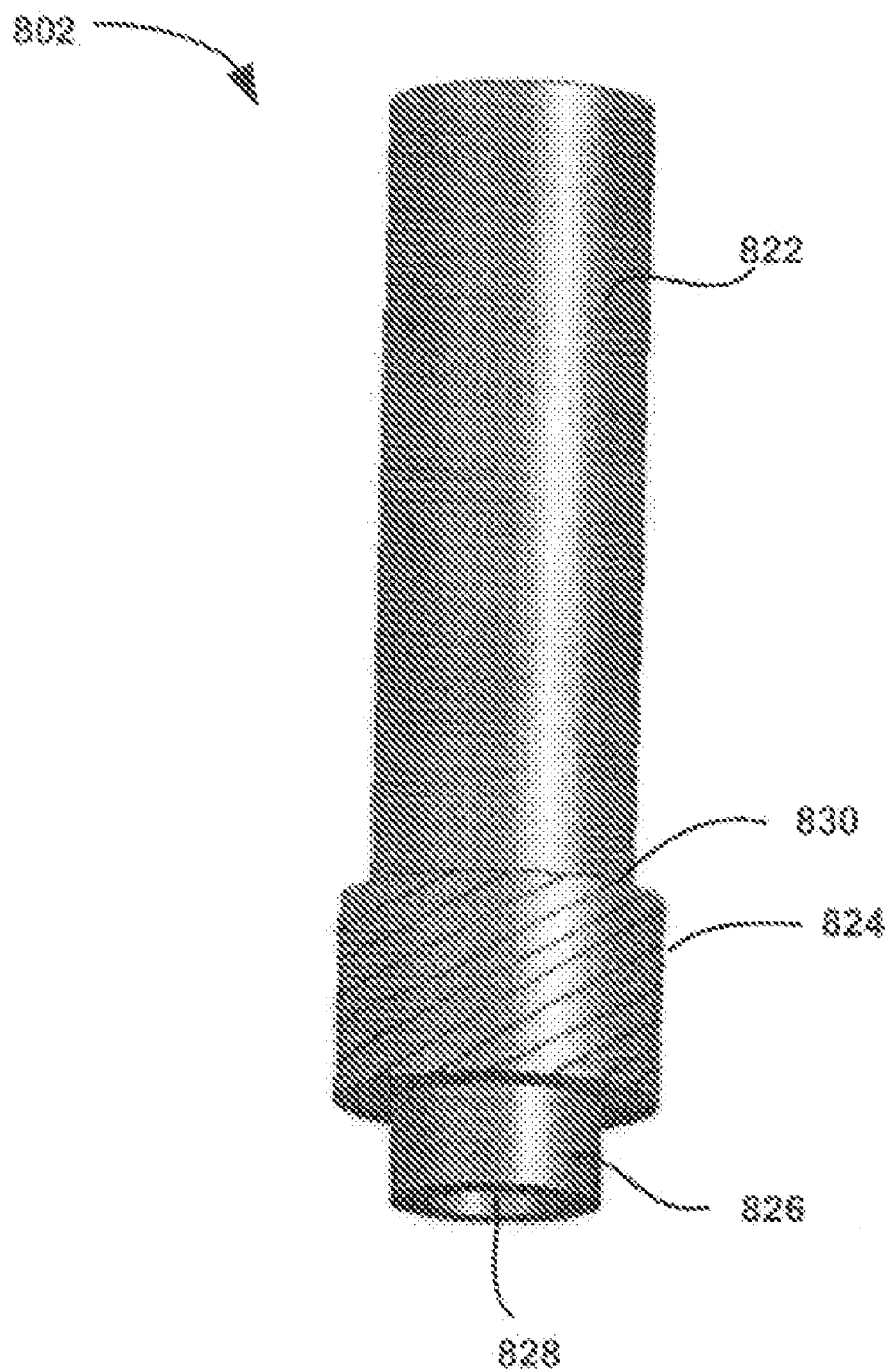
FIG. 57 is a perspective view of an embodiment of a vertical rod system of the invention.

FIG. 57 illustrates the vertical rod 802 used in this embodiment of the invention. The vertical rod 802 includes a vertical rod shaft 822, a threaded band 824, and an end cap 826 having a cavity 828 for accepting the lock tab 812 of the connector 804. In this embodiment, the threaded band 824 and the end cap 826 are both located adjacent to the first end 830 of the vertical rod shaft 822. The diameter of the threaded band 824 can be greater than the diameter of the vertical rod shaft 822 and the end cap 826. In an embodiment, the vertical rod 802 may not include an end cap 826 at all, in which case the threaded band 824 will include a cavity for accepting the lock tab 814 of the connector 804.

Figure 58:
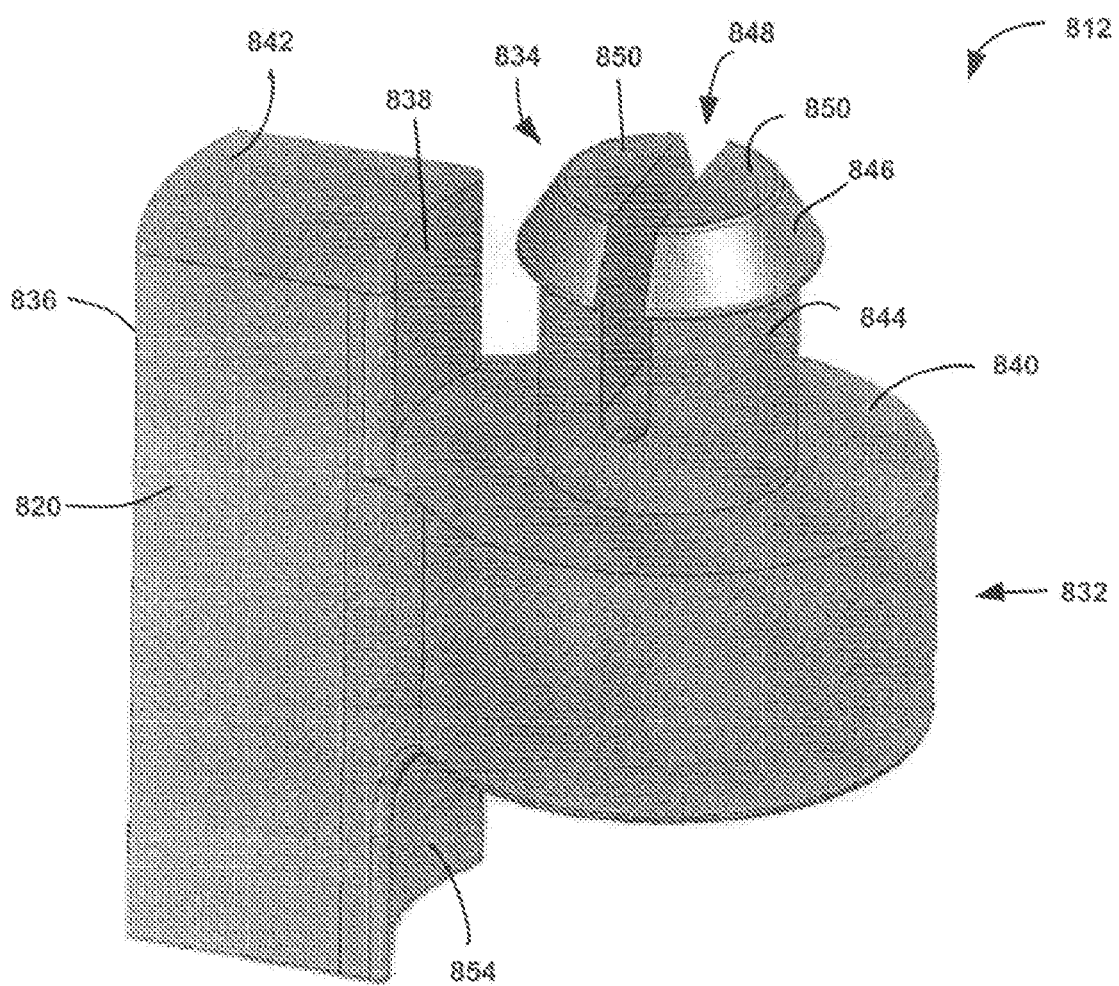
FIG. 58 is a perspective view of an embodiment of a lock tab of a connector of the invention.

FIG. 58 provides a detailed illustration of the lock tab 812 used in this embodiment of the invention. The lock tab 812 includes the exterior panel 820, a cylindrical platform 832 and a knob 834. In this embodiment, the exterior panel 820 can include a convex outer surface 836 and a concave inner surface 838. The cylindrical platform 832 is located along the inner surface 838 of the exterior panel 820, the top surface 840 of the cylindrical platform 832 being parallel to the top surface 842 of the exterior panel 820. The knob 834 is centrally located along the top surface 842 of the cylindrical platform 832. In use within the connector 804, the knob 834 can be used to fasten the lock tab 812 to the vertical rod 802, whereby the inner surface 838 of the exterior panel 820 and the knob 834 both conform to the shape of the end cap 826 of the vertical rod 802 as shown in FIG. 59. In order to secure the knob 834 to the vertical rod 802 the knob 834 includes a cylindrical base 844 having a bevel-shaped collar 846 and a U-shaped slit 848. As the knob 834 is inserted into the cavity 828 within the end cap 826 of the vertical rod 802, the U-shaped slit 848 allows the ends 850 of the knob 834 to pinch in until the collar 846 extends past the top of the end cap 826 of the hollow vertical rod 802. Once the collar 846 extends past the top of the end cap 826, the collar 846 catches under lip 84 and returns to its original unpinched configuration, thereby securing the vertical rod 802 to the lock tab 812 (as shown in FIG. 59).

Referring to FIG. 59, a cross-sectional view of the deflection rod system 800 and the vertical rod 802 within the connector 804 can be seen. The connector 804 has an internal cylindrical bore 808 for accepting the vertical rod 802 which is positioned substantially parallel to the longitudinal axis of the cylindrical body 806. The interior surface of the cylindrical body 806 includes threads 852 for engaging the threaded band 824 of the vertical rod 802. In this embodiment, the vertical rod 802 can be screwed into the cylindrical body 806 until the end cap 826 of the vertical rod 802 is placed in sliding engagement with the lock tab 812 knob 834. Engagement of the vertical rod 802 to the lock tab 812 is accomplished, as set forth above, by inserting the knob 834 into the cavity 828 of the end cap 826 of the vertical rod 802 until the collar 846 of the knob 834 extends past the lip 847 of the end cap 826, whereby the collar 846 of the knob 834 secures the vertical rod 802 to the lock tab 812. In this configuration, the end cap 826 of the vertical rod 802 is free to rotate around the knob 834 of the lock tab 812 while the vertical rod 802 remains engaged to the lock tab 812. Once the vertical rod 802 is placed in engagement with the lock tab 812, the lock tab 812 can be moved up and down by way of threaded movement of the vertical rod 802 within the cylindrical body 806 of the connector 804. In the deployed configuration of the connector 804, the spherical ball or joint 816 of the deflection rod system 800 is inserted into the U-shaped slot 810 of the connector. Once the ball 816 of the deflection rod system 800 is positioned therein, the exterior panel 820 and the locking tab 812 can be moved down to block the opening of the U-shaped slot 810 of the connector 804. In an embodiment, the lower inner surface 854 of the lock tab 812 can be concave and rounded to engage the spherical ball or joint 816 of the deflection rod system 800.

Figure 60:
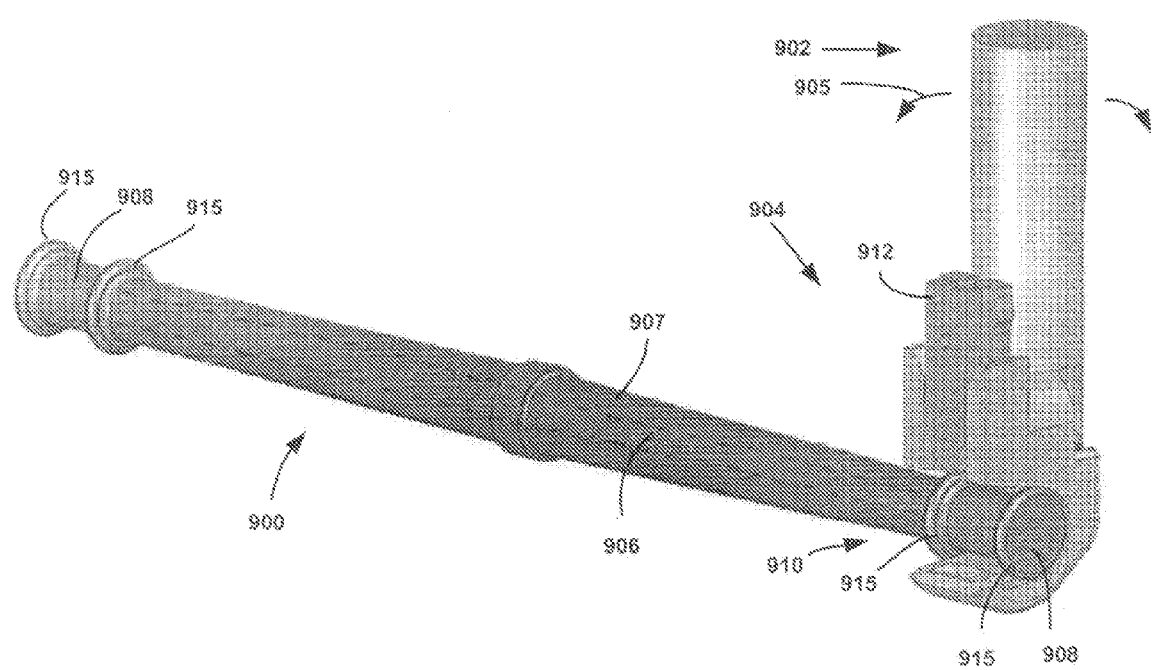
FIG. 60 is a perspective view of an embodiment of a horizontal rod system, a vertical rod system and a connector of the invention.

FIGS. 60-64 illustrate another embodiment of the deflection rod system 900, the vertical rod 902 and the connector 904 used within the dynamic stabilization system 700. As shown in FIG. 60, the deflection rod system 900 used in this embodiment includes a deflection rod 906 having an outer shell 907, the deflection rod 900 further including spool-shaped end caps 908 attached thereto, having circumferential retaining ridges 915, attached to the ends of the end cap 908. The end cap 908 can be screwed, glued, force fit, fused and/or laser welded onto the deflection rod 906. In this embodiment, the spool-shaped cap 908 is not connected to the shell 907. Instead, the shell 907 extends along the rod 906 and is short of the end cap 908. As with other embodiments, the deflection rod 906 can be comprised of a super elastic material and the shell 907 can be comprised of a polymer such as PEEK. The shell 907 protects the rod 906 and adds rigidity to the deflection rod system 900, and the rod 906 includes the deflection and recovery properties of a super elastic material. One of ordinary skill in the art can appreciate that other embodiments of the deflection rod system 900, such as the ones illustrated in FIGS. 68-71 or any other embodiments described herein, can be used in this embodiment of the dynamic stabilization system 700 without deviating from the scope of this invention.

FIG. 60 illustrates the connector 904 used in an embodiment of the invention. The connector 904 can be seen as including a C-shaped slot 910 for accepting the spool-shaped end cap 908 of the deflection rod system 900 and a sliding tab 912 which can close the opening of the C-shaped slot 910 to secure the spool-shaped end cap 908 of the deflection rod system 900 to the connector 904.

Figure 61:
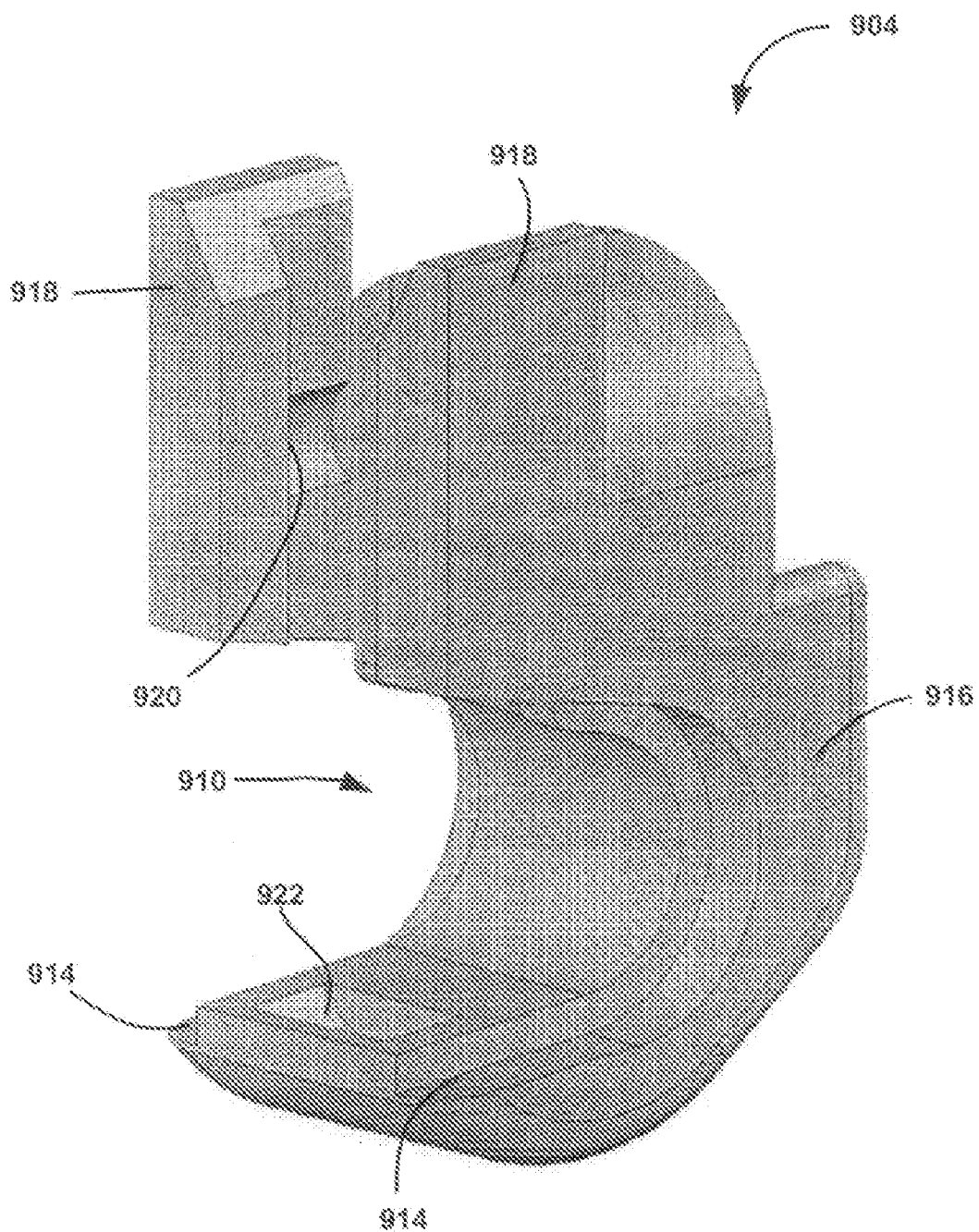
FIG. 61 is a perspective view of an embodiment of a connector of the invention.

Referring now to FIG. 61, a detailed illustration of this embodiment of the connector 904 is provided. The connector 904 can be seen as including the C-shaped slot 910 including two channels 914 adjacent to the side surfaces 916 of the connector 904. The channels 914 allow the C-shaped slot 910 to conform to the shape of the end cap 908 of the deflection rod system 900 (as shown in FIG. 60) and receives the circumferential retaining ridges 915 of the end cap 908. This configuration defines the movement of the deflection rod 900 within the connector 904. The connector 904 further includes L-shaped tab restraints 918 having a pair of grooves 920 along the inner surface of the tab restraints 918 as well as a groove 922 along the lower inner surface of the C-shaped slot 910. The L-shaped tab restraints 918 and various grooves 920, 922 facilitate securing the sliding tab 912 to the connector 904 as will be described in greater detail below.

Figure 62A:
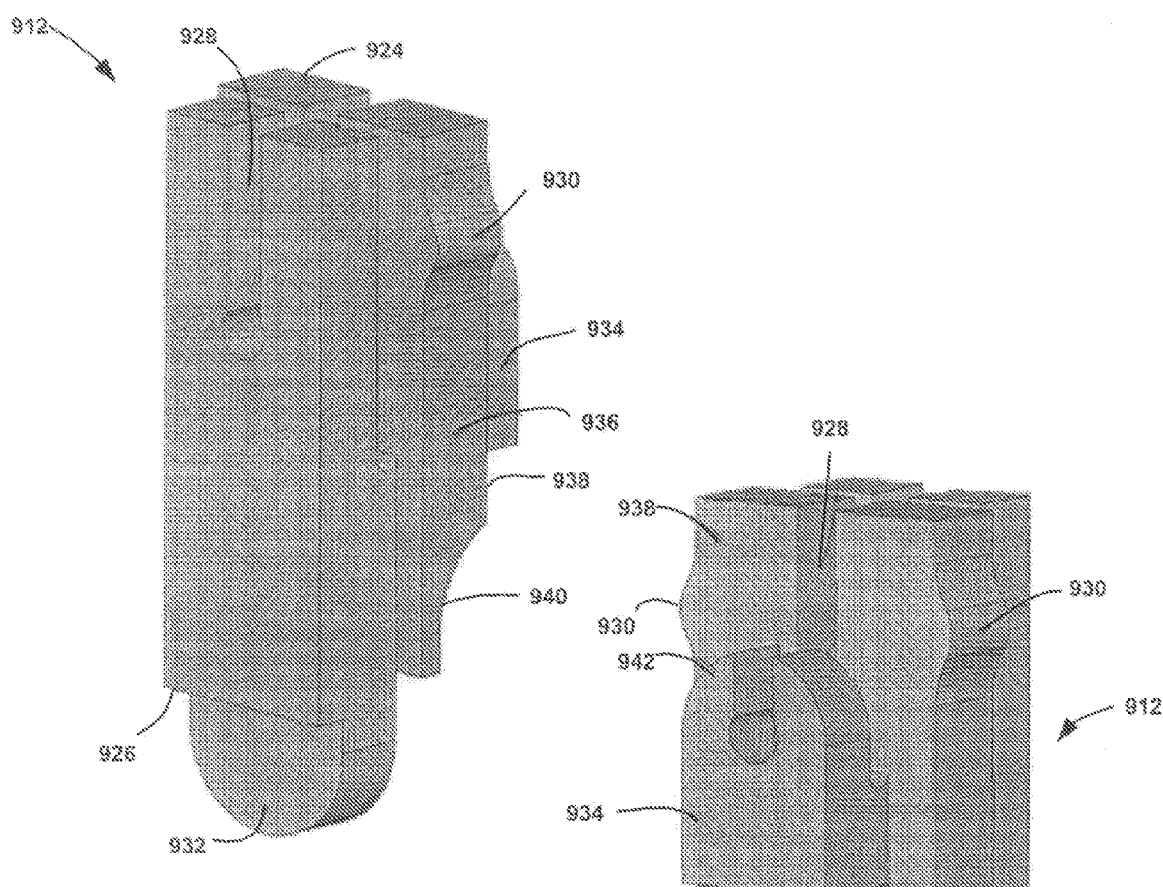
FIG. 62A is a perspective view of an embodiment of a sliding tab of a connector of the invention.
Figure 62B:
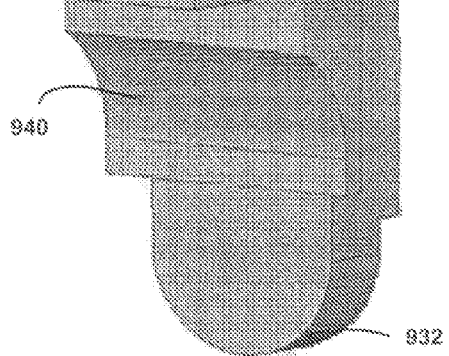
FIG. 62B is a perspective view of an embodiment of a sliding tab of a connector of the invention.

Referring now to FIG. 62A and FIG. 62B, the embodiment of the sliding tab 912 shown in FIG. 60 is illustrated in greater detail. The sliding tab 912 of this embodiment includes a first end 924 and a second end 926. The sliding tab 912 further including a U-shaped slot 928 at end 924, side knobs 930, a bottom lip 932 at end 926 and a rear restraint 934. The U-shaped slot 928, located adjacent to the first end 924 of the sliding tab 912, is positioned parallel to the longitudinal axis of the sliding tab 912. The U-shaped slot 928 allows the first end 924 of the sliding tab 912 to pinch together within the L-shaped tab restraints 918 of the connector 904 (shown in FIG. 61) as the sliding tab 912 is being placed in its deployed position. The side knobs 930 are located on the side surfaces 936 of the sliding tab 912 and conform to the grooves 920 along the inner surface of the tab restraints 918 of the connector 904 (shown in FIG. 61). The bottom lip 932, located adjacent to the second end 924 of the sliding tab 912, conforms to and can be received in the groove 922 along the lower inner surface of the C-shaped slot 910 of the connector 904 (shown in FIG. 61). Referring to FIG. 62B, the back surface 938 of the sliding tab 912 can be seen as including a curved section 940 which can be configured to conform to the cylindrical shape of the spool-shaped end cap 908. The back surface 938 of the sliding tab 912 can also include the rear restraint 934. In this embodiment, the rear restraint 934 can be inserted into a slot 948 within the vertical rod 902 (shown in FIG. 64) to position the vertical rod 902 relative to the connector 904 for deployment into a patient. The side knobs 930 and the bottom lip 932 also facilitate securing the sliding tab 912 to the connector 904 (as shown in FIG. 63).

Figure 63:
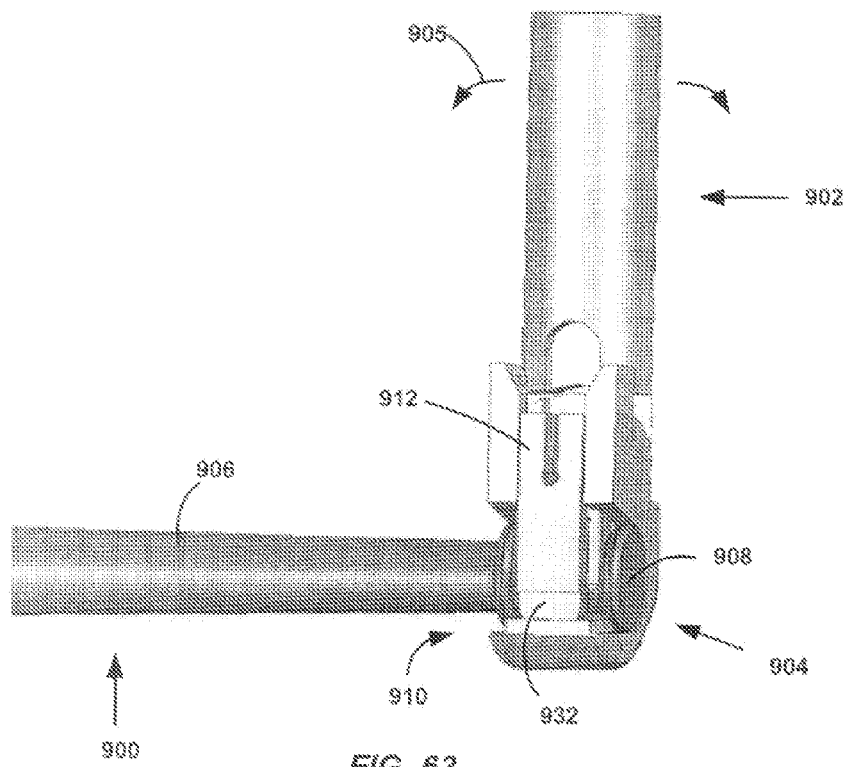
FIG. 63 is a perspective view of an embodiment of a horizontal rod system, a vertical rod system and a connector of the invention.

FIG. 63 illustrates the connector 904 in its deployed configuration. As shown, the deflection rod system 900 is secured to the connector 904 within the C-shaped slot 910 using the sliding tab 912. In this configuration, the side knobs 930 are mated with the grooves 920 along the inner surface of the tab restraints 918 and the bottom lip 932 is mated with the groove 922 along the lower inner surface of the C-shaped slot 910, thereby locking the sliding tab 912 into its deployed position within the connector 904 and locking the connector 904 about the spool-shaped end cap 904. Accordingly, the vertical rod can rotate about the end cap 904 and thus rotate about the longitudinal axis of the torsion rod system 900.

Figure 64:
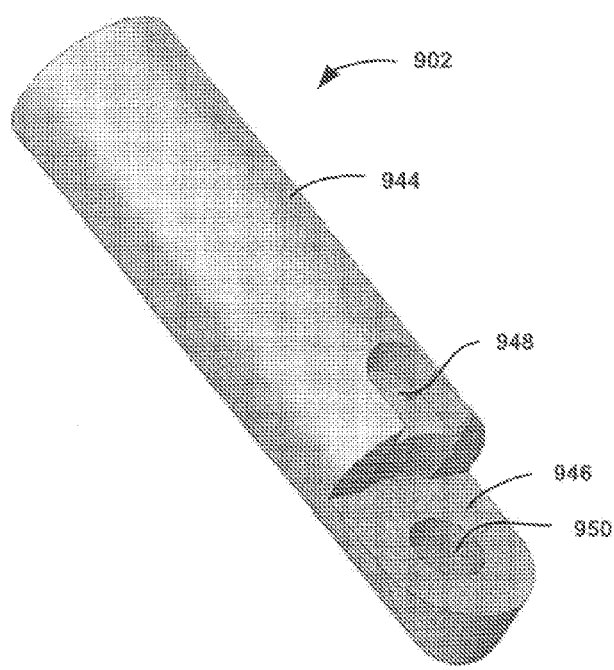
FIG. 64 is a perspective view of an embodiment of a vertical rod of the invention.

As shown in FIG. 64, the vertical rod 902 used in this embodiment of the invention includes a vertical rod shaft 944, a first slot 946 for accepting the connector 904 and a second slot 948 for accepting the rear restraint 934 of the sliding tab 912. The vertical rod 902 also includes an aperture 950 for accepting a screw, rivet or pin. In this embodiment, the back of the connector 904 can be shaped to conform to the shape of the vertical rod 902. Accordingly, the vertical rod 902 can be mated with the connector 904 as shown in FIG. 60, and a screw, rivet or pin can be inserted through the aperture 950 of the vertical rod 902 into the connector 904 to secure the vertical rod 902 to the connector 904 and/or allow the vertical rod 902 to pivot about the screw, rivet or pin (see arrows 905) and relative to the horizontal rod 900. The rear restraint 934 can be held in the slot 948 prior to the sliding tab 912 being lockingly deployed to capture the spool-shaped end cap 918 in the C-shaped slot 910.

Figure 65:
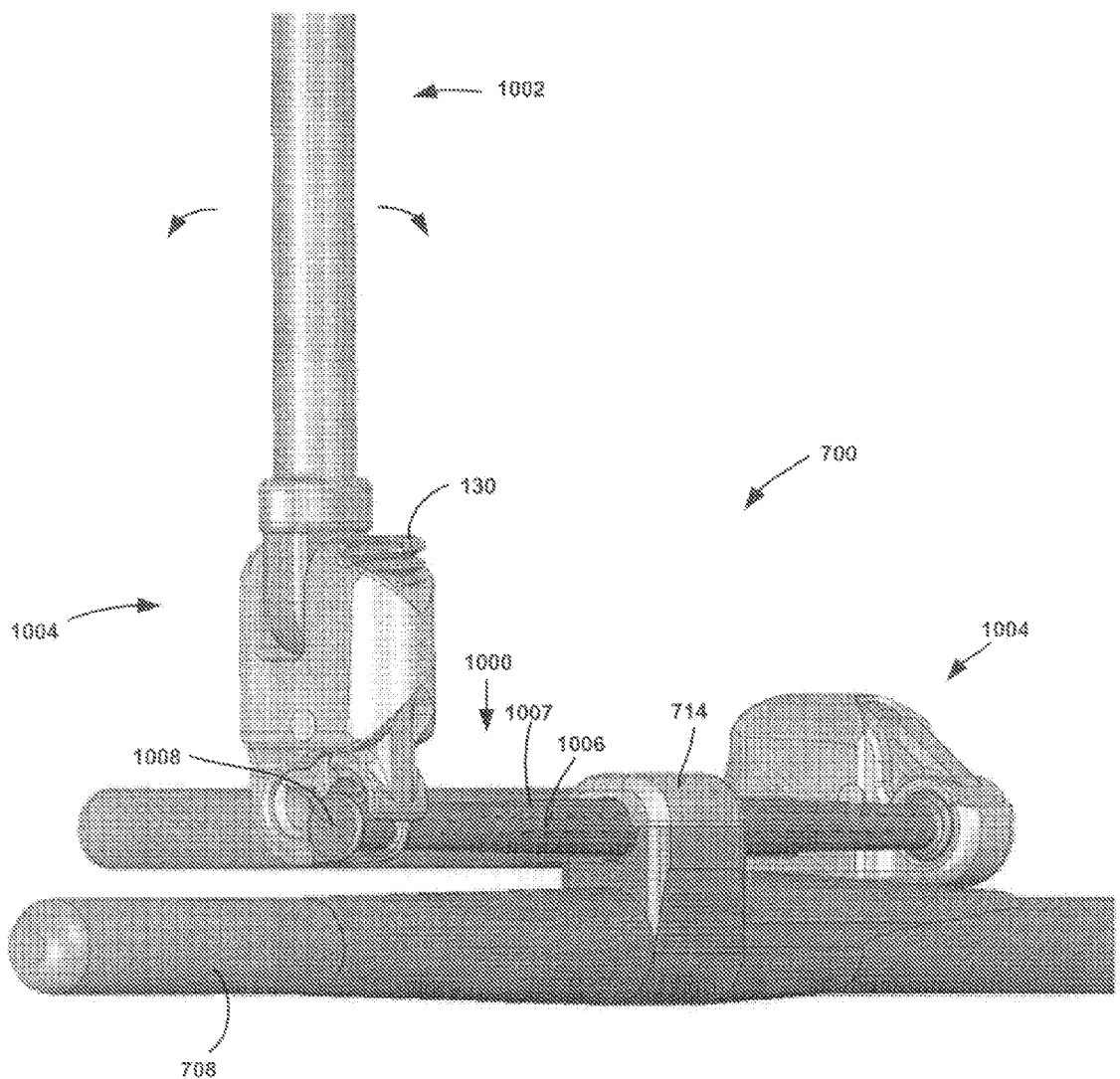
FIG. 65 is a perspective view of an embodiment of a horizontal rod system, a vertical rod system and a connector of the invention.
Figure 66:
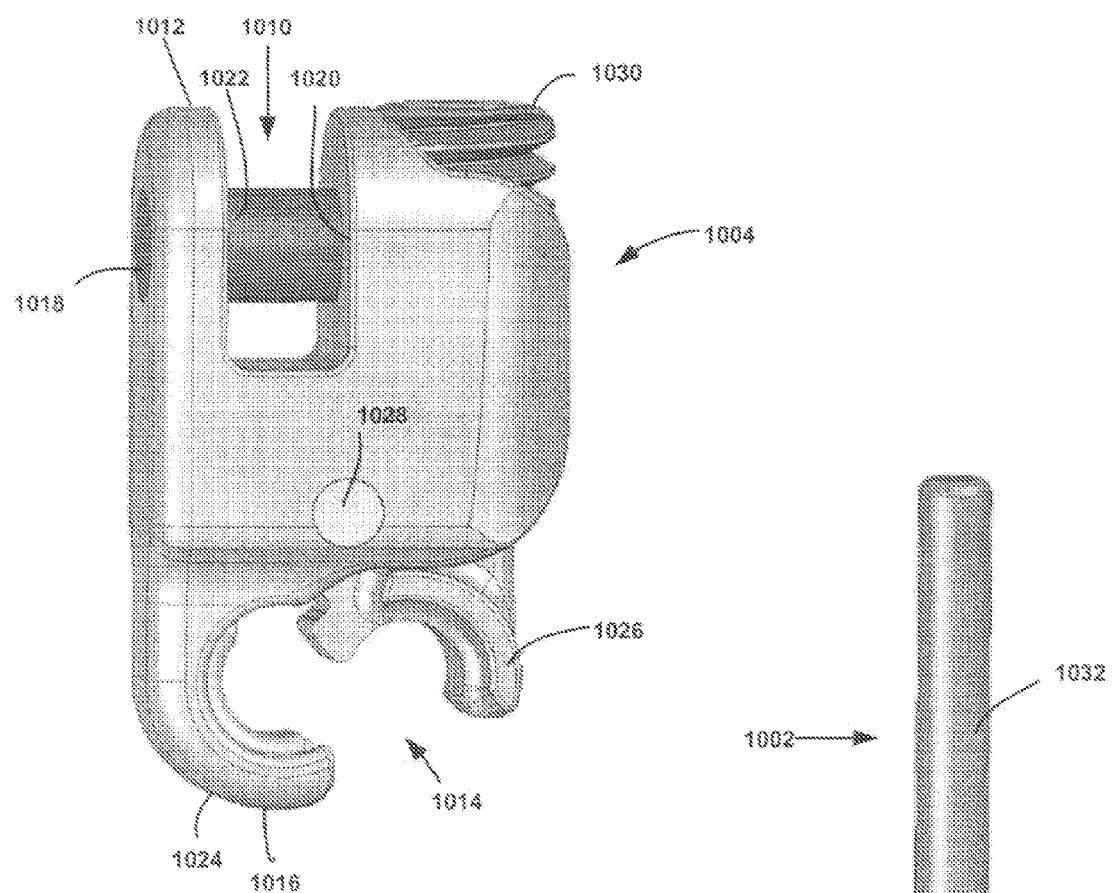
FIG. 66 is a perspective view of an embodiment of a connector of the invention.
Figure 67:
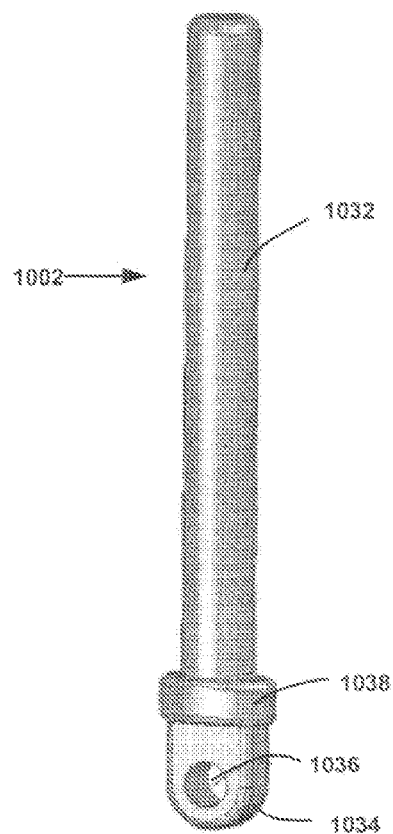
FIG. 67 is a perspective view of an embodiment of a vertical rod of the invention.
Figure 68:
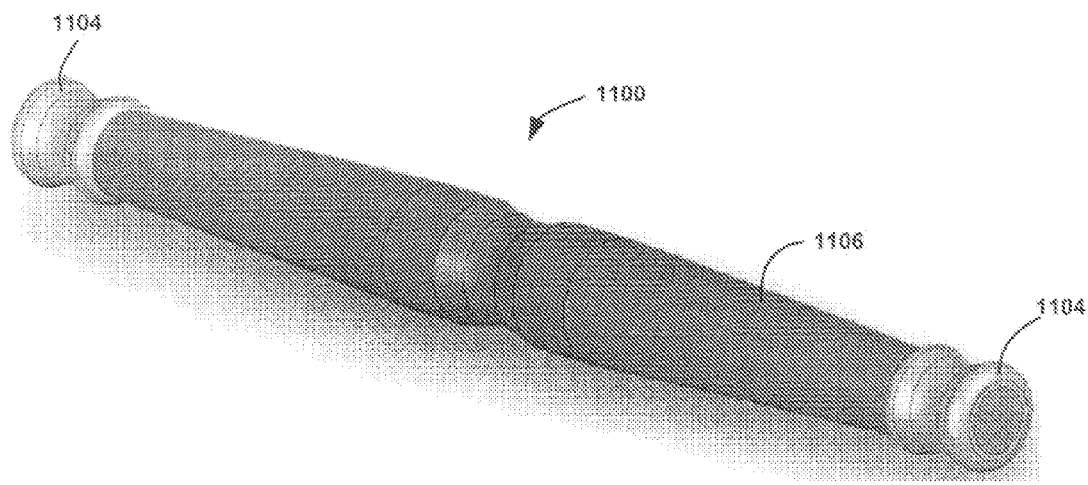
FIG. 68 is a perspective view of an embodiment of a deflection rod of the invention.
Figure 69:
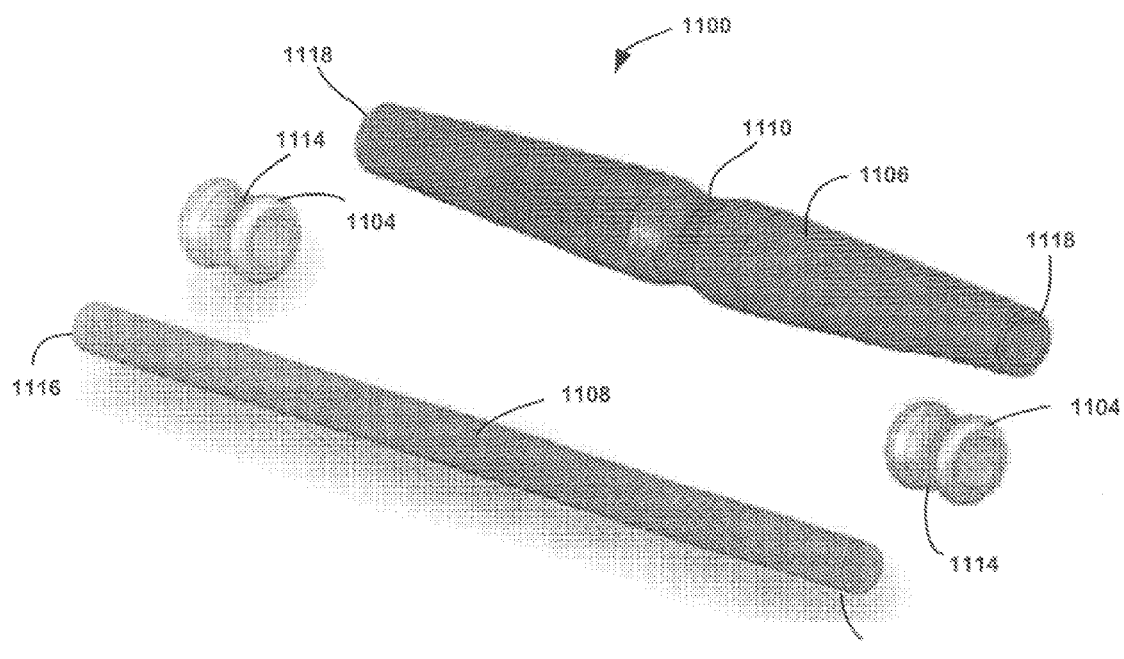
FIG. 69 is a perspective and exploded view of an embodiment of a deflection rod of the invention.

FIGS. 65-67 illustrate yet another embodiment of the deflection rod system 1000, the vertical rod 1002 and the connector 1004 which can be used as a part of the dynamic stabilization system 700. Referring now to FIG. 65, the deflection rod system 1000 can be seen as including a deflection rod 1006 having spool-shaped end caps 1008 attached to the ends of the shaft 1006 and shell 1007 similar to the embodiment depicted in FIG. 60. It is noted that one of ordinary skill in the art can appreciate that other embodiments of the deflection rod system 1000, such as the ones illustrated in FIGS. 68-71 or any other embodiments described herein, can be used in this embodiment of the dynamic stabilization system 700 without deviating from the scope of this invention.

FIG. 66 illustrates the connector 1004 of this embodiment of the invention. The connector 1004 can be seen as having a U-shaped slot 1010 on the first end 1012 of the connector 1004, and a clamp, generally numbered 1014, on the second end 1016 of the connector 1004. The U-shaped slot 1010 can be configured to accept the vertical rod 1002. In an embodiment, the connector 1004 includes apertures 1018, 1020 along the sides of the U-shaped slot 1010 for accepting a pin or screw 1022. Once an aperture 1036 (FIG. 67) of the vertical rod 1002 is placed within the U-shaped slot 1010, the pin or screw 1022 can be inserted into the apertures 1018, 1020 of the connector 1004 as well as the vertical rod 1002 to either fixedly or pivotally secure the vertical rod 1002 to the connector 1004. The pin or screw 1022 can be fused, glued, screwed, force fit and/or laser welded to the connector 1004.

The clamp 1014 includes a C-shaped arm 1024 as well as a C-shaped locking paw 1026 that is pivotally attached to the connector 1004 using a pivot pin 1028. The clamp 1014 also includes a clamp set screw 1030 which can adjust the position of the locking paw 1026. In this embodiment, the end cap 1008 of the deflection rod 1000 can be secured to the connector 1004 between the C-shaped arm 1024 and the locking paw 1026 in the closed configuration of the clamp 1014 as shown in FIG. 65 and held in place by set screw 1030. Accordingly, the vertical rod can pivot about the deflection rod 1006 with the end cap 1008 retained in the clamp 1014.

Referring now to FIG. 67, the vertical rod 1002 used in this embodiment of the invention can be seen as including a cylindrical shaft 1032, a head 1034 having an aperture 1036 for accepting a pin or screw, and a spacer 1038 located between the head 1034 and the shaft 1032. In this embodiment, the head 1034 of the vertical rod 1002 conforms to the U-shaped slot 1010 of the connector 1004.

Figure 70:
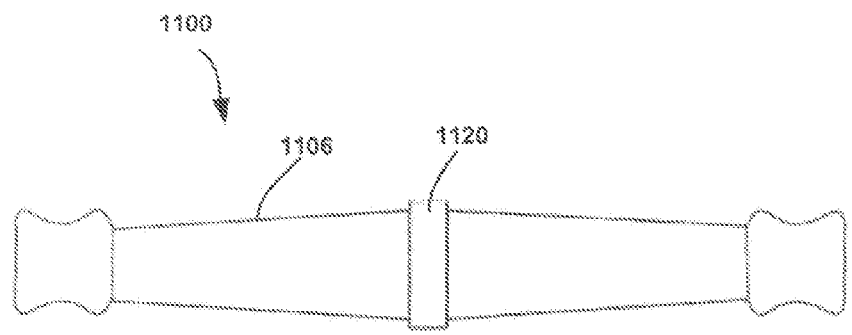
FIG. 70 is a front view of an embodiment of a deflection rod of the invention.

Alternate Embodiments of the Deflection Rod System and the First Horizontal Rod of the Invention:

FIGS. 68-71 illustrate another embodiment of deflection rod system 1100 which can be used within the embodiments of the dynamic stabilization systems 700 described herein. The deflection rod system 1100 generally includes a deflection rod 1108 and two end caps 1104. The end cap 1104 can be, for example, spool-shaped or spherically-shaped as illustrated with respect to other embodiments. The deflection rod system 1100 can also include an outer shell 1106. In an embodiment, the deflection rod 1108 is cylindrical and made of a super elastic material, preferably Nitinol (NiTi). The diameter of the deflection rod 1108 is constant in this embodiment. In this embodiment, the outer shell 1106 of the deflection rod system 1100 is made of a biocompatible material or polymer, preferably PEEK, which is less elastic than the deflection rod 1108. In this embodiment, the deflection rod shell 1106 includes a hollow tube which is generally tapered. The tube increases in diameter from the ends 1118 of the shell 1106 to the central portion 1110 of the outer shell 1106. A channel 1112 can be provided at the central portion of the shell 1106 to facilitate the retention of the deflection rod system 1100 in a mount on a horizontal rod such as, for example, mount 714 on horizontal rod 708 in FIG. 45. Instead of a channel 1112, a ring-shaped plateau or land can be defined having the largest diameter of the shell 1106 (FIG. 70). Either the channel 1112 or the plateau can be received in the mount 714 of the horizontal rod system as seen in FIG. 48. In an embodiment, the end caps 1104 can be made of titanium, stainless steel, a biocompatible polymer such as PEEK or another biocompatible material. In this embodiment, the end caps 1104 are spool shaped or cylindrical shaped and include a central channel 1114.

The deflection rod 1108 can be inserted into the outer shell 1106 of the deflection rod system 1100 so that the ends 1116 of the deflection rod 1108 extend past from the ends 1118 of the outer shell 1106. The end caps 1104 can then be attached to the end 1116 of the deflection rod 1108. The purpose of the deflection rod shell 1106 is to protect the deflection rod 1108, which is made of the super elastic material and to support and restrict the motion of the rod 1108. The outer shell 1106 also serves to reduce the strain on the deflection rod 1108 as force is applied to the ends 1116 of the deflection rod 1108. As increased strain is placed on the ends 1116 of the deflection rod 1108, and spread along the entire length of the deflection rod 1108, the deflection rod shell 1106 can resist such strain along the entire length of the shell 1106. The outer shell 1106 of the deflection rod system 1100 helps to limit the maximum amount of deflection allowed by the deflection rod system 1100 as well as support and protect the deflection rod 1108.

Figure 71:
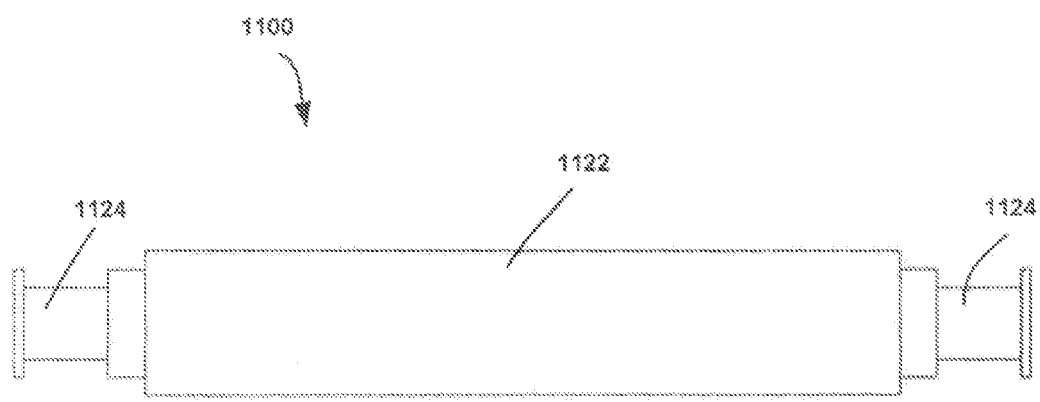
FIG. 71 is a front view of an embodiment of a deflection rod of the invention.

FIGS. 70 and 71 illustrate other embodiments of the deflection rod system 1100. Referring first to FIG. 70, this embodiment of the deflection rod system 1100 is similar to the deflection rod system 1100 embodied in FIG. 68. However, in this embodiment, the central portion of the deflection rod shell 1106 includes a central ring or plateau 1120 as opposed to a channel. Referring now to FIG. 71, this embodiment of the deflection rod system 1100 includes a deflection rod shaft 1122 having a constant diameter and two end caps 1124 also having constant diameters. As can be seen in FIG. 71, the diameter of the deflection rod shaft 1122 is larger than the diameter of the end caps 1124. It is noted that as with the deflection rod system 1100 illustrated in FIGS. 68 and 69, the embodiments of the deflection rod systems illustrated in FIGS. 70-71 include a deflection rod or core 1108 and a deflection rod shell 1106 as described above. The embodiments illustrated in FIGS. 68-71 are not intended to be limiting and it is envisioned that the deflection rod system 1100 may include other embodiments which would be evident to one skilled in the art without deviating from the scope of the invention.

Figure 72A:
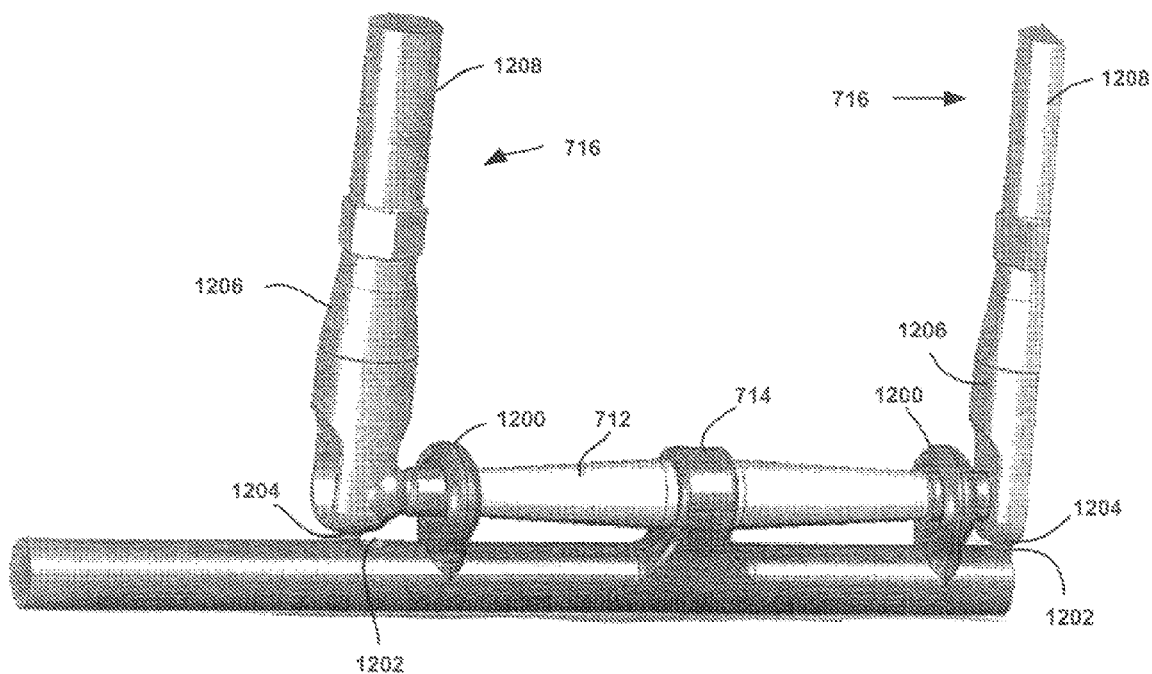
FIG. 72A is a perspective view of an embodiment of a horizontal rod system, a vertical rod system and a connector of the invention.

FIGS. 72A-73C illustrate alternative embodiments of the first horizontal rod 708. Referring now to FIG. 72A, an embodiment of the first horizontal rod 708 is shown as including a mount 714, a pair of guide or deflection restraining rings 1200 and a pair of grooves 1202 proximal to and outboard of the guide rings 1200. In this embodiment, the deflection rod system 712 is secured to the first horizontal rod 708 within the mount 714. The deflection rod system 712 is further contained within the guide rings 1200 proximal to the ends of the deflection rod system 712. The guide rings 1200 can be used to limit the amount of deflection of the deflection rod system 712 in use as well as to prevent the deflection rod system 712 from becoming overextended during use. In this embodiment, the guide rings 1200 are elliptical rings wherein the vertical diameters of the guide rings 1200 are greater than the horizontal diameters of the guide rings (FIG. 72C). Again, horizontal referring to a horizontal orientation with respect to a patient that is standing and vertical referring to a vertical orientation with respect to a patient that is standing. The configuration of the guide ring 1200 allows the deflection rod system 712 to have a greater amount of vertical deflection than horizontal deflection. It is envisioned that the guide rings 1200 can have other configurations and still fall within the scope of this invention.

Figure 72B:
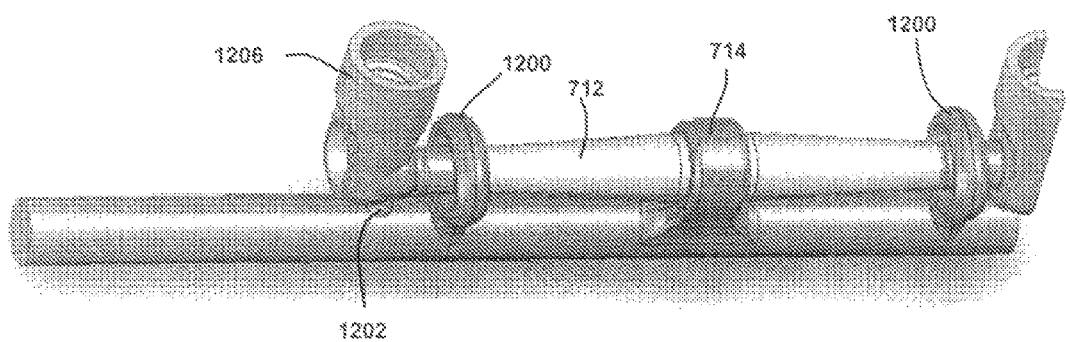
FIG. 72B is a perspective view of an embodiment of a horizontal rod system, a vertical rod system and a connector of the invention.
Figure 72C:
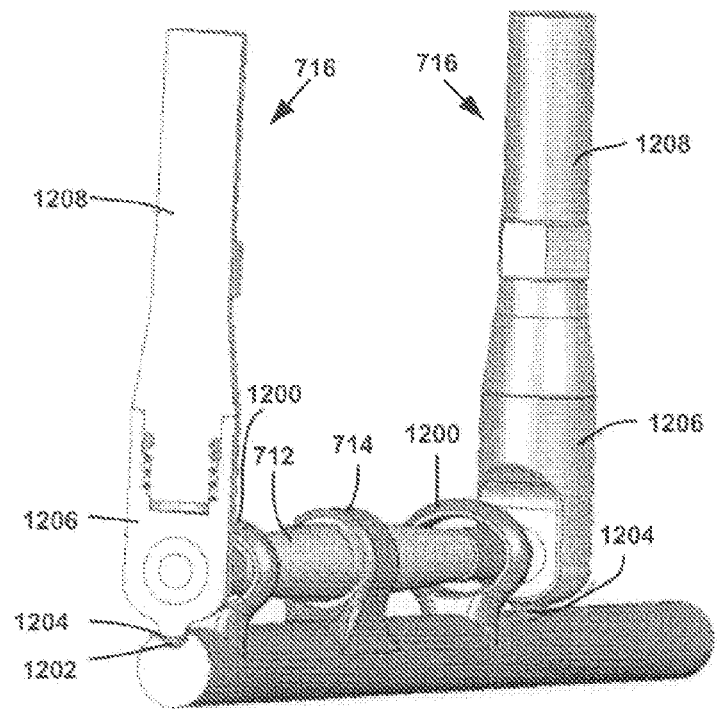
FIG. 72C is a partial sectional view of an embodiment of a horizontal rod system, a vertical rod system and a connector of the invention.

The first horizontal rod 708 also includes the grooves 1202 which can be mated with corresponding knobs 1204 located on the end caps 1206 of a vertical rods 716 to keep the ends caps 1206 and/or the vertical rods 716 aligned during deployment into the patient. Alternatively, such initial alignment technique can be dispensed with. In this embodiment, the vertical rod 716 includes an end cap 1206 and a main vertical shaft 1208 wherein the main vertical shaft 1208 can be screwed into the end cap 1206. It is to be understood that the horizontal system can first be inserted into a patient without the main vertical shaft 1208 being attached (as shown in FIG. 72B). Once the horizontal system has successfully been inserted, the main vertical shafts 1208 can be attached to the end caps 1206, wherein the grooves 1202 and the knobs 1204 can act to align and steady the end caps 1206 as the main vertical shafts 1208 are inserted into the end caps 1206 (as shown in FIG. 72C).

Figure 73A:
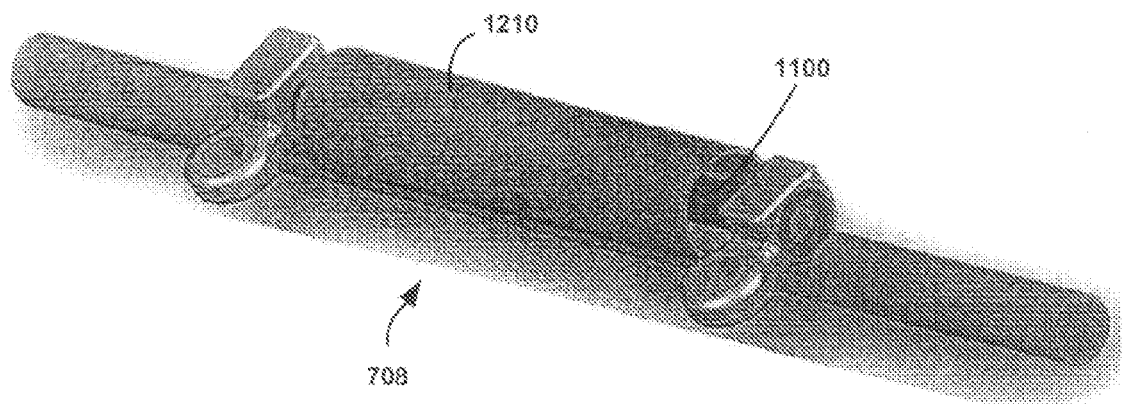
FIG. 73A is a perspective view of an embodiment of a horizontal rod system and a connector of the invention.
Figure 73B:
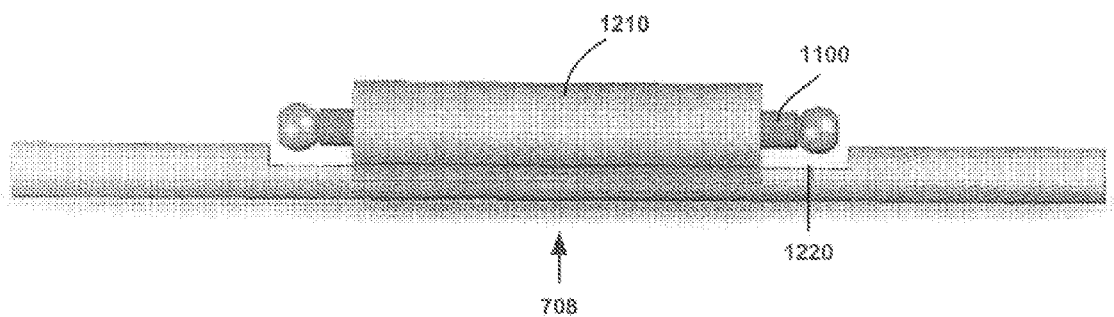
FIG. 73B is a front view of a an embodiment of horizontal rod system of the invention.
Figure 73C:
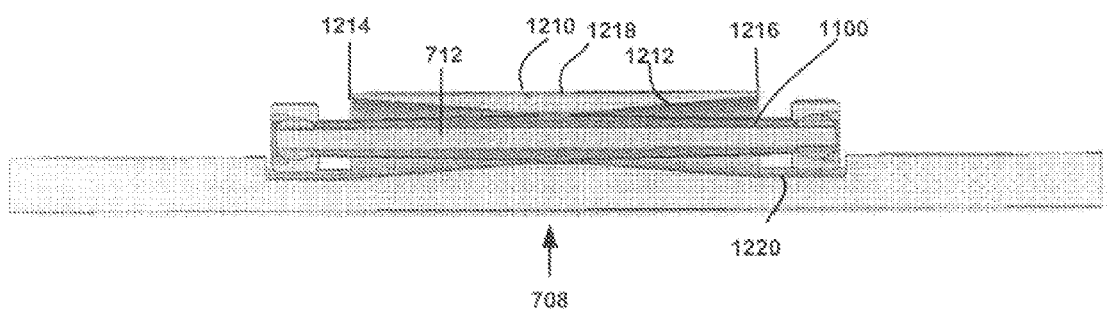
FIG. 73C is a sectional view of an embodiment of a horizontal rod system of the invention.

Referring now to FIGS. 73A-73C, another embodiment of the first horizontal rod is illustrated. As can be seen in FIGS. 73A and 73B, the first horizontal rod 708 of this embodiments includes a deflection rod collar or shield 1210 that wraps around the deflection rod system 1100. The deflection rod shield 1210 is preferably stiff and rigid (and made of titanium, for example). The deflection rod shield 1210 can be used to protect the deflection rod 712 from damage during use. The deflection rod system 1100 includes a rod 1108 and an outer shell 1106 as shown for the deflection rod system 1100 in FIG. 69. The deflection rod shield 1210 can also be used to limit the amount of deflection of the deflection rod system 1100 as well as prevent the deflection rod system 1100 from becoming overextended during use. Referring now to FIG. 73C, the inner surface 1212 of the deflection rod shield 1210 can be seen as being tapered wherein the diameter of the inner surface 1212 of the deflection rod shield 1210 is greater at the ends 1214, 1216 than at the center 1218 of the deflection rod shield 1210. In this configuration, the surface of the deflection rod system 1100 can touch the inner surface 1212 of the deflection rod shield 1210 during use. Accordingly, the deflection rod shell 1210 can limit the movement of the deflection rod system 1100 and assist in spreading the load and strain on the deflection rod system 1100 along the entire length of the deflection rod system 1100. Also in this embodiment, the first horizontal rod 708 includes a cavity 1220 to encompass the deflection rod system 1100 within the deflection rod shield 1210 to give the first horizontal rod 708 a smaller profile when implanted into a patient. It is envisioned that the deflection rod system 1100 can be mounted to any other type of horizontal rod which would be obvious to one skilled in the art without deviating from the scope of the invention.

Figure 74:
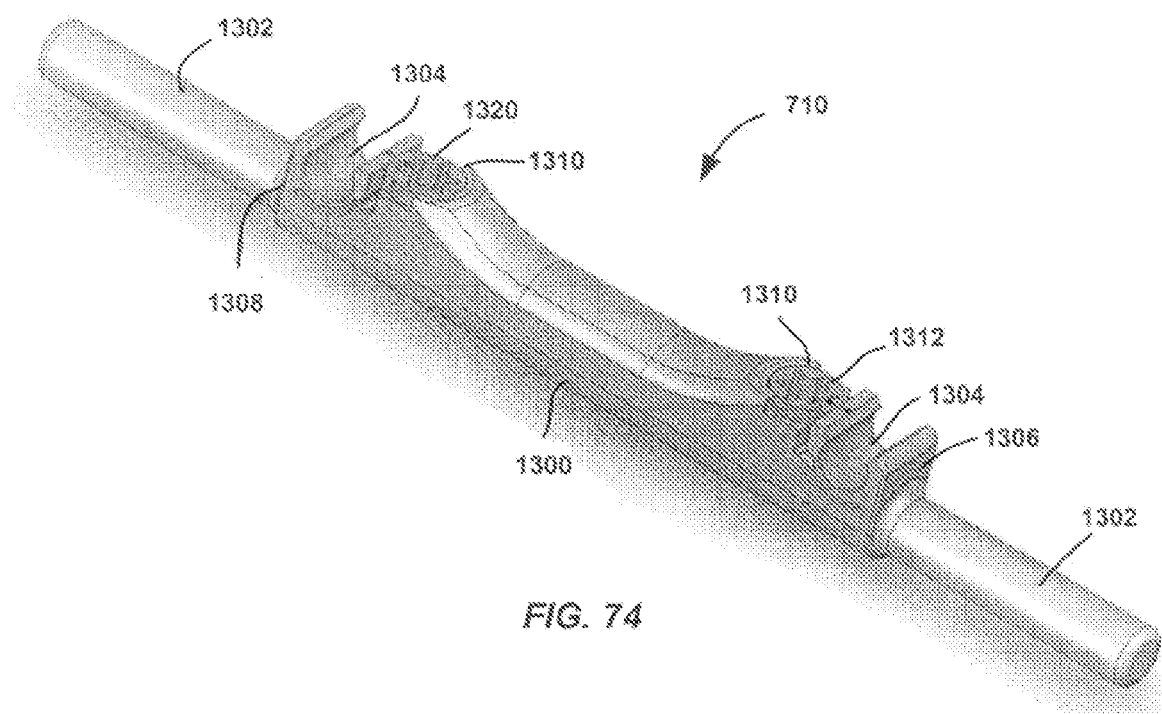
FIG. 74 is a perspective view of an embodiment of a horizontal rod of the invention.

Alternative Embodiments for Connections Used to Mate the Vertical Rod System to the Second Horizontal System:

FIGS. 74-79B illustrate embodiments of a second horizontal rod 710 which can be used within the dynamic stabilization system 700 described above. Referring now to FIG. 74, the horizontal rod 710 can generally be seen as including a main body 1300 and two cylindrical shafts 1302 extending away from each side of the main body 1300. The main body 1300 includes cylindrical slots 1304 adjacent to the ends 1306, 1308 of the main body 1300 and sockets 1310 for accepting a cam 1312. In this embodiment, the cylindrical slots 1304 are about perpendicular to the cylindrical shafts 1302. The two cylindrical shafts 1302 can be connected to the anchor system 702 while the cylindrical slots 1304 can be used to accept and secure the vertical rods 716 to the second horizontal rod 710 as shown in FIG. 48.

Figure 75:
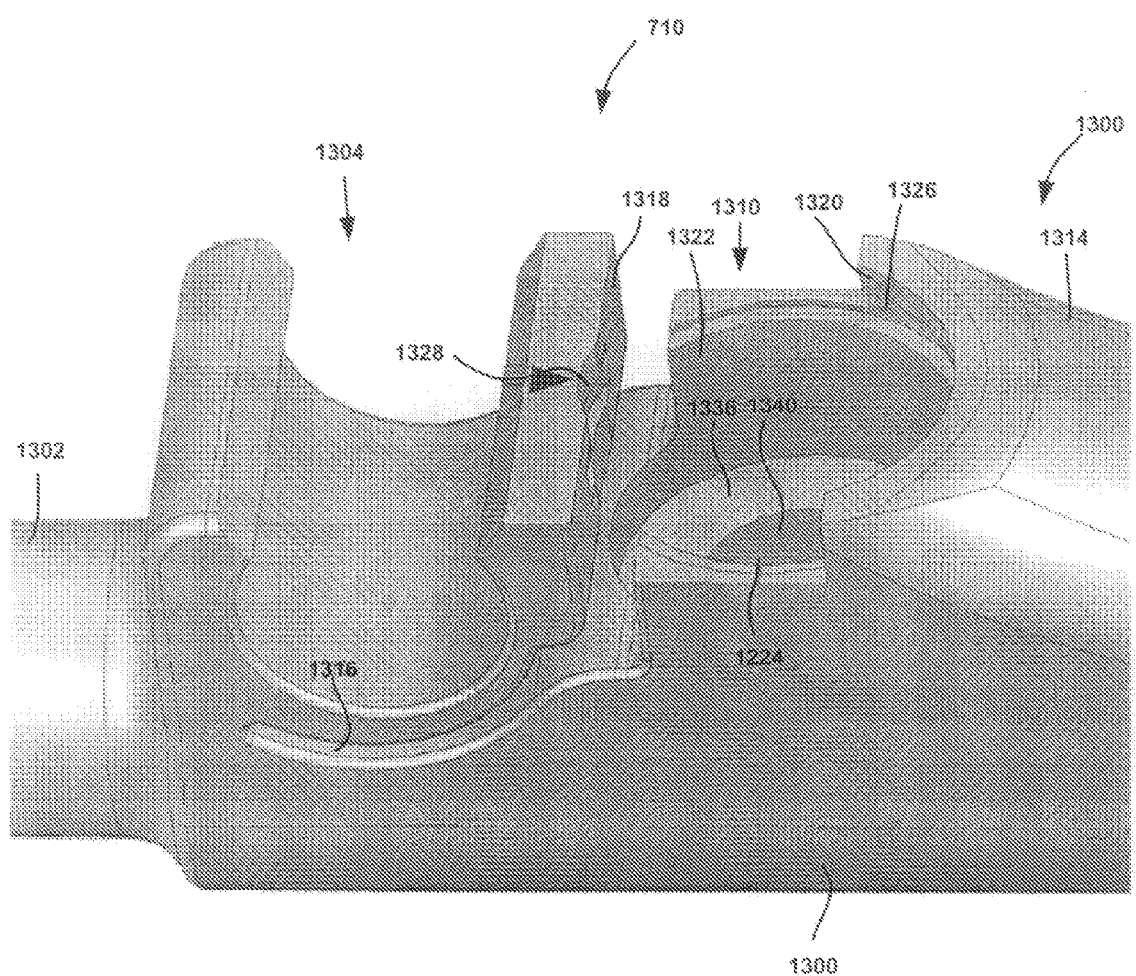
FIG. 75 is a perspective view of an embodiment of a horizontal rod of the invention.

Referring now to FIG. 75, the cylindrical slot 1304 for accepting a vertical rod 716 and the socket 1310 for accepting a cam 1312 can be seen in greater detail. As shown in FIG. 75, the cylindrical slot 1304 is located along the top surface 1314 of the main body 1300 and extends about perpendicular to the longitudinal axis of the second horizontal rod 710. In this embodiment, a slit 1316 is located underneath the cylindrical slot 1304 in order to allow the sides of the cylindrical slot 1304 to pinch together around a vertical rod 716 in the deployed configuration of the second horizontal rod 710.

Figure 77A:
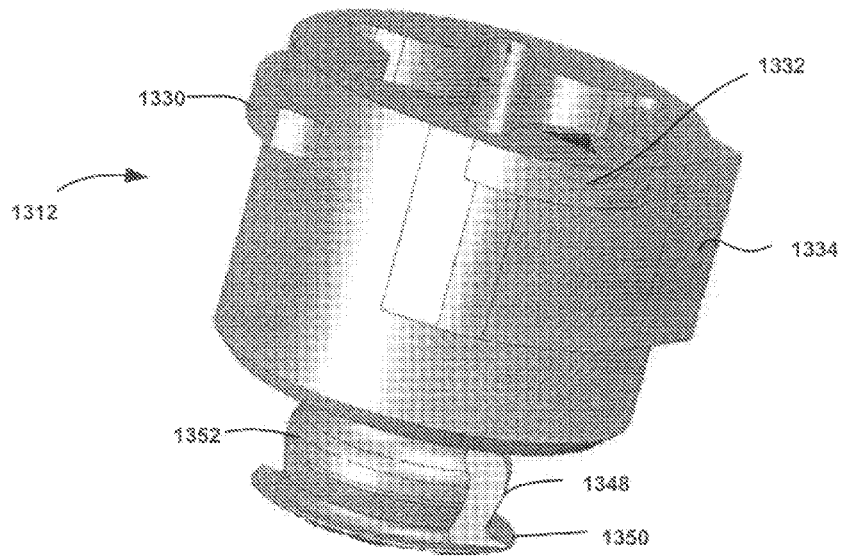
FIG. 77A is a perspective view of an embodiment of a cam of the invention.
Figure 77B:
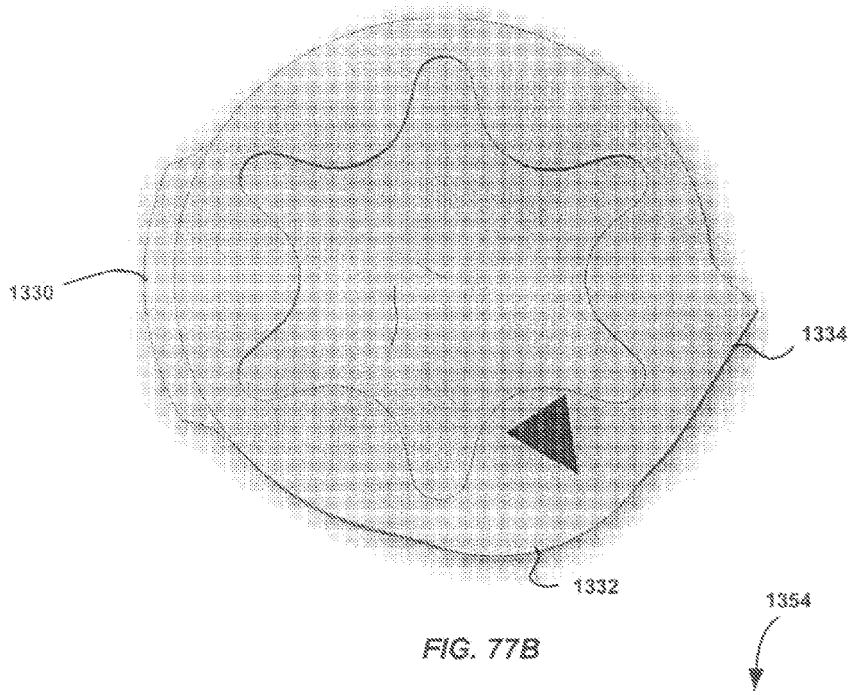
FIG. 77B is a top view of an embodiment of a cam of the invention.

Located adjacent to the cylindrical slot 1304 is the socket 1310 for accepting a cam 1312. One purpose of the cam 1312 is to provide a mechanical means to pinch the sides of the cylindrical slot 1304 together in order to secure the vertical rods 716 to the second horizontal rod 710. The socket 1310 of this embodiment includes a flat front face 1318, a rounded back face 1320, and two rounded side faces 1322, 1324. The front face 1318 includes a groove 1328 while the back face 1320 includes a channel 1326, both of which can be used to help keep the cam 1312 secured within the second horizontal rod 710. The front and back faces 1318, 1320 are also elevated from the side faces 1322, 1324. In this configuration, a cam 1312 having a first side tab 1330 and a second side tab 1332 (as shown in FIGS. 77A, 77B) can be inserted into the socket 1310 wherein the side tabs 1330, 1332 are initially placed adjacent to the side faces 1322, 1324 of the second horizontal rod 710. As a vertical rod 716 is placed within the cylindrical slot 1304, the cam 1312 can be twisted in order to position a first side tab 1332 within the groove 1328 of the front face 1318 and a second side tab 1330 within the channel 1326 of the back face 1320. In this configuration, the first side tab 1332 and the second side tab 1334 of the cam 1312 secure the cam 1312 to the second horizontal rod 710 while also causing the sides of the cylindrical slot 1304 to pinch together, thereby securing the vertical rod 716 to the second horizontal rod 710. In an embodiment, the cam 1312 can also include a tapered ridge 1334 (as shown in FIGS. 77A, 77B) which further helps to pinch the sides of the cylindrical slot 1204 together around the vertical rod 716.

Figure 76:
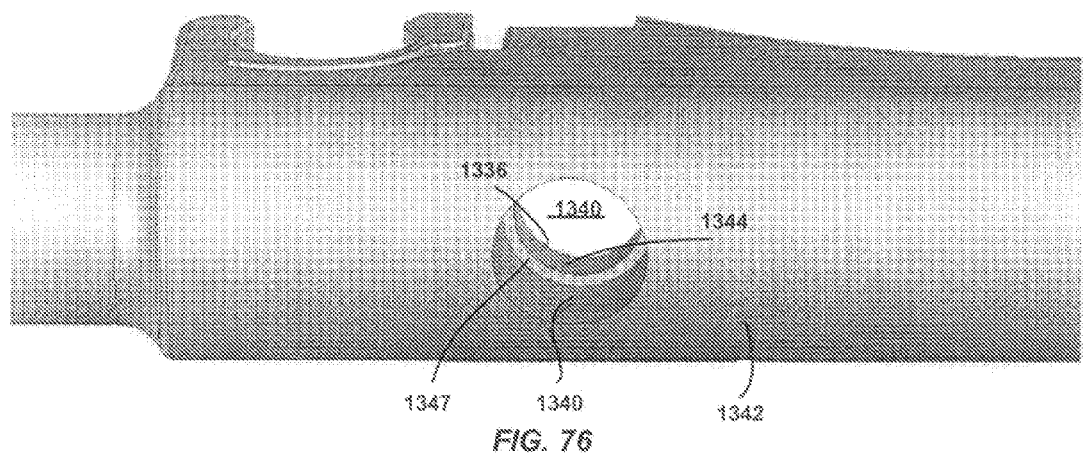
FIG. 76 is a perspective view of an embodiment of a horizontal rod of the invention.

Referring now to FIG. 76, the socket 1310 can also include an aperture 1340, the aperture 1340 extending from the floor 1336 of the socket 1310 to the bottom surface 1342 of the second horizontal rod 710. The aperture 1340 can include a first section 1344 and a second section 1346. In this embodiment, the diameter of the first section 1344 of the aperture 1340 is smaller than the diameter of the second section 1346 of the aperture 1340. The height and diameter of the first section 1344 of the aperture 1340 can be designed to conform to the shape of a fastener located on the bottom of a cam which can be inserted therein. For example, the cam 1312 shown in FIG. 77A includes fasteners 1348 located on the bottom of the cam 1312. The cam fasteners 1348 include ends 1350 which extend away from the main body 1352 of the fasteners 1348. In use, as the fasteners 1348 are inserted into the aperture 1340 of the socket 1310, the fasteners 1348 pinch in until the ends 1350 of the fasteners 1348 extend past the first section 1344 of the aperture 1340. Once the ends 1350 of the fasteners 1348 extend past the first section 1344 of the aperture 1340, the fasteners 1348 return to their relaxed configurations, and engage lip 1347, wherein the main body 1352 of the fasteners 1348 engage the second horizontal rod 710 along the first section 1344 of the aperture 1340 while the ends 1350 of the fasteners 1348 and engage lip 1347 help prevent the cam 1312 from becoming disengaged from the second horizontal rod 710.

Figure 78:
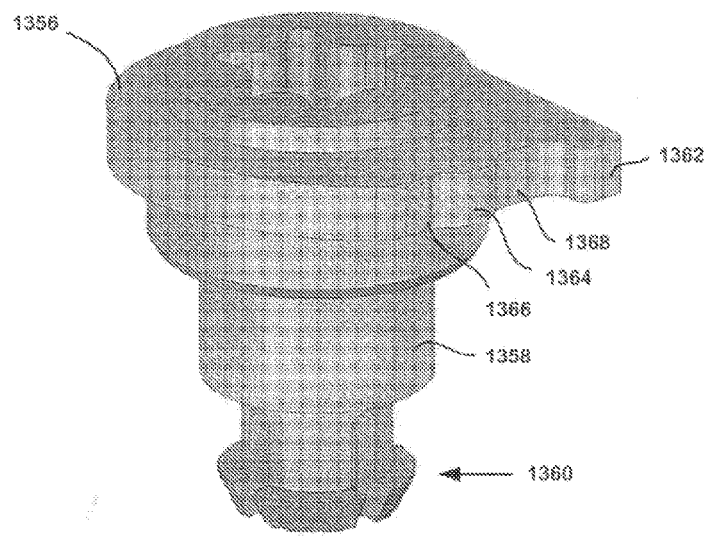
FIG. 78 is a perspective view of an embodiment of a cam of the invention.
Figure 79A:
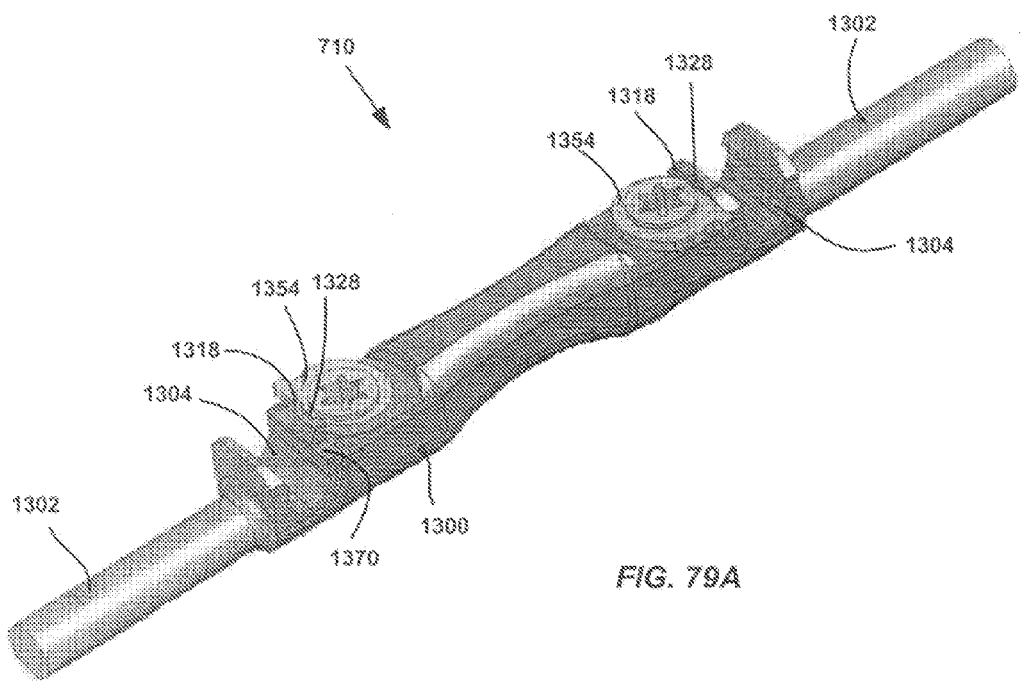
FIG. 79A is a perspective view of an embodiment of a horizontal rod system and a connector of the invention.
Figure 79B:
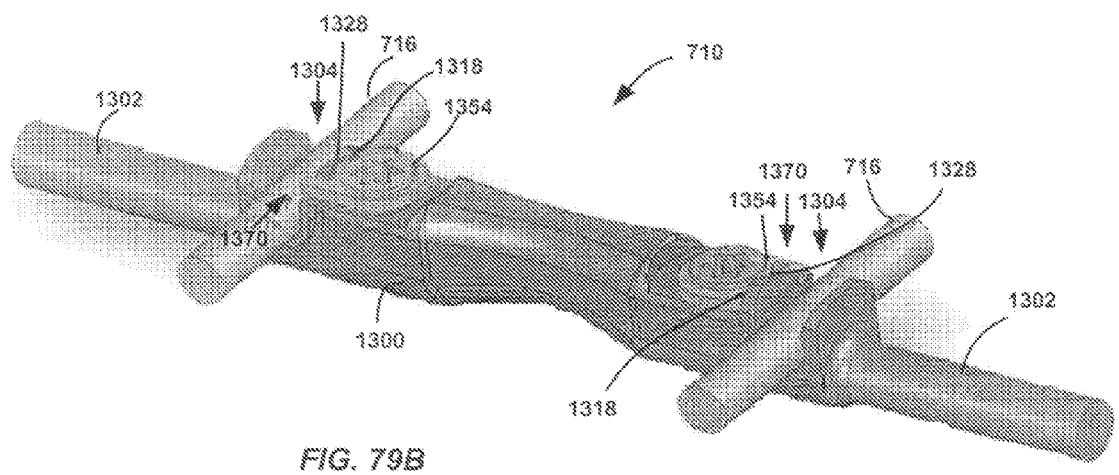
FIG. 79B is a perspective view of an embodiment of a horizontal rod system, a vertical rod system and a connector of the invention.

FIGS. 78-79C illustrate an alternative embodiment of a cam 1354. Referring now to FIG. 78, the cam 1354 of this embodiment can be seen as including a top section 1356, a cylindrical body 1358 and fasteners 1360 on the bottom of the cam 1354. The top section 1356 further includes a restraining tab 1362 and a side tab 1364 located between two grooves 1366, 1368. FIG. 79A illustrates cam 1354 which has been force fit in the socket 1310 of the second horizontal rod 710 in its undeployed configuration. The cam 1354 is secured to the second horizontal rod 710 through the use of the fasteners 1360 in the same manner as set forth above for cam 1312. FIG. 79B illustrates cam 1354 within the second horizontal rod 710 in its deployed configuration. In this configuration, once the vertical rod 716 is placed in the cylindrical slot 1304 of the second horizontal rod 710, the cam 1354 can be rotated until the side tab 1364 of the cam 1354 is aligned with the groove 1328 of the front face 1318 of the socket 1310 and the restraining tab 1362 of the cam 1354 is placed within an indentation 1370 of the front face 1318 of the socket 1310. The side tab 1362 causes the sides of the cylindrical slot 1304 to pinch together, thereby securing the vertical rod 716 to the second horizontal rod 710.

Figure 80:
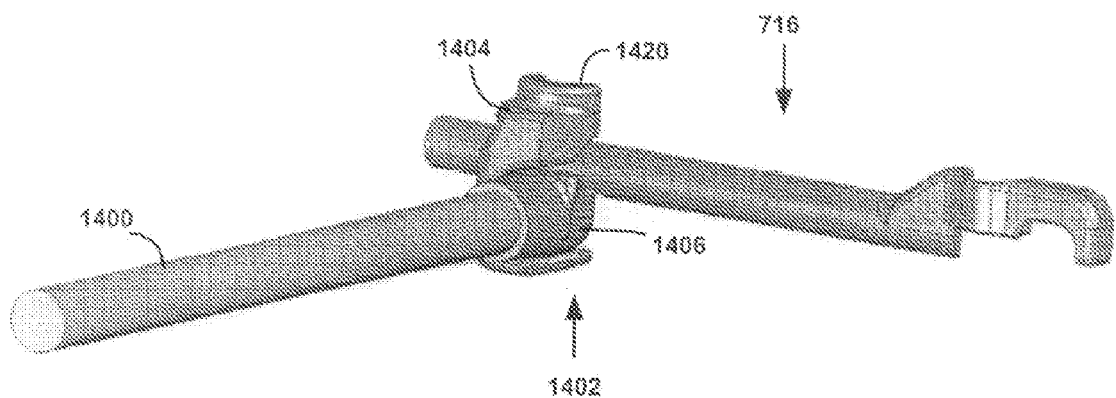
FIG. 80 is a perspective view of an embodiment of a connector of the invention.
Figure 81:
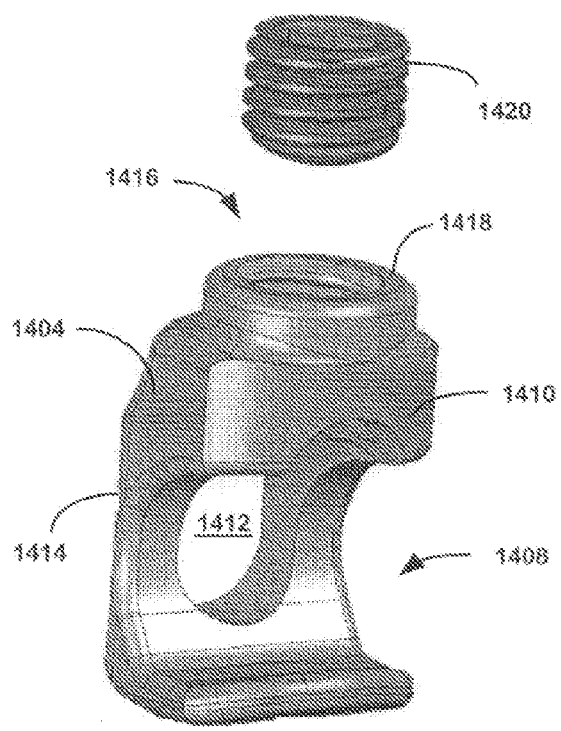
FIG. 81 is a perspective view of an embodiment of a connector of the invention.
Figure 82:
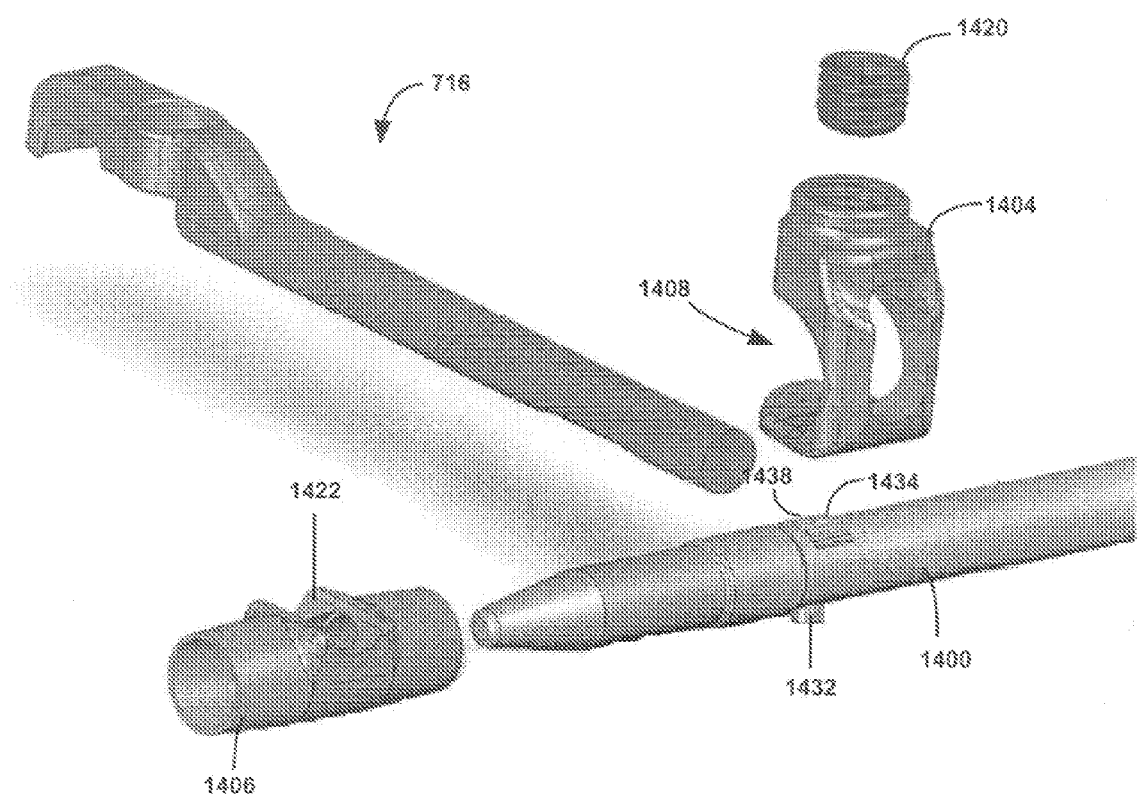
FIG. 82 is a perspective view of an embodiment of a horizontal rod system, a vertical rod system and a connector of the invention.

FIGS. 80-85 illustrate an alternative embodiment of the second horizontal rod which can be used within the dynamic stabilization system 700 described above. Referring now to FIG. 80, a second horizontal rod 1400 (previously shown in FIG. 74 as second horizontal rod 710) includes a connector 1402 to secure the second horizontal rod 1400 to the vertical rod 716. The connector 1402 of this embodiment includes a main body 1404 and a rotating link 1406. FIGS. 81 and 82 illustrate the individual components included in this embodiment of the second horizontal rod 1400 as well as the connector 1402.

Referring now to FIG. 81, the main body 1404 of the connector 1402 can be seen as including a C-shaped slot 1408 for housing the rotating link 1406 along the front face 1410 of the main body 1404. The main body 1404 also includes a first aperture 1412 and a second aperture 1416. The first aperture 1412 is located along the back face 1414 of the main body 1404 and is configured to accept the vertical rod 716. The second aperture 1416 is located at the top 1418 of the main body 1404 and can be threaded to accept a threaded fastening or set screw 1420.

Figure 83:
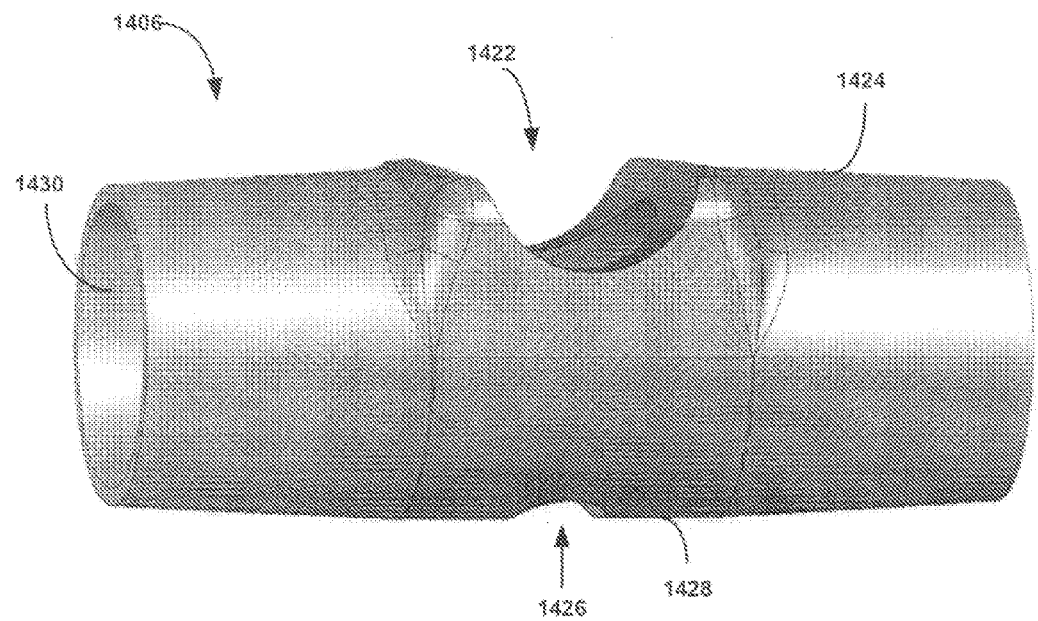
FIG. 83 is a perspective view of an embodiment of a rotating link of a connector of the invention.

Referring now to FIG. 83, the rotating link 1406 can be seen as including a saddle-shaped groove 1422 on the top surface of the rotating link 1446 which is positioned substantially perpendicular to the longitudinal axis of the rotating link 1406. The saddle-shaped groove 1422 includes an aperture 1426 that extends from the top 1424 to the bottom surface 1428 of the rotating link 1406. Finally, the rotating link 1406 includes an internal cylindrical bore 1430 for accepting the second horizontal rod 1400 which is positioned substantially parallel to the longitudinal axis of the rotating link 1406.

Referring back to FIG. 80, this embodiment of the second horizontal rod 1400 can be seen in its deployed configuration. In this configuration, the second horizontal rod 1400 is inserted into the cylindrical bore 1430 of the rotating link 1306. In this embodiment, the second horizontal rod 1400 can include a dowel pin 1432 (as shown in FIG. 82) that extends through the aperture 1426 along the bottom surface 1428 of the rotating link 1406 (as shown in FIG. 83) when the second horizontal rod 1400 is inserted into the rotating link 1406. One purpose of the dowel pin 1432 is to keep the rotating link 1306 positioned on the rod 1400 with restricted motion longitudinally along the rod 1400 and circumferential about the rod 1400 as will be described in greater detail below. It can further be seen in FIG. 80 that the rotating link 1406 is placed within the C-shaped slot 1408 of the main body 1404, with the vertical rod 716 being positioned within the saddle-shaped groove 1422 of the rotating link 1406. In this embodiment, the vertical rod 716 can be inserted into the aperture 1412 located along the back face 1414 of the main body 1404 perpendicular to the second horizontal rod 1400 and the rotating link 1406. The extent that the vertical rod 716 is inserted into the aperture 1412 can be varied to accommodate the specific vertebrae being affected. The fastening screw 1420 is used to secure the vertical rod 716 and the rotating link 1406 to the main body 1404.

Figure 84:
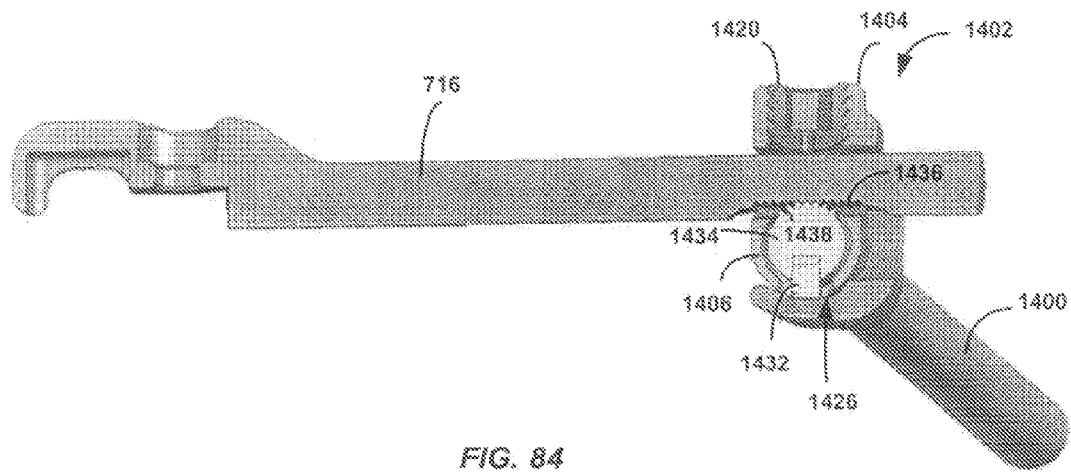
FIG. 84 is a sectional view of an embodiment of a horizontal rod system, a vertical rod system and a connector of the invention.
Figure 85:
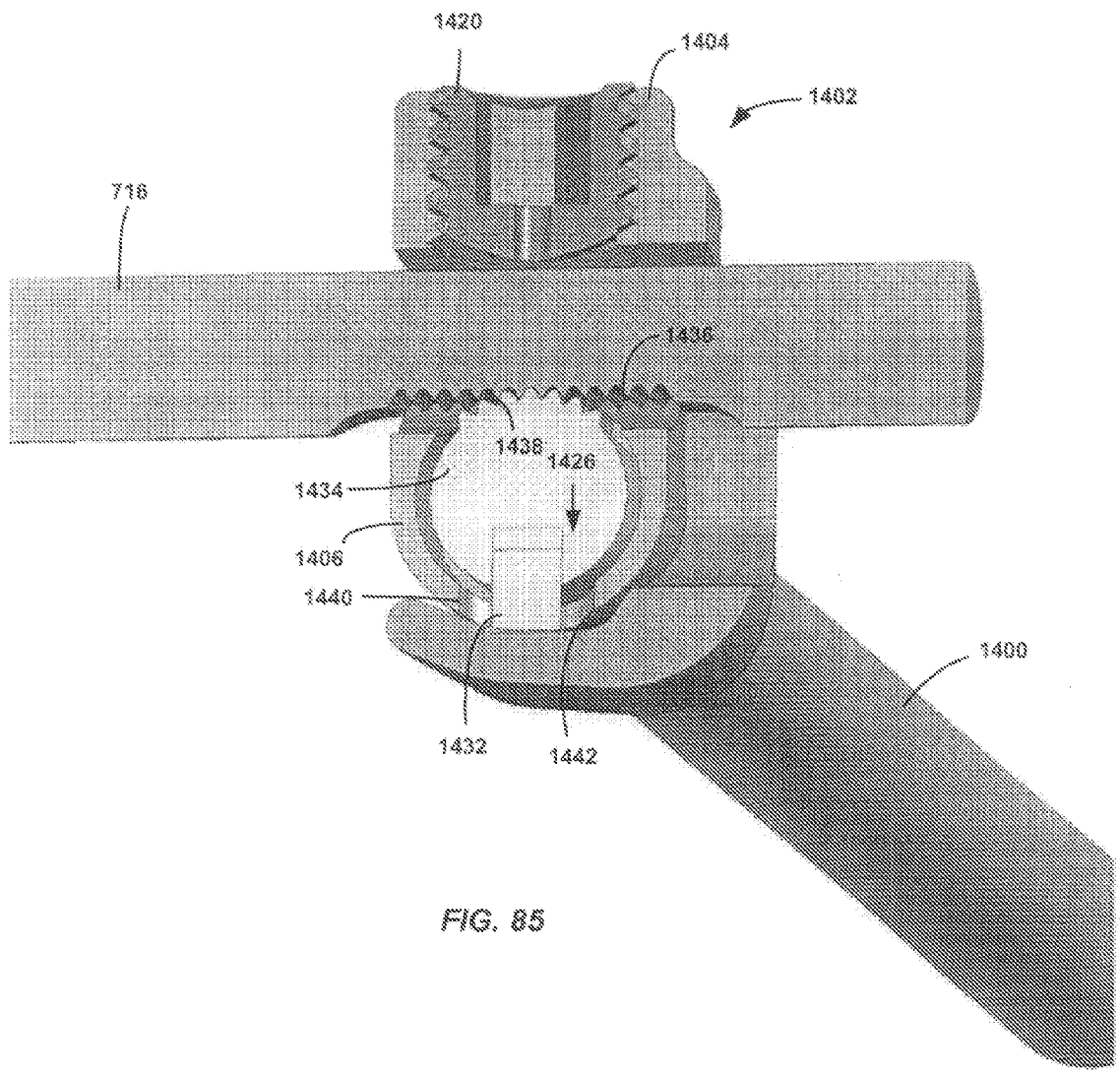
FIG. 85 is a sectional view of an embodiment of a horizontal rod system, a vertical rod system and a connector of the invention.

As shown in FIGS. 82, 84 and 85, the second horizontal rod 1400 can also include a section 1434 having threads or grooves 1438 to engage threads or grooves 1436 on a vertical rod 716. In this embodiment, the threads or grooves 1438 on the section 1434 engage a recessed, threaded or grooved section 1436 of the vertical rod 716 on one side of the section 1434, while a dowel pin 1432 extends on the opposing side, the dowel pin 1432 extending past the aperture 1426 along the bottom surface 1428 of the rotating link 1406. In this configuration, the vertical rod 716 is allowed to have limited vertical movement within the main body 1404 of the connector 1402. The dowel pin 1432 extends through the aperture 1426 of the rotating link 1406, thereby limiting the degrees of freedom of motion and with the help of set screw 1420, fix the position of the horizontal rod 1400 relative to the vertical rod 716. An alternative embodiment of the connector can eliminate one or any combination of two or more of the rotating link 1406, the dowel pin 1432, the threads or grooves 1438, and the threaded or grooved section 1436. It is noted that the second horizontal rod 1400 can be a straight rod having a constant diameter (as shown in FIG. 84) which is made of a stiff and rigid material (titanium, for example). It is also noted that other types of connectors can also be used which would be obvious to one skilled in the art without deviating from the scope of the invention.

Method of Implantation and Revised Implantation:

A method of implantation of the system in the spine of the human patient is as follows. First the vertebral levels that are to receive the system are identified. Then the anchor systems are implanted, generally two anchor systems for each level. The anchor systems can be implanted using a cannula and under guidance imaging such as x-ray imaging. Alternatively, the anchor system can be implanted using traditional spinal surgery techniques. Then the horizontal rods are inserted and secured to the anchor systems. The horizontal rods can be inserted laterally through a cannula or with an incision and the use of, for example, a lead-in cone. Alternatively, the horizontal rods can be inserted using traditional techniques when the anchor systems are implanted. Thereafter, the vertical rods can be connected to or pivoted, rotated or placed into communication with and secured to the appropriate horizontal rod.

Should a dynamic stabilization system such as system 100 be initially implanted and then should there be a desire to make the system more rigid or to accomplish a fusion, the system 100 can be revised by removing the horizontal rod 104 that includes the deflection rods or loading rods and replace it with a horizontal rod 106 which has the vertical rod mounts (FIG. 34) and is thus substantially more rigid. Thus a revision to a fusion configuration can be accomplished with minimal trauma to the bone and tissue structures of the spine.

Materials of Embodiments of the Invention:

In addition to Nitinol or nickel-titanium (NiTi) other super elastic materials include copper-zinc-aluminum and copper-aluminum-nickel. However for biocompatibility the nickel-titanium is the preferred material.

As desired, the implant can be made of titanium or stainless steel. Other suitable material includes by way of example only polyetheretherketone (PEEK), polyetherketoneketone (PEKK), polyetherketone (PEK), polyetherketoneetherketoneketone (PEKEKK), and polyetheretherketoneketone (PEEKK). Still, more specifically, the material can be PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

As will be appreciated by those of skill in the art, other suitable similarly biocompatible thermoplastic or thermoplastic polycondensate materials that resist fatigue, have good memory, are flexible, and/or deflectable have very low moisture absorption, and good wear and/or abrasion resistance, can be used without departing from the scope of the invention.

Reference to appropriate polymers that can be used in the spacer can be made to the following documents. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and PCT Publication WO 02/00270 A1, dated Jan. 3, 2002, entitled "Bio-Compatible Polymeric Materials."

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A spinal implant that is adapted to be mounted to a spine comprising:
   a deflection rod system having a first section and a second section;
   a horizontal rod adapted to be secured at each end by a bone anchor to a vertebra;
   a first mount connected to the first section and adapted to secure the first section of the deflection rod system to a vertical rod which supports a load from an adjacent vertebra;
   a second mount connected to the second section which secures the second section of the deflection rod system to the horizontal rod;
   wherein the deflection rod system is adapted, by bending of the deflection rod system, to permit resilient deflection of the first mount relative to the horizontal rod and thereby supports the load from the adjacent vertebra while accommodating relative movement between the vertebra and the adjacent vertebra;

said deflection rod system including an inner rod and an outer shell;
wherein said inner rod is cylindrical in shape; and
wherein said outer shell increases in diameter going from the first mount towards the second mount.

2. The implant of claim 1, wherein said second mount connects the second section of the deflection rod system to a middle portion of the horizontal rod.

3. The implant of claim 1, wherein said second mount connects the second section of the deflection rod system to the horizontal rod with the deflection rod system substantially parallel to the horizontal rod.

4. The implant of claim 2, wherein said second mount connects the second section of the deflection rod system to the horizontal rod such that the deflection rod system forms a cantilever with respect to the horizontal rod.

5. The implant of claim 1 wherein said inner rod is comprised of a super elastic material.

6. The implant of claim 1, wherein the first mount is ball-shaped and adapted to be received in a socket of the vertical rod.

7. The implant of claim 1 wherein said inner rod is comprised of Nitinol.

8. The implant of claim 1 wherein said outer shell is comprised of a biocompatible polymer.

9. The implant of claim 1 wherein said outer shell is comprised of PEEK.

10. The implant of claim 1 wherein said inner rod is comprised of a first material and the outer shell is comprised of a second material, and wherein said second material is selected such that the outer shell is stiffer than the first material, and wherein said outer shell resists movement of said inner rod.

11. The implant of claim 1 wherein said inner rod is comprised of a first material and the outer shell is comprised of a second material, and wherein said second material causes the load that is placed on the inner rod by the spine to be spread along the elongated inner rod.

12. The implant of claim 1 wherein said inner rod extends past said outer shell at the first section of the deflection rod system.

13. The implant of claim 1, wherein:
said deflection rod system further comprises a third section and wherein the second section is located between the first section and the third section;
and wherein the implant includes a third mount connected to the third section and adapted to secure the third section to a second vertical rod which supports a load from the adjacent vertebra;
wherein the deflection rod system is adapted, by bending of the deflection rod system, to permit resilient deflection of the first mount and third mount relative to the horizontal rod and thereby support the load from the adjacent vertebra while accommodating relative movement between the vertebra and the adjacent vertebra; and
wherein said outer shell also increases in diameter going from the third mount towards the second mount.

14. The implant of claim 13, wherein said second mount connects the second section of the deflection rod system to the spinal rod with the deflection rod system substantially parallel to the horizontal rod.

15. The implant of claim 13, wherein said outer shell is conical in shape between the second mount and the first mount and is conical in shape between the second mount and the third mount.

16. The implant of claim 13, wherein:
the first mount is ball-shaped and adapted to be received in a socket of the vertical rod; and
the third mount is ball-shaped and adapted to be received in a second socket of the second vertical rod.

17. A spinal implant that is adapted to be mounted to a spine comprising:
a deflection rod system including a first section and a second section;
a spinal rod adapted to be mounted at each end by a bone anchor to a vertebra;
a first mount connected to the first section and adapted to secure the first section of the deflection rod system to a vertical rod which supports a load from an adjacent vertebra;
a second mount connected to the second section and adapted to secure the second section of the deflection rod system to the spinal rod;
wherein the deflection rod system is adapted, by bending of the deflection rod system, to permit resilient deflection of the first mount relative to the spinal rod and thereby support the load from the adjacent vertebra while accommodating relative movement between the vertebra and the adjacent vertebra;
said deflection rod system including an inner rod and an outer shell;
wherein said inner rod is elongated and said outer shell is elongated along the elongated inner rod;
wherein said outer shell is conical in shape with a larger diameter adjacent to the second section of the deflection rod system and a smaller diameter located adjacent to the first section of the deflection rod system; and
wherein said inner rod is comprised of a super elastic material.

18. The implant of claim 17 wherein said outer shell is comprised of a biocompatible polymer.

19. A spinal implant that is adapted to be mounted to a spine comprising:
a deflection rod system including a first section and a second section;
a horizontal rod adapted to be mounted to another implant that can be implanted in a vertebra;
a first mount connected to the first section and adapted to secure the first section of the deflection rod system to a vertical rod which supports a load from an adjacent vertebra;
a second mount connected to the second section which secures the second section of the deflection rod system to the horizontal rod;
wherein the deflection rod system is adapted, by bending of the deflection rod system, to permit resilient deflection of the first mount relative to the horizontal rod and thereby support the load from the adjacent vertebra while accommodating relative movement between the vertebra and the adjacent vertebra;
said deflection rod system including an inner rod and an outer shell; and
wherein said inner rod is elongated and said outer shell is elongated along the elongated inner rod.

20. The implant of claim 19 including:
said outer shell is conical in shape with a larger diameter adjacent to the second mount of the deflection rod system and a smaller diameter located adjacent to the first mount of the deflection rod system; and
wherein said inner rod is comprised of a super elastic material.

21. The implant of claim 20 wherein said outer shell is comprised of a biocompatible polymer.

22. The implant of claim 19, wherein the first mount is ball-shaped and adapted to be received in a socket of the vertical rod.

23. The implant of claim 19, wherein the second mount secures the second section of the deflection rod system to a middle portion of the horizontal rod and the horizontal rod is adapted to be secured at each end in fixed relationship to the vertebra by a bone anchor.

24. The implant of claim 19, wherein:
   said deflection rod system further comprises a third section and wherein the second section is located between the first section and the third section;
   and wherein the implant includes a third mount connected to the third section and adapted to secure the third section to another vertical rod which supports a load from the adjacent vertebra; and
   wherein the deflection rod system is adapted, by bending of the deflection rod system, to permit resilient deflection of the first mount and the third mount relative to the horizontal rod and thereby support the load from the adjacent vertebra while accommodating relative movement between the vertebra and the adjacent vertebra.

25. The implant of claim 19, wherein said inner rod comprises Nitinol and said outer shell comprises PEEK.

26. A spinal implant that is adapted to be mounted to a spine comprising:
   a deflection rod system having a first section and a second section;
   a horizontal rod adapted to be secured at each end by a bone anchor to a vertebra;
   a first mount connected to the first section and adapted to secure the first section of the deflection rod system to a vertical rod which supports a load from an adjacent vertebra;
   a second mount connected to the second section which secures the second section of the deflection rod system to the horizontal rod; and
   wherein the deflection rod system is adapted, by bending of the deflection rod system, to permit resilient deflection of the first mount relative to the horizontal rod and thereby support the load from the adjacent vertebra while accommodating relative movement between the vertebra and the adjacent vertebra.

27. The spinal implant of claim 26, wherein
   said deflection rod system further comprises a third section and wherein the second section is located between the first section and the third section;
   and wherein the implant includes a third mount connected to the third section and adapted to secure the third section to another vertical rod which supports a load from the adjacent vertebra; and
   wherein the deflection rod system is adapted, by bending of the deflection rod system, to permit resilient deflection of the first mount and the third mount relative to the horizontal rod and thereby support the load from the adjacent vertebra while accommodating relative movement between the vertebra and the adjacent vertebra.

* * * * *